US010961198B2

(12) United States Patent
Smith et al.

(10) Patent No.: US 10,961,198 B2
(45) Date of Patent: *Mar. 30, 2021

(54) FARNESOID X RECEPTOR AGONISTS AND USES THEREOF

(71) Applicant: Metacrine, Inc., San Diego, CA (US)

(72) Inventors: Nicholas D. Smith, San Diego, CA (US); Steven P. Govek, San Diego, CA (US); Johnny Y. Nagasawa, San Diego, CA (US)

(73) Assignee: METACRINE, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/494,264

(22) PCT Filed: Mar. 14, 2018

(86) PCT No.: PCT/US2018/022489
§ 371 (c)(1),
(2) Date: Sep. 13, 2019

(87) PCT Pub. No.: WO2018/170166
PCT Pub. Date: Sep. 20, 2018

(65) Prior Publication Data
US 2020/0131134 A1 Apr. 30, 2020

Related U.S. Application Data

(60) Provisional application No. 62/471,517, filed on Mar. 15, 2017.

(51) Int. Cl.
*C07D 231/12* (2006.01)
*A61P 1/16* (2006.01)
*A61P 1/00* (2006.01)
*A61K 9/00* (2006.01)
*A61K 9/06* (2006.01)
*A61K 9/20* (2006.01)
*A61K 9/48* (2006.01)
*C07D 401/04* (2006.01)
*C07D 401/14* (2006.01)
*C07D 403/12* (2006.01)
*C07D 405/12* (2006.01)
*C07D 471/04* (2006.01)

(52) U.S. Cl.
CPC .......... *C07D 231/12* (2013.01); *A61K 9/0014* (2013.01); *A61K 9/0029* (2013.01); *A61K 9/0053* (2013.01); *A61K 9/06* (2013.01); *A61K 9/2054* (2013.01); *A61K 9/4866* (2013.01); *A61P 1/00* (2018.01); *A61P 1/16* (2018.01); *C07D 401/04* (2013.01); *C07D 401/14* (2013.01); *C07D 403/12* (2013.01); *C07D 405/12* (2013.01); *C07D 471/04* (2013.01)

(58) Field of Classification Search
CPC .................................. C07D 231/12; A61P 1/16
See application file for complete search history.

(56) References Cited

U.S. PATENT DOCUMENTS

| 6,645,980 | B1 | 11/2003 | Cuny et al. |
| 8,212,006 | B2 | 7/2012 | Downes et al. |
| 2006/0009459 | A1 | 1/2006 | Chakka et al. |
| 2008/0081824 | A1 | 4/2008 | Zheng et al. |
| 2008/0280916 | A1 | 11/2008 | Bilich et al. |
| 2012/0115869 | A1 | 5/2012 | Crosignani et al. |
| 2014/0155247 | A1 | 6/2014 | Aoyagi et al. |
| 2015/0258052 | A1 | 9/2015 | Evans et al. |
| 2017/0066724 | A1 | 3/2017 | Evans et al. |
| 2018/0116993 | A1 | 5/2018 | Li et al. |
| 2018/0282263 | A1 | 10/2018 | Smith et al. |
| 2020/0092932 | A1* | 3/2020 | Youn .................. H04W 80/02 |
| 2020/0102308 | A1 | 4/2020 | Smith et al. |
| 2020/0131129 | A1* | 4/2020 | Smith .................. C07D 241/18 |
| 2020/0131142 | A1 | 4/2020 | Smith et al. |

FOREIGN PATENT DOCUMENTS

| FR | 2839974 A1 | 11/2003 |
| JP | 2006199656 A | 8/2006 |
| JP | 2007530582 A | 11/2007 |
| JP | 2010077109 A | 4/2010 |
| MY | 144229 A | 8/2011 |
| WO | WO-0069810 A1 | 11/2000 |
| WO | WO-0071518 A2 | 11/2000 |
| WO | WO-0185694 A2 | 11/2001 |
| WO | WO-0192226 A1 | 12/2001 |
| WO | WO-0224649 A1 | 3/2002 |
| WO | WO-0230927 A1 | 4/2002 |
| WO | WO-02098852 A2 | 12/2002 |

(Continued)

OTHER PUBLICATIONS

Ali et al. Recent advances in the development of farnesoid X receptor agonists. Ann Transl Med 3(1):5 (2015).
Amidon et al. Colon-Targeted Oral Drug Delivery Systems: Design Trends and Approaches, AAPS PharmSciTech 16(4):731-741 (2015).
Beaulieu et al., Preparation of 2-amido benzoic acid compounds as viral polymerase inhibitors. Chemical Abstracts Service. XP002791354. Database accession No. 2009:771969 (2009).
Berge et al. Pharmaceutical Salts. Journal of Pharmaceutical Sciences 66(1):1-19 (Jan. 1977).

(Continued)

Primary Examiner — D Margaret M Seaman
(74) Attorney, Agent, or Firm — Wilson Sonsini Goodrich & Rosati

(57) ABSTRACT

Described herein are compounds that are farnesoid X receptor agonists, methods of making such compounds, pharmaceutical compositions and medicaments comprising such compounds, and methods of using such compounds in the treatment of conditions, diseases, or disorders associated with farnesoid X receptor activity.

4 Claims, No Drawings

(56) References Cited

FOREIGN PATENT DOCUMENTS

| WO | WO-2004009549 A2 | 1/2004 |
|---|---|---|
| WO | WO-2004026823 A1 | 4/2004 |
| WO | WO-2004009549 A3 | 6/2004 |
| WO | WO-2004045511 A2 | 6/2004 |
| WO | WO-2004046162 A2 | 6/2004 |
| WO | WO-2004096771 A1 | 11/2004 |
| WO | WO-2005011655 A2 | 2/2005 |
| WO | WO-2004046162 A8 | 3/2005 |
| WO | WO-2005058822 A1 | 6/2005 |
| WO | WO-2005113522 A1 | 12/2005 |
| WO | WO-2007110237 A2 | 10/2007 |
| WO | WO-2008065500 A2 | 6/2008 |
| WO | WO-2009076747 A1 | 6/2009 |
| WO | WO-2009106991 A2 | 9/2009 |
| WO | WO-2010001869 A1 | 1/2010 |
| WO | WO-2011006935 A2 | 1/2011 |
| WO | WO-2011008915 A1 | 1/2011 |
| WO | WO-2012011081 A1 | 1/2012 |
| WO | WO-2012129495 A1 | 9/2012 |
| WO | WO-2014133414 A2 | 9/2014 |
| WO | WO-2015040425 A1 | 3/2015 |
| WO | WO-2015138969 A1 | 9/2015 |
| WO | WO-2016149111 A1 | 9/2016 |
| WO | WO-2017018751 A1 | 2/2017 |
| WO | WO-2017049172 A1 | 3/2017 |
| WO | WO-2017049173 A1 | 3/2017 |
| WO | WO-2017049176 A1 | 3/2017 |
| WO | WO-2017049177 A1 | 3/2017 |
| WO | WO-2017170182 A1 | 10/2017 |
| WO | WO-2018170165 A1 | 9/2018 |
| WO | WO-2018170166 A1 | 9/2018 |
| WO | WO-2018170167 A1 | 9/2018 |
| WO | WO-2018170173 A1 | 9/2018 |
| WO | WO-2018170182 A1 | 9/2018 |
| WO | WO-2020061112 A1 | 3/2020 |
| WO | WO-2020061113 A1 | 3/2020 |
| WO | WO-2020061116 A1 | 3/2020 |
| WO | WO-2020061117 A1 | 3/2020 |
| WO | WO-2020061118 A1 | 3/2020 |

OTHER PUBLICATIONS

Boss et al., Preparation of N-benzyl N-piperidin-4-yl benzamides as inhibitors of parasitic aspartyl protease. Chemical Abstracts Service. XP002791357. Database accession No. 2005:570873 (2005).
Boss et al., Preparation of piperidines for the treatment of central nervous system disorders. Chemical Abstracts Service. XP002791361. Database accession No. 2004:80651 (2004).
Boss et al., Preparation of substituted amino-aza-cycloalkanes as anti-malarial agents. Chemical Abstracts Service. XP002791363. Database accession No. 2002:240729 (2002).
Boss et al., Achiral, cheap, and potent inhibitors of Plasmepsins I, II, and IV. ChemMedChem. 1(12):1341-1345 (2006).
Brauer et al., Evolutionary chemistry approach toward finding novel inhibitors of the type 2 diabetes target glucose-6-phosphate translocase. Journal of Combinatorial Chemistry. 7(2):218-226 (2005).
Bromidge et al., Preparation of biaryl compounds having activity at the 5-HT5A receptor. Chemical Abstracts Service. XP002791359. Database accession No. 2004:965222 (2004).
Brough et al., Preparation of resorcinol N-Aryl amide compounds, for use as pyruvate dehydrogenase kinase inhibitors. Chemical Abstracts Service. XP002791352 Database accession No. 2015:512259 (2015).
Bundgaard. Design and Application of Prodrugs. Textbook of Drug Design and Development. Krosgaard-Larsen and Bundgaard. Chapter 5. pp. 113-191 (1991).
Bundgaard. Means to Enhance Penetration: Prodrugs as a Means to Improve the Delivery of Peptide Drugs. Advanced Drug Delivery Review 8:1-38 (1992).
Camilleri. Bile Acid diarrhea: prevalence, pathogenesis, and therapy. Gut Liver 9(3):332-339 (2015).

Chemical Abstract compound, STN express RN 1026708-50-8 (Entered STN: Jun. 9, 2008).
Chourasia et al. Pharmaceutical approaches to colon targeted drug delivery systems. J Pharm Pharm Sci. 6(1):33-66 (2003).
Costantino et al. Molecular Dynamics Simulation of the Ligand Binding Domain of Farnesoid X Receptor. Insights into Helix-12 Stability and Coactivator Peptide Stabilization in Response to Agonist Binding. J Med Chem 48:3251-3259 (2005).
Downes et al. A Chemical, Genetic, and Structural Analysis of the Nuclear Bile Acid Receptor FXR. Molecular Cell 11:1079-1092 (2003).
Erb et al. Sequential One-Pot Access to Molecular Diversity through Aniline Aqueous Borylation. J Organ Chem 79:10568-10580 (2014).
Fang et al. Intestinal FXR agonism promotes adipose tissue browning and reduces obesity and insulin resistance. Nat Med 21(2):159-165 (2015).
Fett et al., Preparation of oxadiazole and pyridazine derivatives as inhibitors of biosynthesis of triglycerides. Chemical Abstracts Service. XP002791353 Database accession No. 2012:125764 (2012).
Fu et al. Fibroblast growth factor 19 increases metabolic rate and reverses dietary and leptin-deficient diabetes. Endocrinology 145:2594-2603 (2004).
Gadaleta et al. Farnesoid X receptor activation inhibits inflammation and preserves the intestinal barrier in inflammatory bowel disease. Gut 60(4):463-472 (2011).
Gangloff et al. Synthesis of 3,5-disubstituted 1,2,4-oxadiazoles using tetrabutylammonium fluoride as a mild and efficient catalyst. Tetrahedron Letters 42(8):1441-1443 (2001).
Gege et al. Knocking on FXR's Door: The "Hammerhead"—Structure Series of FXR Agonists—Amphiphilic Isoxazoles with Potent in Vitro and in Vivo Activi-ties. Current Topics in Medicinal Chemistry 14:2143-2158 (2014).
Genin et al. Discovery of 6-(4-{[5-Cyclopropyl-3-(2,6-dichlorophenyl)isoxazol-4-yl]methoxy}piperidin-1-yl)-1-methyl-1H-indole-3-carboxylic Acid: A Novel FXR Agonist for the Treatment of Dyslipidemia. J Med Chem 58(24):9768-9772 (2015).
Hamada et al. Synthesis and antimicrobial evaluation of some heterocyclic chalcone derivatives. Molecules 16:2304-2312 (2011).
Hambruch et al. On the Pharmacology of Farnesoid X Receptor Agonists: Give me an "A", Like an "Acid". Nuclear Receptor Research 3:Article ID 101207 (2016).
Honorio et al. 3D QSAR Comparative molecular field analysis on nonsteroidal farnesoid X receptor activators. J Mol Graph Model 25:921-927 (2007).
Honorio et al. Hologram quantitative structure-activity relationships for a series of farnesoid X receptor activators. Bioorg Med Chem Letts 15:3119-3125 (2005).
Hu et al. Predicting biological Functions of Compounds based on Chemical-Chemical Interactions. PLoS One 6(12):e29491 (2011).
Inagaki et al. Regulation of antibacterial defense in the small intestine by the nuclear bile acid receptor. PNA USA 103:3920-3925 (2006).
Johnson et al., Preparation of arylheterocyclylamides as motilin antagonists. Chemical Abstracts Service. XP002791364. Database accession No. 2001:833284 (2001).
Jursic et. al. Preparation of 5-substituted 2-methyl-1,3,4-oxadiazoles from 5-substituted tetrazoles and acetic anhydride. Synthetic Communications 24(11):1575-82 (1994).
Kim et al. Inhibitory Effects of Bile Acides and Synthetic Farnesoid X Receptor Agonists on Rotavirus Replication. J Virol 85(23):12570-12577 (2011).
Kumar et al. Colon targeted drug delivery systems—an overview. Curr Drug Deliv 5(3):186-198 (2008).
Lam et al. Bile acids inhibit duodenal secretin expression via orphan nuclear receptor small heterodimer partner (SHP). Am J Physiol Gastrointest Liver Physiol 287:G90-G97 (2009).
Li et al. Microbiome remodelling leads to inhibition of intestinal farnesoid X receptor signalling and decreased obesity. Nat Commun 4:2384 (2013).
Li et al. Progress in the ligands and their complex structures of farnesoid X receptor. ACTA Pharmaceutica Sinica 47(6):704-715 (2012) (English Abstract).

(56) References Cited

OTHER PUBLICATIONS

Ling et al., Preparation of 3-(benzoylamino)propionic acid derivatives as glucagon antagonists/inverse agonists. Chemical Abstracts Service. XP002791365. Database accession No. 2000:824211 (2000).
Merk et al. Medicinal chemistry of farnesoid X receptor ligands: from agonists and antagonists to modulators. Future Med Chem 4(8):1015-1036 (2012).
Misawa et al. Discovery and structural development of small molecules that enhance transport activity of bile salt export pump mutant associated with progressive familial intrahepatic cholestasis type 2. Bioorg Med Chem 20:2940-2949 (2012).
Mokale et al. Synthesis and in-vivo hypolipidemic activity of some novel substituted phenyl isoxazol phenoxy acetic acid derivatives. Bioorg Med Chem Lett 24(9):2155-2158 (2014).
Mueller et al. Synthesis of plasmepsin II inhibitors—potential antimalarial agents. Molecules 8(7):556-564 (2003).
Mueller et al., Synthesis of plasmepsin II inhibitors as potential antimalarial agents. Chemical Abstracts Service. XP002791362. Database accession No. 2003:524478 (2003).
Nicolaou et al. Discovery and optimization of non-steroidal FXR agonists from natural product-like libraries. Org Biomol Chem 1:908-920 (2003).
O'Keefe et al., Preparation of amide and sulfonamidel igands for the estrogen receptor. Chemical Abstracts Service. XP002791360. Database accession No. 2004:267292 (2004).
Patel et al.Therapeutic opportunities in colon-specific drug-delivery systems. Crit Rev Ther Drug Carrier Syst. 24(2):147-202 (2007).
PCT/US2016/052270 International Preliminary Report on Patentability dated Mar. 29, 2018.
PCT/US2016/052270 International Search Report and Written Opinion dated Mar. 3, 2017.
PCT/US2018/022488 International Search Report and Written Opinion dated Jul. 30, 2018.
PCT/US2018/022488 Third Party Observation dated Jul. 15, 2019.
PCT/US2018/022489 International Search Report and Written Opinion dated Jul. 30, 2018.
PCT/US2018/022489 Third Party Observation dated Jul. 15, 2019.
PCT/US2018/022497 International Search Report and Written Opinion dated Jul. 30, 2018.
PCT/US2018/022497 Third Party Observation dated Jul. 15, 2019.
PCT/US2018/022513 International Search Report and Written Opinion dated Jul. 24, 2018.
PCT/US2019/051602 International Search Report and Written Opinion dated Dec. 4, 2019.
PCT/US2019/051603 International Search Report and Written Opinion dated Dec. 4, 2019.
PCT/US2019/051606 International Search Report and Written Opinion dated Dec. 4, 2019.
PCT/US2019/051607 International Search Report and Written Opinion dated Dec. 4, 2019.
PCT/US2019/051608 International Search Report and Written Opinion dated Dec. 4, 2019.
Poondra et al., Discovery of Indoline-Based, Natural-Product-like Compounds as Probes of Focal Adhesion Kinase Signaling Pathways. Chemical Abstracts Service. XP002791355 Database accession No. 2009:61531 (2009).
Ramanathan et al. One-Pot Reactions for Synthesis of 2,5-Substituted Tetrazoles from Aryldiazonium Salts and Amidines. Organic Letters 17(23):5886-5889 (2015).
Reschly et al. Ligand specificity and evolution of liver X receptors. J Steroid Biochem Mol Biol 110(1-2):83-94 (2008).
Sanyal et al. Involvement of corepressor complex subunit GPS2 in transcriptional pathways governing human bile acid biosynthesis. PNAS USA 104(40):15665-15670 (2007).
Schuster et al. Pharmacophore-based discovery of FXR agonists. Part I: Model development and experimental validation. Bioorg Med Chem 19:7168-7180 (2011).
Science IP—The CAS Search Service. Jul. 17, 2015 (316 pgs).
Shen et al. Synthesis and structure-activity relationships of thiadiazole-derivatives as potent and orally active peroxisome proliferator-activated receptors alpha/delta dual agonists. Bioorg Med Chem 16(6):3321-3341 (2008).
Steri et al. Antidiabetic sulfonylureas modulate farnesoid X receptor activation and target gene transcription. Future Med Chem 2(4):575-589 (2010).
U.S. Appl. No. 15/758,707 Office Action dated Sep. 5, 2019.
Vallin et al. Efficient Chemoenzymatic Dynamic Kinetic Resolution of 1-Heteroaryl Ethanols. J Org Chem 74(24):9328-9336 (2009).
Van Den Mooter. Colon drug delivery. Expert Opin Drug Deliv. 3(1):111-125 (2006).
Widder et al. Section III: Prodrugs Kinetics. Method in Enzymology. 112:309-396 (1985).
Yang et al. Syntheses of nicotinamide riboside and derivatives: effective agents for increasing nicotinamide adenine dinucleotide concentrations in mammalian cells. J. Med. Chem. 50:6458-61 (2007).
Zheng et al., Preparation of substituted piperidines as modulators of chemokine receptor activity. Chemical Abstracts Service. XP002791356. Database accession No. 2008:419604 (2008).
Co-pending U.S. Appl. No. 16/886,642, filed May 28, 2020.
PCT/US2018/022513 Third Party Observation dated Jul. 15, 2019.
Braeuer et al. Evolutionary chemistry approach toward finding novel inhibitors of the type 2 diabetes target glucose-6-phosphate translocase. CA, Chemical Abstracts Service, Columbus, Ohio, US, (2005), Database accession No. 2005:154377, URL: STN, XP002791358.
CAS Registry No. 1349456-93-4. CA Index Name: [1,1?-biphenyl]-2-carboxylic acid, 4?-[[[[2-[[acetyl[4-(1-piperidinylmethyl)phenyl]amino]methyl] cyclopropyl]carbonyl]amino]methyl]-3,3?-difluoro-, methyl ester. Entered STN: Dec. 6, 2011.
CAS Registry No. 485347-98-6; CA Index Name: acetamide,N-[2-(aminomethyl)-1H-benzimidazol-6-yl]N-[[2-(phenylmethoxy)phenyl]methyl]Entered STN: Feb. 4, 2003.
Poondra et al. Discovery of Indoline-Based, Natural-Product-like Compounds as Probes of Focal Adhesion Kinase Signaling Pathways. J Comb Chem 11(2):303-309 (2009).

* cited by examiner

FARNESOID X RECEPTOR AGONISTS AND USES THEREOF

CROSS-REFERENCE

This application is filed pursuant to 35 U.S.C. § 371 as a United States National Phase Application of International Application No. PCT/US2018/022489 filed on Mar. 14, 2018, which claims benefit of U.S. Provisional Patent Application No. 62/471,517 filed on Mar. 15, 2017, all of which are incorporated herein by reference in their entireties.

FIELD OF THE INVENTION

Described herein are compounds that are farnesoid X receptor agonists, methods of making such compounds, pharmaceutical compositions and medicaments comprising such compounds, and methods of using such compounds in the treatment of conditions, diseases, or disorders associated with farnesoid X receptor activity.

BACKGROUND OF THE INVENTION

Farnesoid X receptor (FXR) is a nuclear receptor highly expressed in the liver, intestine, kidney, adrenal glands, and adipose tissue. FXR regulates a wide variety of target genes involved in the control of bile acid synthesis and transport, lipid metabolism, and glucose homeostasis. FXR agonism is a treatment modality for many metabolic disorders, liver diseases or conditions, inflammatory conditions, gastrointestinal diseases, or cell proliferation diseases.

SUMMARY OF THE INVENTION

In one aspect, described herein are farnesoid X receptor agonists and uses thereof.

In one aspect, described herein is a compound that has the structure of Formula (I), or a pharmaceutically acceptable salt or solvate thereof:

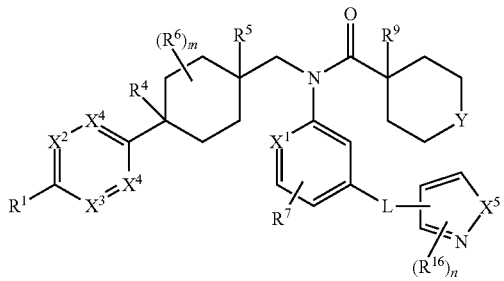

Formula (I)

wherein, $X^1$ is CH or N;

$R^1$ is H, D, halogen, —CN, —OH, —SH, —N($R^{15}$)$_2$, —NR$^{15}$S(=O)$_2$($C_1$-$C_4$alkyl), —S($C_1$-$C_4$alkyl), —S(=O)($C_1$-$C_4$alkyl), —S(=O)$_2$($C_1$-$C_4$alkyl), —S(=O)$_2$N($R^{15}$)$_2$, —OC(=O)($C_1$-$C_4$alkyl), —CO$_2$H, —CO$_2$($C_1$-$C_4$alkyl), —C(=O)N($R^{15}$)$_2$, —NR$^{15}$C(=O)($C_1$-$C_4$alkyl), —NR$^{15}$C(=O)O($C_1$-$C_4$alkyl), —OC(=O)N($R^{15}$)$_2$, —NR$^{15}$C(=O)N($R^{15}$)$_2$, $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, $C_1$-$C_4$heteroalkyl, or substituted or unsubstituted monocyclic $C_2$-$C_5$heterocycloalkyl;

$X^2$ is $CR^2$ or N;

$R^2$ is H, D, halogen, —CN, —OH, —SH, —N($R^{15}$)$_2$, —NR$^{15}$S(=O)$_2$($C_1$-$C_4$alkyl), —S($C_1$-$C_4$alkyl), —S(=O)($C_1$-$C_4$alkyl), —S(=O)$_2$($C_1$-$C_4$alkyl), —S(=O)$_2$N($R^{15}$)$_2$, —OC(=O)($C_1$-$C_4$alkyl), —CO$_2$H, —CO$_2$($C_1$-$C_4$alkyl), —C(=O)N($R^{15}$)$_2$, —NR$^{15}$C(=O)($C_1$-$C_4$alkyl), —NR$^{15}$C(=O)O($C_1$-$C_4$alkyl), —OC(=O)N($R^{15}$)$_2$, —NR$^{15}$C(=O)N($R^{15}$)$_2$, $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, or $C_1$-$C_4$heteroalkyl, or substituted or unsubstituted monocyclic $C_2$-$C_5$heterocycloalkyl;

or $R^1$ and $R^2$ are taken together with the intervening atoms to form a substituted or unsubstituted fused 5-membered ring or substituted or unsubstituted fused 6-membered ring with 0-3 N atoms and 0-2 O or S atoms in the ring;

$X^3$ is $CR^3$ or N;

$R^3$ is H, D, halogen, —CN, —OH, —SH, —N($R^{15}$)$_2$, —NR$^{15}$S(=O)$_2$($C_1$-$C_4$alkyl), —S($C_1$-$C_4$alkyl), —S(=O)($C_1$-$C_4$alkyl), —S(=O)$_2$($C_1$-$C_4$alkyl), —S(=O)$_2$N($R^{15}$)$_2$, —OC(=O)($C_1$-$C_4$alkyl), —CO$_2$H, —CO$_2$($C_1$-$C_4$alkyl), —C(=O)N($R^{15}$)$_2$, —NR$^{15}$C(=O)($C_1$-$C_4$alkyl), $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, $C_1$-$C_4$heteroalkyl, or substituted or unsubstituted monocyclic $C_2$-$C_5$heterocycloalkyl;

each $X^4$ is independently CH or N;

$R^4$ is H, D, F, or —CH$_3$;

$R^5$ is H, D, F, or —CH$_3$;

or $R^4$ and $R^5$ are taken together to form a bridge that is —CH$_2$— or —CH$_2$CH$_2$—;

each $R^6$ is independently H, D, F, —OH, or —CH$_3$;

m is 0, 1, or 2;

$R^7$ is H, D, halogen, —CN, —OH, $C_1$-$C_4$alkyl, $C_2$-$C_4$alkenyl, $C_2$-$C_4$alkynyl, $C_1$-$C_4$alkoxy, C1-$C_4$deuteroalkyl, $C_1$-$C_4$deuteroalkoxy, $C_1$-$C_4$fluoroalkyl, $C_1$-$C_4$fluoroalkoxy, or $C_1$-$C_4$heteroalkyl;

L is absent, —$Y^2$-$L^1$-, -$L^1$-$Y^2$—, cyclopropylene, cyclobutylene or bicyclo[1.1.1]pentylene;

$Y^2$ is absent, —O—, —S—, —S(=O)—, —S(=O)$_2$—, —S(=O)$_2$NR$^{15}$—, —CH$_2$—, —CH=CH—, —C≡C—, —C(=O)—, —C(=O)O—, —OC(=O)—, —OC(=O)O—, —C(=O)NR$^{15}$—, —NR$^{15}$C(=O)—, —OC(=O)NR$^{15}$—, —NR$^{15}$C(=O)O—, —NR$^{15}$C(=O)NR$^{15}$—, —NR$^{15}$S(=O)$_2$—, or —NR$^{15}$—;

$L^1$ is absent or substituted or unsubstituted $C_1$-$C_4$alkylene;

$X^5$ is NR$^8$ or N;

$R^8$ is H, D, $C_1$-$C_6$alkyl, $C_1$-$C_6$deuteroalkyl, $C_1$-$C_6$fluoroalkyl, $C_1$-$C_6$heteroalkyl, —C(=O)($C_1$-$C_4$alkyl), —CO$_2$($C_1$-$C_4$alkyl), —C(=O)N($R^{15}$)$_2$, —S(=O)$_2$($C_1$-$C_4$alkyl), —S(=O)$_2$N($R^{15}$)$_2$, substituted or unsubstituted $C_3$-$C_6$cycloalkyl, or substituted or unsubstituted monocyclic $C_2$-$C_6$heterocycloalkyl, substituted or unsubstituted phenyl, or substituted or unsubstituted monocyclic heteroaryl;

$R^9$ is H, D, F or —CH$_3$;

Y is —CR$^{10}$R$^{11}$—, —O—, —S—, —S(=O)—, —S(=O)$_2$, or —NR$^{17}$—;

$R^{10}$ is H, D, halogen, —CN, —OH, $C_1$-$C_6$alkyl, $C_2$-$C_4$alkenyl, $C_2$-$C_4$alkynyl, $C_1$-$C_6$alkoxy, $C_1$-$C_6$fluoroalkyl, —$SR^{12}$, —S(=O)$R^{14}$, —S(=O)$_2R^{14}$, or —N($R^{12}$)$_2$;

$R^{11}$ is H, D, F or —$CH_3$;

or $R^9$ and $R^{11}$ are taken together to form a bridge that is —$CH_2$— or —$CH_2CH_2$—;

each $R^{12}$ is independently H, $C_1$-$C_4$alkyl, $C_1$-$C_4$deuteroalkyl, $C_1$-$C_4$fluoroalkyl, $C_1$-$C_4$heteroalkyl, substituted or unsubstituted $C_3$-$C_6$cycloalkyl, substituted or unsubstituted $C_2$-$C_6$heterocycloalkyl, substituted or unsubstituted phenyl, substituted or unsubstituted benzyl, substituted or unsubstituted monocyclic heteroaryl;

$R^{14}$ is $C_1$-$C_4$alkyl, $C_1$-$C_4$deuteroalkyl, $C_1$-$C_4$fluoroalkyl, $C_1$-$C_4$heteroalkyl, substituted or unsubstituted $C_3$-$C_6$cycloalkyl, substituted or unsubstituted $C_2$-$C_6$heterocycloalkyl, substituted or unsubstituted phenyl, substituted or unsubstituted benzyl, or substituted or unsubstituted monocyclic heteroaryl;

$R^{15}$ is H or substituted or unsubstituted $C_1$-$C_6$alkyl;

each $R^{16}$ is independently H, D, halogen, —CN, —OH, —N($R^{15}$)$_2$, —$NR^{15}$S(=O)$_2$($C_1$-$C_4$alkyl), —S($C_1$-$C_4$alkyl), —S(=O)($C_1$-$C_4$alkyl), —S(=O)$_2$($C_1$-$C_4$alkyl), —C(=O)($C_1$-$C_4$alkyl), —OC(=O)($C_1$-$C_4$alkyl), —$CO_2$H, —$CO_2$($C_1$-$C_4$alkyl), —$NR^{15}$C(=O)($C_1$-$C_4$alkyl), —C(=O)N($R^{15}$)$_2$, —$NR^{15}$C(=O)O($C_1$-$C_4$alkyl), —OC(=O)N($R^{15}$)$_2$, $C_1$-$C_4$alkyl, $C_2$-$C_4$alkenyl, $C_2$-$C_4$alkynyl, $C_1$-$C_4$alkoxy, $C_1$-$C_4$deuteroalkyl, $C_1$-$C_4$deuteroalkoxy, $C_1$-$C_4$fluoroalkyl, $C_1$-$C_4$fluoroalkoxy, $C_1$-$C_4$heteroalkyl, substituted or unsubstituted $C_3$-$C_6$cycloalkyl, substituted or unsubstituted monocyclic $C_2$-$C_6$heterocycloalkyl, substituted or unsubstituted phenyl, or substituted or unsubstituted monocyclic heteroaryl;

n is 0, 1, or 2;

$R^{17}$ is -$L^5$-$R^{14}$; and $L^5$ is absent, —S(=O)$_2$—, —C(=O)—, —$CO_2$—, or —C(=O)N($R^{15}$).

Any combination of the groups described above for the various variables is contemplated herein. Throughout the specification, groups and substituents thereof are chosen by one skilled in the field to provide stable moieties and compounds.

In one aspect, described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by intravenous administration, subcutaneous administration, or oral administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

In another aspect, described herein is a method of treating a disease or condition in a mammal that would benefit from FXR agonism comprising administering a compound as described herein, or pharmaceutically acceptable salt, or solvate thereof, to the mammal in need thereof. In some embodiments, the disease or condition is a metabolic condition. In some embodiments, the disease or condition is a liver condition.

In some embodiments, the compound is administered to the mammal by intravenous administration, subcutaneous administration, oral administration, inhalation, nasal administration, dermal administration, or ophthalmic administration.

In one aspect, described herein is a method of treating or preventing any one of the diseases or conditions described herein comprising administering a therapeutically effective amount of a compound described herein, or a pharmaceutically acceptable salt, or solvate thereof, to a mammal in need thereof.

In one aspect, described herein is a method for the treatment or prevention of a metabolic or liver condition in a mammal comprising administering a therapeutically effective amount of a compound described herein, or a pharmaceutically acceptable salt, or solvate thereof, to the mammal in need thereof. In other embodiments, the metabolic or liver condition is amenable to treatment with a FXR agonist. In some embodiments, the method further comprises administering a second therapeutic agent to the mammal in addition to the compound described herein, or a pharmaceutically acceptable salt, or solvate thereof.

In one aspect, described herein is a method of treating or preventing a liver disease or condition in a mammal, comprising administering to the mammal a compound of Formula (I), or a pharmaceutically acceptable salt or solvate thereof. In some embodiments, the liver disease or condition is an alcoholic or non-alcoholic liver disease. In some embodiments, the liver disease or condition is primary biliary cirrhosis, primary sclerosing cholangitis, cholestasis, nonalcoholic steatohepatitis (NASH), or nonalcoholic fatty liver disease (NAFLD). In some embodiments, the alcoholic liver disease or condition is fatty liver (steatosis), cirrhosis, or alcoholic hepatitis. In some embodiments, the non-alcoholic liver disease or condition is nonalcoholic steatohepatitis (NASH), or nonalcoholic fatty liver disease (NAFLD). In some embodiments, the non-alcoholic liver disease or condition is nonalcoholic steatohepatitis (NASH). In some embodiments, the non-alcoholic liver disease or condition is nonalcoholic steatohepatitis (NASH) and is accompanied by liver fibrosis. In some embodiments, the non-alcoholic liver disease or condition is nonalcoholic steatohepatitis (NASH) without liver fibrosis. In some embodiments, the non-alcoholic liver disease or condition is intrahepatic cholestasis or extrahepatic cholestasis.

In one aspect, described herein is a method of treating or preventing a liver fibrosis in a mammal, comprising administering to the mammal a compound of Formula (I), or a pharmaceutically acceptable salt or solvate thereof. In some embodiments, the mammal is diagnosed with hepatitis C virus (HCV), nonalcoholic steatohepatitis (NASH), primary sclerosing cholangitis (PSC), cirrhosis, Wilson's disease, hepatitis B virus (HBV), HIV associated steatohepatitis and cirrhosis, chronic viral hepatitis, non-alcoholic fatty liver disease (NAFLD), alcoholic steatohepatitis (ASH), nonalcoholic steatohepatitis (NASH), primary biliary cirrhosis (PBC), or biliary cirrhosis. In some embodiments, the mammal is diagnosed with nonalcoholic steatohepatitis (NASH).

In one aspect, described herein is a method of treating or preventing a liver inflammation in a mammal, comprising administering to the mammal a compound of Formula (I), or a pharmaceutically acceptable salt or solvate thereof. In some embodiments, the mammal is diagnosed with hepatitis C virus (HCV), nonalcoholic steatohepatitis (NASH), primary sclerosing cholangitis (PSC), cirrhosis, Wilson's disease, hepatitis B virus (HBV), HIV associated steatohepatitis and cirrhosis, chronic viral hepatitis, non-alcoholic fatty liver disease (NAFLD), alcoholic steatohepatitis (ASH), nonalcoholic steatohepatitis (NASH), primary biliary cirrhosis (PBC), or biliary cirrhosis. In some embodiments, the mammal is diagnosed with nonalcoholic steatohepatitis (NASH). In some embodiments, the liver inflammation is associated with inflammation in the gastrointestinal tract. In some embodiments, the mammal is diagnosed with inflammatory bowel disease.

In one aspect, described herein is a method of treating or preventing a gastrointestinal disease or condition in a mammal, comprising administering to the mammal a compound of Formula (I), or a pharmaceutically acceptable salt or solvate thereof. In some embodiments, the gastrointestinal disease or condition is necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, post-surgical inflammation, gastric carcinogenesis, graft versus host disease or any combination thereof. In some embodiments, the gastrointestinal disease is irritable bowel syndrome (IBS), irritable bowel syndrome with diarrhea (IBS-D), irritable bowel syndrome with constipation (BS-C), mixed IBS (IBS-M), unsubtyped IBS (IBS-U), or bile acid diarrhea (BAD)

In one aspect, described herein is a method of treating or preventing a disease or condition in a mammal that would benefit from treatment with a FXR agonist, comprising administering to the mammal a compound of Formula (I), or a pharmaceutically acceptable salt or solvate thereof. In some embodiments, the methods described herein further comprise administering at least one additional therapeutic agent in addition to the compound of Formula (I), or a pharmaceutically acceptable salt or solvate thereof.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the aforementioned aspects involving the treatment of a disease or condition are further embodiments comprising administering at least one additional agent in addition to the administration of a compound of Formula (I) described herein, or a pharmaceutically acceptable salt thereof. In various embodiments, each agent is administered in any order, including simultaneously.

In any of the embodiments disclosed herein, the mammal or subject is a human.

In some embodiments, compounds provided herein are administered to a human.

In some embodiments, compounds provided herein are orally administered.

In some embodiments, described herein is method of treating or preventing a metabolic disorder in a subject, comprising: administering to a gastrointestinal tract of the subject a therapeutically effective amount of one or more of the compounds described herein, or a pharmaceutically acceptable salt or solvate thereof, thereby activating farnesoid X receptors (FXR) in the intestines, and treating or preventing a metabolic disorder in the subject. In some embodiments, the compound's absorption is preferentially restricted to within the intestines. In some embodiments, the method substantially enhances FXR target gene expression in the intestines while not substantially enhancing FXR target gene expression in the liver or kidney. In some embodiments, the method substantially enhances FXR target gene expression in the intestines while minimizing systemic plasma levels of the delivered compound. In some embodiments, the method substantially enhances FXR target gene expression in the intestines and the liver while minimizing systemic plasma levels of the delivered compound. In some embodiments, the method substantially enhances FXR target gene expression in the intestines while not substantially enhancing FXR target gene expression in the liver or kidney, and while minimizing systemic plasma levels. In some embodiments, the method substantially enhances FXR target gene expression in the intestines and the liver and provides sustained systemic plasma levels of the delivered compound. In some embodiments, the method reduces or prevents diet-induced weight gain. In some embodiments, the method increases a metabolic rate in the subject. In some embodiments, the increasing the metabolic rate comprises enhancing oxidative phosphorylation in the subject. In some embodiments, the method further comprises improving glucose and/or lipid homeostasis in the subject. In some embodiments, the method results in no substantial change in food intake and/or fat consumption in the subject. In some embodiments, the method results in no substantial change in appetite in the subject. In some embodiments, the metabolic disorder is selected from obesity, diabetes, insulin resistance, dyslipidemia or any combination thereof. In some embodiments, the metabolic disorder is non-insulin dependent diabetes mellitus. In some embodiments, the method protects against diet-induced weight gain, reduces inflammation, enhances thermogenesis, enhances insulin sensitivity in the liver, reduces hepatic steatosis, promotes activation of BAT, decreases blood glucose, increases weight loss, or any combination thereof. In some embodiments, the method enhances insulin sensitivity in the liver and promotes brown adipose tissue (BAT) activation. In some embodiments, the method further comprises administering to the subject an insulin sensitizing drug, an insulin secretagogue, an alpha-glucosidase inhibitor, a glucagon-like peptide (GLP) agonist, a dipeptidyl peptidase-4 (DPP-4) inhibitor, nicotinamide ribonucleoside, an analog of nicotinamide ribonucleoside, or combinations thereof.

In some embodiments, described herein is a method of treating or preventing inflammation in an intestinal region of a subject, comprising: administering to a gastrointestinal tract of the subject a therapeutically effective amount of one or more of the compounds described herein, or a pharmaceutically acceptable salt or solvate thereof, thereby activating FXR receptors in the intestines, and thereby treating or preventing inflammation in the intestinal region of the subject. In some embodiments, the compound's absorption is preferentially restricted to within the intestines. In some embodiments, the method substantially enhances FXR target gene expression in the intestines while not substantially enhancing FXR target gene expression in the liver or kidney. In some embodiments, the inflammation is associated with a clinical condition selected from necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, post-surgical inflammation, gastric carcinogenesis or any combination thereof. In some embodiments, the one or more FXR target genes comprises IBABP, OSTα, Perl, FGF15, FGF19, SHP or combinations thereof. In some embodiments, the method further comprises administering a therapeutically effective amount of an antibiotic therapy to the subject, wherein the method treats or prevents inflammation associated with pseudomembranous colitis in the subject. In some embodiments, the method further comprises administering to the subject a therapeutically effective amount of an oral corticosteroid, other anti-inflammatory or immunomodulatory therapy, nicotinamide ribonucleoside, an analog of nicotinamide ribonucleoside, or combinations thereof. In some embodiments, the method increases HSL phosphorylation and β3-adrenergic receptor expression. In some embodiments, a serum concentration of the compound in the subject remains below its $EC_{50}$ following administration of the compound.

In some embodiments, described herein is a method of treating or preventing a cell proliferation disease in a subject, comprising administering to a gastrointestinal tract of the subject a therapeutically effective amount of one or more of the compounds described herein or a pharmaceutically acceptable salt or solvate thereof. In some embodiments, the cell proliferation disease is an adenocarcinoma. In some embodiments, the adenocarcinoma is a colon cancer. In some embodiments, the treating the adenocarcinoma reduces the size of the adenocarcinoma, the volume of the adenocarcinoma, the number of adenocarcinomas, cachexia due to the adenocarcinoma, delays progression of the adenocarcinoma, increases survival of the subject, or combinations thereof. In some embodiments, the method further comprises administering to the subject an additional therapeutic compound selected from the group consisting of a chemotherapeutic, a biologic, a radiotherapeutic, or combinations thereof.

In some embodiments, described herein is a method of treating or preventing a liver disease or condition in a subject, comprising administering to the subject a therapeutically effective amount of one or more of the compounds described herein, or a pharmaceutically acceptable salt or solvate thereof. In some embodiments, the liver disease or condition is an alcoholic or non-alcoholic liver disease. In some embodiments, the liver disease or condition is primary biliary cirrhosis, primary sclerosing cholangitis, cholestasis, nonalcoholic steatohepatitis (NASH), or nonalcoholic fatty liver disease (NAFLD). In some embodiments, the alcoholic liver disease or condition is fatty liver (steatosis), cirrhosis, or alcoholic hepatitis. In some embodiments, the non-alcoholic liver disease or condition is nonalcoholic steatohepatitis (NASH), or nonalcoholic fatty liver disease (NAFLD). In some embodiments, the non-alcoholic liver disease or condition is intrahepatic cholestasis or extrahepatic cholestasis.

Articles of manufacture, which include packaging material, a compound described herein, or a pharmaceutically acceptable salt thereof, within the packaging material, and a label that indicates that the compound or composition, or pharmaceutically acceptable salt, pharmaceutically active metabolite, pharmaceutically acceptable prodrug, or pharmaceutically acceptable solvate thereof, is used for the treatment, prevention or amelioration of one or more symptoms of a disease or condition that would benefit from FXR agonism, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

The nuclear hormone receptor farnesoid X receptor (also known as FXR or nuclear receptor subfamily 1, group H, member 4 (NR1H4)) (OMIM: 603826) functions as a regulator for bile acid metabolism. FXR is a ligand-activated transcriptional receptor expressed in diverse tissues including the adrenal gland, kidney, stomach, duodenum, jejunum, ileum, colon, gall bladder, liver, macrophages, and white and brown adipose tissue. FXRs are highly expressed in tissues that participate in bile acid metabolism such as the liver, intestines, and kidneys. Bile acids function as endogenous ligands for FXR such that enteric and systemic release of bile acids induces FXR-directed changes in gene expression networks. Bile acids are the primary oxidation product of cholesterol, and in some cases, upon secretion into the intestines, are regulators of cholesterol absorption. The rate-limiting step for conversion of cholesterol into bile acids is catalyzed by cytochrome p450 enzyme cholesterol 7-α-hydroxylase (CYP7A1) and occurs in the liver. The cytochrome p450 enzyme sterol 12-α-hydroxylase (CYP8B1) mediates production of cholic acid and determines the relative amounts of the two primary bile acids, cholic acid and chenodeoxycholic acid. Activation of FXR can represses the transcription of CYP7A1 and CYP8B1 by increasing the expression level of the hepatic small heterodimer partner (SHP) (also known as nuclear receptor subfamily 0, group B, member 2; or NR0B2) and intestinal expression of fibroblast growth factor 15 (FGF15) in mice and fibroblast growth factor 19 (FGF19) in human. SHP represses the liver receptor homolog (LRH-1) and hepatocyte nuclear factor 4alpha (HNFa4), transcription factors that regulate CYP7A1 and CYP8B1 gene expression. CYP8B1 repression by FXR can be species-specific and FXR activation may in some cases increase CYP8B1 expression in humans (Sanyal et al PNAS, 2007, 104, 15665). In some cases, FGF15/19 released from the intestine then activates the fibroblast growth factor receptor 4 in the liver, leading to activation of the mitogen-activated protein kinase (MAPK) signaling pathway which suppress CYP7A1 and CYP8B1.

In some embodiments, elevated levels of bile acids have been associated with insulin resistance. For example, insulin resistance sometimes leads to a decreased uptake of glucose from the blood and increased de novo glucose production in the liver. In some instances, intestinal sequestration of bile acids has been shown to improve insulin resistance by promoting the secretion of glucagon-like peptide-1 (GLP1) from intestinal L-cells. GLP-1 is an incretin derived from the transcription product of the proglucagon gene. It is released in response to the intake of food and exerts control in appetite and gastrointestinal function and promotes insulin secretion from the pancreas. The biologically active forms of GLP-1 include GLP-1-(7-37) and GLP-1-(7-36)$NH_2$, which result from selective cleavage of the proglucagon molecule. In such cases, activation of FXR leading to decreased production of bile acids correlates to a decrease in insulin resistance.

In some embodiments, the activation of FXR also correlates to the secretion of pancreatic polypeptide-fold such as peptide YY (PYY or PYY3-36). In some instances, peptide YY is a gut hormone peptide that modulates neuronal activity within the hypothalamic and brainstem, regions of the brain involved in reward processing. In some instances, reduced level of PYY correlates to increased appetite and weight gain.

In some instances, the activation of FXR indirectly leads to a reduction of plasma triglycerides. The clearance of triglycerides from the bloodstream is due to lipoprotein lipase (LPL). LPL activity is enhanced by the induction of its activator apolipoprotein CII, and the repression of its inhibitor apolipoprotein CIII in the liver occurs upon FXR activation.

In some cases, the activation of FXR further modulates energy expenditure such as adipocyte differentiation and function. Adipose tissue comprises adipocytes or fat cells. In some instances, adipocytes are further differentiated into brown adipose tissue (BAT) or white adipose tissue (WAT). The function of BAT is to generate body heat, while WAT functions as fat storing tissues.

In some instances, FXR is widely expressed in the intestine. In some cases, the activation of FXR has been shown to induce the expression and secretion of FGF19 (or FGF15 in mouse) in the intestine. FGF19 is a hormone that regulates bile acid synthesis as well as exerts an effect on glucose metabolism, lipid metabolism, and on energy expenditure.

In some instances, FGF19 has also been observed to modulate adipocyte function and differentiation. Indeed, a study has shown that the administration of FGF19 to high-fat diet-fed mice increased energy expenditure, modulated adipocytes differentiation and function, reversed weight gain, and improved insulin resistance (see, Fu et al., "Fibroblast growth factor 19 increases metabolic rate and reverses dietary and leptin-deficient diabetes." *Endocrinology* 145: 2594-2603 (2004)).

In some cases, intestinal FXR activity has also been shown to be involved in reducing overgrowth of the microbiome, such as during feeding (Li et al., *Nat Commun* 4:2384, 2013). For example, a study had shown that activation of FXR correlated with increased expression of several genes in the ileum such as Ang2, iNos, and I118, which have established antimicrobial actions (Inagaki et al., *Proc Natl Acad Sci USA* 103:3920-3925, 2006).

In some cases, FXR has been implicated in barrier function and immune modulation in the intestine. FXR modulates transcription of genes involved in bile salt synthesis, transport and metabolism in the liver and intestine, and in some cases has been shown to lead to improvements in intestinal inflammation and prevention of bacterial translocation into the intestinal tract (Gadaleta et al., *Gut*. 2011 April; 60(4):463-72).

In some cases, over production of bile acids or improper transport and re-cycling of bile acids can lead to diarrhea. FXR modulates transcription of genes involved in bile salt synthesis, transport and metabolism in the liver and intestine, and in some cases may lead to improvements in diarrhea Camilleri, *Gut Liver*. 2015 May; 9(3): 332-339.

G protein-coupled bile acid receptor 1 (also known as GPBAR2, GPCR19, membrane-type receptor for bile acids or M-BAR, or TGR5) is a cell surface receptor for bile acids. Upon activation with bile acid, TGR5 induces the production of intracellular cAMP, which then triggers an increase in triiodothyronine due to the activation of deiodinase (DIO02) in BAT, resulting in increased energy expenditure.

Hence in some embodiments, regulation of metabolic processes such as bile acid synthesis, bile-acid circulation, glucose metabolism, lipid metabolism, or insulin sensitivity is modulated by the activation of FXR. Furthermore, in some embodiments, dis-regulation of metabolic processes such as bile acid synthesis, bile-acid circulation, glucose metabolism, lipid metabolism, or insulin sensitivity results in metabolic diseases such as diabetes or diabetes-related conditions or disorders, alcoholic or non-alcoholic liver disease or condition, intestinal inflammation, or cell proliferative disorders.

Disclosed herein, in certain embodiments, are compounds that have activity as FXR agonists. In some embodiments, the FXR agonists described herein are structurally distinct from bile acids, other synthetic FXR ligands, and other natural FXR ligands.

In some embodiments, also disclosed herein are methods of treating or preventing a metabolic disorder, such as diabetes, obesity, impaired glucose tolerance, dyslipidemia, or insulin resistance by administering a therapeutically effective amount of an FXR agonist. In some instances, the compounds are administered to the GI tract of a subject.

In additional embodiments, disclosed herein are methods for treating or preventing alcoholic or non-alcoholic liver disease or conditions (e.g., cholestasis, primary biliary cirrhosis, steatosis, cirrhosis, alcoholic hepatitis, non-alcoholic steatohepatitis (NASH), non-alcoholic fatty liver disease (NAFLD), primary sclerosing cholangitis (PSC) or elevated liver enzymes) by administering a therapeutically effective amount of an FXR agonist to a subject in need thereof (e.g., via the GI tract). In additional embodiments, disclosed herein include methods for treating or preventing cholestasis, cirrhosis, primary biliary cirrhosis, non-alcoholic steatohepatitis (NASH), non-alcoholic fatty liver disease (NAFLD), or primary sclerosing cholangitis (PSC) by administering a therapeutically effective amount of an FXR agonist to a subject in need thereof. In some embodiments, disclosed herein include methods for treating or preventing cholestasis by administering a therapeutically effective amount of an FXR agonist to a subject in need thereof. In some embodiments, disclosed herein include methods for treating or preventing primary biliary cirrhosis by administering a therapeutically effective amount of an FXR agonist to a subject in need thereof. In some embodiments, disclosed herein include methods for treating or preventing NASH by administering a therapeutically effective amount of an FXR agonist to a subject in need thereof. In some embodiments, disclosed herein include methods for treating or preventing NAFLD by administering a therapeutically effective amount of an FXR agonist to a subject in need thereof.

In further embodiments, disclosed herein include methods for treating or preventing inflammation in the intestines and/or a cell proliferative disorder, such as cancer, by administering a therapeutically effective amount of an FXR agonist to a subject in need thereof (e.g., via the GI tract).

In still further embodiments, disclosed herein include FXR agonists that modulate one or more of the proteins or genes associated with a metabolic process such as bile acid synthesis, glucose metabolism, lipid metabolism, or insulin sensitivity, such as for example, increase in the activity of FGF19 (FGF15 in mouse), increase in the secretion of GLP-1, or increase in the secretion of PYY.

Metabolic Disorders

Disclosed herein, in certain embodiments, are methods of treating a metabolic disorder in a subject in need thereof. Also described herein include methods of preventing a metabolic disorder in a subject in need thereof. In some instances, these methods include administering to the subject in need thereof a therapeutically effective amount of one or more of the compounds disclosed herein. In some instances, the one or more compounds disclosed herein are absorbed in the gastrointestinal (GI) tract. In additional instances, the one or more disclosed compounds absorbed in the GI tract activates FXR receptors thereby treating or preventing a metabolic disorder in the subject.

In some embodiments, the disclosed compounds demonstrate systemic exposure. In some instances, the disclosed compounds have local exposure in the intestines, but limited exposure in the liver or systemically. In some embodiments, local exposure of the disclosed compounds in the intestines maybe demonstrated by regulation of FXR target genes in the intestines. In some embodiments, the target genes may include: SHP, FGF19 (FGF15), IBABP, C3, OST α/β. In some embodiments, exposure of the disclosed compounds is about 40%, 50%, 55%, 60%, 65%, 70%, 75%, 80%, 85%, 90%, 95%, 99%, 99.5%, or more in the intestines. In some instances, exposure of the disclosed compounds is about 0.5%, 1%, 5%, 10%, 15%, 20%, 25%, 30%, 40%, 50%, or less in the systemic circulation. In some embodiments, the exposure of the FXR agonists in the intestinal lumen reduces the chance of side effects which results from systemic action, thereby improving the safety profile of the therapy. In additional embodiments, the disclosed compounds enhance FXR target gene expression in the intestines. In additional embodiments, the disclosed compounds further modulate gene expressions in the FXR-mediated pathway, such as for example, FGF19 (FGF15) which inhibits CYP7A1 and CYP8B1 gene expression in the liver. In some instances, the disclosed compounds enhance gene expression in the FXR-mediated pathway.

In other instances, the disclosed compounds reduce or inhibit gene expression in the FXR-mediated pathway. In some instances, enhancing is about 1%, 5%, 10%, 15%, 20%, 25%, 30%, 40%, 50%, 60%, 70%, 80%, 90%, 100%, 200%, 300%, 500%, 1,000%, 5,000%, 10,000%, 50,000%, 100,000%, 500,000%, or higher in gene expression in the intestines, liver, kidney, or other tissues relative to the gene expression in the absence of the disclosed compound. In some cases, reducing is about 100%, 90%, 80%, 70%, 60%, 50%, 40%, 30%, 25%, 20%, 15%, 10%, 5%, 1%, or less in gene expression in the intestines, liver, kidney, or other tissues relative to the gene expression in the absence of the disclosed compound.

In some embodiments, the method substantially enhances FXR target gene expression in the intestines while minimizing systemic plasma levels of the delivered compound. In some embodiments, the method substantially enhances FXR target gene expression in the intestines and the liver while minimizing systemic plasma levels of the delivered compound. In some embodiments, the method substantially enhances FXR target gene expression in the intestines while not substantially enhancing FXR target gene expression in the liver or kidney, and while minimizing systemic plasma levels. In some embodiments, the method substantially enhances FXR target gene expression in the intestines and the liver and provides sustained systemic plasma levels of the delivered compound.

In some embodiments, metabolic disorder refers to any disorder that involves an alteration in the normal metabolism of carbohydrates, lipids, proteins, nucleic acids or a combination thereof. In some instances, a metabolic disorder is associated with either a deficiency or excess in a metabolic pathway resulting in an imbalance in metabolism of nucleic acids, proteins, lipids, and/or carbohydrates. Factors affecting metabolism include, but are not limited to, the endocrine (hormonal) control system (e.g., the insulin pathway, the enteroendocrine hormones including GLP-1, oxyntomodulin, PYY or the like), or the neural control system (e.g., GLP-1 in the brain). Exemplary metabolic disorders include, but are not limited to, diabetes, insulin resistance, dyslipidemia, liver disease, inflammation related intestinal conditions, cell proliferative disorders, or the like.

Diabetes Mellitus and Diabetes-Related Conditions or Disorders

In some embodiments, disclosed herein are methods of treating a subject having diabetes mellitus or diabetes-related condition or disorder with administration of a FXR agonist described herein. In some instances, diabetes is type II diabetes or non-insulin-dependent diabetes mellitus (NIDDM). In some instances, diabetes-related conditions or disorders include obesity, impaired glucose tolerance, dyslipidemia, and insulin resistance. In some instances, diabetes-related conditions or disorders further include secondary complications such as atherosclerosis, stroke, fatty liver disease, blindness, gallbladder disease, or polycystic ovary disease. In some cases, a FXR agonist is administered for the treatment of type II diabetes, obesity, impaired glucose tolerance, dyslipidemia, insulin resistance, or secondary complications such as atherosclerosis, stroke, fatty liver disease, blindness, gallbladder disease, or polycystic ovary disease.

In some embodiments, a diabetic subject (e.g., a type II diabetic subject) is further characterized with a body mass index (BMI) of 25 or greater, 30 or greater, 35 or greater, 40 or greater, such as a BMI of 25 to 29, 30 to 34, or 35 to 40.

In some examples, a FXR agonist described herein reduces or prevents weight gain in a subject. In some instances, the weight gain is diet-induced weight gain. In other instances, the weight gain is non-diet-related, such as familial/genetic obesity or obesity resulting from medication. In some examples, such methods reduce or prevent weight gain in the subject by at least 5%, at least 10%, at least 15%, at least 20%, at least 30%, at least 40%, at least 50%, or more. In some instances, weight gain is reduced or prevented by about 5% to about 50%, by about 5% to about 25%, by about 10% to about 20%, or by about 10% to about 30%. In some cases, the reduction or prevention of weight gain is relative to the reduction or prevention of weight gain observed in a subject not treated with the FXR agonist.

Similarly, in some cases, the FXR agonist reduces the BMI of a subject. In some examples, such methods reduce the BMI of a subject by at least 5%, at least 10%, at least 15%, at least 20%, at least 25%, at least 30%, or more, relative to a subject not treated with the FXR agonist. In some instances, the subject is overweight but not obese. In other instances, the subject is neither overweight nor obese.

In some instances, administration of a FXR agonist results in a decrease in the amount of serum lipids. In some examples, the decrease in the amount of serum lipids is by at least 5%, at least 10%, at least 15%, at least 20%, at least 30%, at least 50%, at least 60%, at least 70%, at least 75%, or more. In some cases, the decrease in the amount of serum lipids is by about 5% to about 50%, by about 5% to about 25%, by about 10% to about 20%, by about 10% to about 70%, or by about 10% to about 30%. In some cases, the decrease in the amount of serum lipids is relative to the amount of serum lipids observed in a subject not treated with the FXR agonist.

In some examples, administration of a FXR agonist results in a decrease in triglyceride (e.g., hepatic triglyceride) level. In some instances, the decrease in triglyceride (e.g., hepatic triglyceride) level is by at least 5%, at least 10%, at least 15%, at least 20%, at least 30%, at least 50%, at least 60%, at least 70%, at least 75%, or more. In some instances, the decrease in triglyceride (e.g., hepatic triglyceride) level is by about 5% to about 50%, by about 5% to about 25%, by about 10% to about 20%, by about 10% to about 70%, or by about 10% to about 30%. In some cases, the decrease in triglyceride (e.g., hepatic triglyceride) level is relative to the triglyceride (e.g., hepatic triglyceride) level observed in a subject not treated with the FXR agonist.

In some examples, administration of a FXR agonist results in an increased insulin sensitivity to insulin in the liver. In some instances, the increase in insulin sensitivity is by at least 5%, at least 10%, at least 15%, at least 20%, at least 30%, at least 40%, at least 50%, or more. In some cases, the increase in insulin sensitivity is by about 5% to about 50%, by about 5% to about 25%, by about 10% to about 20%, or by about 10% to about 30%. In some cases, the increase in insulin sensitivity is relative to sensitivity observed in a subject not treated with the FXR agonist.

In some embodiments, administration of a FXR agonist results in a decrease in the amount of serum insulin in the subject. In some examples, the decrease in serum insulin is by at least 5%, at least 10%, at least 15%, at least 20%, at least 30%, at least 50%, at least 60%, at least 70%, at least 75%, or more. In some instances, serum insulin is decreased by about 5% to about 50%, by about 5% to about 25%, by about 10% to about 20%, by about 10% to about 70%, or by about 10% to about 30%. In some cases, the decrease in serum insulin level is relative to levels observed in a subject not treated with the FXR agonist.

In some embodiments, administration of a FXR agonist results in a decrease in the amount of serum glucose in the subject. In some examples, the decrease in serum glucose is by at least 5%, at least 10%, at least 15%, at least 20%, at least 30%, at least 50%, at least 60%, at least 70%, at least 75%, or more. In some instances, serum glucose is decreased by about 5% to about 50%, by about 5% to about 25%, by about 10% to about 20%, by about 10% to about 70%, or by about 10% to about 30%. In some cases, the decrease in serum glucose level is relative to levels observed in a subject not treated with the FXR agonist.

In some examples, a FXR agonist described herein increases browning of white adipose tissue in a subject. In some examples, the rate of increase of browning of white adipose tissue in the subject is by at least 5%, at least 10%, at least 15%, at least 20%, at least 30%, at least 40%, at least 50%, or more, relative to a subject not treated with the FXR agonist.

In some embodiments, administration of a FXR agonist does not result in substantial change in food intake and/or fat consumption in the subject. In some instances, food intake and/or fat consumption is reduced, such as by less than 15%, less than 10%, or less than 5%.

In some embodiments, no substantial change in appetite in the subject results. In other embodiments, reduction in appetite is minimal as reported by the subject.

In some embodiments, administration of a FXR agonist results in an increase in the metabolic rate in the subject. In some instances, the FXR agonist increases the metabolic rate in a subject. In some cases, the metabolic rate in the subject is increased by at least 5%, at least 10%, at least 15%, at least 20%, at least 30%, at least 40%, at least 50%, at least 60%, at least 70%, at least 75%, or more. In some instances, the metabolic rate is increased by about 5% to about 50%, by about 5% to about 25%, by about 10% to about 20%, by about 10% to about 70%, or by about 10% to about 30%). In some cases, the increase in metabolic rate is relative to the rate observed in a subject not treated with the FXR agonist.

In some embodiments, the increase in metabolism results from enhanced oxidative phosphorylation in the subject, which in turn leads to increased energy expenditure in tissues (such as BAT). In such instances, the FXR agonist helps to increase the activity of BAT. In some examples, the activity of BAT is increased by at least 5%, at least 10%, at least 15%, at least 20%, at least 30%, at least 50%, at least 60%, at least 70%, at least 75%, or more. In some instances, the activity of BAT is increased by about 5% to about 50%, by about 5% to about 25%, by about 10% to about 20%, by about 10% to about 70%, or by about 10% to about 30%. In some cases, the increase in BAT activity is relative to the activity of BAT observed in a subject not treated with the FXR agonist.

Alcoholic and Non-Alcoholic Liver Disease or Condition

Disclosed herein include methods of preventing and/or treating alcoholic or non-alcoholic liver diseases or conditions. Exemplary alcoholic or non-alcoholic liver diseases or conditions include, but are not limited to cholestasis, cirrhosis, steatosis, alcoholic hepatitis, non-alcoholic steatohepatitis (NASH), non-alcoholic fatty liver disease (NAFLD), primary sclerosing cholangitis (PSC), elevated liver enzymes, and elevated triglyceride levels. In some embodiments, a FXR agonist is used in the prevention or treatment of alcoholic or non-alcoholic liver diseases. In some embodiments, a FXR agonist is used in the prevention or treatment of cholestasis, cirrhosis, steatosis, alcoholic hepatitis, non-alcoholic steatohepatitis (NASH), non-alcoholic fatty liver disease (NAFLD), or primary sclerosing cholangitis (PSC).

Cholestasis

In some embodiments, a FXR agonist disclosed herein is used in the treatment of cholestasis in a subject. Cholestasis, an impairment or cessation in the flow of bile, which in some cases, causes hepatotoxicity due to the buildup of bile acids and other toxins in the liver. In some instances, cholestasis is a component of many liver diseases, including cholelithiasis, cholestasis of pregnancy, primary biliary cirrhosis (PBC), and primary sclerosing cholangitis (PSC). In some instances, the obstruction is due to gallstone, biliary trauma, drugs, one or more additional liver diseases, or to cancer. In some cases, the enterohepatic circulation of bile acids enables the absorption of fats and fat-soluble vitamins from the intestine and allows the elimination of cholesterol, toxins, and metabolic by-products such as bilirubin from the liver. In some cases, activation of FXR induces expression of the canalicular bile transporters BSEP (ABCB 11) and multidrug resistance-related protein 2 (MRP2; ABCC2, cMOAT), and represses genes involved in bile acid biosynthesis, such as for example sterol 12α-hydroxylase (CYP8B1) and CYP7A1.

In some examples, the FXR agonist reduces cholestasis in the subject by at least 5%, at least 10%, at least 15%, at least 20%, at least 30%, at least 40%, at least 50%, or more. In some cases, cholestasis is reduced by about 5% to about 50%, by about 5% to about 25%, by about 10% to about 20%, or by about 10% to about 30%. In some instances, the level of cholestasis is relative to the level of cholestasis in a subject not treated with the FXR agonist.

Primary Biliary Cirrhosis and Cirrhosis

In some embodiments, a FXR agonist disclosed herein is used in the treatment of primary biliary cirrhosis (PBC) in a subject. PBC is a liver disease that primarily results from autoimmune destruction of the bile ducts that transport bile acids (BAs) out of the liver, resulting in cholestasis. As PBC progresses, persistent toxic buildup of BAs causes progressive liver damage. Chronic inflammation and fibrosis can advance to cirrhosis. In some examples, the FXR agonist reduces PBC in the subject by at least 5%, at least 10%, at least 15%, at least 20%, at least 30%, at least 40%, at least 50%, or more. In some cases, PBC is reduced by about 5% to about 50%, by about 5% to about 25%, by about 10% to about 20%, or by about 10% to about 30%. In some instances, the level of PBC is relative to the level of PBC in a subject not treated with the FXR agonist.

In some embodiments, a FXR agonist disclosed herein reduces cirrhosis in a subject. In some examples, the FXR agonist reduces cirrhosis in the subject by at least 5%, at least 10%, at least 15%, at least 20%, at least 30%, at least 40%, at least 50%, or more. In some cases, cirrhosis is reduced by about 5% to about 50%, by about 5% to about 25%, by about 10% to about 20%, or by about 10% to about 30%. In some instances, the level of cirrhosis is relative to the level of cirrhosis in a subject not treated with the FXR agonist.

Non-Alcoholic Fatty Liver Disease and Non-Alcoholic Steatohepatitis

Non-alcoholic fatty liver disease (NAFLD) is associated with excessive fat in the liver (steatosis) and in some cases progresses to NASH, which is defined by the histologic hallmarks of inflammation, cell death, and fibrosis. In some instances, primary NASH is associated with insulin resistance, while secondary NASH is caused by medical or surgical conditions, or drugs such as, but not limited to, tamoxifen. In some cases, NASH progresses to advanced fibrosis, hepatocellular carcinoma, or end-stage liver disease requiring liver transplantation.

In some instances, NASH develops as a result of triglyceride (TGs) imbalance. For example, dysfunctional adipocytes secrete pro-inflammatory molecules such as cytokines and chemokines leading to insulin resistance and a failure of lipolysis suppression in the adipocytes. In some instances, this failure of lipolysis suppression leads to a release of free fatty acids (FFAs) into the circulation and uptake within the liver. In some cases, over accumulation of FFAs in the form of triglycerides (TGs) in lipid droplets leads to oxidative stress, mitochondrial dysfunction, and upregulation of pro-inflammatory molecules.

In some instances, activation of FXR inhibits triglyceride (TG)/fatty acid (FA) synthesis facilitated by suppressing sterol regulatory element-binding protein 1c (SREBP1c) via activation of SHP. In some cases, FXR additionally increases the clearance of TG by stimulating lipoprotein lipase (LPL) activity as well as the hepatic uptake of remnants and low-density lipoprotein by inducing syndecan 1 (SDC1) and the VLDL receptor (VLDLR).

In some embodiments, a FXR agonist disclosed herein is used in the treatment of non-alcoholic steatohepatitis (NASH). In some examples, the FXR agonist reduces NASH the subject by at least 5%, at least 10%, at least 15%, at least 20%, at least 30%, at least 40%, at least 50%, or more. In some cases, NASH is reduced by about 5% to about 50%, by about 5% to about 25%, by about 10% to about 20%, or by about 10% to about 30%. In some instances, the level of NASH is relative to the level of NASH in a subject not treated with the FXR agonist.

In some embodiments, a FXR agonist disclosed herein is used in the treatment of NAFLD. In some examples, the FXR agonist reduces NAFLD in the subject by at least 5%, at least 10%, at least 15%, at least 20%, at least 30%, at least 40%, at least 50%, or more. In some cases, NAFLD is reduced by about 5% to about 50%, by about 5% to about 25%, by about 10% to about 20%, or by about 10% to about 30%. In some instances, the level of NAFLD is relative to the level of NAFLD in a subject not treated with the FXR agonist.

Steatosis

In some embodiments, a FXR agonist disclosed herein reduces fatty liver (steatosis) in a subject. In some examples, the FXR agonist reduces steatosis in the subject by at least 5%, at least 10%, at least 15%, at least 20%, at least 30%, at least 40%, at least 50%, or more. In some instances, steatosis is reduced by about 5% to about 50%, by about 5% to about 25%, by about 10% to about 20%, or by about 10% to about 30%. In some instances, the level of steatosis is relative to the level of steatosis in a subject not treated with the FXR agonist.

Ballooning

Hepatocyte ballooning, a feature denoting cellular injury, is a feature of NASH.

Ballooning is a feature that denotes progressive NAFL (types 3 and 4). The term applies to enlarged, swollen-appearing hepatocytes; the affected cells are often intermixed in areas of steatosis and, in classic steatohepatitis, in the perivenular regions. Hepatocellular ballooning is most commonly noted in regions of H & E-detectable perisinusoidal fibrosis. Ballooned hepatocytes are most easily noted when they contain MH (either typical or poorly formed). Hepatocyte ballooning is a structural manifestation of microtubular disruption and severe cell injury.

In some embodiments, a FXR agonist disclosed herein reduces liver ballooning in a subject. In some examples, the FXR agonist reduces liver ballooning in the subject by at least 5%, at least 10%, at least 15%, at least 20%, at least 30%, at least 40%, at least 50%, or more. In some instances, liver ballooning is reduced by about 5% to about 50%, by about 5% to about 25%, by about 10% to about 20%, or by about 10% to about 30%. In some instances, the liver ballooning is relative to the level of liver ballooning in a subject not treated with the FXR agonist.

Alcoholic Hepatitis

In some embodiments, a FXR agonist disclosed herein reduces alcoholic hepatitis in a subject. In some examples, the FXR agonist reduces alcoholic hepatitis in the subject by at least 5%, at least 10%, at least 15%, at least 20%, at least 30%, at least 40%, at least 50%, or more. In some instances, the level of alcoholic hepatitis is reduced by about 5% to about 50%, by about 5% to about 25%, by about 10% to about 20%, or by about 10% to about 30%. In some instances, the level of alcoholic hepatitis is relative to the level of alcoholic hepatitis in a subject not treated with the FXR agonist.

Primary Sclerosing Cholangitis

In some embodiments, a FXR agonist disclosed herein is used in the treatment of primary sclerosing cholangitis (PSC). PSC is a chronic and progressive cholestatic liver disease. PSC is characterized by progressive inflammation, fibrosis, and stricture formation in liver ducts. Common symptoms include pruritus and jaundice. The disease is strongly associated with inflammatory bowel disease (IBD)—about 5% of patients with ulcerative colitis will have PSC. Up to 70% of patients with PSC also have IBD, most commonly ulcerative colitis.

Additional Alcoholic and Non-Alcoholic Liver Diseases or Conditions

In some embodiments, a FXR agonist disclosed herein reduces liver enzymes in a subject. In some examples, the FXR agonist reduce liver enzymes (e.g., serum ALT and/or AST levels) in the subject by at least 5%, at least 10%, at least 15%, at least 20%, at least 30%, at least 40%, at least 50%, or more. In some instances, the level of liver enzymes is reduced by about 5% to about 50%, by about 5% to about 25%, by about 10% to about 20%, or by about 10% to about 30%. In some instances, the level of liver enzymes is relative to the level of liver enzymes in a subject not treated with the FXR agonist.

In some embodiments, a FXR agonist disclosed herein reduces liver triglycerides in a subject. In some examples, the FXR agonist reduces liver triglycerides in the subject by at least 5%, at least 10%, at least 15%, at least 20%, at least 30%, at least 40%, at least 50%, or more. In some instances, the level of liver triglycerides is reduced by about 5% to about 50%, by about 5% to about 25%, by about 10% to about 20%, or by about 10% to about 30%. In some instances, the level of liver triglycerides is relative to the level of liver triglycerides in a subject not treated with the FXR agonist.

Inflammatory Intestinal Condition

Disclosed herein are methods of treating or preventing an inflammatory intestinal condition. Exemplary inflammatory conditions include necrotizing enterocolitis (NEC), gastritis, ulcerative colitis, inflammatory bowel disease, irritable bowel syndrome, pseudomembranous colitis, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection. In some embodiments, the inflammatory condition is NEC and the subject is a newborn or prematurely born infant. In some embodiments, the subject is enterally-fed infant or formula-fed infant.

In some embodiments, a FXR agonist disclosed herein is administered to a subject having an inflammatory intestinal condition. In some embodiments, a FXR agonist disclosed herein is administered to a subject having necrotizing enterocolitis (NEC), gastritis, ulcerative colitis, inflammatory bowel disease, irritable bowel syndrome, pseudomembranous colitis, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection.

In some embodiments, a FXR agonist disclosed herein reduces inflammation of the intestines in a subject (such as a human). In some examples, the FXR agonist reduces intestinal inflammation in the subject by at least 5%, at least 10%, at least 15%, at least 20%, at least 30%, at least 40%, at least 50%, or more. In some instances, intestinal inflammation is reduced by about 5% to about 50%, by about 5% to about 25%, by about 10% to about 20%, or by about 10% to about 30%. In some instances, the level of intestinal inflammation is relative to the level of intestinal inflammation in a subject not treated with the FXR agonist.

Gastrointestinal Diseases

Disclosed herein, in certain embodiments, are methods of treating or preventing a gastrointestinal disease in a subject in need thereof, comprising administering to the subject a farnesoid X receptor (FXR) agonist as described herein. In some embodiments, the gastrointestinal disease is irritable bowel syndrome (iBS), irritable bowel syndrome with diarrhea (BS-D), irritable bowel syndrome with constipation (BS-C), mixed IBS (IBS-M), unsubtyped IBS (IBS-U), or bile acid diarrhea (BAD).

Irritable Bowel Syndrome

Irritable bowel syndrome (IBS) is a combination of symptoms including abdominal pain and changes in bowel movement patterns that persists over an extended period of time, often years. The causes of IBS remain unclear; however, gut motility problems, food sensitivity, genetic factors, small intestinal bacterial overgrowth, and gut-brain axis problems are thought to have a potential role. In some instances, IBS is accompanied with diarrhea and is categorized as IBS with diarrhea (BS-D). In some instances, IBS is accompanied with constipation and is categorized as IBS with constipation (BS-C). In some instances, IBS is accompanied with an alternating pattern of diarrhea and constipation and is categorized as mixed IBS (IBS-M). In some instances, IBS is not accompanied with either diarrhea or constipation and is categorized as unsubtyped IBS (IBS-U). In some instances, IBS has four different variations: BS-D, BS-C, BS-M, and IBS-U.

In some embodiments, the symptoms of IBS are mimicked by a different condition. In some embodiments, sugar maldigestion, celiac disease, gluten intolerance without celiac disease, pancreatic exocrine insufficiency, small bowel bacterial overgrowth, microscopic colitis, or bile acid malabsorption (BAM) mimic IBS-D. In some embodiments, anismus, pelvic floor dyssynergia or puborectalis spasm, or descending perineum syndrome mimic IBS-C.

In some embodiments, an FXR agonist disclosed herein is used in the treatment of IBS or any of its variations in a mammal. In some examples, an FXR agonist therapeutic agent reduce IBS symptoms in the mammal by at least 5%, at least 10%, at least 15%, at least 20%, at least 30%, at least 40%, at least 50%, or more.

Bile Acid Malabsorption

Bile acid malabsorption (BAM), also known as bile acid diarrhea (BAD), bile acid-induced diarrhea, cholerheic or choleretic enteropathy, or bile salt malabsorption, is a condition in which the presence of bile acids in the colon causes diarrhea. BAM is caused by a number of conditions such as Crohn's disease, cholecystectomy, coeliac disease, radiotherapy, and pancreatic diseases. In some instances, BAM is caused by medications such as metformin. In some embodiments, BAM is caused by an overproduction of bile acids. Bile acid synthesis is negatively regulated by the ileal hormone fibroblast growth factor 19 (FGF-19); low levels of FGF-19 lead to an increase in bile acids. FXR activation promotes the synthesis of FGF-19, consequently lowering the levels of bile acids.

In some embodiments, an FXR agonist disclosed herein is used in the treatment of BAM in a mammal. In some embodiments, an FXR agonist disclosed herein decreases bile acid synthesis. In some embodiments, an FXR agonist disclosed herein decreases bile acid levels. In some embodiments, an FXR agonist and an additional therapeutic agent disclosed herein prevent BAD. In some examples, an FXR agonist reduces BAM symptoms in the mammal by at least 5%, at least 10%, at least 15%, at least 20%, at least 30%, at least 40%, at least 50%, or more.

Graft Vs. Host Disease (GvHD)

Graft vs. host disease (GvHD) is a medical complication that arises after a transplant of tissue or cells from a histo-incompatible donor (i.e. a genetically or immunologically different donor). Immune cells in the donated tissue or cells (graft) recognize the recipient (the host) as foreign and initiate and attack. Non-limiting examples of transplanted tissue or cells that give rise to GvHD are blood products, stem cells such as bone marrow cells, and organs. There are different types of GvHD depending on where the symptoms manifest or develop: skin GvHD, liver GvHD, eye GvHD, neuromuscular GvHD, genitourinary tract GvHD, and gastrointestinal (GI) tract GvHD. Symptoms of GI tract GvHD include difficulty swallowing, pain with swallowing, weight loss, nausea, vomiting, diarrhea, and/or abdominal cramping. GI tract GvHD results in sloughing of the mucosal membrane and severe intestinal inflammation. Inflammation of the biliary epithelium is amenable to be controlled by nuclear receptors such as the glucocorticoid receptor (GR), FXR, or the peroxisome proliferator-activated receptors (PPARs).

In some embodiments, an FXR agonist disclosed herein is used in the treatment of GvHD or a complication of GvHD in a mammal. In some embodiments, an FXR agonist disclosed herein is used in the treatment of GI tract GvHD or a complication of GI tract GvHD in a mammal. In some examples, an FXR agonist reduces GI tract GvHD or a complication of GI tract GvHD in the mammal by at least 5%, at least 10%, at least 15%, at least 20%, at least 30%, at least 40%, at least 50%, or more. In some cases, GI tract GvHD or a complication of GI tract GvHD is reduced by about 5% to about 50%, by about 5% to about 25%, by about 10% to about 20%, or by about 10% to about 30%. In some embodiments, an FXR agonist disclosed herein decreases intestinal inflammation caused by GI tract GvHD. In some embodiments, an FXR agonist disclosed herein reduces intestinal inflammation caused by GI tract GvHD reduced by about 5% to about 50%, by about 5% to about 25%, by about 10% to about 20%, or by about 10% to about 30%.

Kidney Diseases

Disclosed herein, in certain embodiments, are methods of treating or preventing a kidney disease in a subject in need thereof, comprising administering to the subject a farnesoid X receptor (FXR) agonist described herein. In some embodiments, the kidney disease is associated with a liver disease. In some embodiments, the kidney disease is associated with a fibrotic liver disease. In some embodiments, the kidney disease is associated with a metabolic liver disease. In some embodiments, the kidney disease is associated with a metabolic condition such as but not limited to diabetes, metabolic syndrome, NAFLD, insulin resistance, fatty acid metabolism disorder, and cholestasis. In some embodiments, the kidney disease is diabetic nephropathy, kidney disease associated with fibrosis, kidney disease not associated with fibrosis, renal fibrosis, or any combination thereof.

Diabetic Nephropathy

Diabetic nephropathy is a kidney disease characterized by damage to the kidney's glomeruli. Diabetes contributes to an excessive production of reactive oxygen species, which leads to nephrotic syndrome and scarring of the glomeruli. As diabetic nephropathy progresses, the glomerular filtration barrier (GFB) is increasingly damaged and consequently, proteins in the blood leak through the barrier and accumulate in the Bowman's space.

In some embodiments, an FXR agonist disclosed herein is used in the treatment of diabetic nephropathy in a mammal.

Renal Fibrosis

Renal fibrosis is characterized by activation of fibroblasts and excessive deposition of extracellular matrix or connective tissue in the kidney, which is a hallmark of chronic kidney disease. FXR plays an important role in protecting against renal fibrosis. Activation of FXR suppresses renal fibrosis and decreases accumulation of extracellular matrix proteins in the kidney.

In some embodiments, an FXR agonist disclosed herein is used in the treatment of renal fibrosis in a mammal.

In one aspect, described herein is a method of treating or preventing a kidney disease or condition in a mammal, comprising administering to the mammal an FXR agonist disclosed herein, or a pharmaceutically acceptable salt or solvate thereof. In some embodiments, the kidney disease or condition is diabetic nephropathy, kidney disease associated with fibrosis, kidney disease not associated with fibrosis, renal fibrosis, kidney disease associated with a metabolic disease, chronic kidney disease, polycystic kidney disease, acute kidney disease, or any combination thereof.

Cell Proliferation Disease

Further disclosed herein are methods of preventing or treating cell proliferation diseases, for example, in certain types of cancer. In some embodiments, the FXR agonists disclosed herein are used in the prevention or treatment of adenocarcinomas, or a carcinoma derived from glandular tissue or in which the tumor cells form recognizable glandular structures. In some embodiments, adenocarcinomas are classified according to the predominant pattern of cell arrangement, as papillary, alveolar, or according to a particular product of the cells, as mucinous adenocarcinoma. In some instances, adenocarcinomas are observed for example, in colon, kidney, breast, cervix, esophagus, gastric, pancreas, prostate, or lung.

In some embodiments, the compounds disclosed herein are used in the prevention or treatment of a cancer of the intestine, such as colon cancer, e.g. cancer that forms in the tissues of the colon (the longest part of the large intestine), or a cancer of another part of the intestine, such as the jejunum, and/or ileum. In some instances, colon cancer is also referred to as "colorectal cancer." In some instances, the most common type of colon cancer is colon adenocarcinoma.

In some cases, cancer progression is characterized by stages, or the extent of cancer in the body. Staging is usually based on the size of the tumor, the presence of cancer in the lymph nodes, and the presence of the cancer in a site other than the primary cancer site. Stages of colon cancer include stage I, stage II, stage III and stage IV. In some embodiments, colon adenocarcinoma is from any stage. In other embodiments, colon adenocarcinoma is a stage I cancer, a stage II cancer or a stage III cancer.

In some embodiments, a FXR agonist described herein is administered to a subject having a stage I, stage II, stage III, or stage IV cancer. In some instances, a FXR agonist described herein is administered to a subject having a stage I, stage II, or stage III colon adenocarcinoma.

In some embodiments, a FXR agonist disclosed herein further reduces the tumor burden in a subject. In some examples, the FXR agonist reduces tumor burden (such as colon tumor burden) in the subject by at least 5%, at least 10%, at least 15%, at least 20%, at least 30%, at least 40%, at least 50%, or more. In some instances, tumor burden is reduced by about 5% to about 50%, by about 5% to about 25%, by about 10% to about 20%, or by about 10% to about 30%. In some instances, the level of tumor burden is relative to the level of tumor burden in a subject not treated with the FXR agonist.

In some instances, a FXR agonist disclosed herein further reduces tumor size and/or volume in a subject. In some cases, the FXR agonist reduces tumor size and/or volume (such as a colon tumor) in the subject by at least 5%, at least 10%, at least 15%, at least 20%, at least 30%, at least 40%, at least 50%, or more. In some instances, tumor size is reduced by about 5% to about 50%, by about 5% to about 25%, by about 10% to about 20%, or by about 10% to about 30%. In some instances, the tumor size is relative to the tumor size in a subject not treated with the FXR agonist.

In additional embodiments, a FXR agonist disclosed herein reduces effects of cachexia due to a tumor in a subject. In some examples, the FXR agonist reduce the effect of cachexia (such as due to a colon tumor) in the subject by at least 5%, at least 10%, at least 15%, at least 20%, at least 30%, at least 40%, at least 50%, or more. In some instances, the effect of cachexia is reduced by about 5% to about 50%, by about 5% to about 25%, by about 10% to about 20%, or by about 10% to about 30%. In some instances, the effect of cachexia is relative to the effect of cachexia in a subject not treated with the FXR agonist.

In other embodiments, a FXR agonist disclosed herein increases survival rates of a subject with a tumor. In some cases, the FXR agonist increases the survival rate of a subject with a tumor (such as a colon cancer) in the subject by at least 5%, at least 10%, at least 15%, at least 20%, at least 30%, at least 40%, at least 50%, or more. In some instances, survival rate is increased by about 5% to about 50%, by about 5% to about 25%, by about 10% to about 20%, or by about 10% to about 30%. In some instances, the survival rate is relative to the survival rate in a subject not treated with the FXR agonist.

Compounds

Compounds described herein, including pharmaceutically acceptable salts, prodrugs, active metabolites and pharmaceutically acceptable solvates thereof, are farnesoid X receptor agonists.

In one aspect, described herein are farnesoid X receptor agonists and uses thereof. In one aspect, described herein is a compound that has the structure of Formula (I), or a pharmaceutically acceptable salt or solvate thereof:

Formula (I)

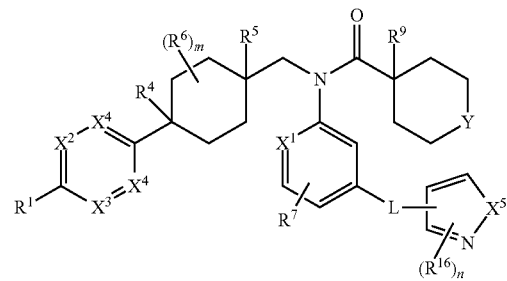

wherein, $X^1$ is CH or N;

$R^1$ is H, D, halogen, —CN, —OH, —SH, —N($R^{15}$)$_2$, —NR$^{15}$S(=O)$_2$(C$_1$-C$_4$alkyl), —S(C$_1$-C$_4$alkyl), —S(=O)(C$_1$-C$_4$alkyl), —S(=O)$_2$(C$_1$-C$_4$alkyl), —S(=O)$_2$N($R^{15}$)$_2$, —OC(=O)(C$_1$-C$_4$alkyl), —CO$_2$H, —CO$_2$(C$_1$-C$_4$alkyl), —C(=O)N($R^{15}$)$_2$, —NR$^{15}$C(=O)(C$_1$-C$_4$alkyl), —NR$^{15}$C(=O)O(C$_1$-C$_4$alkyl), —OC(=O)N($R^{15}$)$_2$, —NR$^{15}$C(=O)N($R^{15}$)$_2$, C$_1$-C$_4$alkyl, C$_2$-C$_4$alkenyl, C$_2$-C$_4$alkynyl, C$_1$-C$_4$alkoxy, C$_1$-C$_4$deuteroalkyl, C$_1$-C$_4$deuteroalkoxy, C$_1$-C$_4$fluoroalkyl, C$_1$-C$_4$fluoroalkoxy, C$_1$-C$_4$heteroalkyl, or substituted or unsubstituted monocyclic C$_2$-C$_5$heterocycloalkyl;

$X^2$ is CR$^2$ or N;

$R^2$ is H, D, halogen, —CN, —OH, —SH, —N($R^{15}$)$_2$, —NR$^{15}$S(=O)$_2$(C$_1$-C$_4$alkyl), —S(C$_1$-C$_4$alkyl), —S(=O)(C$_1$-C$_4$alkyl), —S(=O)$_2$(C$_1$-C$_4$alkyl), —S(=O)$_2$N($R^{15}$)$_2$, —OC(=O)(C$_1$-C$_4$alkyl), —CO$_2$H, —CO$_2$(C$_1$-C$_4$alkyl), —C(=O)N($R^{15}$)$_2$, —NR$^{15}$C(=O)(C$_1$-C$_4$alkyl), —NR$^{15}$C(=O)O(C$_1$-C$_4$alkyl), —OC(=O)N($R^{15}$)$_2$, —NR$^{15}$C(=O)N($R^{15}$)$_2$, C$_1$-C$_4$alkyl, C$_2$-C$_4$alkenyl, C$_2$-C$_4$alkynyl, C$_1$-C$_4$alkoxy, C$_1$-C$_4$deuteroalkyl, C$_1$-C$_4$deuteroalkoxy, C$_1$-C$_4$fluoroalkyl, C$_1$-C$_4$fluoroalkoxy, or C$_1$-C$_4$heteroalkyl, or substituted or unsubstituted monocyclic C$_2$-C$_5$heterocycloalkyl;

or R$^1$ and R$^2$ are taken together with the intervening atoms to form a substituted or unsubstituted fused 5-membered ring or substituted or unsubstituted fused 6-membered ring with 0-3 N atoms and 0-2 O or S atoms in the ring;

$X^3$ is CR$^3$ or N;

$R^3$ is H, D, halogen, —CN, —OH, —SH, —N($R^{15}$)$_2$, —NR$^{15}$S(=O)$_2$(C$_1$-C$_4$alkyl), —S(C$_1$-C$_4$alkyl), —S(=O)(C$_1$-C$_4$alkyl), —S(=O)$_2$(C$_1$-C$_4$alkyl), —S(=O)$_2$ N($R^{15}$)$_2$, —OC(=O)(C$_1$-C$_4$alkyl), —CO$_2$H, —CO$_2$(C$_1$-C$_4$alkyl), —C(=O)N($R^{15}$)$_2$, —NR$^{15}$C(O)(C$_1$-C$_4$alkyl), C$_1$-C$_4$alkyl, C$_2$-C$_4$alkenyl, C$_2$-C$_4$alkynyl, C$_1$-C$_4$alkoxy, C$_1$-C$_4$deuteroalkyl, C$_1$-C$_4$deuteroalkoxy, C$_1$-C$_4$fluoroalkyl, C$_1$-C$_4$fluoroalkoxy, C$_1$-C$_4$heteroalkyl, or substituted or unsubstituted monocyclic C$_2$-C$_5$heterocycloalkyl;

each X$^4$ is independently CH or N;

R$^4$ is H, D, F, or —CH$_3$;

R$^5$ is H, D, F, or —CH$_3$;

or R$^4$ and R$^5$ are taken together to form a bridge that is —CH$_2$— or —CH$_2$CH$_2$—;

each R$^6$ is independently H, D, F, —OH, or —CH$_3$;

m is 0, 1, or 2;

R$^7$ is H, D, halogen, —CN, —OH, C$_1$-C$_4$alkyl, C$_2$-C$_4$alkenyl, C$_2$-C$_4$alkynyl, C$_1$-C$_4$alkoxy, C₁-C₄deuteroalkyl, C₁-C₄deuteroalkoxy, C₁-C₄fluoroalkyl, C₁-C₄fluoroalkoxy, or C₁-C₄heteroalkyl;

L is absent, —Y²-L¹-, -L¹-Y²—, cyclopropylene, cyclobutylene or bicyclo[1.1.1]pentylene;

Y² is absent, —O—, —S—, —S(=O)—, —S(=O)₂—, —S(=O)₂NR¹⁵—, —CH₂—, —CH=CH—, —C≡C—, —C(=O)—, —C(=O)O—, —OC(=O)—, —OC(=O)O—, —C(=O)NR¹⁵—, —NR¹⁵C(=O)—, —OC(=O)NR¹⁵—, —NR¹⁵C(=O)O—, —NR¹⁵C(=O)NR¹⁵—, —NR¹⁵S(=O)₂—, or —NR¹⁵—;

L¹ is absent or substituted or unsubstituted C₁-C₄alkylene;

X⁵ is NR⁸ or N;

R⁸ is H, D, C₁-C₆alkyl, C₁-C₆deuteroalkyl, C₁-C₆fluoroalkyl, C₁-C₆heteroalkyl, —C(=O)(C₁-C₄alkyl), —CO₂(C₁-C₄alkyl), —C(=O)N(R¹⁵)₂, —S(=O)₂(C₁-C₄alkyl), —S(=O)₂N(R¹⁵)₂, substituted or unsubstituted C₃-C₆cycloalkyl, or substituted or unsubstituted monocyclic C₂-C₆heterocycloalkyl, substituted or unsubstituted phenyl, or substituted or unsubstituted monocyclic heteroaryl;

R⁹ is H, D, F or —CH₃;

Y is —CR¹⁰R¹¹—, —O—, —S—, —S(=O)—, —S(=O)₂—, or —NR¹⁷—;

R¹⁰ is H, D, halogen, —CN, —OH, C₁-C₆alkyl, C₂-C₄alkenyl, C₂-C₄alkynyl, C₁-C₆alkoxy, C₁-C₆fluoroalkyl, —SR¹², —S(=O)R¹⁴, —S(=O)₂R¹⁴, or —N(R¹²)₂;

R¹¹ is H, D, F or —CH₃;

or R⁹ and R¹¹ are taken together to form a bridge that is —CH₂— or —CH₂CH₂—;

each R¹² is independently H, C₁-C₄alkyl, C₁-C₄deuteroalkyl, C₁-C₄fluoroalkyl, C₁-C₄heteroalkyl, substituted or unsubstituted C₃-C₆cycloalkyl, substituted or unsubstituted C₂-C₆heterocycloalkyl, substituted or unsubstituted phenyl, substituted or unsubstituted benzyl, substituted or unsubstituted monocyclic heteroaryl;

R¹⁴ is C₁-C₄alkyl, C₁-C₄deuteroalkyl, C₁-C₄fluoroalkyl, C₁-C₄heteroalkyl, substituted or unsubstituted C₃-C₆cycloalkyl, substituted or unsubstituted C₂-C₆heterocycloalkyl, substituted or unsubstituted phenyl, substituted or unsubstituted benzyl, or substituted or unsubstituted monocyclic heteroaryl;

R¹⁵ is H or substituted or unsubstituted C₁-C₆alkyl;

each R¹⁶ is independently H, D, halogen, —CN, —OH, —N(R¹⁵)₂, —NR¹⁵S(=O)₂(C₁-C₄alkyl), —S(C₁-C₄alkyl), —S(=O)(C₁-C₄alkyl), —S(=O)₂(C₁-C₄alkyl), —C(=O)(C₁-C₄alkyl), —OC(=O)(C₁-C₄alkyl), —CO₂H, —CO₂(C₁-C₄alkyl), —NR¹⁵C(=O)(C₁-C₄alkyl), —C(=O)N(R¹⁵)₂, —NR¹⁵C(=O)O(C₁-C₄alkyl), —OC(=O)N(R¹⁵)₂, C₁-C₄alkyl, C₂-C₄alkenyl, C₂-C₄alkynyl, C₁-C₄alkoxy, C₁-C₄deuteroalkyl, C₁-C₄deuteroalkoxy, C₁-C₄fluoroalkyl, C₁-C₄fluoroalkoxy, C₁-C₄heteroalkyl, substituted or unsubstituted C₃-C₆cycloalkyl, substituted or unsubstituted monocyclic C₂-C₆heterocycloalkyl, substituted or unsubstituted phenyl, or substituted or unsubstituted monocyclic heteroaryl;

n is 0, 1, or 2;

R¹⁷ is -L⁵-R¹⁴; and

L⁵ is absent, —S(=O)₂—, —C(=O)—, —CO₂—, or —C(=O)N(R¹⁵).

In another aspect, described herein is a compound of Formula (I), or a pharmaceutically acceptable salt, or solvate thereof:

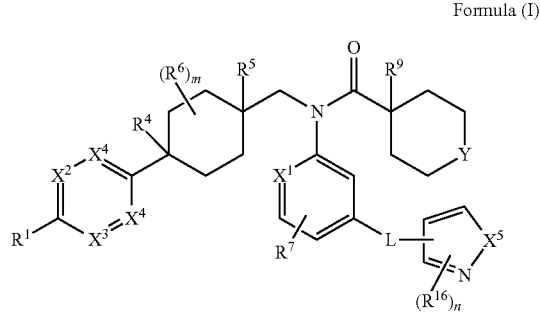

Formula (I)

wherein,

X¹ is CH or N;

R¹ is H, D, halogen, —CN, —OH, —N(R¹⁵)₂, —NR¹⁵S(=O)₂(C₁-C₄alkyl), —OC(=O)(C₁-C₄alkyl), —CO₂H, —CO₂(C₁-C₄alkyl), —NR¹⁵C(=O)(C₁-C₄alkyl), —NR¹⁵C(=O)O(C₁-C₄alkyl), —OC(=O)N(R¹⁵)₂, —NR¹⁵C(=O)N(R¹⁵)₂, C₁-C₄alkyl, C₂-C₄alkenyl, C₂-C₄alkynyl, C₁-C₄alkoxy, C₁-C₄deuteroalkyl, C₁-C₄deuteroalkoxy, C₁-C₄fluoroalkyl, C₁-C₄fluoroalkoxy, C₁-C₄heteroalkyl, or substituted or unsubstituted monocyclic C₂-C₅heterocycloalkyl;

X² is CR² or N;

R² is H, D, halogen, —CN, —OH, —N(R¹⁵)₂, —NR¹⁵S(=O)₂(C₁-C₄alkyl), —OC(=O)(C₁-C₄alkyl), —CO₂H, —CO₂(C₁-C₄alkyl), —NR¹⁵C(=O)(C₁-C₄alkyl), —NR¹⁵C(=O)O(C₁-C₄alkyl), —OC(=O)N(R¹⁵)₂, —NR¹⁵C(=O)N(R¹⁵)₂, C₁-C₄alkyl, C₂-C₄alkenyl, C₂-C₄alkynyl, C₁-C₄alkoxy, C₁-C₄deuteroalkyl, C₁-C₄deuteroalkoxy, C₁-C₄fluoroalkyl, C₁-C₄fluoroalkoxy, or C₁-C₄heteroalkyl;

or R¹ and R² are taken together with the intervening atoms to form a substituted or unsubstituted fused 5-membered ring with 0-3 N atoms and 0-2 O or S atoms in the ring;

X³ is CR³ or N;

R³ is H, D, halogen, —CN, —OH, —N(R¹⁵)₂, —NR¹⁵S(=O)₂(C₁-C₄alkyl), —OC(=O)(C₁-C₄alkyl), —CO₂H, —CO₂(C₁-C₄alkyl), —NR¹⁵C(=O)(C₁-C₄alkyl), C₁-C₄alkyl, C₂-C₄alkenyl, C₂-C₄alkynyl, C₁-C₄alkoxy, C₁-C₄deuteroalkyl, C₁-C₄deuteroalkoxy, C₁-C₄fluoroalkyl, C₁-C₄fluoroalkoxy, or C₁-C₄heteroalkyl;

each X⁴ is independently CH or N;

R⁴ is H, D, F, or —CH₃;

R⁵ is H, D, F, or —CH₃;

or R⁴ and R⁵ are taken together to form a bridge that is —CH₂— or —CH₂CH₂—;

each R⁶ is independently H, D, F, —OH, or —CH₃;

m is 0, 1, or 2;

R⁷ is H, D, halogen, —CN, —OH, C₁-C₄alkyl, C₁-C₄alkoxy, C₁-C₄deuteroalkyl, C₁-C₄deuteroalkoxy, C₁-C₄fluoroalkyl, C₁-C₄fluoroalkoxy, or C₁-C₄heteroalkyl;

L is absent, —Y²-L¹-, -L¹-Y²—, cyclopropylene, cyclobutylene or bicyclo[1.1.1]pentylene;

Y² is absent, —O—, —S—, —S(=O)—, —S(=O)₂—, —S(=O)₂NR¹⁵—, —CH₂—, —CH=CH—, —C≡C—, —C(=O)—, —C(=O)O—, —OC(=O)—, —OC(=O)O—, —C(=O)NR¹⁵—, —NR¹⁵C(=O)—, —OC(=O)NR¹⁵—, —NR¹⁵C(=O)O—, —NR¹⁵C(=O)NR¹⁵—, —NR¹⁵S(=O)₂—, or —NR¹⁵—;

L¹ is absent or substituted or unsubstituted C₁-C₄alkylene;

X⁵ is NR⁸ or N;

R⁸ is H, D, C₁-C₆alkyl, C₁-C₆deuteroalkyl, C₁-C₆fluoroalkyl, C₁-C₆heteroalkyl, —C(=O)(C₁-C₄alkyl), —CO₂(C₁-C₄alkyl), —C(=O)N(R¹⁵)₂, —S(=O)₂(C₁-C₄alkyl), —S(=O)₂N(R¹⁵)₂, substituted or unsubstituted C₃-C₆cycloalkyl, or substituted or unsubstituted monocyclic C₂-C₆heterocycloalkyl, substituted or unsubstituted phenyl, or substituted or unsubstituted monocyclic heteroaryl;

R⁹ is H, D, or —CH₃;

Y is —CR¹⁰R¹¹—, —O—, —S—, —S(=O)—, —S(=O)₂, or —NR¹⁷—;

R¹⁰ is H, D, halogen, —CN, —OH, C₁-C₆alkyl, C₁-C₆alkoxy, C₁-C₆fluoroalkyl, —SR¹², S(=O)R¹⁴, —S(=O)₂R¹⁴, or —N(R¹²)₂;

R¹¹ is H, D, or —CH₃;

or R⁹ and R¹¹ are taken together to form a bridge that is —CH₂— or —CH₂CH₂—;

each R¹² is independently H, C₁-C₄alkyl, C₁-C₄deuteroalkyl, C₁-C₄fluoroalkyl, C₁-C₄heteroalkyl, substituted or unsubstituted C₃-C₆cycloalkyl, substituted or unsubstituted C₂-C₆heterocycloalkyl, substituted or unsubstituted phenyl, substituted or unsubstituted benzyl, substituted or unsubstituted monocyclic heteroaryl;

R¹⁴ is C₁-C₄alkyl, C₁-C₄deuteroalkyl, C₁-C₄fluoroalkyl, C₁-C₄heteroalkyl, substituted or unsubstituted C₃-C₆cycloalkyl, substituted or unsubstituted C₂-C₆heterocycloalkyl, substituted or unsubstituted phenyl, substituted or unsubstituted benzyl, or substituted or unsubstituted monocyclic heteroaryl;

R¹⁵ is H or substituted or unsubstituted C₁-C₆alkyl;

each R¹⁶ is independently H, D, halogen, —CN, —OH, —N(R¹⁵)₂, —NR¹⁵S(=O)₂(C₁-C₄alkyl), —S(C₁-C₄alkyl), —S(=O)₂(C₁-C₄alkyl), —C(=O)(C₁-C₄alkyl), —OC(=O)(C₁-C₄alkyl), —CO₂H, —CO₂(C₁-C₄alkyl), —NR¹⁵C(=O)(C₁-C₄alkyl), —C(=O)N(R¹⁵)₂, —NR¹⁵C(=O)O(C₁-C₄alkyl), —OC(=O)N(R¹⁵)₂, C₁-C₄alkyl, C₂-C₄alkenyl, C₂-C₄alkynyl, C₁-C₄alkoxy, C₁-C₄deuteroalkyl, C₁-C₄deuteroalkoxy, C₁-C₄fluoroalkyl, C₁-C₄fluoroalkoxy, C₁-C₄heteroalkyl, substituted or unsubstituted C₃-C₆cycloalkyl, substituted or unsubstituted monocyclic C₂-C₆heterocycloalkyl, substituted or unsubstituted phenyl, or substituted or unsubstituted monocyclic heteroaryl;

n is 0, 1, or 2;

R¹⁷ is -L⁵-R¹⁴; and

L⁵ is absent, —S(=O)₂—, —C(=O)—, —CO₂—, or —C(=O)N(R¹⁵).

For any and all of the embodiments, substituents are selected from among a subset of the listed alternatives. For example, in some embodiments Y is —CR¹⁰R¹¹—, —O—, —S—, —S(=O)—, —S(=O)₂, or —NR¹⁷—. In other embodiments, Y is —CR¹⁰R¹¹—, —O—, or —NR¹⁷—. In some embodiments, Y is —CR¹⁰R¹¹—.

In some embodiments, m is 0, 1, or 2. In some embodiments, m is 0 or 1. In some embodiements, m is 0. In some embodiments, n is 0, 1, or 2. In some embodiments, n is 0 or 1. In some embodiments, n is 0.

In some embodiments, L is absent, —O—, —S—, —CH₂—, —CH₂CH₂—, —CH₂O—, —OCH₂—, —CH₂NR¹⁵—, —NR¹⁵CH₂—, —CH=CH—, —C≡C—, —C(=O)—, —C(=O)O—, —OC(=O)—, —OC(=O)O—, —C(=O)NR¹⁵—, —NR¹⁵C(=O)—, —OC(=O)NR¹⁵—, —NR¹⁵C(=O)O—, —NR¹⁵C(=O)NR¹⁵—, —NR¹⁵S(=O)₂—, —NR¹⁵—, cyclopropylene, cyclobutylene or bicyclo[1.1.1]pentylene.

In some embodiments, L is absent, —O—, —S—, —CH₂—, —CH₂CH₂—, —CH₂O—, —OCH₂—, —CH₂NR¹⁵—, —NR¹⁵CH₂—, —CH=CH—, —C≡C—, —C(=O)NR¹⁵—, —NR¹⁵C(=O)—, —OC(=O)NR¹⁵—, —NR¹⁵C(=O)O—, —NR¹⁵C(=O)NR¹⁵—, —NR¹⁵S(=O)₂—, —NR¹⁵, cyclopropylene, cyclobutylene or bicyclo[1.1.1]pentylene.

In some embodiments, L is absent or —C≡C—.

In some embodiments, R⁹ is H; R¹¹ is H; or R⁹ and R¹¹ are taken together to form a bridge that is —CH₂CH₂—. In some embodiments, R⁹ is H; and R¹¹ is H.

In some embodiments, the compound has the structure of Formula (II), or a pharmaceutically acceptable salt or solvate thereof:

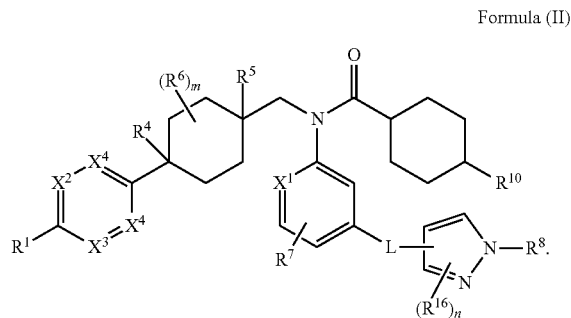

Formula (II)

In some embodiments, L is absent.

In some embodiments, the compound has the structure of Formula (III), or a pharmaceutically acceptable salt or solvate thereof:

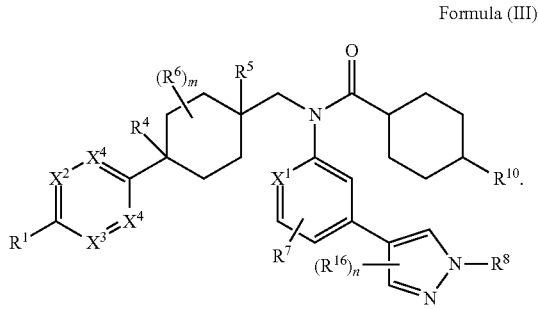

Formula (III)

In some embodiments, R⁴ is H; R⁵ is H; or R⁴ and R⁵ are taken together to form a bridge that is —CH₂CH₂—.

In some embodiments, R⁴ is H; R⁵ is H.

In some embodiments, R⁴ and R⁵ are taken together to form a bridge that is —CH₂CH₂—.

In some embodiments, the compound has the structure of Formula (IV), or a pharmaceutically acceptable salt or solvate thereof:

Formula (IV)

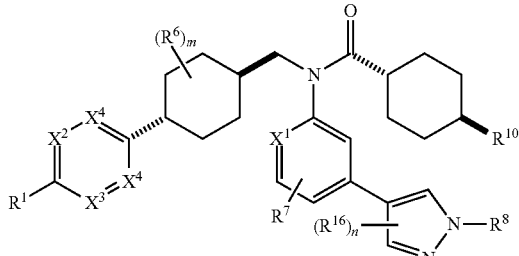

In some embodiments, the compound has the structure of Formula (V), or a pharmaceutically acceptable salt or solvate thereof:

Formula (V)

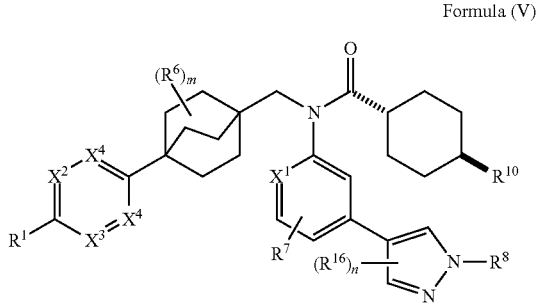

In some embodiments, the compound has the structure of Formula (VI), or a pharmaceutically acceptable salt or solvate thereof:

Formula (VI)

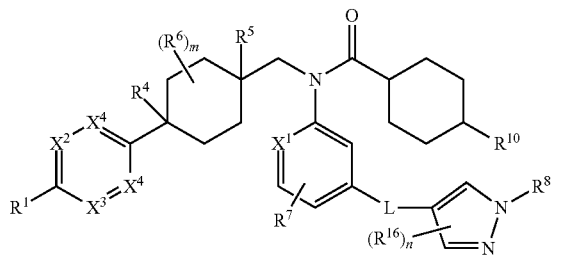

In some embodiments, R is H; $R^5$ is H; or $R^4$ and $R^5$ are taken together to form a bridge that is —CH$_2$CH$_2$—.

In some embodiments, the compound has the structure of Formula (VII), or a pharmaceutically acceptable salt or solvate thereof:

Formula (VII)

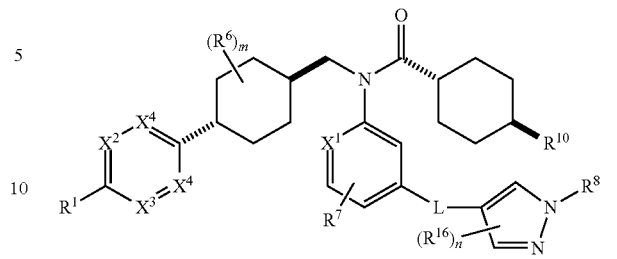

In some embodiments, the compound has the structure of Formula (VIII), or a pharmaceutically acceptable salt or solvate thereof:

Formula (VIII)

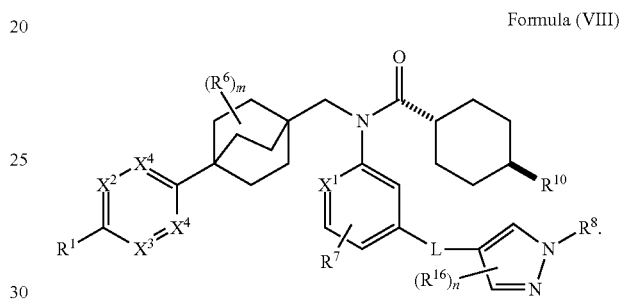

In some embodiments, $R^{10}$ is H, D, F, —CN, —OH, $C_1$-$C_6$alkyl, $C_1$-$C_6$alkoxy, $C_1$-$C_6$fluoroalkyl, or —N($R^{12}$)$_2$. In some embodiments, $R^{10}$ is H, D, F, —OH, $C_1$-$C_6$alkyl, $C_1$-$C_6$alkoxy, or —N($R^{12}$)$_2$. In some embodiments, $R^{10}$ is H, D, F, —CN, —OH, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —OCH$_3$, —OCH$_2$CH$_3$, —OCH(CH$_3$)$_2$, —CH$_2$F, —CHF$_2$, —CF$_3$, —CH$_2$CF$_3$, —NH$_2$, —NH(CH$_3$), or —N(CH$_3$)$_2$. In some embodiments, $R^{10}$ is H, —OH, —CH$_3$, —OCH$_3$, —NH$_2$, —NH(CH$_3$), or —N(CH$_3$)$_2$. In some embodiments, $R^{10}$ is H, —OH, or —NH$_2$.

In some embodiments, $R^{10}$ is —OH.

In some embodiments, no more than two $X^2$, $X^3$, $X^4$, $X^4$ are N.

In some embodiments, if both $X^4$ are N then $X^2$ is $CR^2$ and $X^3$ is $CR^3$; or if one $X^4$ is N and the other $X^4$ is CH then only one of $X^2$ and $X^3$ is N.

In some embodiments, the 6-membered ring containing $X^2$, $X^3$, $X^4$, $X^4$ has no more than two N atoms in the ring.

In some embodiments, $X^2$ is $CR^2$; $X^3$ is $CR^3$ or N; each $X^4$ is CH; or each $X^4$ is N; or one $X^4$ is N and the other $X^4$ is CH.

In some embodiments, $X^2$ is $CR^2$; $X^3$ is $CR^3$; each $X^4$ is CH; or each $X^4$ is N; or one $X^4$ is N and the other $X^4$ is CH.

In some embodiments, $X^2$ is $CR^2$; $X^3$ is $CR^3$; each $X^4$ is CH.

In some embodiments, $R^1$ is H, D, F, Cl, —CN, —OH, —SH, —NH$_2$, —NH(CH$_3$), —N(CH$_3$)$_2$, —NHS(=O)$_2$CH$_3$, —OC(=O)CH$_3$, —CO$_2$H, —CO$_2$CH$_3$, —NHC(=O)CH$_3$, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —OCH$_3$, —OCH$_2$CH$_3$, —OCH(CH$_3$)$_2$, —SCH$_3$, —SCH$_2$CH$_3$, —SCH(CH$_3$)$_2$, —CD$_3$, —OCD$_3$, —CH$_2$F, —CHF$_2$, —CF$_3$, —CH$_2$CF$_3$, —OCH$_2$F, —OCHF$_2$, —OCF$_3$, —OCH$_2$CF$_3$, —CH$_2$OH, —CH₂OCH₃, —CH₂OCH₂CH₃, —CH₂NH₂, —CH₂NHCH₃, or —CH₂N(CH₃)₂; R² is H, D, F, Cl, —CN, —OH, —SH, —NH₂, —NH(CH₃), —N(CH₃)₂, —NHS(═O)₂CH₃, —OC(═O)CH₃, —CO₂H, —CO₂CH₃, —NHC(═O)CH₃, —CH₃, —CH₂CH₃, —CH₂CH₂CH₃, —CH(CH₃)₂, —CH₂CH₂CH₂CH₃, —CH₂CH(CH₃)₂, —C(CH₃)₃, —OCH₃, —OCH₂CH₃, —OCH(CH₃)₂, —SCH₃, —SCH₂CH₃, —SCH(CH₃)₂, —CD₃, —OCD₃, —CH₂F, —CHF₂, —CF₃, —CH₂CF₃, —OCH₂F, —OCHF₂, —OCF₃, —OCH₂CF₃, —CH₂OH, —CH₂OCH₃, —CH₂OCH₂CH₃, —CH₂NH₂, —CH₂NHCH₃, or —CH₂N(CH₃)₂; or R¹ and R² are taken together with the intervening atoms to form a substituted or unsubstituted fused 5-membered ring or substituted or unsubstituted fused 6-membered ring with 0-3 N atoms and 0-2 O or S atoms in the ring that is a substituted or unsubstituted dihydrofuranyl, a substituted or unsubstituted dihydropyrrolyl, substituted or unsubstituted dioxolyl, substituted or unsubstituted furanyl, substituted or unsubstituted thienyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted isoxazolyl or substituted or unsubstituted isothiazolyl, substituted or unsubstituted piperidinyl, substituted or unsubstituted piperazinyl, substituted or unsubstituted pyridinyl, substituted or unsubstituted pyrimidinyl, substituted or unsubstituted pyrazinyl, or substituted or unsubstituted pyridazinyl; R³ is H, D, F, Cl, —CN, —OH, —SH, —NH₂, —NH(CH₃), —N(CH₃)₂, —NHS(═O)₂CH₃, —OC(═O)CH₃, —CO₂H, —CO₂CH₃, —NHC(═O)CH₃, —CH₃, —CH₂CH₃, —CH₂CH₂CH₃, —CH(CH₃)₂, —CH₂CH₂CH₂CH₃, —CH₂CH(CH₃)₂, —C(CH₃)₃, —OCH₃, —OCH₂CH₃, —OCH(CH₃)₂, —SCH₃, —SCH₂CH₃, —SCH(CH₃)₂, —CD₃, —OCD₃, —CH₂F, —CHF₂, —CF₃, —CH₂CF₃, —OCH₂F, —OCHF₂, —OCF₃, —OCH₂CF₃, —CH₂OH, —CH₂OCH₃, —CH₂OCH₂CH₃, —CH₂NH₂, —CH₂NHCH₃, or —CH₂N(CH₃)₂.

In some embodiments, R¹ is H, D, F, Cl, —CN, —OH, —NH₂, —NH(CH₃), —N(CH₃)₂, —NHS(═O)₂CH₃, —OC(═O)CH₃, —CO₂H, —CO₂CH₃, —NHC(═O)CH₃, —CH₃, —CH₂CH₃, —CH₂CH₂CH₃, —CH(CH₃)₂, —CH₂CH₂CH₂CH₃, —CH₂CH(CH₃)₂, —C(CH₃)₃, —OCH₃, —OCH₂CH₃, —OCH(CH₃)₂, —CD₃, —OCD₃, —CH₂F, —CHF₂, —CF₃, —CH₂CF₃, —OCH₂F, —OCHF₂, —OCF₃, —OCH₂CF₃, —CH₂OH, —CH₂OCH₃, —CH₂OCH₂CH₃, —CH₂NH₂, —CH₂NHCH₃, or —CH₂N(CH₃)₂;

R² is H, D, F, Cl, —CN, —OH, —NH₂, —NH(CH₃), —N(CH₃)₂, —NHS(═O)₂CH₃, —OC(═O)CH₃, —CO₂H, —CO₂CH₃, —NHC(═O)CH₃, —CH₃, —CH₂CH₃, —CH₂CH₂CH₃, —CH(CH₃)₂, —CH₂CH₂CH₂CH₃, —CH₂CH(CH₃)₂, —C(CH₃)₃, —OCH₃, —OCH₂CH₃, —OCH(CH₃)₂, —CD₃, —OCD₃, —CH₂F, —CHF₂, —CF₃, —CH₂CF₃, —OCH₂F, —OCHF₂, —OCF₃, —OCH₂CF₃, —CH₂OH, —CH₂OCH₃, —CH₂OCH₂CH₃, —CH₂NH₂, —CH₂NHCH₃, or —CH₂N(CH₃)₂; or R¹ and R² are taken together with the intervening atoms to form a substituted or unsubstituted fused 5-membered ring with 0-3 N atoms and 0-2 O or S atoms in the ring that is a substituted or unsubstituted dihydrofuranyl, substituted or unsubstituted dioxolyl, substituted or unsubstituted furanyl, substituted or unsubstituted thienyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted isoxazolyl or substituted or unsubstituted isothiazolyl; R³ is H, D, F, Cl, —CN, —OH, —NH₂, —NH(CH₃), —N(CH₃)₂, —NHS(═O)₂CH₃, —OC(═O)CH₃, —CO₂H, —CO₂CH₃, —NHC(═O)CH₃, —CH₃, —CH₂CH₃, —CH₂CH₂CH₃, —CH(CH₃)₂, —CH₂CH₂CH₂CH₃, —CH₂CH(CH₃)₂, —C(CH₃)₃, —OCH₃, —OCH₂CH₃, —OCH(CH₃)₂, —CD₃, —OCD₃, —CH₂F, —CHF₂, —CF₃, —CH₂CF₃, —OCH₂F, —OCHF₂, —OCF₃, —OCH₂CF₃, —CH₂OH, —CH₂OCH₃, —CH₂OCH₂CH₃, —CH₂NH₂, —CH₂NHCH₃, or —CH₂N(CH₃)₂.

In some embodiments, R¹ is H, D, F, Cl, —CN, —OH, —SH, —NH₂, —NH(CH₃), —N(CH₃)₂, —CH₃, —CH₂CH₃, —OCH₃, —OCH₂CH₃, —SCH₃, —SCH₂CH₃, —CD₃, —OCD₃, —CH₂F, —CHF₂, —CF₃, —CH₂CF₃, —OCH₂F, —OCHF₂, —OCF₃, or —OCH₂CF₃; R² is H, D, F, Cl, —CH₃, —CH₂CH₃, —OCH₃, —OCH₂CH₃, —SCH₃, —SCH₂CH₃, —CD₃, —OCD₃, —CH₂F, —CHF₂, —CF₃, —OCH₂F, —OCHF₂, —OCF₃, or —OCH₂CF₃; R³ is H, D, F, Cl, —CH₃, —OCH₃, —SCH₃, —CD₃, —OCD₃, —CH₂F, —CHF₂, —CF₃, —CH₂CF₃, —OCH₂F, —OCHF₂, or —OCF₃.

In some embodiments, R¹ is H, D, F, Cl, —CN, —OH, —NH₂, —NH(CH₃), —N(CH₃)₂, —CH₃, —CH₂CH₃, —OCH₃, —OCH₂CH₃, —CD₃, —OCD₃, —CH₂F, —CHF₂, —CF₃, —CH₂CF₃, —OCH₂F, —OCHF₂, —OCF₃, or —OCH₂CF₃; R² is H, D, F, Cl, —CH₃, —CH₂CH₃, —OCH₃, —OCH₂CH₃, —CD₃, —OCD₃, —CH₂F, —CHF₂, —CF₃, —OCH₂F, —OCHF₂, —OCF₃, or —OCH₂CF₃; R³ is H, D, F, Cl, —CH₃, —OCH₃, —CD₃, —OCD₃, —CH₂F, —CHF₂, —CF₃, —CH₂CF₃, —OCH₂F, —OCHF₂, or —OCF₃.

In some embodiments, R¹ is —OH, —SH, —NH₂, —NH(CH₃), —N(CH₃)₂, —CH₃, —OCH₃, —SCH₃, —CD₃, —OCD₃, —CH₂F, —CHF₂, —CF₃, —OCH₂F, —OCHF₂, —OCF₃, or —OCH₂CF₃; R² is H, D, F, Cl, —CH₃, —CD₃, —CH₂F, —CHF₂, or —CF₃; R³ is H.

In some embodiments, R¹ is —OH, —NH₂, —NH(CH₃), —N(CH₃)₂, —CH₃, —OCH₃, —CD₃, —OCD₃, —CH₂F, —CHF₂, —CF₃, —OCH₂F, —OCHF₂, —OCF₃, or —OCH₂CF₃; R² is H, D, F, Cl, —CH₃, —CD₃, —CH₂F, —CHF₂, or —CF₃; R³ is H.

In some embodiments, R¹ is H, D, F, Cl, —CN, —OH, —NH₂, —NH(CH₃), —N(CH₃)₂, —CH₃, —OCH₃, —OCH₂CH₃, —OCH(CH₃)₂, —CD₃, —OCD₃, —CH₂F, —CHF₂, —CF₃, —CH₂CF₃, —OCH₂F, —OCHF₂, or —OCF₃; R² is H, D, F, Cl, —CN, —OH, —CH₃, —OCH₃, —OCH₂CH₃, —OCH(CH₃)₂, —CD₃, —OCD₃, —CH₂F, —CHF₂, —CF₃, or —OCF₃.

In some embodiments, R¹ is —OH, —NH₂, —NH(CH₃), —N(CH₃)₂, —OCH₃, —OCD₃, —OCH₂F, —OCHF₂, or —OCF₃; R² is F, Cl, —CN, —OH, —CH₃, —OCH₃, —CD₃, —OCD₃, —CH₂F, —CHF₂, —CF₃, or —OCF₃. In some embodiments, R¹ is —OH, or —OCH₃; R² is H, D, F, Cl, —CH₃, or —CF₃.

In some embodiments,

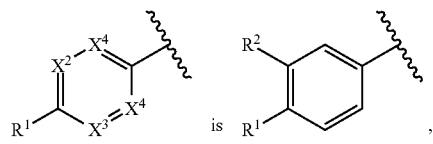

is

-continued

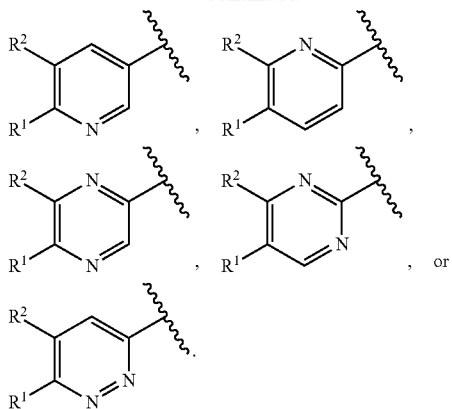

In some embodiments,

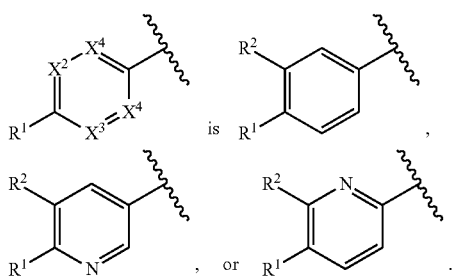

In some embodiments,

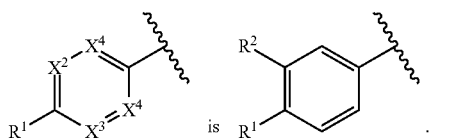

In some embodiments,

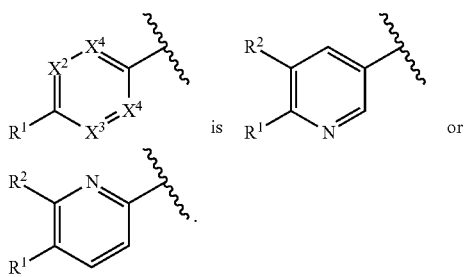

In some embodiments

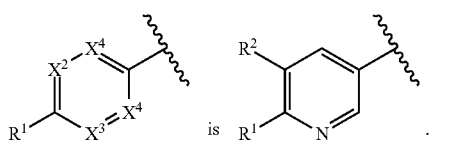

In some embodiments,

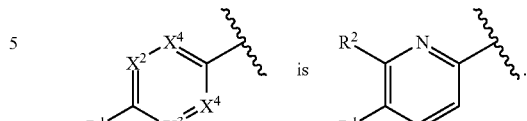

In some embodiments,

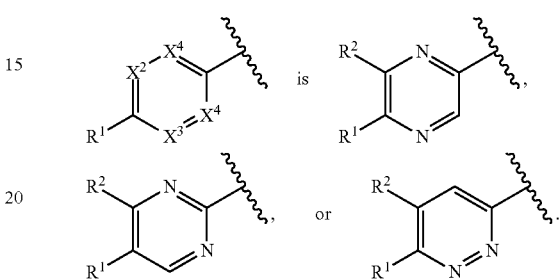

In some embodiments, $X^2$ is N; $X^3$ is N; each $X^4$ is CH. In some embodiments,

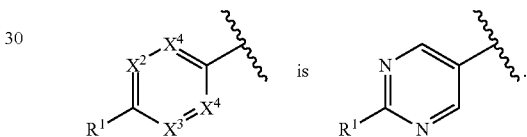

In some embodiments, the compound has the structure of Formula (IX), or a pharmaceutically acceptable salt or solvate thereof:

Formula (IX)

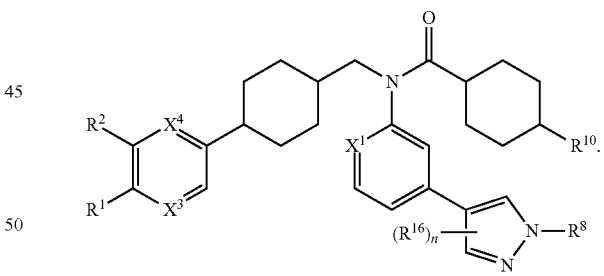

In some embodiments, $R^1$ is H, D, F, Cl, —CN, —OH, —SH, —NH$_2$, —NH(CH$_3$), —N(CH$_3$)$_2$, —NHS(=O)$_2$CH$_3$, —OC(=O)CH$_3$, —CO$_2$H, —CO$_2$CH$_3$, —NHC(=O)CH$_3$, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —OCH$_3$, —OCH$_2$CH$_3$, —OCH(CH$_3$)$_2$, —SCH$_3$, —SCH$_2$CH$_3$, —SCH(CH$_3$)$_2$, —CD$_3$, —OCD$_3$, —CH$_2$F, —CHF$_2$, —CF$_3$, —CH$_2$CF$_3$, —OCH$_2$F, —OCHF$_2$, —OCF$_3$, —OCH$_2$CF$_3$, —CH$_2$OH, —CH$_2$OCH$_3$, —CH$_2$OCH$_2$CH$_3$, —CH$_2$NH$_2$, —CH$_2$NHCH$_3$, or —CH$_2$N(CH$_3$)$_2$.

In some embodiments, $R^1$ is H, D, F, Cl, —CN, —OH, —NH$_2$, —NH(CH$_3$), —N(CH$_3$)$_2$, —NHS(=O)$_2$CH$_3$, —OC(=O)CH$_3$, —CO$_2$H, —CO$_2$CH$_3$, —NHC(=O)CH$_3$, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —OCH$_3$, —OCH$_2$CH$_3$, —OCH(CH$_3$)$_2$, —CD$_3$, —OCD$_3$, —CH$_2$F, —CHF$_2$, —CF$_3$, —CH$_2$CF$_3$, —OCH$_2$F, —OCHF$_2$, —OCF$_3$, —OCH$_2$CF$_3$, —CH$_2$OH, —CH$_2$OCH$_3$, —CH$_2$OCH$_2$CH$_3$, —CH$_2$NH$_2$, —CH$_2$NHCH$_3$, or —CH$_2$N(CH$_3$)$_2$.

In some embodiments, R$^1$ is H, D, F, Cl, —CN, —OH, —SH, —NH$_2$, —NH(CH$_3$), —N(CH$_3$)$_2$, —CH$_3$, —CH$_2$CH$_3$, —OCH$_3$, —OCH$_2$CH$_3$, —SCH$_3$, —SCH$_2$CH$_3$, —CD$_3$, —OCD$_3$, —CH$_2$F, —CHF$_2$, —CF$_3$, —CH$_2$CF$_3$, —OCH$_2$F, —OCHF$_2$, —OCF$_3$, or —OCH$_2$CF$_3$.

In some embodiments, R$^1$ is H, D, F, Cl, —CN, —OH, —NH$_2$, —NH(CH$_3$), —N(CH$_3$)$_2$, —CH$_3$, —CH$_2$CH$_3$, —OCH$_3$, —OCH$_2$CH$_3$, —CD$_3$, —OCD$_3$, —CH$_2$F, —CHF$_2$, —CF$_3$, —CH$_2$CF$_3$, —OCH$_2$F, —OCHF$_2$, —OCF$_3$, or —OCH$_2$CF$_3$.

In some embodiments, R$^1$ is —OH, —SH, —NH$_2$, —NH(CH$_3$), —N(CH$_3$)$_2$, —CH$_3$, —OCH$_3$, —SCH$_3$, —CD$_3$, —OCD$_3$, —CH$_2$F, —CHF$_2$, —CF$_3$, —OCH$_2$F, —OCHF$_2$, —OCF$_3$, or —OCH$_2$CF$_3$.

In some embodiments, R$^1$ is —OH, —NH$_2$, —NH(CH$_3$), —N(CH$_3$)$_2$, —CH$_3$, —OCH$_3$, —CD$_3$, —OCD$_3$, —CH$_2$F, —CHF$_2$, —CF$_3$, —OCH$_2$F, —OCHF$_2$, —OCF$_3$, or —OCH$_2$CF$_3$.

In some embodiments, R$^8$ is H, D, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CD$_3$, —CH$_2$F, —CHF$_2$, —CF$_3$, —CH$_2$CF$_3$, —CHFCH$_3$, —CH$_2$CH$_2$F, —CH$_2$CH$_2$OH, —CH$_2$CH$_2$OCH$_3$, —CH$_2$CH$_2$NH$_2$, —CH$_2$CH$_2$NHCH$_3$, —CH$_2$CH$_2$N(CH$_3$)$_2$, —C(=O)CH$_3$, —C(=O)CH$_2$CH$_3$, —C(=O)CH(CH$_3$)$_2$, —CO$_2$CH$_3$, —CO$_2$CH$_2$CH$_3$, —CO$_2$CH(CH$_3$)$_2$, —C(=O)NHCH$_3$, —S(=O)$_2$CH$_3$, —S(=O)$_2$NHCH$_3$, substituted or unsubstituted cyclopropyl, substituted or unsubstituted cyclobutyl, substituted or unsubstituted cyclopentyl, substituted or unsubstituted cyclohexyl, substituted or unsubstituted oxetanyl, substituted or unsubstituted tetrahydrofuranyl, substituted or unsubstituted tetrahydropyranyl, or substituted or unsubstituted tetrahydrothiopyranyl.

In some embodiments, R$^8$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CD$_3$, —CH$_2$F, —CHF$_2$, —CF$_3$, —CH$_2$CF$_3$, —CHFCH$_3$, —CH$_2$CH$_2$F, —CH$_2$CH$_2$OH, —CH$_2$CH$_2$OCH$_3$, —CH$_2$CH$_2$NH$_2$, —CH$_2$CH$_2$NHCH$_3$, —CH$_2$CH$_2$N(CH$_3$)$_2$, substituted or unsubstituted cyclopropyl, substituted or unsubstituted cyclobutyl, substituted or unsubstituted cyclopentyl, substituted or unsubstituted cyclohexyl, substituted or unsubstituted oxetanyl, substituted or unsubstituted tetrahydrofuranyl, or substituted or unsubstituted tetrahydropyranyl.

In some embodiments, R$^8$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CD$_3$, —CH$_2$F, —CHF$_2$, —CF$_3$, —CH$_2$CF$_3$, —CHFCH$_3$, —CH$_2$CH$_2$F, —CH$_2$CH$_2$OH, —CH$_2$CH$_2$OCH$_3$, —CH$_2$CH$_2$NH$_2$, —CH$_2$CH$_2$NHCH$_3$, —CH$_2$CH$_2$N(CH$_3$)$_2$, substituted or unsubstituted cyclopropyl, substituted or unsubstituted cyclobutyl, substituted or unsubstituted cyclopentyl, substituted or unsubstituted cyclohexyl, substituted or unsubstituted oxetanyl, substituted or unsubstituted tetrahydrofuranyl, or substituted or unsubstituted tetrahydropyranyl.

In some embodiments, R$^8$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CD$_3$, —CH$_2$F, —CHF$_2$, —CF$_3$, —CH$_2$CF$_3$, —CHFCH$_3$, —CH$_2$CH$_2$F, —CH$_2$CH$_2$OH, —CH$_2$CH$_2$OCH$_3$, —CH$_2$CH$_2$NH$_2$, —CH$_2$CH$_2$NHCH$_3$, —CH$_2$CH$_2$N(CH$_3$)$_2$, cyclopropyl, cyclobutyl, cyclopentyl, cyclohexyl, oxetanyl, tetrahydrofuranyl, or tetrahydropyranyl. In some embodiments, R$^8$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CD$_3$, —CH$_2$F, —CHF$_2$, —CF$_3$, —CH$_2$CF$_3$, cyclopropyl, cyclobutyl, cyclopentyl, cyclohexyl, oxetanyl, tetrahydrofuranyl, or tetrahydropyranyl. In some embodiments, R$^8$ is —CH$_3$, —CH$_2$CH$_3$, —CH$_2$CH$_2$CH$_3$, —CH(CH$_3$)$_2$, or cyclopropyl. In some embodiments, R$^8$ is —CH(CH$_3$)$_2$, or cyclopropyl.

In some embodiments, each R$^{12}$ is independently H, C$_1$-C$_4$alkyl, C$_1$-C$_4$deuteroalkyl, C$_1$-C$_4$fluoroalkyl, C$_1$-C$_4$heteroalkyl, substituted or unsubstituted C$_3$-C$_6$cycloalkyl, substituted or unsubstituted C$_2$-C$_6$heterocycloalkyl, substituted or unsubstituted phenyl, substituted or unsubstituted benzyl, or substituted or unsubstituted monocyclic heteroaryl. In some embodiments, each R$^{12}$ is independently H, C$_1$-C$_4$alkyl, C$_1$-C$_4$heteroalkyl, substituted or unsubstituted C$_3$-C$_6$cycloalkyl, substituted or unsubstituted C$_2$-C$_6$heterocycloalkyl, substituted or unsubstituted phenyl, substituted or unsubstituted benzyl, substituted or unsubstituted monocyclic heteroaryl. In some embodiments, each R$^{12}$ is independently H, C$_1$-C$_4$alkyl, C$_1$-C$_4$heteroalkyl, substituted or unsubstituted C$_2$-C$_6$heterocycloalkyl, substituted or unsubstituted phenyl, substituted or unsubstituted benzyl, or substituted or unsubstituted monocyclic heteroaryl. In some embodiments, each R$^{12}$ is independently H, C$_1$-C$_4$alkyl, or substituted or unsubstituted C$_2$-C$_6$heterocycloalkyl. In some embodiments, each R$^{12}$ is independently H or C$_1$-C$_4$alkyl.

In some embodiments, when two R$^{12}$ are attached to an N atom, then one R$^{12}$ is H or C$_1$-C$_4$alkyl. In some embodiments, when two R$^{12}$ are attached to an N atom, then one R$^{12}$ is H or C$_1$-C$_4$alkyl and the other R$^{12}$ is H, C$_1$-C$_4$alkyl, C$_1$-C$_4$heteroalkyl, substituted or unsubstituted C$_3$-C$_6$cycloalkyl, substituted or unsubstituted C$_2$-C$_6$heterocycloalkyl, substituted or unsubstituted phenyl, substituted or unsubstituted benzyl, substituted or unsubstituted monocyclic heteroaryl.

In some embodiments, when two R$^{12}$ are attached to an N atom, then one R$^{12}$ is H or C$_1$-C$_4$alkyl and the other R$^{12}$ is H, C$_1$-C$_4$alkyl, C$_1$-C$_4$heteroalkyl, substituted or unsubstituted C$_2$-C$_6$heterocycloalkyl, or substituted or unsubstituted monocyclic heteroaryl.

In some embodiments, when two R$^{12}$ are attached to an N atom, then one R$^{12}$ is H or C$_1$-C$_4$alkyl and the other R$^{12}$ is H, C$_1$-C$_4$alkyl, C$_1$-C$_4$deuteroalkyl, C$_1$-C$_4$fluoroalkyl, C$_1$-C$_4$heteroalkyl, substituted or unsubstituted C$_3$-C$_6$cycloalkyl, substituted or unsubstituted C$_2$-C$_6$heterocycloalkyl, substituted or unsubstituted phenyl, substituted or unsubstituted benzyl, substituted or unsubstituted monocyclic heteroaryl.

In some embodiments, each R$^{16}$ is independently H, D, F, Cl, —CN, —OH, —NH$_2$, —NH(CH$_3$), —N(CH$_3$)$_2$, —NHS(=O)$_2$CH$_3$, —C(=O)CH$_3$, —OC(=O)CH$_3$, —CO$_2$H, —CO$_2$CH$_3$, —NHC(=O)CH$_3$, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH=CH$_2$, —CH=CHCH$_3$, —C≡CH, —C≡CCH$_3$, —C≡CCH$_2$CH$_3$, —OCH$_3$, —OCH$_2$CH$_3$, —OCH(CH$_3$)$_2$, —SCH$_3$, —SCH$_2$CH$_3$, —SCH(CH$_3$)$_2$, —S(=O)CH$_3$, —S(=O)CH$_2$CH$_3$, —S(=O)CH(CH$_3$)$_2$, —S(=O)$_2$CH$_3$, —S(=O)$_2$CH$_2$CH$_3$, —S(=O)$_2$CH(CH$_3$)$_2$, —CD$_3$, —OCD$_3$, —CH$_2$F, —CHF$_2$, —CF$_3$, —CH$_2$CF$_3$, —OCH$_2$F, —OCHF$_2$, —OCF$_3$, —OCH$_2$CF$_3$, —CH$_2$OH, —CH$_2$CH$_2$OH, —CH$_2$OCH$_3$, —CH$_2$OCH$_2$CH$_3$, —CH$_2$NH$_2$, —CH$_2$NHCH$_3$, or —CH$_2$N(CH$_3$)$_2$, substituted or unsubstituted cyclopropyl, substituted or unsubstituted cyclobutyl, substituted or unsubstituted cyclopentyl, substituted or unsubstituted cyclohexyl, substituted or unsubstituted aziridinyl, substituted or unsubstituted azetidinyl, substituted or unsubstituted pyrrolidinyl, substituted or unsubstituted piperidinyl, substituted or unsubstituted tetrahydrofuranyl, substituted or unsubstituted tetrahydropyranyl, substituted or unsubstituted tetrahydrothiopyranyl, substituted or unsubstituted morpholinyl, substituted or unsubstituted thiomorpholinyl, or substituted or unsubstituted piperazinyl.

In some embodiments, each R$^{16}$ is independently H, D, F, Cl, —CN, —OH, —NH$_2$, —NH(CH$_3$), —N(CH$_3$)$_2$, —NHS(=O)$_2$CH$_3$, —S(=O)$_2$CH$_3$, —C(=O)CH$_3$, —OC(=O)CH$_3$, —CO$_2$H, —CO$_2$CH$_3$, —NHC(=O)CH$_3$, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —C(CH$_3$)$_3$, —CH=CH$_2$, —CH=CHCH$_3$, —C≡CH, —C≡CCH$_3$, —C≡CCH$_2$CH$_3$, —OCH$_3$, —OCH$_2$CH$_3$, —OCH(CH$_3$)$_2$, —CD$_3$, —OCD$_3$, —CH$_2$F, —CHF$_2$, —CF$_3$, —CH$_2$CF$_3$, —OCH$_2$F, —OCHF$_2$, —OCF$_3$, —OCH$_2$CF$_3$, —CH$_2$OH, —CH$_2$CH$_2$OH, —CH$_2$OCH$_3$, —CH$_2$OCH$_2$CH$_3$, —CH$_2$NH$_2$, —CH$_2$NHCH$_3$, or —CH$_2$N(CH$_3$)$_2$, substituted or unsubstituted cyclopropyl, substituted or unsubstituted cyclobutyl, substituted or unsubstituted cyclopentyl, substituted or unsubstituted cyclohexyl, substituted or unsubstituted aziridinyl, substituted or unsubstituted azetidinyl, substituted or unsubstituted pyrrolidinyl, substituted or unsubstituted piperidinyl, substituted or unsubstituted tetrahydrofuranyl, substituted or unsubstituted tetrahydropyranyl, substituted or unsubstituted tetrahydrothiopyranyl, substituted or unsubstituted morpholinyl, substituted or unsubstituted thiomorpholinyl, or substituted or unsubstituted piperazinyl.

In some embodiments, each R$^{16}$ is independently H, D, F, Cl, —CH$_3$, —CH$_2$CH$_3$, —CH(CH$_3$)$_2$, —C(CH$_3$)$_3$, —OCH$_3$, —OCH$_2$CH$_3$, —OCH(CH$_3$)$_2$, —SCH$_3$, —SCH$_2$CH$_3$, —SCH(CH$_3$)$_2$, —CD$_3$, —CH$_2$F, —CHF$_2$, —CF$_3$, —CH$_2$CF$_3$, substituted or unsubstituted cyclopropyl, or substituted or unsubstituted cyclobutyl.

In some embodiments, each R$^{16}$ is independently H, D, F, Cl, —CH$_3$, —CH$_2$CH$_3$, —CH(CH$_3$)$_2$, —C(CH$_3$)$_3$, —CD$_3$, —CH$_2$F, —CHF$_2$, —CF$_3$, —CH$_2$CF$_3$, substituted or unsubstituted cyclopropyl, or substituted or unsubstituted cyclobutyl.

In some embodiments, each R$^{16}$ is independently H, D, F, Cl, —CH$_3$, —CH$_2$CH$_3$, —CD$_3$, —CH$_2$F, —CHF$_2$, —CF$_3$, or —CH$_2$CF$_3$.

In some embodiments, the compound has the structure of Formula (X), or a pharmaceutically acceptable salt or solvate thereof:

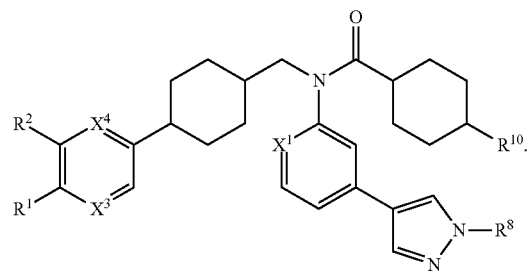

Formula (X)

In some embodiments, the compound has the structure of Formula (XI), or a pharmaceutically acceptable salt or solvate thereof:

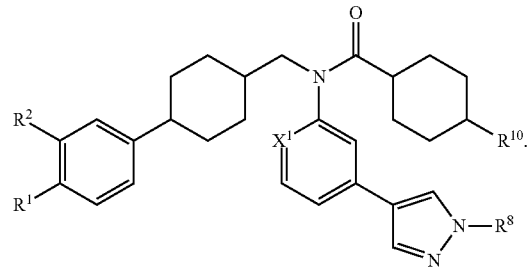

Formula (XI)

Any combination of the groups described above for the various variables is contemplated herein. Throughout the specification, groups and substituents thereof are chosen by one skilled in the field to provide stable moieties and compounds.

In some embodiments, compounds described herein include, but are not limited to, those described in Table 1.

TABLE 1

| Compound | Structure | Chemical Name |
|---|---|---|
| 1 | (structure) | trans-4-Hydroxy-N-((trans-4-(4-methoxy-3-methylphenyl)cyclohexyl)methyl)-N-(3-(4-methyl-1H-pyrazol-1-yl)phenyl)cyclohexanecarboxamide |

TABLE 1-continued

| Compound | Structure | Chemical Name |
| --- | --- | --- |
| 2 | 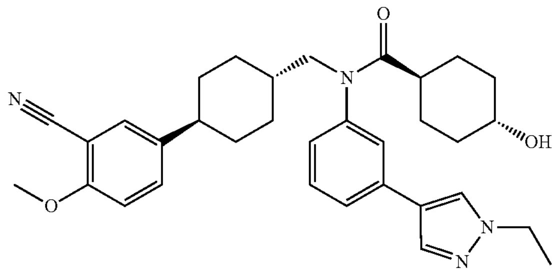 | trans-N-((trans-4-(3-Cyano-4-methoxyphenyl)cyclohexyl)methyl)-N-(3-(1-ethyl-1H-pyrazol-4-yl)phenyl)-4-hydroxycyclohexanecarboxamide |
| 2.01 | 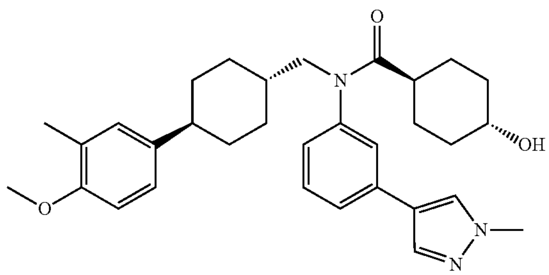 [SMILES: COc1ccc([C@H]2CC[C@H](CN(c3cccc(-c4cnn(C)c4)c3)C(=O)[C@H]3CC[C@H](O)CC3)CC2)cc1C] | trans-4-Hydroxy-N-((trans-4-(4-methoxy-3-methylphenyl)cyclohexyl)methyl)-N-(3-(1-methyl-1H-pyrazol-4-yl)phenyl)cyclohexanecarboxamide |
| 2.02 | 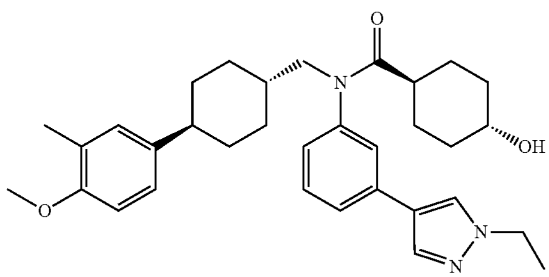 [SMILES: CCn1cc(-c2cccc(N(C[C@H]3CC[C@H](c4ccc(OC)c(C)c4)CC3)C(=O)[C@H]3CC[C@H](O)CC3)c2)cn1] | trans-N-(3-(1-Ethyl-1H-pyrazol-4-yl)phenyl)-4-hydroxy-N-((trans-4-(4-methoxy-3-methylphenyl)cyclohexyl)methyl)cyclohexanecarboxamide |
| 2.03 | 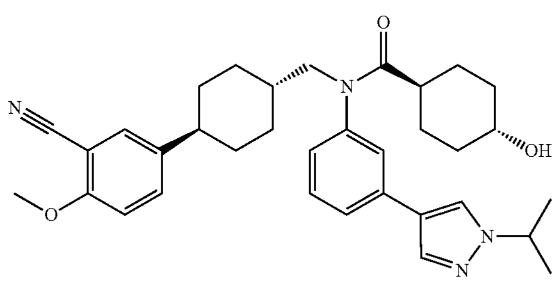 [SMILES: COc1ccc([C@H]2CC[C@H](CN(c3cccc(-c4cnn(C(C)C)c4)c3)C(=O)[C@H]3CC[C@H](O)CC3)CC2)cc1C#N] | trans-N-((trans-4-(3-Cyano-4-methoxyphenyl)cyclohexyl)methyl)-4-hydroxy-N-(3-(1-isopropyl-1H-pyrazol-4-yl)phenyl)cyclohexanecarboxamide |
| 2.04 | 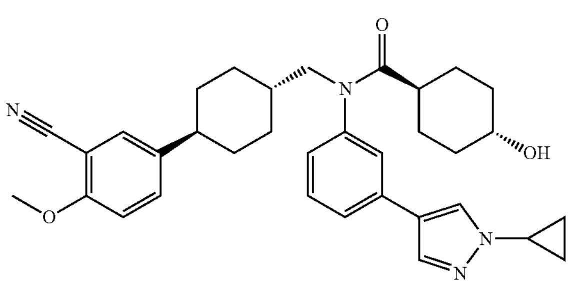 [SMILES: COc1ccc([C@H]2CC[C@H](CN(c3cccc(-c4cnn(C5CC5)c4)c3)C(=O)[C@H]3CC[C@H](O)CC3)CC2)cc1C#N] | trans-N-((trans-4-(3-Cyano-4-methoxyphenyl)cyclohexyl)methyl)-N-(3-(1-cyclopropyl-1H-pyrazol-4-yl)phenyl)-4-hydroxycyclohexanecarboxamide |

TABLE 1-continued

| Compound | Structure | Chemical Name |
|---|---|---|
| 2.05 | 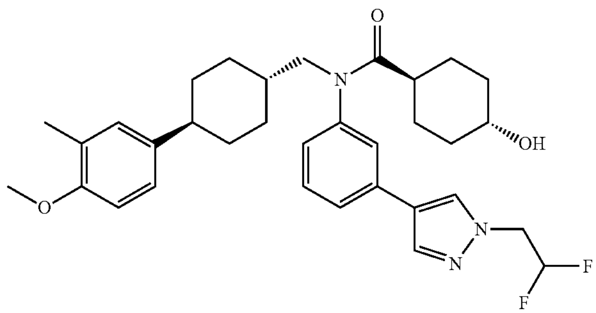 [SMILES: COc1ccc([C@H]2CC[C@H](CN(c3cccc(-c4cnn(CC(F)F)c4)c3)C(=O)[C@H]3CC[C@H](O)CC3)CC2)cc1C] | trans-N-(3-(1-(2,2-Difluoroethyl)-1H-pyrazol-4-yl)phenyl)-4-hydroxy-N-((trans-4-(4-methoxy-3-methylphenyl)cyclohexyl)methyl)cyclohexanecarboxamide |
| 2.06 | 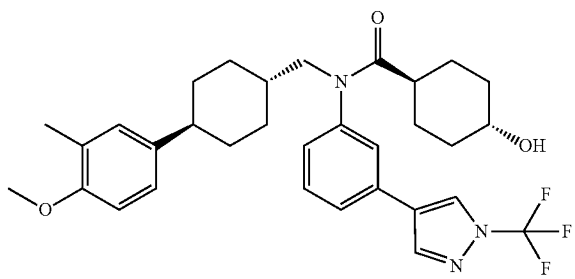 [SMILES: COc1ccc([C@H]2CC[C@H](CN(c3cccc(-c4cnn(C(F)(F)F)c4)c3)C(=O)[C@H]3CC[C@H](O)CC3)CC2)cc1C] | trans-4-Hydroxy-N-((trans-4-(4-methoxy-3-methylphenyl)cyclohexyl)methyl)-N-(3-(1-(trifluoromethyl)-1H-pyrazol-4-yl)phenyl)cyclohexanecarboxamide |
| 2.07 | 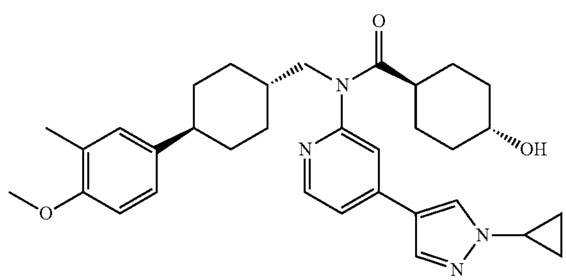 [SMILES: COc1ccc([C@H]2CC[C@H](CN(c3cc(-c4cnn(C5CC5)c4)ccn3)C(=O)[C@H]3CC[C@H](O)CC3)CC2)cc1C] | trans-N-(4-(1-Cyclopropyl-1H-pyrazol-4-yl)pyridin-2-yl)-4-hydroxy-N-((trans-4-(4-methoxy-3-methylphenyl)cyclohexyl)methyl)cyclohexanecarboxamide |
| 2.08 | 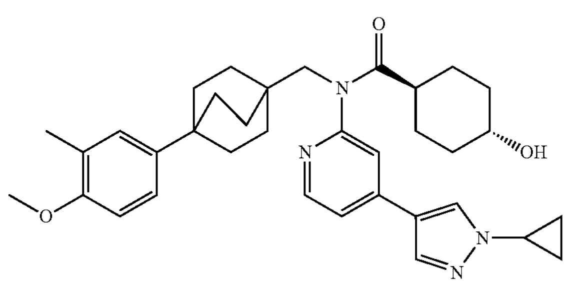 [SMILES: COc1ccc(C23CCC(CN(c4cc(-c5cnn(C6CC6)c5)ccn4)C(=O)[C@H]4CC[C@H](O)CC4)(CC2)CC3)cc1C] | trans-N-(4-(1-Cyclopropyl-1H-pyrazol-4-yl)pyridin-2-yl)-4-hydroxy-N-((4-(4-methoxy-3-methylphenyl)bicyclo[2.2.2]octan-1-yl)methyl)cyclohexanecarboxamide |
| 2.09 | 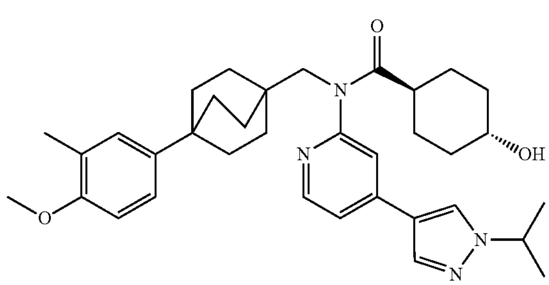 [SMILES: COc1ccc(C23CCC(CN(c4cc(-c5cnn(C(C)C)c5)ccn4)C(=O)[C@H]4CC[C@H](O)CC4)(CC2)CC3)cc1C] | trans-4-Hydroxy-N-(4-(1-isopropyl-1H-pyrazol-4-yl)pyridin-2-yl)-N-(4-(4-methoxy-3-methylphenyl)bicyclo[2.2.2]octan-1-yl)methyl)cyclohexanecarboxamide |

TABLE 1-continued

| Compound | Structure | Chemical Name |
|---|---|---|
| 3 | 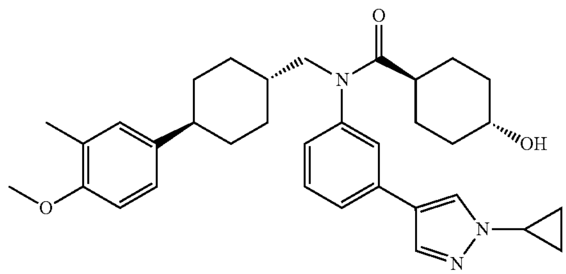 [SMILES: COc1ccc([C@H]2CC[C@H](CN(c3cccc(-c4cnn(C5CC5)c4)c3)C(=O)[C@H]3CC[C@H](O)CC3)CC2)cc1C] | trans-N-(3-(1-Cyclopropyl-1H-pyrazol-4-yl)phenyl)-4-hydroxy-N-((trans-4-(4-methoxy-3-methylphenyl)cyclohexyl)methyl)cyclohexanecarboxamide |
| 3.01 | 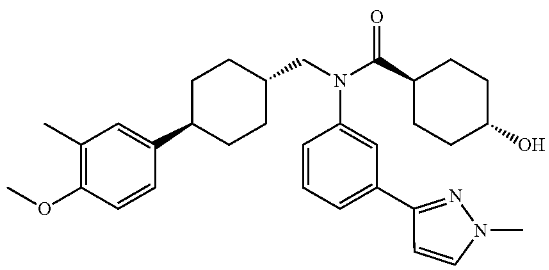 [SMILES: COc1ccc([C@H]2CC[C@H](CN(c3cccc(-c4ccn(C)n4)c3)C(=O)[C@H]3CC[C@H](O)CC3)CC2)cc1C] | trans-4-Hydroxy-N-((trans-4-(4-methoxy-3-methylphenyl)cyclohexyl)methyl)-N-(3-(1-methyl-1H-pyrazol-3-yl)phenyl)cyclohexanecarboxamide |
| 3.02 | 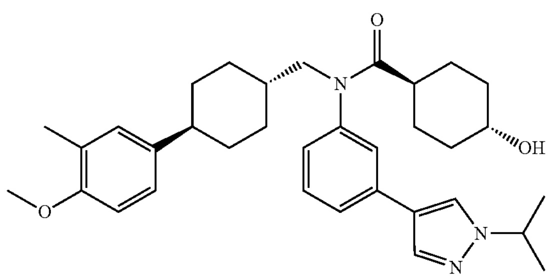 [SMILES: COc1ccc([C@H]2CC[C@H](CN(c3cccc(-c4cnn(C(C)C)c4)c3)C(=O)[C@H]3CC[C@H](O)CC3)CC2)cc1C] | trans-4-Hydroxy-N-(3-(1-isopropyl-1H-pyrazol-4-yl)phenyl)-N-((trans-4-(4-methoxy-3-methylphenyl)cyclohexyl)methyl)cyclohexanecarboxamide |
| 3.03 | 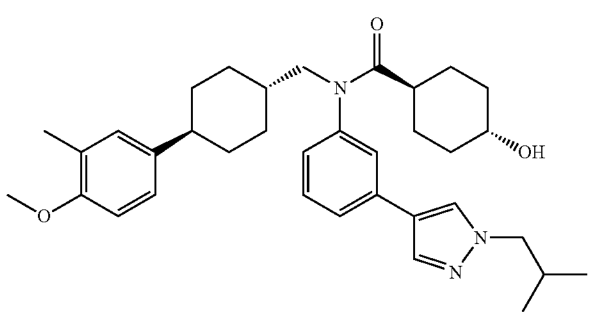 [SMILES: COc1ccc([C@H]2CC[C@H](CN(c3cccc(-c4cnn(CC(C)C)c4)c3)C(=O)[C@H]3CC[C@H](O)CC3)CC2)cc1C] | trans-4-Hydroxy-N-(3-(1-isobutyl-1H-pyrazol-4-yl)phenyl)-N-((trans-4-(4-methoxy-3-methylphenyl)cyclohexyl)methyl)cyclohexanecarboxamide |
| 3.04 | 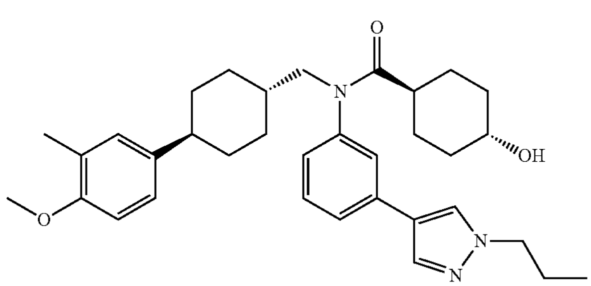 [SMILES: CCCn1cc(-c2cccc(N(C[C@H]3CC[C@H](c4ccc(OC)c(C)c4)CC3)C(=O)[C@H]3CC[C@H](O)CC3)c2)cn1] | trans-4-Hydroxy-N-((trans-4-(4-methoxy-3-methylphenyl)cyclohexyl)methyl)-N-(3-(1-propyl-1H-pyrazol-4-yl)phenyl)cyclohexanecarboxamide |

TABLE 1-continued

| Compound | Structure | Chemical Name |
| --- | --- | --- |
| 3.05 | 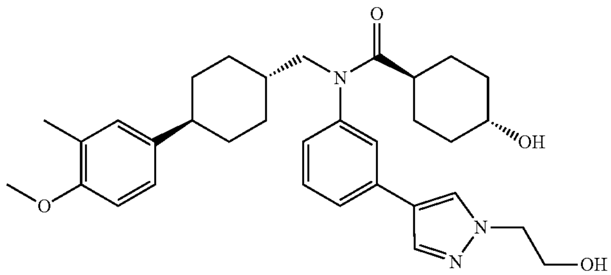 [SMILES: COc1ccc([C@H]2CC[C@H](CN(c3cccc(-c4cnn(CCO)c4)c3)C(=O)[C@H]3CC[C@H](O)CC3)CC2)cc1C] | trans-4-Hydroxy-N-(3-(1-(2-hydroxyethyl)-1H-pyrazol-4-yl)phenyl)-N-((trans-4-(4-methoxy-3-methylphenyl)cyclohexyl)methyl)cyclohexanecarboxamide |
| 3.06 | 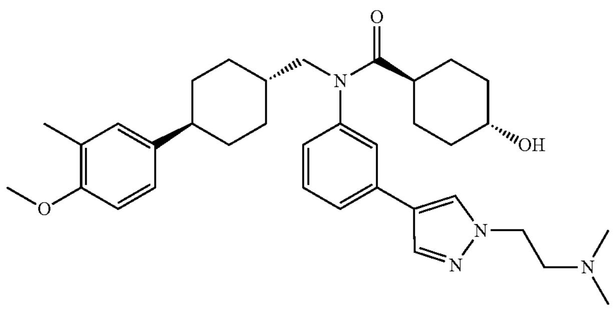 | trans-N-(3-(1-(2-(Dimethylamino)ethyl)-1H-pyrazol-4-yl)phenyl)-4-hydroxy-N-((trans-4-(4-methoxy-3-methylphenyl)cyclohexyl)methyl)cyclohexanecarboxamide |
| 3.07 | 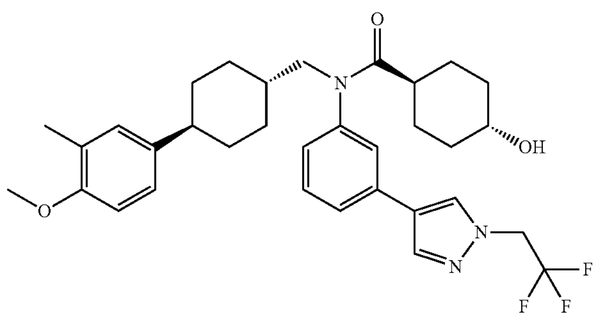 [SMILES: COc1ccc([C@H]2CC[C@H](CN(c3cccc(-c4cnn(CC(F)(F)F)c4)c3)C(=O)[C@H]3CC[C@H](O)CC3)CC2)cc1C] | trans-4-Hydroxy-N-((trans-4-(4-methoxy-3-methylphenyl)cyclohexyl)methyl)-N-(3-(1-(2,2,2-trifluoroethyl)-1H-pyrazol-4-yl)phenyl)cyclohexanecarboxamide |
| 3.08 | 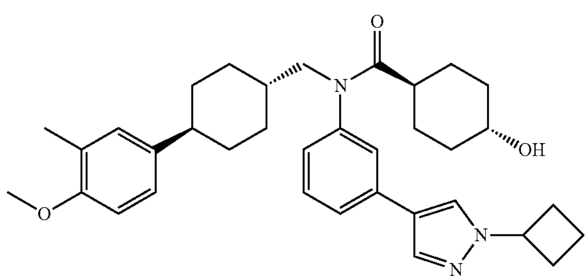 [SMILES: COc1ccc([C@H]2CC[C@H](CN(c3cccc(-c4cnn(C5CCC5)c4)c3)C(=O)[C@H]3CC[C@H](O)CC3)CC2)cc1C] | trans-N-(3-(1-Cyclobutyl-1H-pyrazol-4-yl)phenyl)-4-hydroxy-N-((trans-4-(4-methoxy-3-methylphenyl)cyclohexyl)methyl)cyclohexanecarboxamide |
| 3.09 | 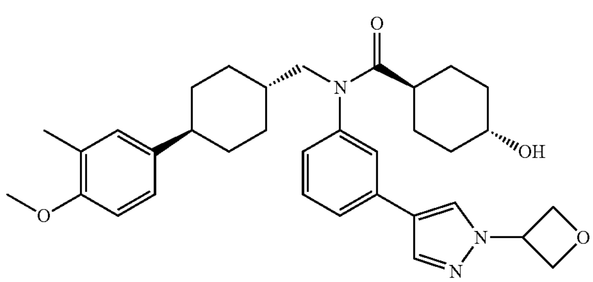 [SMILES: COc1ccc([C@H]2CC[C@H](CN(c3cccc(-c4cnn(C5COC5)c4)c3)C(=O)[C@H]3CC[C@H](O)CC3)CC2)cc1C] | trans-4-Hydroxy-N-((trans-4-(4-methoxy-3-methylphenyl)cyclohexyl)methyl)-N-(3-(1-(oxetan-3-yl)-1H-pyrazol-4-yl)phenyl)cyclohexanecarboxamide |

TABLE 1-continued

| Compound | Structure | Chemical Name |
| --- | --- | --- |
| 3.10 | 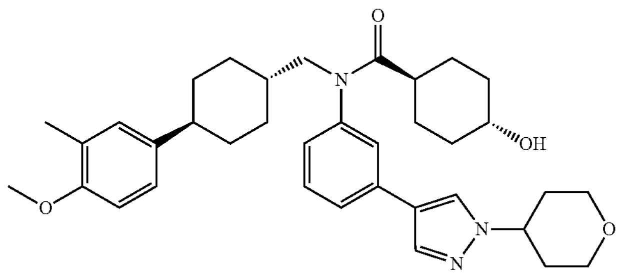 [SMILES: COc1ccc([C@H]2CC[C@H](CN(c3cccc(-c4cnn(C5CCOCC5)c4)c3)C(=O)[C@H]3CC[C@H](O)CC3)CC2)cc1C] | trans-4-Hydroxy-N-((trans-4-(4-methoxy-3-methylphenyl)cyclohexyl)methyl)-N-(3-(1-(tetrahydro-2H-pyran-4-yl)-1H-pyrazol-4-yl)phenyl)cyclohexanecarboxamide |
| 3.11 | 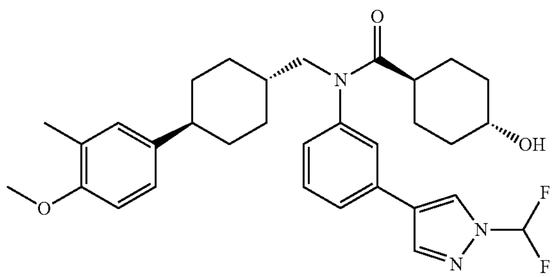 [SMILES: COc1ccc([C@H]2CC[C@H](CN(c3cccc(-c4cnn(C(F)F)c4)c3)C(=O)[C@H]3CC[C@H](O)CC3)CC2)cc1C] | trans-N-(3-(1-(Difluoromethyl)-1H-pyrazol-4-yl)phenyl)-4-hydroxy-N-((trans-4-(4-methoxy-3-methylphenyl)cyclohexyl)methyl)cyclohexanecarboxamide |
| 3.12 | 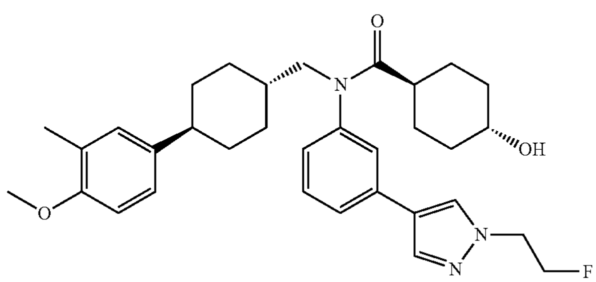 [SMILES: COc1ccc([C@H]2CC[C@H](CN(c3cccc(-c4cnn(CCF)c4)c3)C(=O)[C@H]3CC[C@H](O)CC3)CC2)cc1C] | trans-N-(3-(1-(2-Fluoroethyl)-1H-pyrazol-4-yl)phenyl)-4-hydroxy-N-((trans-4-(4-methoxy-3-methylphenyl)cyclohexyl)methyl)cyclohexanecarboxamide |
| 3.13 | 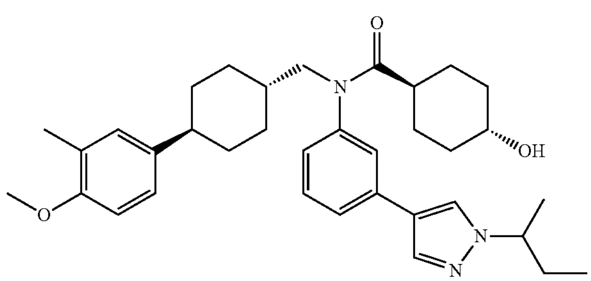 [SMILES: CCC(C)n1cc(-c2cccc(N(C[C@H]3CC[C@H](c4ccc(OC)c(C)c4)CC3)C(=O)[C@H]3CC[C@H](O)CC3)c2)cn1] | trans-N-(3-(1-(sec-Butyl)-1H-pyrazol-4-yl)phenyl)-4-hydroxy-N-((trans-4-(4-methoxy-3-methylphenyl)cyclohexyl)methyl)cyclohexanecarboxamide |
| 4 | 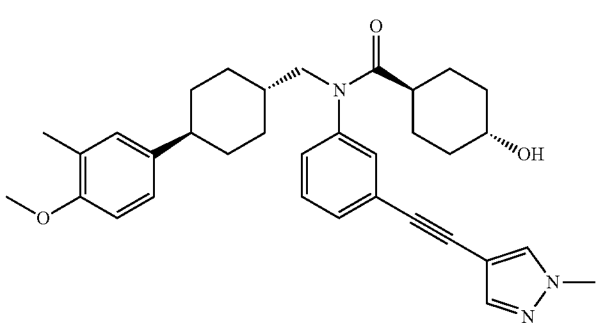 | trans-4-Hydroxy-N-((trans-4-(4-methoxy-3-methylphenyl)cyclohexyl)methyl)-N-(3-((1-methyl-1H-pyrazol-4-yl)ethynyl)phenyl)cyclohexanecarboxamide |

TABLE 1-continued

| Compound | Structure | Chemical Name |
|---|---|---|
| 4.01 | 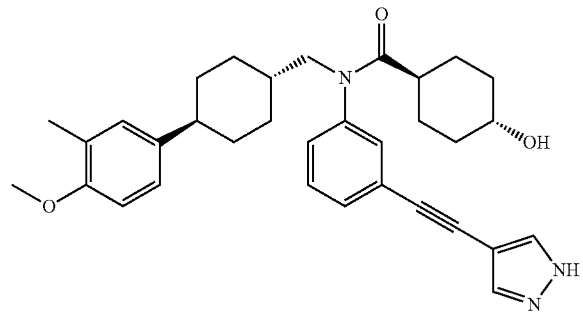 [SMILES: COc1ccc([C@H]2CC[C@H](CN(c3cccc(C#Cc4cn[nH]c4)c3)C(=O)[C@H]3CC[C@H](O)CC3)CC2)cc1C] | trans-N-(3-((1H-Pyrazol-4-yl)ethynyl)phenyl)-4-hydroxy-N-((trans-4-(4-methoxy-3-methylphenyl)cyclohexyl)methyl)cyclohexanecarboxamide |
| 4.02 | 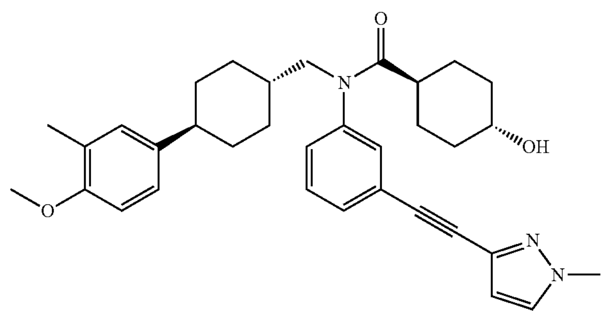 | trans-4-Hydroxy-N-((trans-4-(4-methoxy-3-methylphenyl)cyclohexyl)methyl)-N-(3-((1-methyl-1H-pyrazol-3-yl)ethynyl)phenyl)cyclohexanecarboxamide |
| 4.03 | 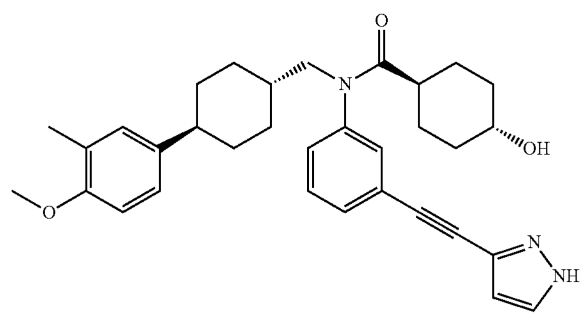 [SMILES: COc1ccc([C@H]2CC[C@H](CN(c3cccc(C#Cc4cc[nH]n4)c3)C(=O)[C@H]3CC[C@H](O)CC3)CC2)cc1C] | trans-N-(3-((1H-Pyrazol-3-yl)ethynyl)phenyl)-4-hydroxy-N-((trans-4-(4-methoxy-3-methylphenyl)cyclohexyl)methyl)cyclohexanecarboxamide |
| 5 | 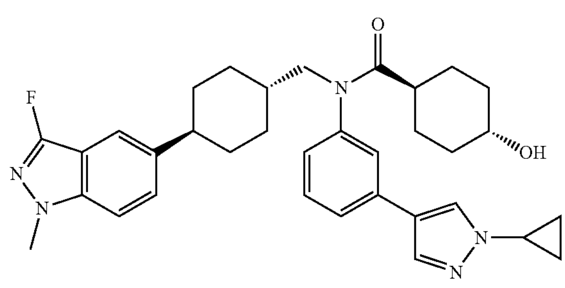 [SMILES: Cn1nc(F)c2cc([C@H]3CC[C@H](CN(c4cccc(-c5cnn(C6CC6)c5)c4)C(=O)[C@H]4CC[C@H](O)CC4)CC3)ccc21] | trans-N-(3-(1-Cyclopropyl-1H-pyrazol-4-yl)phenyl)-N-((trans-4-(3-fluoro-1-methyl-1H-indazol-5-yl)cyclohexyl)methyl)-4-hydroxycyclohexanecarboxamide |
| 5.01 | 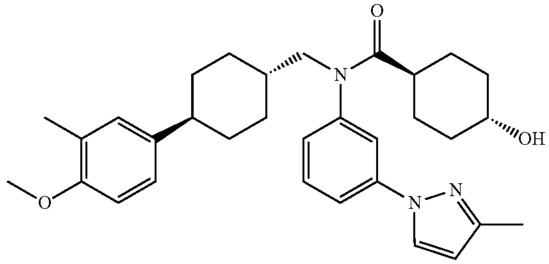 [SMILES: COc1ccc([C@H]2CC[C@H](CN(c3cccc(-n4ccc(C)n4)c3)C(=O)[C@H]3CC[C@H](O)CC3)CC2)cc1C] | trans-4-Hydroxy-N-((trans-4-(4-methoxy-3-methylphenyl)cyclohexyl)methyl)-N-(3-(3-methyl-1H-pyrazol-1-yl)phenyl)cyclohexanecarboxamide |

TABLE 1-continued

| Compound | Structure | Chemical Name |
|---|---|---|
| 5.02 | 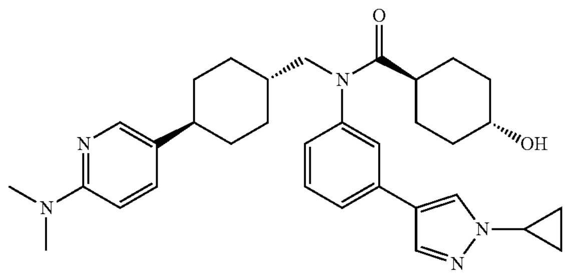 [SMILES: CN(C)c1ccc([C@H]2CC[C@H](CN(c3cccc(-c4cnn(C5CC5)c4)c3)C(=O)[C@H]3CC[C@H](O)CC3)CC2)cn1] | trans-N-(3-(1-Cyclopropyl-1H-pyrazol-4-yl)phenyl)-N-((trans-4-(6-(dimethylamino)pyridin-3-yl)cyclohexyl)methyl)-4-hydroxycyclohexanecarboxamide |
| 5.03 | 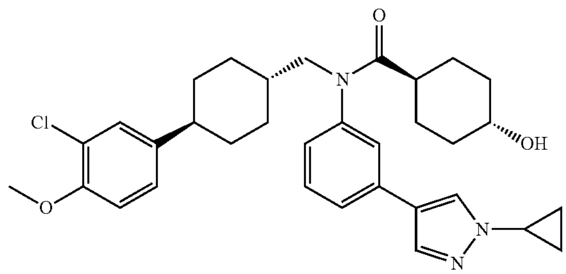 [SMILES: COc1ccc([C@H]2CC[C@H](CN(c3cccc(-c4cnn(C5CC5)c4)c3)C(=O)[C@H]3CC[C@H](O)CC3)CC2)cc1Cl] | trans-N-((trans-4-(3-Chloro-4-methoxyphenyl)cyclohexyl)methyl)-N-(3-(1-cyclopropyl-1H-pyrazol-4-yl)phenyl)-4-hydroxycyclohexanecarboxamide |
| 5.04 | 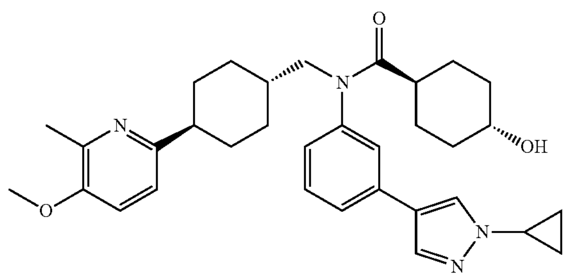 [SMILES: COc1ccc([C@H]2CC[C@H](CN(c3cccc(-c4cnn(C5CC5)c4)c3)C(=O)[C@H]3CC[C@H](O)CC3)CC2)nc1C] | trans-N-(3-(1-cyclopropyl-1H-pyrazol-4-yl)phenyl)-4-hydroxy-N-((trans-4-(5-methoxy-6-methylpyridin-2-yl)cyclohexyl)methyl)cyclohexanecarboxamide |
| 5.05 | 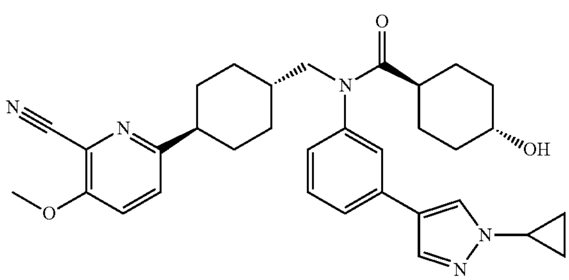 | trans-N-((trans-4-(6-Cyano-5-methoxypyridin-2-yl)cyclohexyl)methyl)-N-(3-(1-cyclopropyl-1H-pyrazol-4-yl)phenyl)-4-hydroxycyclohexanecarboxamide |
| 5.06 | 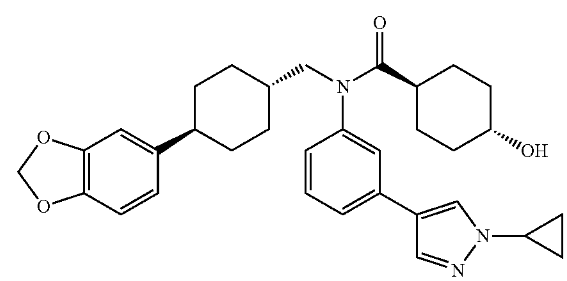 [SMILES: O=C([C@H]1CC[C@H](O)CC1)N(C[C@H]1CC[C@H](c2ccc3c(c2)OCO3)CC1)c1cccc(-c2cnn(C3CC3)c2)c1] | trans-N-((trans-4-(Benzo[d][1,3]dioxol-5-yl)cyclohexyl)methyl)-N-(3-(1-cyclopropyl-1H-pyrazol-4-yl)phenyl)-4-hydroxycyclohexanecarboxamide |

TABLE 1-continued

| Compound | Structure | Chemical Name |
|---|---|---|
| 5.07 | 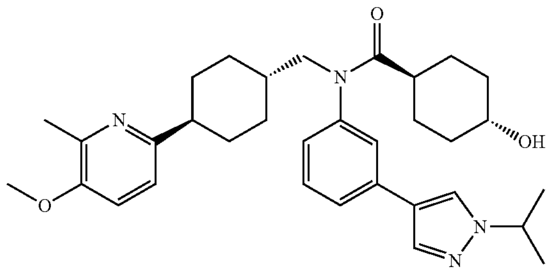 [SMILES: COc1ccc([C@H]2CC[C@H](CN(c3cccc(-c4cnn(C(C)C)c4)c3)C(=O)[C@H]3CC[C@H](O)CC3)CC2)nc1C] | trans-4-Hydroxy-N-(3-(1-isopropyl-1H-pyrazol-4-yl)phenyl)-N-((trans-4-(5-methoxy-6-methylpyridin-2-yl)cyclohexyl)methyl)cyclohexanecarboxamide |
| 5.08 | 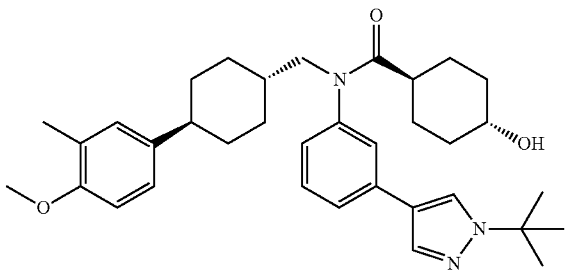 | trans-N-(3-(1-(tert-Butyl)-1H-pyrazol-4-yl)phenyl)-4-hydroxy-N-((trans-4-(4-methoxy-3-methylphenyl)cyclohexyl)methyl)cyclohexanecarboxamide |
| 5.09 | 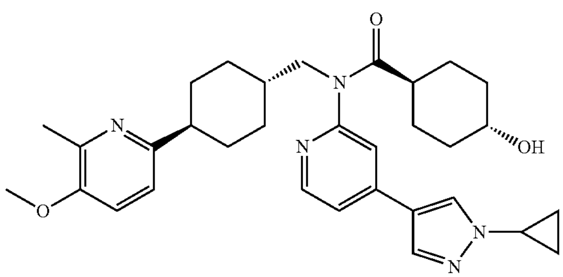 [SMILES: COc1ccc([C@H]2CC[C@H](CN(c3cc(-c4cnn(C5CC5)c4)ccn3)C(=O)[C@H]3CC[C@H](O)CC3)CC2)nc1C] | trans-N-(4-(1-Cyclopropyl-1H-pyrazol-4-yl)pyridin-2-yl)-4-hydroxy-N-((trans-4-(5-methoxy-6-methylpyridin-2-yl)cyclohexyl)methyl)cyclohexanecarboxamide |
| 5.10 | 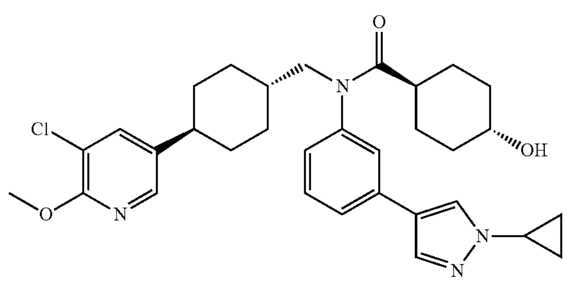 | trans-N-((trans-4-(5-chloro-6-methoxypyridin-3-yl)cyclohexyl)methyl)-N-(3-(1-cyclopropyl-1H-pyrazol-4-yl)phenyl)-4-hydroxycyclohexanecarboxamide |
| 5.11 | 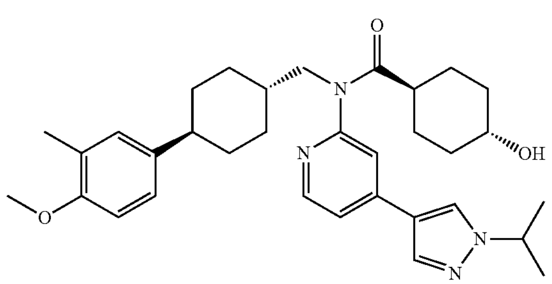 [SMILES: COc1ccc([C@H]2CC[C@H](CN(c3cc(-c4cnn(C(C)C)c4)ccn3)C(=O)[C@H]3CC[C@H](O)CC3)CC2)cc1C] | trans-4-Hydroxy-N-(4-(1-isopropyl-1H-pyrazol-4-yl)pyridin-2-yl)-N-((trans-4-(4-methoxy-3-methylphenyl)cyclohexyl)methyl)cyclohexanecarboxamide |

TABLE 1-continued

| Compound | Structure | Chemical Name |
| --- | --- | --- |
| 5.12 | 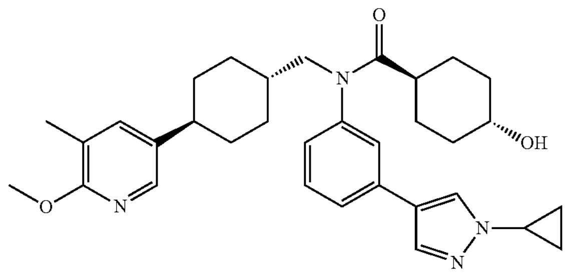 | trans-N-(3-(1-Cyclopropyl-1H-pyrazol-4-yl)phenyl)-4-hydroxy-N-((trans-4-(6-methoxy-5-methylpyridin-3-yl)cyclohexyl)methyl)cyclohexanecarboxamide |
| 5.13 | 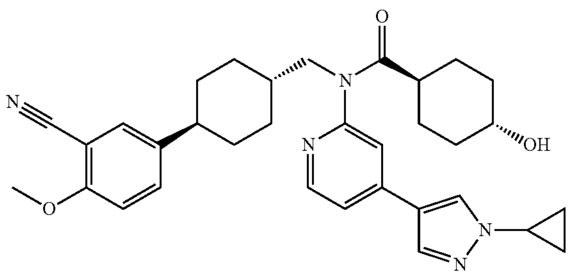 [SMILES: COc1ccc([C@H]2CC[C@H](CN(c3cc(-c4cnn(C5CC5)c4)ccn3)C(=O)[C@H]3CC[C@H](O)CC3)CC2)cc1C#N] | trans-N-((trans-4-(3-Cyano-4-methoxyphenyl)cyclohexyl)methyl)-N-(4-(1-cyclopropyl-1H-pyrazol-4-yl)pyridin-2-yl)-4-hydroxycyclohexanecarboxamide |
| 5.14 | 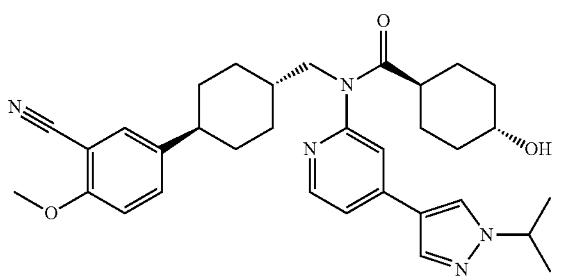 | trans-N-((trans-4-(3-Cyano-4-methoxyphenyl)cyclohexyl)methyl)-4-hydroxy-N-(4-(1-isopropyl-1H-pyrazol-4-yl)pyridin-2-yl)cyclohexanecarboxamide |
| 5.15 | 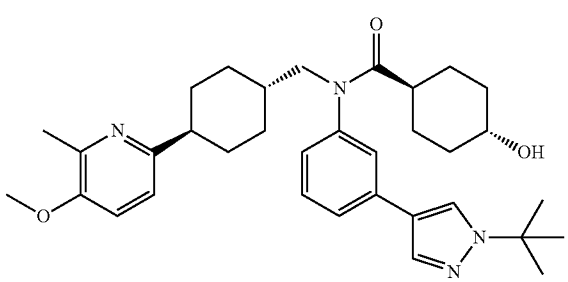 | trans-N-(3-(1-(tert-Butyl)-1H-pyrazol-4-yl)phenyl)-4-hydroxy-N-((trans-4-(5-methoxy-6-methylpyridin-2-yl)cyclohexyl)methyl)cyclohexanecarboxamide |
| 5.16 | 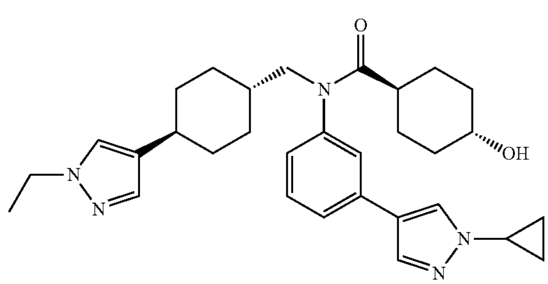 [SMILES: CCn1cc([C@H]2CC[C@H](CN(c3cccc(-c4cnn(C5CC5)c4)c3)C(=O)[C@H]3CC[C@H](O)CC3)CC2)cn1] | trans-N-(3-(1-Cyclopropyl-1H-pyrazol-4-yl)phenyl)-N-((trans-4-(1-ethyl-1H-pyrazol-4-yl)cyclohexyl)methyl)-4-hydroxycyclohexanecarboxamide |

TABLE 1-continued

| Compound | Structure | Chemical Name |
| --- | --- | --- |
| 5.17 | 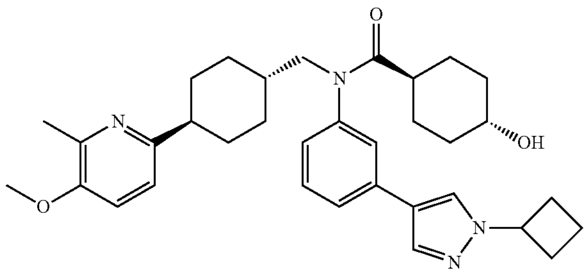 | trans-N-(3-(1-Cyclobutyl-1H-pyrazol-4-yl)phenyl)-4-hydroxy-N-((trans-4-(5-methoxy-6-methylpyridin-2-yl)cyclohexyl)methyl)cyclohexanecarboxamide |
| 5.18 | 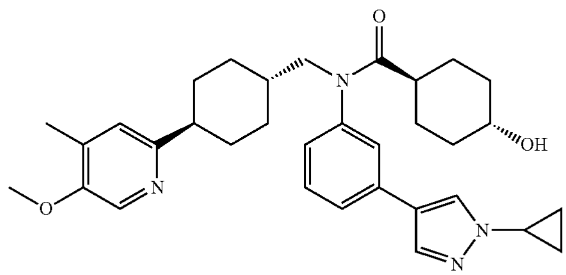 | trans-N-(3-(1-Cyclopropyl-1H-pyrazol-4-yl)phenyl)-4-hydroxy-N-((trans-4-(5-methoxy-4-methylpyridin-2-yl)cyclohexyl)methyl)cyclohexanecarboxamide |
| 5.19 | 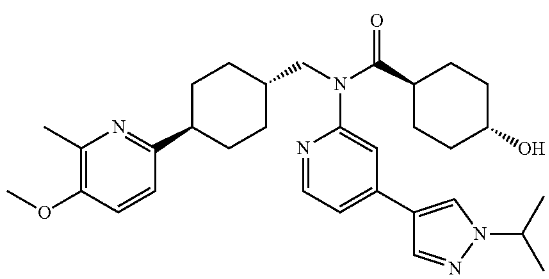 [SMILES: COc1ccc([C@H]2CC[C@H](CN(c3cc(-c4cnn(C(C)C)c4)ccn3)C(=O)[C@H]3CC[C@H](O)CC3)CC2)nc1C] | trans-4-Hydroxy-N-(4-(1-isopropyl-1H-pyrazol-4-yl)pyridin-2-yl)-N-((trans-4-(5-methoxy-6-methylpyridin-2-yl)cyclohexyl)methyl)cyclohexanecarboxamide |
| 5.20 | 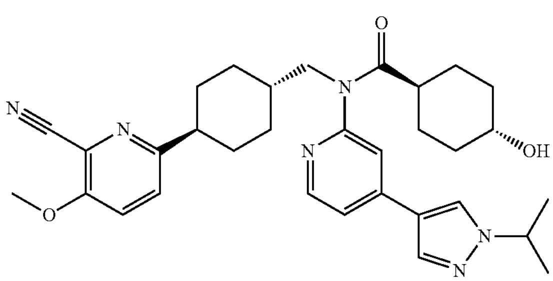 | trans-N-((trans-4-(6-Cyano-5-methoxypyridin-2-yl)cyclohexyl)methyl)-4-hydroxy-N-(4-(1-isopropyl-1H-pyrazol-4-yl)pyridin-2-yl)cyclohexanecarboxamide |
| 5.21 | 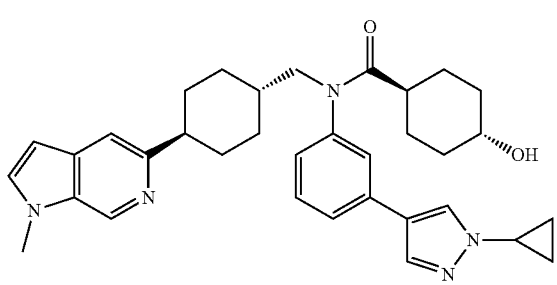 [SMILES: Cn1ccc2cc([C@H]3CC[C@H](CN(c4cccc(-c5cnn(C6CC6)c5)c4)C(=O)[C@H]4CC[C@H](O)CC4)CC3)ncc21] | trans-N-(3-(1-Cyclopropyl-1H-pyrazol-4-yl)phenyl)-4-hydroxy-N-((trans-4-(1-methyl-1H-pyrrolo[2,3-c]pyridin-5-yl)cyclohexyl)methyl)cyclohexanecarboxamide |

TABLE 1-continued

| Compound | Structure | Chemical Name |
|---|---|---|
| 5.22 | 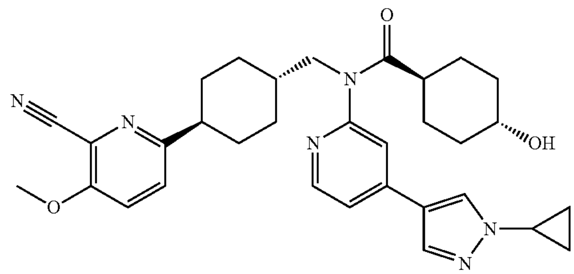 [SMILES: COc1ccc([C@H]2CC[C@H](CN(c3cc(-c4cnn(C5CC5)c4)ccn3)C(=O)[C@H]3CC[C@H](O)CC3)CC2)nc1C#N] | trans-N-((trans-4-(6-Cyano-5-methoxypyridin-2-yl)cyclohexyl)methyl)-N-(4-(1-cyclopropyl-1H-pyrazol-4-yl)pyridin-2-yl)-4-hydroxycyclohexanecarboxamide |
| 5.23 | 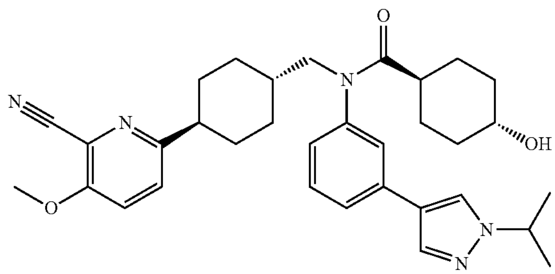 | trans-N-((trans-4-(6-Cyano-5-methoxypyridin-2-yl)cyclohexyl)methyl)-4-hydroxy-N-(3-(1-isopropyl-1H-pyrazol-4-yl)phenyl)cyclohexanecarboxamide |
| 5.24 | 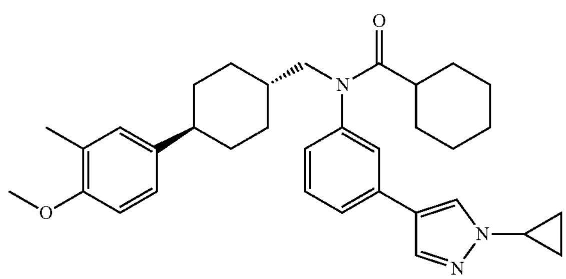 [SMILES: COc1ccc([C@H]2CC[C@H](CN(C(=O)C3CCCCC3)c3cccc(-c4cnn(C5CC5)c4)c3)CC2)cc1C] | N-(3-(1-Cyclopropyl-1H-pyrazol-4-yl)phenyl)-N-((trans-4-(4-methoxy-3-methylphenyl)cyclohexyl)methyl)cyclohexanecarboxamide |
| 5.25 | 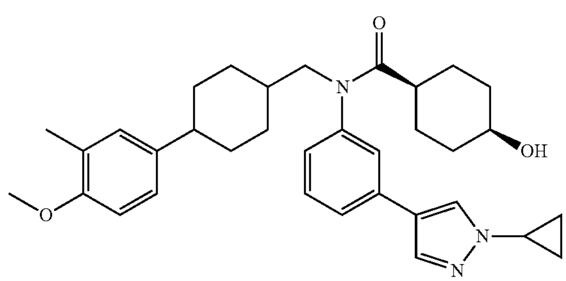 [SMILES: COc1ccc(C2CCC(CN(c3cccc(-c4cnn(C5CC5)c4)c3)C(=O)[C@H]3CC[C@@H](O)CC3)CC2)cc1C] | cis-N-(3-(1-Cyclopropyl-1H-pyrazol-4-yl)phenyl)-4-hydroxy-N-((4-(4-methoxy-3-methylphenyl)cyclohexyl)methyl)cyclohexanecarboxamide |
| 5.26 | 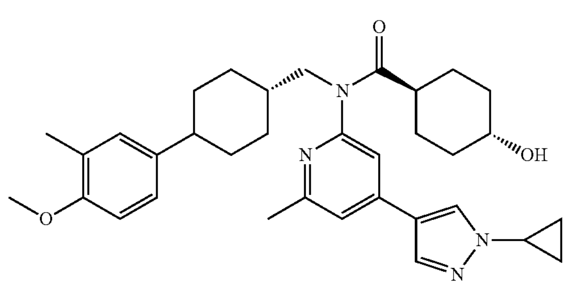 | trans-N-(4-(1-cyclopropyl-1H-pyrazol-4-yl)-6-methylpyridin-2-yl)-4-hydroxy-N-((trans-4-(4-methoxy-3-methylphenyl)cyclohexyl)methyl)cyclohexanecarboxamide |

TABLE 1-continued

| Compound | Structure | Chemical Name |
|---|---|---|
| 5.27 | 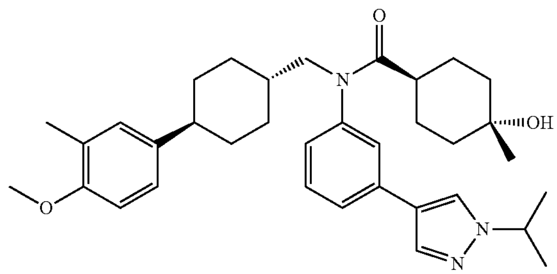 [SMILES: COc1ccc([C@H]2CC[C@H](CN(c3cccc(-c4cnn(C(C)C)c4)c3)C(=O)[C@H]3CC[C@](C)(O)CC3)CC2)cc1C] | (1r,4r)-4-Hydroxy-N-(3-(1-isopropyl-1H-pyrazol-4-yl)phenyl)-N-((trans-4-(4-methoxy-3-methylphenyl)cyclohexyl)methyl)-4-methylcyclohexanecarboxamide |
| 5.28 | 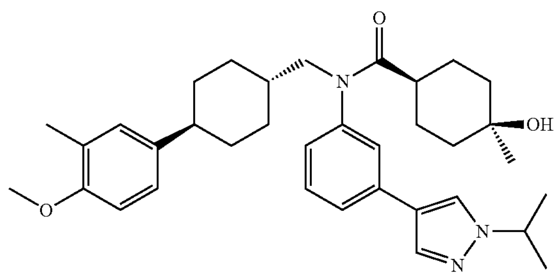 [SMILES: COc1ccc([C@H]2CC[C@H](CN(c3cccc(-c4cnn(C(C)C)c4)c3)C(=O)[C@H]3CC[C@@](C)(O)CC3)CC2)cc1C] | (1s, 4s)-4-Hydroxy-N-(3-(1-isopropyl-1H-pyrazol-4-yl)phenyl)-N-((trans-4-(4-methoxy-3-methylphenyl)cyclohexyl)methyl)-4-methylcyclohexanecarboxamide |
| 5.29 | 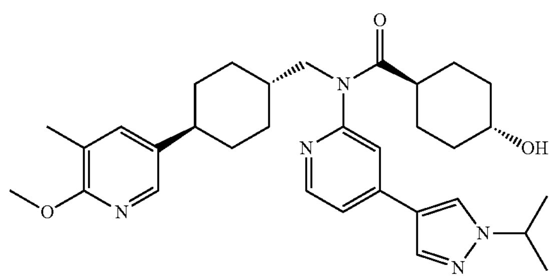 [SMILES: COc1ncc([C@H]2CC[C@H](CN(c3cc(-c4cnn(C(C)C)c4)ccn3)C(=O)[C@H]3CC[C@H](O)CC3)CC2)cc1C] | trans-4-Hydroxy-N-(4-(1-Isopropyl-1H-pyrazol-4-yl)pyridin-2-yl)-N-((trans-4-(6-methoxy-5-methylpyridin-3-yl)cyclohexyl)methyl)cyclohexanecarboxamide |
| 5.30 | 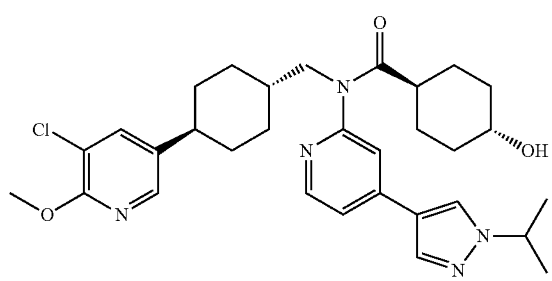 [SMILES: COc1ncc([C@H]2CC[C@H](CN(c3cc(-c4cnn(C(C)C)c4)ccn3)C(=O)[C@H]3CC[C@H](O)CC3)CC2)cc1Cl] | trans-N-((trans-4-(5-Chloro-6-methoxypyridin-3-yl)cyclohexyl)methyl)-4-hydroxy-N-(4-(1-isopropyl-1H-pyrazol-4-yl)pyridin-2-yl)cyclohexanecarboxamide |
| 6 | 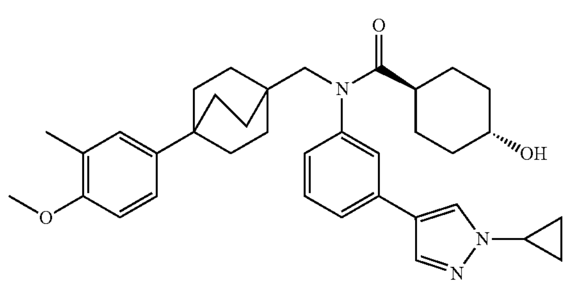 | trans-N-(3-(1-Cyclopropyl-1H-pyrazol-4-yl)phenyl)-4-hydroxy-N-((4-(4-methoxy-3-methylphenyl)bicyclo[2.2.2]octan-1-yl)methyl)cyclohexanecarboxamide |

TABLE 1-continued

| Compound | Structure | Chemical Name |
|---|---|---|
| 6.01 | 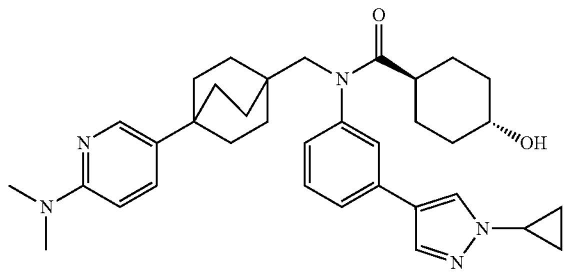 [SMILES: CN(C)c1ccc(C23CCC(CN(c4cccc(-c5cnn(C6CC6)c5)c4)C(=O)[C@H]4CC[C@H](O)CC4)(CC2)CC3)cn1] | trans-N-(3-(1-Cyclopropyl-1H-pyrazol-4-yl)phenyl)-N-((4-(6-(dimethylamino)pyridin-3-yl)bicyclo[2.2.2]octan-1-yl)methyl)-4-hydroxycyclohexanecarboxamide |
| 6.02 | 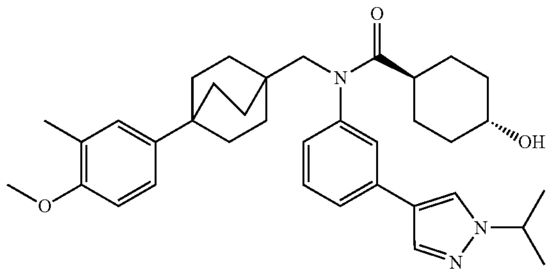 | trans-4-Hydroxy-N-(3-(1-isopropyl-1H-pyrazol-4-yl)phenyl)-N-((4-(4-methoxy-3-methylphenyl)bicyclo[2.2.2]octan-1-yl)methyl)cyclohexanecarboxamide |
| 7 | 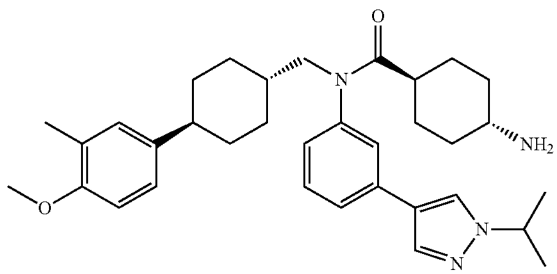 [SMILES: COc1ccc([C@H]2CC[C@H](CN(c3cccc(-c4cnn(C(C)C)c4)c3)C(=O)[C@H]3CC[C@H](N)CC3)CC2)cc1C] | trans-4-Amino-N-(3-(1-isopropyl-1H-pyrazol-4-yl)phenyl)-N-((trans-4-(4-methoxy-3-methylphenyl)cyclohexyl)methyl)cyclohexanecarboxamide |
| 7.01 | 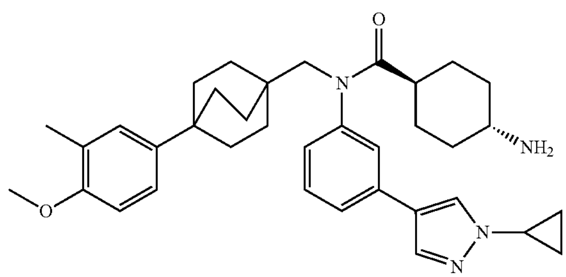 [SMILES: COc1ccc(C23CCC(CN(c4cccc(-c5cnn(C6CC6)c5)c4)C(=O)[C@H]4CC[C@H](N)CC4)(CC2)CC3)cc1C] | trans-4-Amino-N-(3-(1-cyclopropyl-1H-pyrazol-4-yl)phenyl)-N-((4-(4-methoxy-3-methylphenyl)bicyclo[2.2.2]octan-1-yl)methyl)cyclohexanecarboxamide |
| 8 | 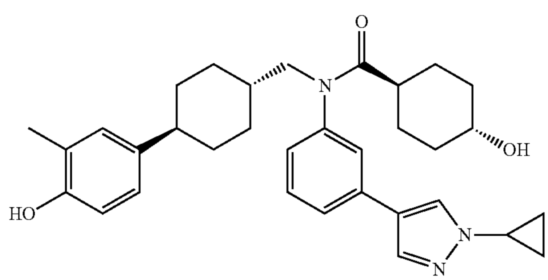 [SMILES: Cc1cc([C@H]2CC[C@H](CN(c3cccc(-c4cnn(C5CC5)c4)c3)C(=O)[C@H]3CC[C@H](O)CC3)CC2)ccc1O] | trans-N-(3-(1-Cyclopropyl-1H-pyrazol-4-yl)phenyl)-4-hydroxy-N-((trans-4-(4-hydroxy-3-methylphenyl)cyclohexyl)methyl)cyclohexanecarboxamide |

In some embodiments, provided herein is a pharmaceutically acceptable salt or solvate of a compound that is described in Table 1

In one aspect, compounds described herein are in the form of pharmaceutically acceptable salts. As well, active metabolites of these compounds having the same type of activity are included in the scope of the present disclosure.

In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible, and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound described herein with an acid to provide a "pharmaceutically acceptable acid addition salt." In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (-L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (-L); salicylic acid; sebacic acid; stearic acid; succinic acid; sulfuric acid; tartaric acid (+L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt.

In some embodiments, pharmaceutically acceptable salts are obtained by reacting a compound described herein with a base to provide a "pharmaceutically acceptable base addition salt."

In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of isolating or purifying the compound with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions.

Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogen atoms of the compounds described herein is replaced with deuterium.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley and Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. The prodrug may be a substrate for a transporter. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound. In some embodiments, a prodrug of the compound disclosed herein permits targeted delivery of the compound to a particular region of the gastrointestinal tract. Formation of a pharmacologically active metabolite by the colonic metabolism of drugs is a commonly used "prodrug" approach for the colon-specific drug delivery systems.

In some embodiments, a prodrug is formed by the formation of a covalent linkage between drug and a carrier in such a manner that upon oral administration the moiety remains intact in the stomach and small intestine. This approach involves the formation of prodrug, which is a pharmacologically inactive derivative of a parent drug molecule that requires spontaneous or enzymatic transformation in the biological environment to release the active drug. Formation of prodrugs has improved delivery properties over the parent drug molecule.

The problem of stability of certain drugs from the adverse environment of the upper gastrointestinal tract can be eliminated by prodrug formation, which is converted into parent drug molecule once it reaches into the colon. Site specific drug delivery through site specific prodrug activation may be accomplished by the utilization of some specific property at the target site, such as altered pH or high activity of certain enzymes relative to the non-target tissues for the prodrug-drug conversion.

In some embodiments, covalent linkage of the drug with a carrier forms a conjugate conjugate. Such conjugates include, but are not limited to, azo bond conjugates, glycoside conjugates, glucuronide conjugates, cyclodextrin conjugates, dextran conjugates or amino-acid conjugates.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

In some embodiments, the compounds described herein are rapidly metabolized following absorption from the gastro-intestinal tract to metabolites that have greatly reduced FXR agonist activity.

In additional or further embodiments, the compounds are rapidly metabolized in plasma.

In additional or further embodiments, the compounds are rapidly metabolized by the intestines.

In additional or further embodiments, the compounds are rapidly metabolized by the liver.

Synthesis of Compounds

Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared.

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

The compounds described herein are prepared by the general synthetic routes described below in Schemes 1 to 11.

In some embodiments, intermediates used in the preparation of compounds described herein are prepared as outlined in Scheme 1.

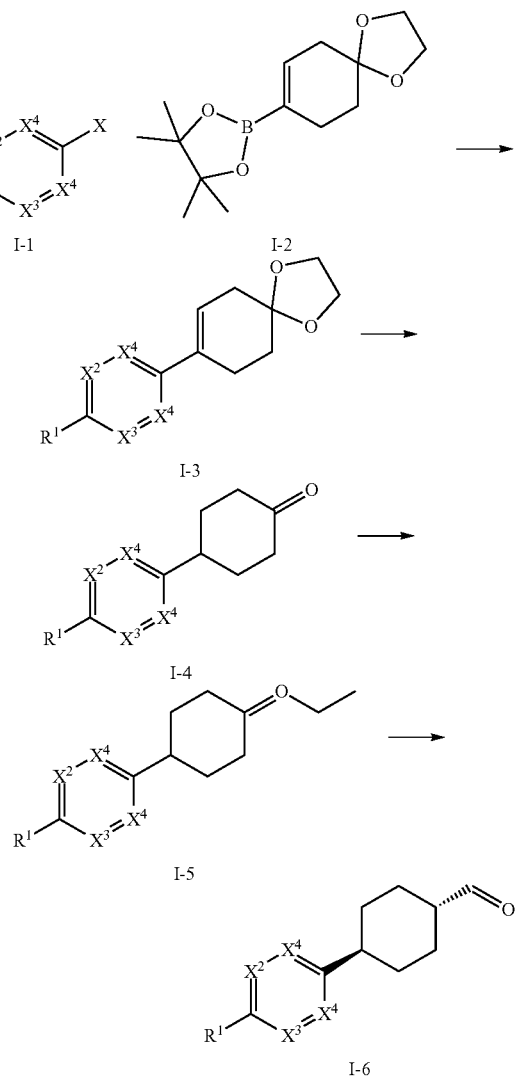

Scheme 1

In Scheme 1, substituents $X^2$, $X^3$, $X^4$, $R^1$, and $R^2$ are as described herein. In some embodiments, $X^2$ is C—$R^2$, $X^3$ is C—H, and each $X^4$ is C—H. In some embodiments, X is a halide. In some embodiments, X is chloro, bromo, or iodo.

In some embodiments, boronic ester I-2 is reacted with halide I-1 under suitable metal-catalyzed cross-coupling reaction conditions to provide I-3. In some embodiments, suitable metal-catalyzed cross-coupling conditions include the use of palladium. In some embodiments, suitable palladium-catalyzed cross-coupling reaction conditions include Pd(dppf)Cl$_2$ or Pd(PPh$_3$)$_4$ with an appropriate base, with an appropriate solvent or solvent mixture for an appropriate time and at an appropriate temperature. In some embodiments, the base is an inorganic base. In some embodiments, the inorganic base is a carbonate base such as Na$_2$CO$_3$ or Cs$_2$CO$_3$. In some embodiments, the appropriate solvent or solvent mixture is dioxane, acetonitrile, DME/EtOH, or ethanol. In some embodiments, the appropriate time and appropriate temperature is about 2 hours to about 18 hours (overnight) at about 50° C. or about 100° C.

In some embodiments, I-3 is subjected to suitable hydrogenation conditions followed by treatment under appropriate acidic conditions to provide cyclohexanone I-4. In some embodiments, suitable hydrogenation conditions include the use of palladium.

Palladium-catalyzed hydrogenation conditions include the use of 10% Pd/C with hydrogen (1 atm) in a suitable solvent, such as EtOAc, ethanol, methanol or a combination of these solvents, for an appropriate amount of time at an appropriate temperature. In some embodiments, the appropriate amount of time is about 4.5 hours to about 18 hours (overnight) at about rt. In some embodiments, appropriate acidic conditions include formic acid in water and toluene for a suitable amount of time at an appropriate temperature. In some embodiments, the suitable amount of time at an appropriate temperature is about 4 hours at about 120° C. In some embodiments, the suitable amount of time at an appropriate temperature is about 18 hours (overnight) at reflux. In some embodiments, appropriate acidic conditions include PPTS in acetone and water for a suitable amount of time at an appropriate temperature. In some embodiments, the suitable amount of time at an appropriate temperature is about 10 hours at about 60° C. In some embodiments, appropriate acidic conditions include 3 M HCl and THF for a suitable amount of time at an appropriate temperature. In some embodiments, the suitable amount of time at an appropriate temperature is about 3 hours to about overnight at about 60° C.

In some embodiments, I-4 is reacted under suitable one carbon-homologation conditions to provide I-5. In some embodiments, suitable one carbon-homologation conditions include the use of phosphonium reagents. In some embodiments, suitable one-carbon-homologation conditions, includes pre-treating (methoxymethyl)triphenyl phosphonium [Ph$_3$P$^+$CH$_2$OCH$_3$ Cl$^-$] with an appropriate base, with an appropriate solvent for an appropriate amount of time at an appropriate temperature before the addition of cyclohexanone I-4. In some embodiments, the appropriate base is NaHMDS. In some embodiments, the appropriate base is KHMDS or LiHMDS. In some embodiments, the appropriate solvent is THF. In some embodiments, the appropriate amount of time before addition of cyclohexanone I-4 at an appropriate temperature is about 30 mins to about 2 hours at about 0° C. In some embodiments, after I-4 is added the reaction is continued for an additional about 30 mins to about 3 hours at about 0° C. In some embodiments, the reaction is allowed to warm to about room temperature overnight.

In some embodiments, I-5 is then subjected under suitable acidic conditions to provide a mixture of cis and trans aldehydes I-6. In some embodiments, suitable acidic conditions include formic acid in water/toluene at about 120° C. to about 130° C. for about 2 hours to about overnight. In some embodiments, suitable acidic conditions include HCl in THF at about 60° C. for about 1 hour or about 6 hours. In some embodiments, further subjection of aldehyde I-6 under appropriate basic conditions provides a mostly trans aldehyde I-6. In some embodiments, appropriate basic conditions include NaOH in a suitable solvent mixture, such as H$_2$O, EtOH, and PhMe, for an appropriate amount of time at an appropriate temperature. In some embodiments, THF is used instead of PhMe. In some embodiments, the appropriate amount of time at an appropriate temperature is about 5.5 hours to about overnight at about rt. In some embodiments, appropriate basic conditions include NaOMe in a suitable solvent, such as MeOH, for an appropriate amount of time at an appropriate temperature. In some embodiments, the appropriate amount of time at an appropriate temperature is at about 4 hours to about 18 hours at about room temperature. In some embodiments, further purification via crystallization or chromatography provides pure trans aldehyde I-6.

In some embodiments, intermediates used in the preparation of compounds described herein are prepared as outlined in Scheme 2.

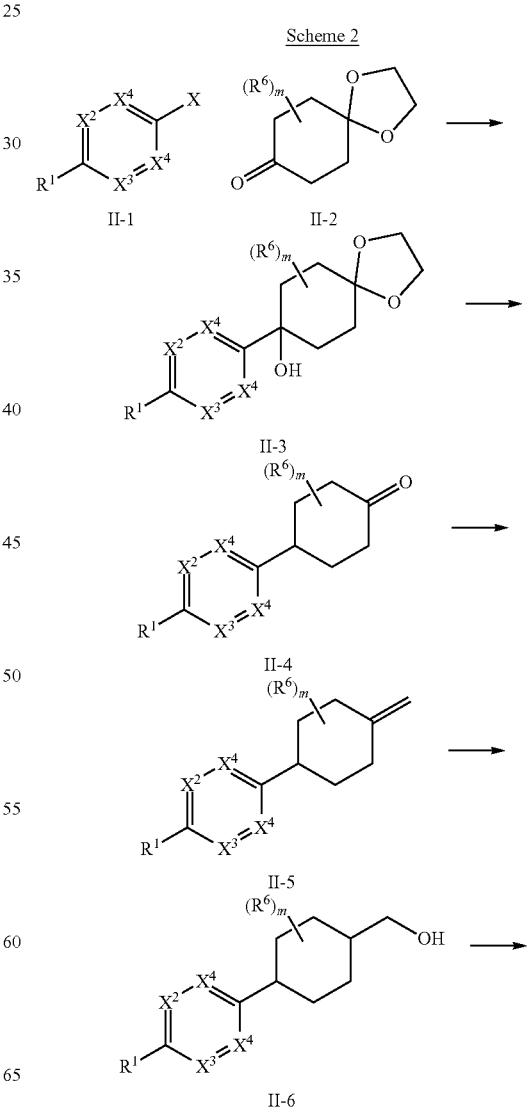

-continued

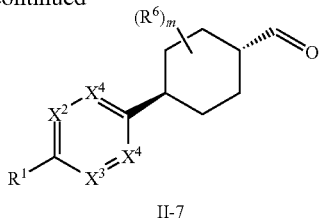

II-7

In Scheme 2, substituents $X^2$, $X^3$, $X^4$, $R^1$, $R^2$, and m are as described herein. In some embodiments, $X^2$ is C—$R^2$, $X^3$ is C—H, and each $X^4$ is C—H. In some embodiments, $R^6$ is alkyl.

In some embodiments, $R^6$ is methyl. In some embodiments, X is a halogen. In some embodiments, X is chloro, bromo, or iodo.

In some embodiments, II-1 is cooled to a suitable temperature, reacted under suitable metal-halogen exchange conditions with an appropriate solvent for an appropriate time and at an appropriate temperature, and then later reacted with an appropriate ketone II-2 for an appropriate time and at an appropriate temperature to provide II-3. In some embodiments, suitable metal-halogen exchange conditions include an organometallic reagent. In some embodiments, an appropriate solvent is THF. In some embodiments, the organometallic reagent is an alkyl lithium. In some embodiments, the alkyllithium is n-butyl lithium. In some embodiments, II-1 is cooled to about −78° C. before addition of an organometallic reagent. In some embodiments, II-1 is reacted for about two hours at about −78° C. before addition of the appropriate ketone II-2. In some embodiments, the intermediate organometallic reagent is reacted for about 3 hours after the addition of ketone II-2. In some embodiments, the intermediate organometallic reagent is reacted at about −78° C. after the addition of ketone II-2.

In some embodiments, alcohol II-3 is reacted under appropriate reduction conditions with an appropriate solvent for an appropriate time and at an appropriate temperature to form a mixture of dehydrated and reduced products. In some embodiments, conditions include the use of trifluoroacetic acid and a silyl hydride. In some embodiments, the silyl hydride is triethylsilane. In some embodiments, the appropriate solvent is dichloromethane. In some embodiments, the temperature is about 0° C. to about rt or about 0° C. In some embodiments, the appropriate time is about overnight or about 1 hour. In some embodiments, the mixture of reduced and dehydrated products is reacted under the appropriate conditions with an appropriate solvent for an appropriate time and at an appropriate temperature to form a ketone. In some embodiments, the appropriate solvent is a formic acid, toluene, and water mixture. In some embodiments, the appropriate temperature is about 130° C. In some embodiments, the appropriate time is about overnight. In some embodiments, the appropriate solvent is a formic acid, THF, and water mixture. In some embodiments, the appropriate temperature is about 80° C. In some embodiments, the appropriate time is about 18 hours. In some embodiments, this ketone, containing the dehydrated side product, is fully reduced under suitable reduction conditions with an appropriate solvent for an appropriate time and at an appropriate temperature to form II-4. In some embodiments, the appropriate reduction conditions include the use of hydrogen as a reducing agent. In some embodiments, the hydrogen is at a pressure of about 15 psi or about 30 psi. In some embodiments, the alkene reduction includes use of a palladium catalyst. In some embodiments, the palladium catalyst is 10% palladium on carbon. In some embodiments, the solvent is ethyl acetate and concentrated HCl. In some embodiments, the solvent is ethyl acetate. In some embodiments, the temperature is about rt. In some embodiments, the appropriate time is about 30 min to about 18 hours.

In some embodiments, II-4 is pre-treated with an electrophile $R^6X$ in an appropriate solvent and at an appropriate temperature. In some embodiments, the electrophile is an alkyl halide. In some embodiments, X is chloro, bromo, or iodo. In some embodiments, the electrophile is methyl iodide. In some embodiments, the temperature is about −78° C. In some embodiments, the mixture is further reacted with a base for an appropriate time and at an appropriate temperature to form an alkylated product. In some embodiments, the base is lithium diisopropyldiamide. In some embodiments, the appropriate time is about 2 hours. In some embodiments, the temperature is about −78° C. In some embodiments, the mixture is further allowed to warm to about rt over a suitable amount of time. In some embodiments, a suitable amount of time is about overnight.

In some embodiments, ketone II-4 is transformed into aldehyde II-7 as described in Scheme 1.

Alternatively in some embodiments, II-4 is reacted under suitable one carbon-homologation conditions to provide alkene II-5. In some embodiments, suitable one carbon-homologation conditions include the use of phosphonium reagents. In some embodiments, suitable one-carbon-homologation conditions, includes pre-treating methyltriphenyl phosphonium bromide [$Ph_3P^+CH_3\ Br^-$] with an appropriate base in an appropriate solvent for an appropriate amount of time at an appropriate temperature before the addition of cyclohexanone II-4. In some embodiments, the appropriate base is an organic base. In some embodiments, the appropriate base is an alkoxide base. In some embodiments, the appropriate base is potassium tert-butoxide. In some embodiments, the appropriate solvent is toluene. In some embodiments, the appropriate time before adding the ketone is about 30 min. In some embodiments, the temperature of the reaction before adding the ketone is about 100° C. In some embodiments, ketone II-4 is added in the appropriate solvent, at the appropriate temperature, and for the appropriate amount of time. In some embodiments, the reaction temperature is about 50° C. after the addition of the ketone. In some embodiments, the ketone is added in toluene. In some embodiments, the ketone is further reacted at a suitable temperature for a suitable amount of time. In some embodiments, the ketone is further reacted at about 100° C. In some embodiments, the ketone is further reacted for about 2 hours.

In some embodiments, alkene II-5 is subjected to hydration conditions to form II-6. In some embodiments, the hydration conditions include treatment with a reducing agent followed by an oxidizing agent. The reducing agent is reacted with II-5 in the appropriate solvent, at the appropriate temperature, and for the appropriate amount of time. In some embodiments, the reducing agent is a borane. In some embodiments, the reducing agent is $BH_3$—$SMe_2$. In some embodiments, the reducing agent is reacted with II-5 in THF. In some embodiments, the reaction temperature is about 0° C. In some embodiments, the reaction proceeds for about one hour after addition of the reducing agent. In some embodiments, the reaction further continues at about rt. In some embodiments, the reaction further continues for about 3 hours. In some embodiments, the intermediate borane product is further oxidized with an oxidizing agent to form alcohol II-6 in the appropriate solvent, at the appropriate temperature, and for the appropriate amount of time. In some embodiments, the oxidizing agent is 30% H$_2$O$_2$. In some embodiments, the oxidation reaction is carried out in the prescence of a base. In some embodiments, the base is NaOH. In some embodiments, the solvent is H$_2$O. In some embodiments, the appropriate amount of time is about overnight. In some embodiments, the appropriate temperature is about rt.

In some embodiments, alcohol II-6 is subjected to an oxidizing agent to form aldehyde II-7. In some embodiments, the oxidizing agent is a Swern oxidant in the appropriate solvent, at the appropriate temperature, and for the appropriate amount of time.

In some embodiments, the Swern oxidant is formed with DMSO and oxalyl chloride. In some embodiments, the appropriate solvent is dichloromethane. In some embodiments, the appropriate temperature for Swern oxidant formation is about −78° C. In some embodiments, the appropriate time for Swern oxidant formation is 30 min. In some embodiments, II-6 is reacted with the Swern oxidant at about −78° C. In some embodiments, II-6 is reacted with the Swern oxidant for about one hour. In some embodiments, a base is then added at the appropriate temperature for the appropriate amount of time. In some embodiments, the base is an amine base. In some embodiments, the amine base is triethylamine. In some embodiments, the appropriate temperature is about −78° C. In some embodiments, the appropriate reaction time after addition of the base is about one hour. In some embodiments, oxidation produces II-7 as a mixture of cis and trans isomers.

In some embodiments, the cis/trans mixture of II-7 is equilibrated to mostly trans II-7 with an appropriate reagent, in the appropriate solvent, at the appropriate temperature, and for the appropriate time. In some embodiments, the appropriate reagent is a base. In some embodiments, the base is an inorganic base. In some embodiments, the base is sodium hydroxide. In some embodiments, the appropriate solvent is a mixture, such as H$_2$O, EtOH and PhMe. In some embodiments, the appropriate time is about 3 hours. In some embodiments, the appropriate temperature is about rt. In some embodiments, further purification via crystallization or chromatography provides pure trans aldehyde II-7.

In some embodiments, intermediates used in the preparation of compounds described herein are prepared as outlined in Scheme 3.

Scheme 3

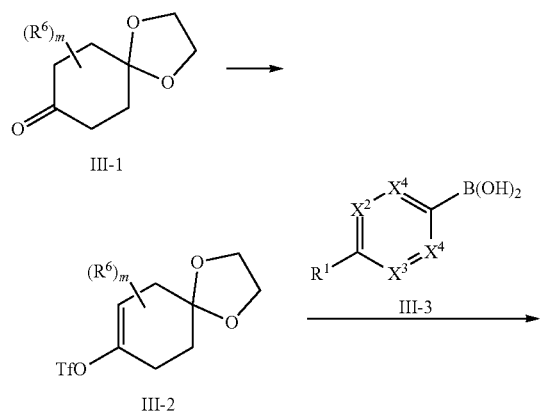

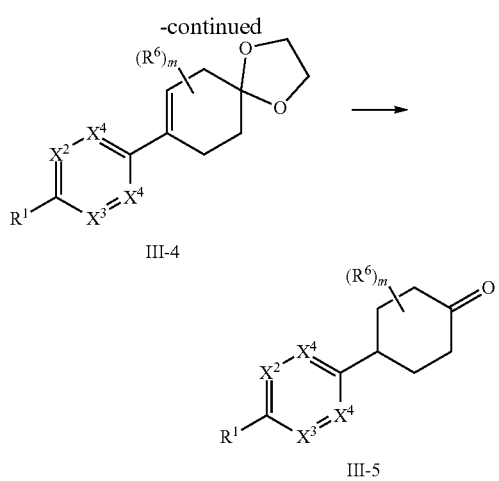

In Scheme 3, substituents X$^2$, X$^3$, X$^4$, R$^1$, R$^2$, and m are as described herein. In some embodiments, X$^2$ is C—R$^2$, X$^3$ is C—H, and each X$^4$ is C—H. In some embodiments, R$^6$ is alkyl.

In some embodiments, R$^6$ is methyl.

In some embodiments, ketone III-1 is treated with a base to form an enolate with an appropriate base, in an appropriate solvent, for an appropriate amount of time, at an appropriate temperature. In some embodiments, the base is an organic base. In some embodiments, the organic base is LiHMDS. In some embodiments, enolate formation takes place at about −78° C. In some embodiments, the appropriate solvent is THF. In some embodiments, the appropriate time is about one hour. In some embodiments, the enolate of ketone III-1 is reacted with a suitable electrophile in an appropriate solvent to form enol ether III-2 at the appropriate temperature, for an appropriate amount of time. In some embodiments, the electrophile forms a sulfate ester. In some embodiments, the electrophile is PhNTf$_2$. In some embodiments, the appropriate temperature is about −78° C. and the appropriate time is about 2 hours. In some embodiments, the reaction is further warmed to a suitable temperature over a suitable period of time. In some embodiments, the suitable temperature is about rt for about overnight.

In some embodiments, boronic acid III-3 is reacted with enol triflate III-2 under suitable metal-catalyzed cross-coupling reaction conditions to provide III-4. In some embodiments, suitable metal-catalyzed cross-coupling conditions include palladium. In some embodiments, suitable palladium-catalyzed cross-coupling reaction conditions include Pd(dppf)Cl$_2$ with an appropriate base, with an appropriate solvent for an appropriate time and at an appropriate temperature. In some embodiments, the base is an inorganic base. In some embodiments, the inorganic base is a carbonate base such as Na$_2$CO$_3$. In some embodiments, the appropriate solvent is a dioxane/water mixture. In some embodiments, the appropriate time and appropriate temperature is about 6 hours at about 30° C.

In some embodiments, III-4 is subjected under suitable olefin reduction conditions followed by treatment under appropriate acidic conditions to provide cyclohexanone III-5. In some embodiments, suitable reduction conditions include palladium-catalyzed hydrogenation conditions. In some embodiments, palladium-catalyzed hydrogenation conditions include use of 10% Pd/C with hydrogen (1 atm) in a suitable solvent, such as EtOAc, for an appropriate amount of time at an appropriate temperature. In some embodiments, the appropriate amount of time is about overnight at about rt. In some embodiments, appropriate acidic conditions include the use of formic acid in water and toluene for a suitable amount of time at an appropriate temperature. In some embodiments, the suitable amount of time at an appropriate temperature is about overnight at about 120° C.

In some embodiments, ketone III-5 is transformed into aldehyde I-6 or II-7, as shown in Scheme 1 and Scheme 2, respectively.

In some embodiments, compounds described herein are prepared as outlined in Scheme 4.

acid in an appropriate solvent, such as methanol, at an appropriate temperature for a suitable amount of time before the addition of the reducing agent. In some embodiments, the appropriate temperature and time is about rt for about 5 minutes to about 4 hours. In some embodiments, the reaction is then further subjected to a suitable reducing agent, such as NaBH$_3$CN, for the appropriate time and at the appropriate temperature. In some embodiments, the appropriate amount of time is about overnight at about rt.

In some embodiments, the acylation of amine IV-3 with an acyl chloride affords compound IV-4. Suitable acylation conditions include but are not limited to the use of a suitable

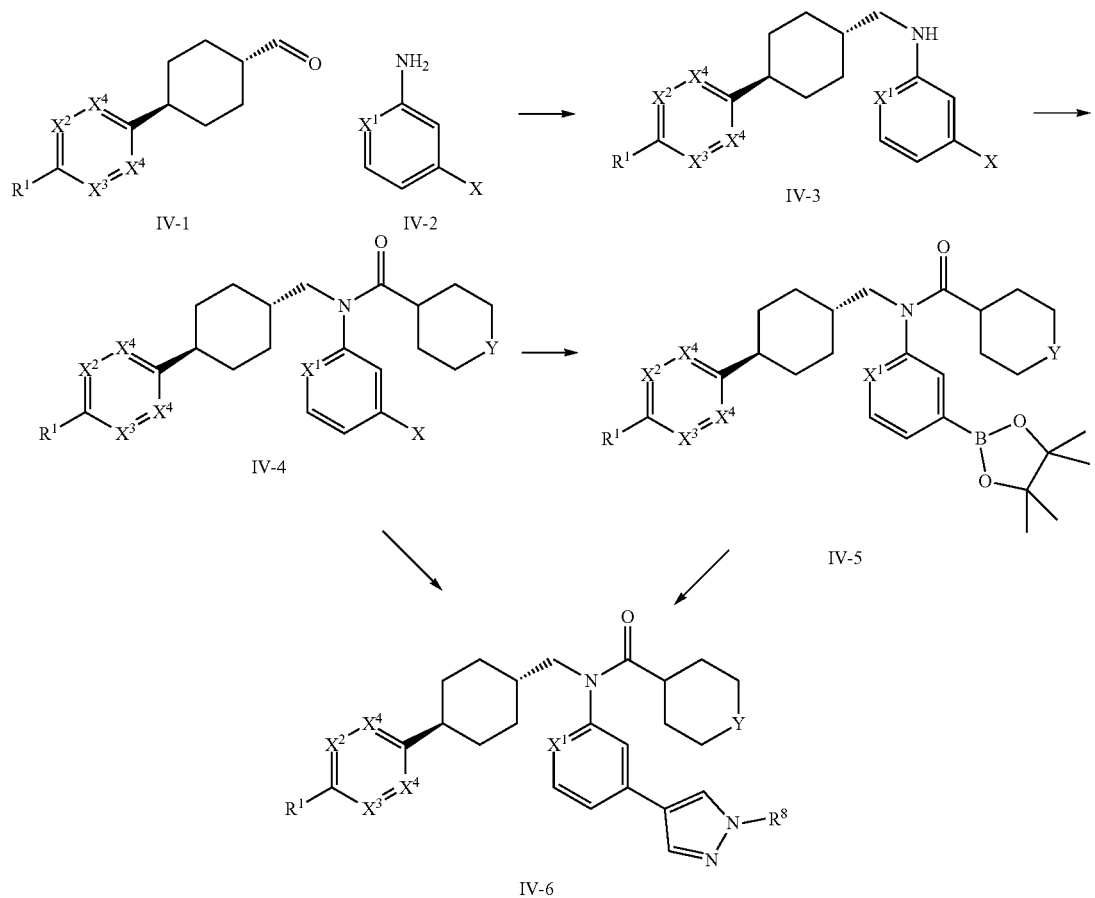

Scheme 4

In Scheme 4, substituents Y, $X^1$, $X^2$, $X^3$, $X^4$, $R^1$, $R^2$, and $R^8$ are as described herein.

In some embodiments, $X^2$ is C—$R^2$, $X^3$ is C—H, and each $X^4$ is C—H. In some embodiments, X is a halide. In some embodiments, X is iodo or bromo.

In some embodiments, trans aldehyde IV-1 is reacted with an appropriate aniline IV-2 under suitable reductive amination conditions. In some embodiments, suitable reductive amination conditions include the use of a suitable reducing agent and acetic acid in an appropriate solvent, such as DCE or DCM, at an appropriate temperature for a suitable amount of time. In some embodiments, NaBH(OAc)$_3$ is used as a reducing agent. In some embodiments, the appropriate temperature is about rt. In some embodiments, the suitable amount of time is about one hour to about 2.5 hours. In some embodiments, suitable reaction conditions include acetic base, such as TEA or pyridine in a suitable solvent, such as DCM or toluene, for an appropriate amount of time and at a suitable temperature, such as about rt to about 80° C. for about 1 hour to about overnight. In some embodiments, pyridine is used as both the base and the solvent. Other suitable conditions include the addition of DMAP.

Boronic ester IV-5 may be prepared from IV-4 using boron-halogen exchange conditions in some embodiments. Suitable boron-halogen exchange conditions include but are not limited to use of a suitable organometallic reagent and a suitable boron reagent. In some embodiments, suitable organometallic reagents include palladium. In some embodiments, suitable boron reagents include bis(pinacolato)diboron. In some embodiments, suitable palladium-catalyzed boron-halogen exchange conditions include Pd(dppf)Cl$_2$ with an appropriate base, in an appropriate solvent for an appropriate time and at an appropriate temperature. In some embodiments, the base is an inorganic base. In some embodiments, the inorganic base is an acetate base such as KOAc. In some embodiments, the appropriate solvent is toluene. In some embodiments, the appropriate time and appropriate temperature is about 4 hours to about overnight and about 100° C. to about 115° C.

In some embodiments, boronic ester IV-5 is reacted with a heteroaryl halide under suitable metal-catalyzed cross-coupling reaction conditions to provide IV-6. In some embodiments, the heteroaryl halide is a heteroaryl bromide. In some embodiments, the heteroaryl halide is a pyrazolyl halide. In some embodiments, suitable metal-catalyzed cross-coupling conditions include use of palladium. In some embodiments, suitable palladium-catalyzed cross-coupling reaction conditions include Pd(dppf)Cl$_2$ or Pd(PPh$_3$)$_4$ with an appropriate base, with an appropriate solvent for an appropriate time and at an appropriate temperature. In some embodiments, the base is an inorganic base. In some embodiments, the inorganic base is a carbonate base such as K$_2$CO$_3$, Na$_2$CO$_3$ or Cs$_2$CO$_3$. In some embodiments, the appropriate solvent is dioxane or DMF. In some embodiments, water is a co-solvent. In some embodiments, the appropriate time and appropriate temperature is about 10 min to about 4 hours at about 50° C. to about 80° C. In some embodiments, the appropriate time and appropriate temperature is about 0.5 hours to about 6 hours at about 80° C.

In some embodiments, aryl halide IV-4 is reacted with a boron reagent under suitable metal-catalyzed cross-coupling reaction conditions to provide IV-6. In some embodiments, the boron reagent is a heteroaryl boronic acid. In some embodiments, the boron reagent is a heteroaryl boronic ester. In some embodiments, the boron reagent is a heteroaryl pinacolyl boronic ester. In some embodiments, the heteroaryl boron reagent is a pyrazolyl boron reagent. In some embodiments, suitable metal-catalyzed cross-coupling conditions include palladium. In some embodiments, suitable palladium-catalyzed cross-coupling reaction conditions include Pd(dppf)Cl$_2$ or Pd(PPh$_3$)$_4$ with an appropriate base, with an appropriate solvent for an appropriate time and at an appropriate temperature. In some embodiments, the base is an inorganic base. In some embodiments, the inorganic base is a carbonate base such as Cs$_2$CO$_3$, Na$_2$CO$_3$, or K$_2$CO$_3$. In some embodiments, the appropriate solvent is a dioxane/water or DMF/water mixture. In some embodiments, the appropriate time and appropriate temperature is about 10 min to about 2 hours at about 50° C. to about 100° C. or at about 80° C.

In some embodiments, Y contains a protected alcohol. In some embodiments, Y is protected with a silyl ether. In some embodiments, protecting groups are removed to produce a free alcohol using suitable deprotection conditions including appropriate solvent, temperature and time to produce IV-6. In some embodiments, suitable deprotection conditions include the use of aqueous HCl. In some embodiments, the appropriate solvent is water, THF, methanol, or a combination of solvents. In some embodiments, the appropriate time at the appropriate temperature is about 30 min to about 1 hour at about 0° C. to about rt.

In some embodiments, compounds described herein are prepared as outlined in Scheme 5.

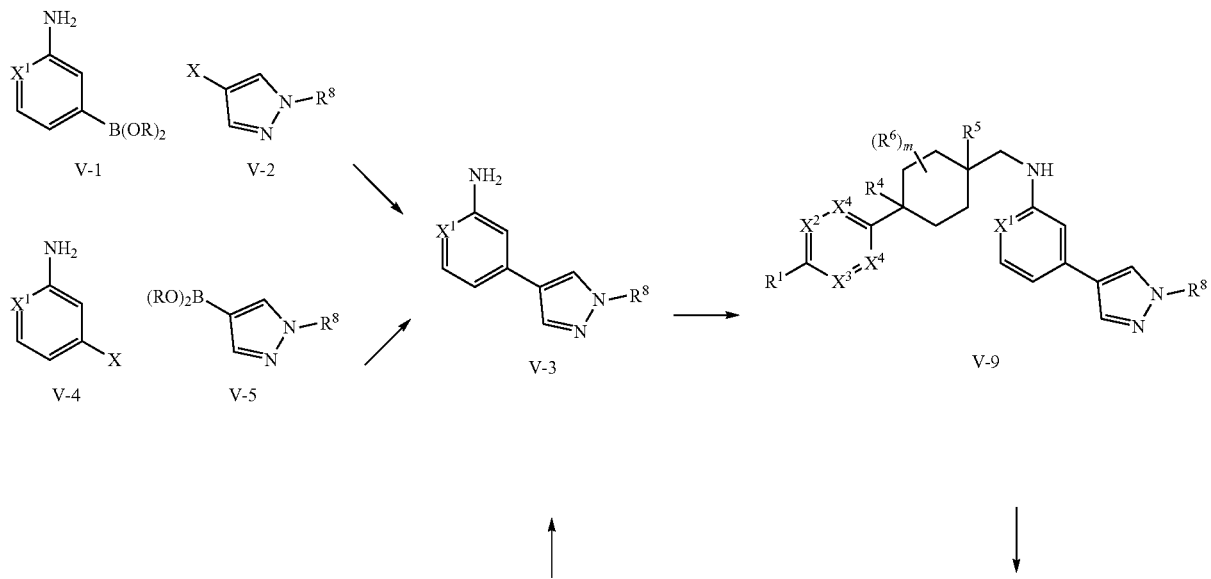

-continued

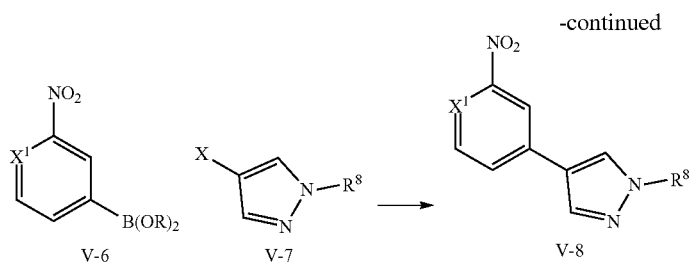 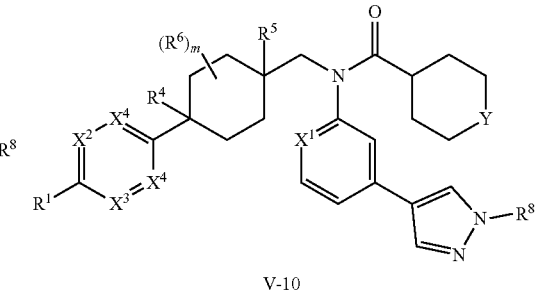

In Scheme 5, substituents Y, $X^1$, $X^2$, $X^3$, $X^4$, $R^1$, $R^2$, $R^4$, $R^5$, $R^6$, $R^8$, and m are as described herein. In some embodiments, $X^2$ is C—$R^2$, $X^3$ is C—H, and each $X^4$ is C—H. In some embodiments, X is a halide. In some embodiments, X is iodo or bromo. In some embodiments, R is an alkyl group. In some embodiments, R is hydrogen.

In some embodiments, boron reagent V-1 is reacted with a heteroaryl halide V-2 under suitable metal-catalyzed cross-coupling reaction conditions to provide V-3. In some embodiments, the heteroaryl halide is heteroaryl bromide or heteroaryl iodide. In some embodiments, the heteroaryl halide is a pyrazolyl halide. In some embodiments, suitable metal-catalyzed cross-coupling conditions include palladium. In some embodiments, suitable palladium-catalyzed cross-coupling reaction conditions include Pd(dppf)Cl$_2$ with an appropriate base, with an appropriate solvent for an appropriate time and at an appropriate temperature. In some embodiments, the base is an inorganic base. In some embodiments, the inorganic base is a carbonate base such as K$_2$CO$_3$. In some embodiments, the appropriate solvent is a dioxane/water mixture. In some embodiments, the appropriate time and appropriate temperature is about 4 hours at about 80° C.

In some embodiments, aryl halide V-4 is reacted with boron reagent V-5 under suitable metal-catalyzed cross-coupling reaction conditions to provide V-3. In some embodiments, the boron reagent is a heteroaryl boronic acid. In some embodiments, the boron reagent is a heteroaryl boronic ester. In some embodiments, the boron reagent is a heteroaryl pinacolyl boronic ester. In some embodiments, the heteroaryl boron reagent is a pyrazolyl boron reagent. In some embodiments, suitable metal-catalyzed cross-coupling conditions include palladium. In some embodiments, suitable palladium-catalyzed cross-coupling reaction conditions include Pd(dppf)Cl$_2$ with an appropriate base, with an appropriate solvent for an appropriate time and at an appropriate temperature. In some embodiments, the base is an inorganic base. In some embodiments, the inorganic base is a carbonate base such as K$_2$CO$_3$. In some embodiments, the appropriate solvent is a dioxane/water mixture. In some embodiments, the appropriate time and appropriate temperature is about about 20 min at about 90° C.

In some embodiments, an aldehyde is reacted with aniline V-3 under suitable reductive amination conditions to form amine V-9. In some embodiments, suitable reductive amination conditions include use of a suitable reducing agent in an appropriate solvent, such as DCE or DCM, at an appropriate temperature for a suitable amount of time. In some embodiments, acetic acid is added. In some embodiments, NaBH(OAc)$_3$ is used as a reducing agent. In some embodiments, the appropriate temperature is about rt. In some embodiments, the suitable amount of time is about one hour to about overnight. In some embodiments, suitable reaction conditions include acetic acid in an appropriate solvent, such as methanol, at an appropriate temperature for a suitable amount of time before the addition of the reducing agent. In some embodiments, the appropriate temperature and time is about rt for about 5 minutes to about 4 hours. In some embodiments, the reaction is subjected to a suitable reducing agent, such as NaBH$_3$CN, for the appropriate time and at the appropriate temperature. In some embodiments, the appropriate amount of time is about overnight at about rt.

In some embodiments, the acylation of aniline V-9 with an acyl chloride affords amide V-10. Suitable acylation conditions include but are not limited to the use of a suitable base, such as TEA or pyridine in a suitable solvent, such as DCM, toluene or pyridine, for an appropriate amount of time and at a suitable temperature, such as about 0° C. to about 50° C. or about 0° C. to about 80° C. for about 10 min to about overnight. Other suitable conditions include the addition of DMAP.

In some embodiments, Y contains a protected alcohol. In some embodiments, Y is protected with a silyl ether. In some embodiments, protecting groups are removed to produce a free alcohol using suitable deprotection conditions including appropriate solvent, temperature and time to produce V-10. In some embodiments, suitable deprotection conditions include the use of aqueous HCl. In some embodiments, the appropriate solvent is water, THF, methanol, or a combination of solvents. In some embodiments, the appropriate time at the appropriate temperature is about 30 min to about 1 hour at about 0° C. to about rt.

In some embodiments, boron reagent V-6 is reacted with a heteroaryl halide V-7 under suitable metal-catalyzed cross-coupling reaction conditions to provide V-8. In some embodiments, the heteroaryl halide is heteroaryl bromide or heteroaryl iodide. In some embodiments, the heteroaryl halide is a pyrazolyl halide. In some embodiments, suitable metal-catalyzed cross-coupling conditions include palladium. In some embodiments, suitable palladium-catalyzed cross-coupling reaction conditions include Pd(dppf)Cl$_2$ with an appropriate base, with an appropriate solvent for an appropriate time and at an appropriate temperature. In some embodiments, the base is an inorganic base. In some embodiments, the inorganic base is a carbonate base such as Na$_2$CO$_3$. In some embodiments, the appropriate solvent is a mixture of dioxane, ethanol and water. In some embodiments, the appropriate time and appropriate temperature is about about overnight at about 80° C.

In some embodiments, V-8 is subjected to suitable nitro reduction conditions to provide aniline V-3. Suitable nitro reduction conditions include palladium-catalyzed hydrogenation conditions. In some embodiments, suitable palladium-catalyzed hydrogenation conditions include use of 10% Pd/C with hydrogen (1 atm) in a suitable solvent, such as methanol, for an appropriate amount of time at an appropriate temperature.

In some embodiments, appropriate conditions include addition of HCl in water. In some embodiments, the appropriate amount of time is at the appropriate temperature is about one hour at about rt.

In some embodiments, compounds described herein are prepared as outlined in Scheme 6.

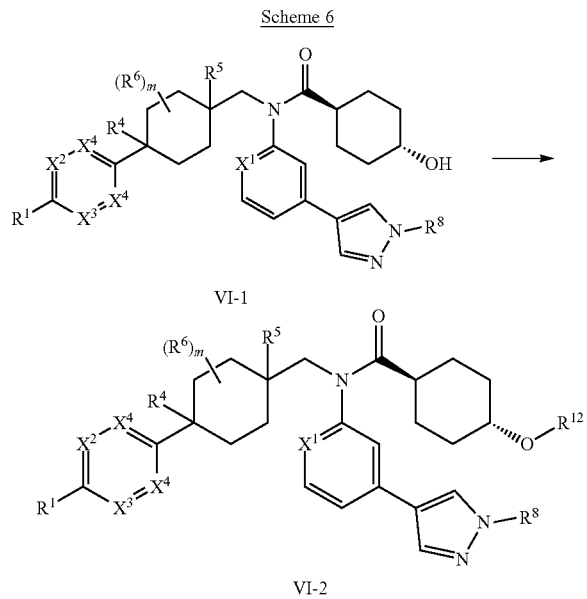

Scheme 6

VI-1

VI-2

In Scheme 6, substituents $X^1$, $X^2$, $X^3$, $X^4$, $R^1$, $R^2$, $R^4$, $R^5$, $R^6$, $R^8$, $R^{12}$, and m are as described herein. In some embodiments, $X^2$ is C—$R^2$, $X^3$ is C—H, and each $X^4$ is C—H.

In some embodiments, compound VI-2 is prepared from the O-alkylation of VI-1 with $R^{12}X$, a suitable base, and suitable solvent, such as THF, at a suitable temperature for a suitable amount of time. In some embodiments, X is a halide. In some embodiments, a suitable base is NaH. In some embodiments, the compound VI-1 is pretreated with the suitable base for an appropriate amount of time at an appropriate temperature, such as about 0.5 h at about 0° C., before the addition of the halide $R^{12}X$. In some embodiments, the appropriate time and temperature is about overnight at about 60° C.

In some embodiments, compounds described herein are prepared as outlined in Scheme 7.

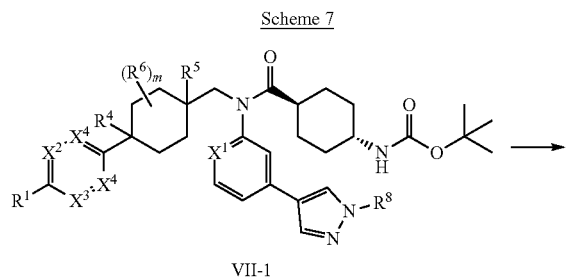

Scheme 7

VII-1

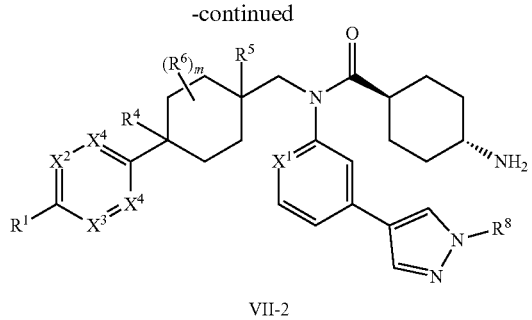

VII-2

In Scheme 7, substituents $X^1$, $X^2$, $X^3$, $X^4$, $R^1$, $R^2$, $R^4$, $R^5$, $R^6$, $R^8$, and m are as described herein. In some embodiments, $X^2$ is C—$R^2$, $X^3$ is C—H, and each $X^4$ is C—H.

In some embodiments, VII-1 is subjected under appropriate acidic conditions to provide an amine VII-2. In some embodiments, the appropriate acidic conditions include the use of TFA in a suitable solvent, such as DCM, at an appropriate temperature for an appropriate amount of time. In some embodiments, the appropriate acidic conditions include the use of HCl in a suitable solvent, such as dioxane, at an appropriate temperature for an appropriate amount of time. In some embodiments, the appropriate temperature for an appropriate amount of time is about 0° C. to about rt for about 0.5 hours to about 2 hours.

In some embodiments, intermediates used in the preparation of compounds described herein are prepared as outlined in Scheme 8.

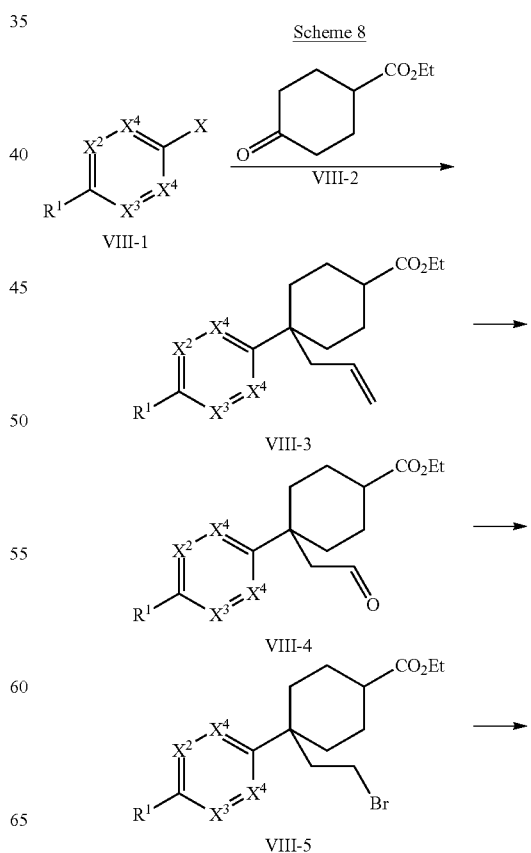

Scheme 8

VIII-1     VIII-2

VIII-3

VIII-4

VIII-5

-continued

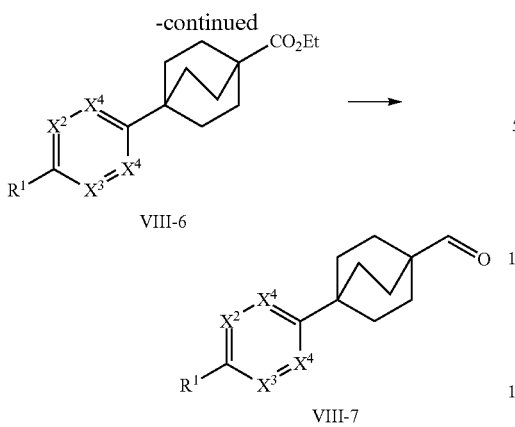

VIII-6

VIII-7

In Scheme 8, substituents $X^2$, $X^3$, $X^4$, $R^1$, and $R^2$ are as described herein. In some embodiments, $X^2$ is C—$R^2$, $X^3$ is C—H, and each $X^4$ is C—H. In some embodiments, X is a halide. In some embodiments, X is chloro, bromo or iodo.

In some embodiments, halide VIII-1 is cooled to a suitable temperature, reacted under suitable metal-halogen exchange conditions with an appropriate solvent for an appropriate time and at an appropriate temperature, and then later reacted with an appropriate ketone VIII-2 for an appropriate time and at an appropriate temperature to provide a tertiary alcohol. In some embodiments, suitable metal-halogen exchange conditions include an organometallic reagent. In some embodiments, an appropriate solvent is THF. In some embodiments, the organometallic reagent is an alkyl lithium. In some embodiments, the alkyllithium is n-butyl lithium. In some embodiments, VIII-1 is cooled to about −78° C. before addition of an organometallic reagent. In some embodiments, VIII-1 is reacted for about one hour at about −78° C. before addition of the appropriate ketone VIII-2. In some embodiments, VIII-1 is reacted for about 2 hours after the addition of ketone VIII-2. In some embodiments, the appropriate temperature for reacting VIII-1 and ketone VIII-2 is about −78° C. In some embodiments, the tertiary alcohol is reacted under appropriate allylation conditions which include use of an allylating reagent and a Lewis acid, in an appropriate solvent for an appropriate time and at an appropriate temperature to form VIII-3.

In some embodiments, the appropriate allylating reagent is allyltrimethylsilane. In some embodiments, the appropriate Lewis acid is $BF_3$—$OEt_2$. In some embodiments, the appropriate solvent is DCM. In some embodiments, the appropriate temperature for the appropriate time is about −78° C. for about 1 hour. In some embodiments, the reaction is further warmed to about rt for about overnight. In some embodiments, the appropriate temperature for the appropriate time is about 0° C. for about overnight.

In some embodiments, VIII-3 is reacted under suitable oxidative cleavage conditions for the appropriate time period, in the appropriate solvent, and at the appropriate temperature to produce VIII-4. In some embodiments, oxidative cleavage conditions include the use of an osmium reagent and N-methylmorpholine N-oxide to form an intermediate diol. In some embodiments, the osmium reagent is $OsO_4$ or $K_2OsO_4 \cdot 2H_2O$. In some embodiments, an appropriate solvent is an ACN/water mixture. In some embodiments, an appropriate temperature for the appropriate time is about 0° C. to about rt for about overnight. In some embodiments, the diol is cleaved to form VIII-4 under the appropriate oxidative cleavage conditions for the appropriate time period, in the appropriate solvent, and at the appropriate temperature. In some embodiments, appropriate oxidative cleavage conditions include the use of $NaIO_4$. In some embodiments, an appropriate solvent is a THF/water mixture. In some embodiments, the appropriate temperature for the appropriate time is is about 0° C. to about rt for about overnight.

In some embodiments, VIII-4 is reduced to a primary alcohol under suitable reducing conditions, and then halogenated under suitable halogenation conditions to produce VIII-5. In some embodiments, suitable reducing conditions include the use of a borohydride reagent. In some embodiments, reducing conditions include the use of $NaBH_4$ in the appropriate solvent, at an appropriate temperature for the appropriate amount of time. In some embodiments, an appropriate solvent is THF. In some embodiments, an appropriate temperature for the appropriate time is about 0° C. for about one hour. In some embodiments, the reaction is warmed to about rt for about overnight. The alcohol is reacted under suitable halogenation conditions to produce an alkyl halide in some embodiments. In some embodiments, suitable halogenation conditions are bromination conditions that include use of $CBr_4$ in an appropriate solvent at an appropriate initial temperature followed by $PPh_3$ in the appropriate solvent, at an appropriate temperature for an appropriate time. In some embodiments, the appropriate solvent is a halogenated solvent, such as DCM. In some embodiments, an appropriate initial temperature is about 0° C. In some embodiments, an appropriate temperature and time after addition of $PPh_3$ is about 0° C. for about one hour. In some embodiments, an appropriate solvent for addition of $PPh_3$ is THF. In some embodiments, the reaction is further warmed to about rt for about overnight.

In some embodiments, VIII-5 is subjected to intramolecular alkylation conditions to form VIII-6. In some embodiments, intramolecular alkylation conditions include a suitable base. In some embodiments, the suitable base is lithium diisopropylamide in the appropriate solvent, at an appropriate temperature for an appropriate amount of time. In some embodiments, the appropriate solvent is a HMPA and THF mixture. In some embodiments, the appropriate temperature for the appropriate amount of time is about −78° C. for about 3 hours or about −78° C. to rt for about overnight.

Ester VIII-6 is reduced to an alcohol by suitable reduction conditions followed by oxidation to aldehyde VIII-7 by suitable oxidation conditions in some embodiments. In some embodiments, suitable reduction conditions include the use of DIBALH in an appropriate solvent at an appropriate temperature for an appropriate time. In some embodiments, the appropriate solvent is DCM. In some embodiments, the appropriate temperature for the appropriate time is about −78° C. for about one hour. In some embodiments, the reaction is further warmed to about rt for about two hours to produce an alcohol. In some embodiments, suitable oxidation conditions are chromium-based oxidations. In some embodiments, suitable oxidation conditions include the use of PCC in an appropriate solvent at an appropriate temperature for an appropriate time. In some embodiments, silica gel is added. In some embodiments, the appropriate solvent is DCM. In some embodiments, the appropriate temperature is about rt for about 2 hours. Alternatively in some embodiments, the oxidations conditions include the use of oxalyl chloride and DMSO with an amine base in an appropriate solvent at an appropriate temperature for an appropriate time. In some embodiments, the appropriate amine base is TEA. In some embodiments, the appropriate solvent is DCM. In some embodiments, the appropriate temperature for an appropriate amount of time is about −78° C. for about one hour.

In some embodiments, intermediates used in the preparation of compounds described herein are prepared as outlined in Scheme 9.

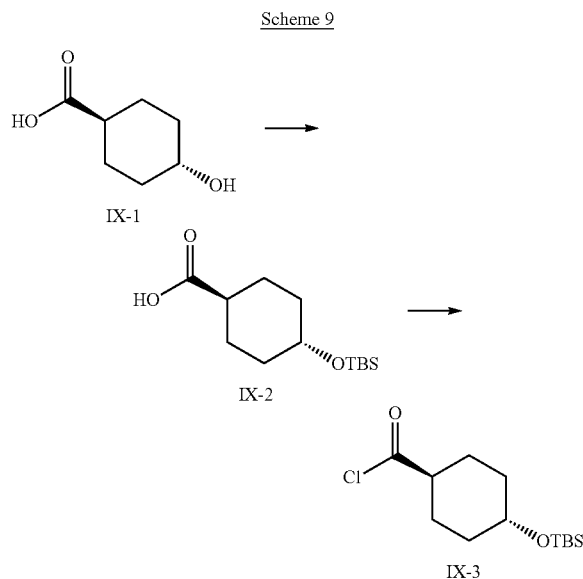

Scheme 9

In some embodiments, IX-1 is subjected to alcohol protection conditions to form a bis-silyl intermediate, followed by hydrolysis conditions to form IX-2. In some embodiments, the alcohol protection conditions include the use of TBSCl and an appropriate base at the appropriate temperature, in the appropriate solvent, and for an appropriate period of time. In some embodiments, the appropriate solvent is DMF. In some embodiments, the appropriate base is imidazole. In some embodiments, the appropriate temperature for the appropriate time is about rt for about 2 hours. In some embodiments, the intermediate silyl ester is subjected to hydrolysis conditions to form IX-2. In some embodiments, hydrolysis conditions include treatment with a base, at an appropriate temperature, in an appropriate solvent, and for an appropriate period of time. In some embodiments, the appropriate solvent is an EtOH, $H_2O$, THF mixture. In some embodiments, the appropriate base is $K_2CO_3$. In some embodiments, the appropriate temperature for the appropriate time is about rt for about 3 hours.

Compound IX-2 is converted to acid chloride IX-3 in some embodiments under chlorinating conditions. In some embodiments, chlorinating conditions include the use of (chloromethylene)dimethyliminium chloride and a base at a suitable temperature, in a suitable solvent. In some embodiments, the suitable base is anhydrous $K_2CO_3$. In some embodiments, the suitable temperature is about 0° C. In some embodiments, a suitable solvent is toluene. In some embodiments, IX-2 is added and the mixture stirred at a suitable temperature for a suitable time to produce IX-3. In some embodiments, the suitable temperature for the suitable time is about rt for about 0.5 to about one hour.

In some embodiments, compounds described herein are prepared as outlined in Scheme 10.

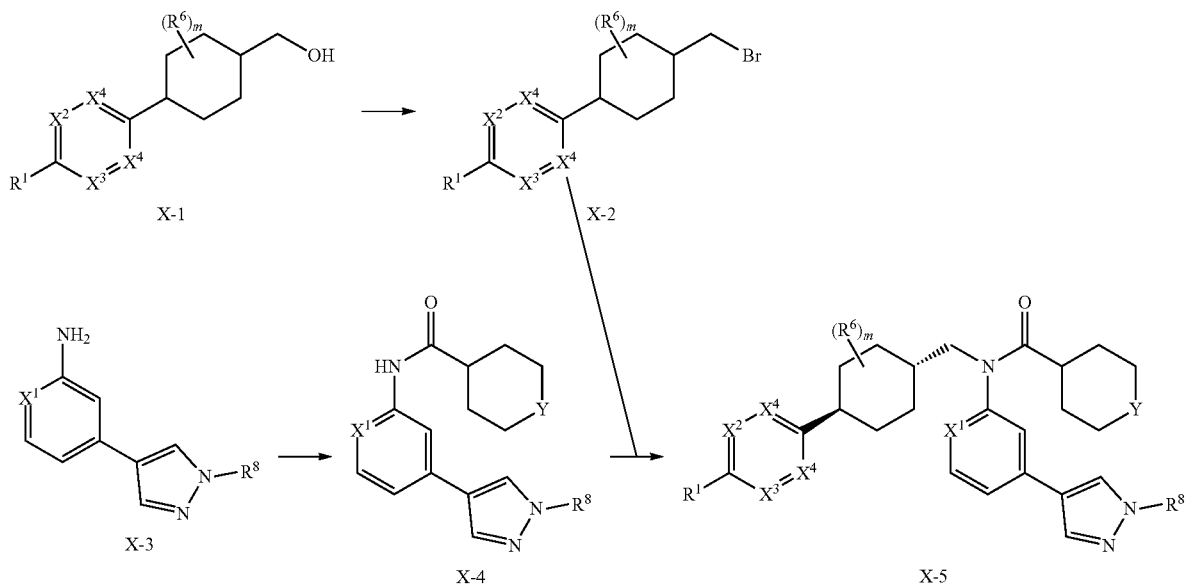

Scheme 10

In Scheme 10, substituents Y, $X^1$, $X^2$, $X^3$, $X^4$, $R^1$, $R^2$, $R^6$, $R^8$, and m are as described herein. In some embodiments, $X^2$ is C—$R^2$, $X^3$ is C—H, and each $X^4$ is C—H.

Alcohol X-1 is reacted under suitable halogenation conditions to produce an alkyl halide X-2 in some embodiments. In some embodiments, suitable halogenation conditions are bromination conditions including the use of CBr$_4$ in an appropriate solvent at an appropriate initial temperature followed by PPh$_3$ in the appropriate solvent, at an appropriate temperature for an appropriate time. In some embodiments, the appropriate solvent is a halogenated solvent, such as DCM. In some embodiments, an appropriate initial temperature is about 0° C. In some embodiments, an appropriate temperature and time after addition of PPh$_3$ is about 0° C. for about one hour. In some embodiments, the reaction is further warmed to about rt for about overnight.

In some embodiments, the acylation of amine X-3 with an acyl chloride affords compound X-4. Suitable acylation conditions include but are not limited to the use of a suitable base, such as pyridine in a suitable solvent, such as DCM or toluene at a suitable temperature, such as about 0° C. In some embodiments, an acyl chloride is added in an appropriate solvent at an appropriate temperature for an appropriate amount of time. In some embodiments, the appropriate solvent is toluene. In some embodiments, the appropriate temperature is about 0° C. then warming to rt for about overnight.

In some embodiments, compound X-5 is prepared from the N-alkylation of X-4 with bromide X-2 and a suitable base in suitable solvent, such as DMF, at a suitable temperature for a suitable amount of time. Suitable bases include NaH. In some embodiments, the compound X-4 is pretreated with the suitable base for an appropriate amount of time at an appropriate temperature, such as about two hours at about 0° C. to about rt, before the addition of bromide X-2. In some embodiments, the appropriate time and temperature after addition of bromide X-2 is about rt for about overnight. In some embodiments, Y contains a protected alcohol. In some embodiments, Y is protected with a silyl ether. In some embodiments, protecting groups are removed to produce a free alcohol using suitable deprotection conditions including an appropriate solvent, temperature and time to produce X-5. In some embodiments, suitable deprotection conditions include the use of fluoride reagents. In some embodiments, the fluoride reagent is NH$_4$F. In some embodiments, the appropriate solvent is methanol. In some embodiments, the appropriate time at the appropriate temperature is about overnight at about 60° C.

In some embodiments, compounds described herein are prepared as outlined in Scheme 11.

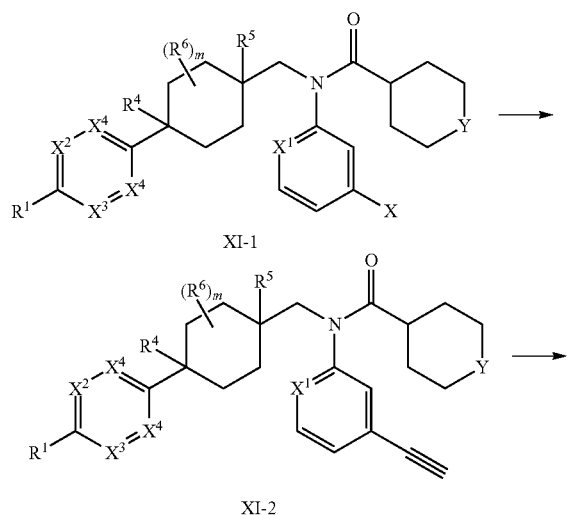

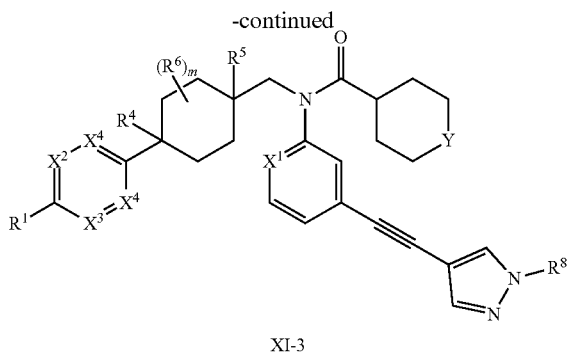

XI-3

In Scheme 11, substituents Y, X$^1$, X$^2$, X$^3$, X$^4$, R$^1$, R$^2$, R$^4$, R$^5$, R$^6$, R$^8$, and m are as described herein. In some embodiments, X$^2$ is C—R$^2$, X$^3$ is C—H, and each X$^4$ is C—H. In some embodiments, X is a suitable cross-coupling substituent. In some embodiments, X is a halide. In some embodiments, X is chloro, bromo, or iodo.

In some embodiments, compound XI-1 is reacted with a suitable acetylene source under suitable metal-catalyzed cross-coupling reaction conditions to provide XI-2. In some embodiments, suitable metal-catalyzed cross-coupling conditions include palladium. In some embodiments, a suitable acetylene source is trimethylsilylacetylene. In some embodiments, suitable palladium-catalyzed cross-coupling reaction conditions include Pd(PPh$_3$)$_2$Cl$_2$, a copper catalyst, with an appropriate base, for an appropriate time and at an appropriate temperature. In some embodiments, the copper catalyst is CuI. In some embodiments, the base is an amine base, such as TEA. In some embodiments, the appropriate time and appropriate temperature is about 6 hours at about 90° C. In some embodiments, the TMS-group is removed after the cross-coupling, under suitable deprotection conditions including an appropriate solvent, temperature and time to produce to form XI-2. In some embodiments, suitable deprotection conditions include the use of fluoride reagents. In some embodiments, the fluoride reagent is NH$_4$F. In some embodiments, the appropriate solvent is methanol. In some embodiments, the appropriate time is about one hour at about 60° C.

In some embodiments, acetylene XI-2 is reacted with a suitable heteroaromatic halide under suitable metal-catalyzed cross-coupling reaction conditions to provide XI-3. In some embodiments, suitable metal-catalyzed cross-coupling conditions include palladium. In some embodiments, a suitable heteroaromatic halide is a pyrazolyl halide. In some embodiments, the heteroaromatic halide is a heteroaromatic iodide. In some embodiments, suitable palladium-catalyzed cross-coupling reaction conditions include Pd(PPh$_3$)$_2$Cl$_2$, a copper catalyst, with an appropriate base, for an appropriate time and at an appropriate temperature. In some embodiments, the copper catalyst is CuI. In some embodiments, the base is an amine base, such as TEA. In some embodiments, the appropriate time and appropriate temperature is about one hour at about 80° C. to about 90° C. or about 70° C. to about 90° C.

In some embodiments, Y contains a protected alcohol. In some embodiments, Y is protected with a silyl ether. In some embodiments, protecting groups are removed to produce a free alcohol using suitable deprotection conditions including appropriate solvent, temperature and time to produce XI-3. In some embodiments, suitable deprotection conditions include the use of aqueous HCl. In some embodiments, the appropriate solvent is water, THF, methanol, or a combination of solvents. In some embodiments, the appropriate time at the appropriate temperature is about 30 min to about 1 hour at about 0° C. to about rt.

In some embodiments, compounds are prepared as described in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, 4 carbon atoms, 5 carbon atoms, 6 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect, the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers refers to a divalent alkyl radical. Any of the above mentioned monovalent alkyl groups may be an alkylene by abstraction of a second hydrogen atom from the alkyl. In some embodiments, an alkylene is a $C_1$-$C_6$alkylene. In other embodiments, an alkylene is a $C_1$-$C_4$alkylene. In certain embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises two carbon atoms (e.g., $C_2$ alkylene). In other embodiments, an alkylene comprises two to four carbon atoms (e.g., $C_2$-$C_4$ alkylene). Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R) =$CR_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=$CH_2$, —C(CH$_3$)=$CH_2$, —CH=CHCH$_3$, —C(CH$_3$)=CHCH$_3$, and —CH$_2$CH=CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$—C≡CCH$_2$CH$_3$, —CH$_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon or nitrogen atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycle includes cycloalkyl and aryl.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicyclo[1.1.1] pentyl. In some embodiments, a cycloalkyl is a $C_3$-$C_6$cycloalkyl. In some embodiments, a cycloalkyl is a monocyclic cycloalkyl. Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.1]heptanyl), norbornenyl, decalinyl, 7,7-dimethyl-bicyclo[2.2.1]heptanyl, and the like The term "halo" or, alternatively, "halogen" or "halide" means fluoro, chloro, bromo or iodo. In some embodiments, halo is fluoro, chloro, or bromo.

The term "haloalkyl" refers to an alkyl in which one or more hydrogen atoms are replaced by a halogen atom. In one aspect, a fluoroalkyl is a $C_1$-$C_6$fluoroalkyl.

The term "fluoroalkyl" refers to an alkyl in which one or more hydrogen atoms are replaced by a fluorine atom. In one aspect, a fluoroalkyl is a $C_1$-$C_6$fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heteroalkylene" refers refers to a divalent heteroalkyl radical.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. In some embodiments, heterocycles are monocyclic, bicyclic, polycyclic, spirocyclic or bridged compounds. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, alkenyl, alkynyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$($C_1$-$C_4$alkyl), —C(=O)NH$_2$, —C(=O)NH($C_1$-$C_4$alkyl), —C(=O)N($C_1$-$C_4$alkyl)$_2$, —S(=O)$_2$NH$_2$, —S(=O)$_2$NH ($C_1$-$C_4$alkyl), —S(=O)$_2$N($C_1$-$C_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —S$C_1$-$C_4$alkyl, —S(=O)$C_1$-$C_4$alkyl, and —S(=O)$_2$$C_1$-$C_4$alkyl. In some embodiments, optional substituents are independently selected from D, halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be affected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream.

In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

In some embodiments, a compound disclosed herein is formulated in such a manner that delivery of the compound to a particular region of the gastrointestinal tract is achieved.

For example, a compound disclosed herein is formulated for oral delivery with bioadhesive polymers, pH-sensitive coatings, time dependent, biodegradable polymers, microflora activated systems, and the like, in order to effect delivering of the compound to a particular region of the gastrointestinal tract.

In some embodiments, a compound disclosed herein is formulated to provide a controlled release of the compound. Controlled release refers to the release of the compound described herein from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

Approaches to deliver the intact therapeutic compound to the particular regions of the gastrointestinal tract (e.g. such as the colon), include:

(i) Coating with polymers: The intact molecule can be delivered to the colon without absorbing at the upper part of the intestine by coating of the drug molecule with the suitable polymers, which degrade only in the colon.

(ii) Coating with pH-sensitive polymers: The majority of enteric and colon targeted delivery systems are based on the coating of tablets or pellets, which are filled into conventional hard gelatin capsules. Most commonly used pH-dependent coating polymers are methacrylic acid copolymers, commonly known as Eudragit® S, more specifically Eudragit® L and Eudragit® S. Eudragit® L100 and S 100 are copolymers of methacrylic acid and methyl methacrylate.

(iii) Coating with biodegradable polymers;
(iv) Embedding in matrices;
(v) Embedding in biodegradable matrices and hydrogels;
(vi) Embedding in pH-sensitive matrices;
(vii) Timed release systems;
(viii) Redox-sensitive polymers;
(ix) Bioadhesive systems;
(x) Coating with microparticles;
(xi) Osmotic controlled drug delivery;

Another approach towards colon-targeted drug delivery or controlled-release systems includes embedding the drug in polymer matrices to trap it and release it in the colon. These matrices can be pH-sensitive or biodegradable. Matrix-Based Systems, such as multi-matrix (MMX)-based delayed-release tablets, ensure the drug release in the colon.

Additional pharmaceutical approaches to targeted delivery of therapeutics to particular regions of the gastrointestinal tract are known. Chourasia M K, Jain S K, Pharmaceutical approaches to colon targeted drug delivery systems. J Pharm Pharm Sci. 2003 January-April; 6(1):33-66. Patel M, Shah T, Amin A. Therapeutic opportunities in colon-specific drug-delivery systems Crit Rev Ther Drug Carrier Syst. 2007; 24(2):147-202. Kumar P, Mishra B. Colon targeted drug delivery systems—an overview. Curr Drug Deliv. 2008 July; 5(3):186-98. Van den Mooter G. Colon drug delivery. Expert Opin Drug Deliv. 2006 January; 3(1): 111-25. Seth Amidon, Jack E. Brown, and Vivek S. Dave, Colon-Targeted Oral Drug Delivery Systems: Design Trends and Approaches, AAPS PharmSciTech. 2015 August; 16(4): 731-741.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from administration of a FXR agonist.

Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

Disclosed herein, are methods of administering a FXR agonist in combination with an additional therapeutic agent. In some embodiments, the additional therapeutic agent comprises a therapeutic agent for treatment of diabetes or diabetes related disorder or conditions, alcoholic or non-alcoholic liver disease, inflammation related intestinal conditions, or cell proliferative disorders.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments, wherein the patient's condition does not improve, upon the doctor's discretion, the compounds are administered chronically, that is, for an extended period of time, including throughout the duration of the patient's life in order to ameliorate or otherwise control or limit the symptoms of the patient's disease or condition.

In certain embodiments, wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt thereof, is co-administered with a second therapeutic agent, wherein the compound described herein, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, a FXR agonist is administered in combination with an additional therapeutic agent for the treatment of diabetes or diabetes related disorder or conditions.

In some instances, the additional therapeutic agent comprises a statin, an insulin sensitizing drug, an insulin secretagogue, an alpha-glucosidase inhibitor, a GLP agonist, a DPP-4 inhibitor (such as sitagliptin, vildagliptin, saxagliptin, linagliptin, anaglptin, teneligliptin, alogliptin, gemigleptin, or dutoglpitin), a catecholamine (such as epinephrine, norepinephrine, or dopamine), peroxisome proliferator-activated receptor (PPAR)-gamma agonist (e.g., a thiazolidinedione (TZD) [such as pioglitazone, rosiglitazone, rivoglitazone, or troglitazone], aleglitazar, farglitazar, muraglitazar, or tesaglitazar), or a combination thereof.

In some cases, the statin is a HMG-CoA reductase inhibitor. In other instances, additional therapeutic agents include fish oil, fibrate, vitamins such as niacin, retinoic acid (e.g., 9 cis-retinoic acid), nicotinamide ribonucleoside or its analogs thereof, or combinations thereof. In some instances, nicotinamide ribonucleoside or its analogs thereof, which promote $NAD^+$ production, a substrate for many enzymatic reactions including p450s which is a target for FXR (e.g., see Yang et al., *J. Med. Chem.* 50:6458-61, 2007).

In some embodiments, a FXR agonist is administered in combination with an additional therapeutic agent such as a statin, an insulin sensitizing drug, an insulin secretagogue, an alpha-glucosidase inhibitor, a GLP agonist, a DPP-4 inhibitor (such as sitagliptin, vildagliptin, saxagliptin, linagliptin, anaglptin, teneligliptin, alogliptin, gemigleptin, or dutoglpitin), a catecholamine (such as epinephrine, norepinephrine, or dopamine), peroxisome proliferator-activated receptor (PPAR)-gamma agonist (e.g., a thiazolidinedione (TZD) [such as pioglitazone, rosiglitazone, rivoglitazone, or troglitazone], aleglitazar, farglitazar, muraglitazar, or tesaglitazar), or combinations thereof, for the treatment of diabetes or diabetes related disorder or conditions. In some embodiments, a FXR agonist is administered in combination with an additional therapeutic agent such as fish oil, fibrate, vitamins such as niacin, retinoic acid (e.g., 9 cis-retinoic acid), nicotinamide ribonucleoside or its analogs thereof, or combinations thereof, for the treatment of diabetes or diabetes related disorder or conditions.

In some embodiments, a FXR agonist is administered in combination with a statin such as a HMG-CoA reductase inhibitor, fish oil, fibrate, niacin or a combination thereof, for the treatment of dyslipidemia.

In additional embodiments, a FXR agonist is administered in combination with a vitamin such as retinoic acid for the treatment of diabetes and diabetes related disorder or condition such as lowering elevated body weight and/or lowering elevated blood glucose from food intake.

In some embodiments, the farnesoid X receptor agonist is administered with at least one additional therapy. In some embodiments, the at least one additional therapy is a glucose-lowering agent. In some embodiments, the at least one additional therapy is an anti-obesity agent. In some embodiments, the at least one additional therapy is selected from among a peroxisome proliferator activated receptor (PPAR) agonist (gamma, dual, or pan), a dipeptidyl peptidase (IV) inhibitor, a glucagon-like peptide-1 (GLP-I) analog, insulin or an insulin analog, an insulin secretagogue, a sodium glucose co-transporter 2 (SGLT2) inhibitor, a glucophage, a human amylin analog, a biguanide, an alpha-glucosidase inhibitor, a meglitinide, a thiazolidinedione, and sulfonylurea. In some embodiments, the at least one additional therapy is metformin, sitagliptin, saxaglitpin, repaglinide, nateglinide, exenatide, liraglutide, insulin lispro, insulin aspart, insulin glargine, insulin detemir, insulin isophane, and glucagon-like peptide 1, or any combination thereof. In some embodiments, the at least one additional therapy is a lipid-lowering agent. In certain embodiments, the at least one additional therapy is administered at the same time as the farnesoid X receptor agonist. In certain embodiments, the at least one additional therapy is administered less frequently than the farnesoid X receptor agonist. In certain embodiments, the at least one additional therapy is administered more frequently than the farnesoid X receptor agonist. In certain embodiments, the at least one additional therapy is administered prior to administration of the farnesoid X receptor agonist. In certain embodiments, the at least one additional therapy is administered after administration of the farnesoid X receptor agonist.

In some embodiments, a compound described herein, or a pharmaceutically acceptable salt thereof, is administered in combination with chemotherapy, anti-inflammatory agents, radiation therapy, monoclonal antibodies, or combinations thereof.

In some embodiments, a FXR agonist is administered in combination with an additional therapeutic agent for the treatment of alcoholic or non-alcoholic liver disease. In some embodiments, the additional therapeutic agent includes antioxidant, corticosteroid, anti-tumor necrosis factor (TNF) or a combination thereof.

In some embodiments, a FXR agonist is administered in combination with an additional therapeutic agent such as antioxidant, corticosteroid, anti-tumor necrosis factor (TNF), or a combination thereof, for the treatment of alcoholic or non-alcoholic liver disease.

In some embodiments, a FXR agonist is administered in combination with an antioxidant, a vitamin precursor, a corticosteroid, an anti-tumor necrosis factor (TNF), or a combination thereof, for the treatment of alcoholic or non-alcoholic liver disease.

In some embodiments, a FXR agonist is administered in combination with an additional therapeutic agent for the treatment of inflammation related intestinal conditions.

In some instances, the additional therapeutic agent comprises an antibiotic (such as metronidazole, vancomycin, and/or fidaxomicin), a corticosteroid, or an additional anti-inflammatory or immuno-modulatory therapy.

In some instances, a FXR agonist is administered in combination with an additional therapeutic agent such as an antibiotic, a corticosteroid, or an additional anti-inflammatory or immuno-modulatory therapy, for the treatment of inflammation related intestinal conditions.

In some cases, a FXR agonist is administered in combination with metronidazole, vancomycin, fidaxomicin, corticosteroid, or combinations thereof, for the treatment of inflammation related intestinal conditions.

As discussed above, inflammation is sometimes associated with pseudomembranous colitis. In some instances, pseudomembranous colitis is associated with bacterial overgrowth (such as *C. dificile* overgrowth). In some embodiments, a FXR agonist is administered in combination with an antibiotic such as metronidazole, vancomycin, fidaxomicin, or a combination thereof, for the treatment of inflammation associated with bacterial overgrowth (e.g., pseudomembranous colitis).

In some embodiments, the FXR agonist is administered in combination with an additional therapeutic agent for the treatment of cell proliferative disorders. In some embodiments, the additional therapeutic agent includes a chemotherapeutic, a biologic (e.g., antibody, for example bevacizumab, cetuximab, or panitumumab), a radiotherapeutic (e.g., FOLFOX, FOLFIRI, CapeOX, 5-FU, leucovorin, regorafenib, irinotecan, or oxaliplatin), or combinations thereof.

In some embodiments, the FXR agonist is administered in combination with an additional therapeutic agent for the treatment of primary biliary cirrhosis. In some embodiments, the additional therapeutic agent includes ursodeoxycholic acid (UDCA).

In some embodiments, a FXR agonist is administered in combination with an additional therapeutic agent such as a chemotherapeutic, a biologic, a radiotherapeutic, or combinations thereof, for the treatment of a cell proliferative disorder. In some instances, a FXR agonist is administered in combination with an antibody (e.g., bevacizumab, cetuximab, or panitumumab), chemotherapeutic, FOLFOX, FOLFIRI, CapeOX, 5-FU, leucovorin, regorafenib, irinotecan, oxaliplatin, or combinations thereof, for the treatment of a cell proliferative disorder.

EXAMPLES

The following examples are provided for illustrative purposes only and not to limit the scope of the claims provided herein.

As used above, and throughout the description of the invention, the following abbreviations, unless otherwise indicated, shall be understood to have the following meanings:

ACN or MeCN acetonitrile
AcOH acetic acid
Ac acetyl
BINAP 2,2'-bis(diphenylphosphino)-1,1'-binaphthalene
Bn benzyl
BOC or Boc tert-butyl carbamate
t-Bu tert-butyl
Cy cyclohexyl
DBA or dba dibenzylideneacetone
DCE dichloroethane (ClCH$_2$CH$_2$Cl)
DCM dichloromethane (CH$_2$Cl$_2$)
DIPEA or DIEA diisopropylethylamine
DMAP 4-(N,N-dimethylamino)pyridine
DME 1,2-dimethoxyethane
DMF N,N-dimethylformamide
DMA N,N-dimethylacetamide
DMSO dimethylsulfoxide
Dppf or dppf 1,1'-bis(diphenylphosphino)ferrocene
EEDQ 2-Ethoxy-1-ethoxycarbonyl-1,2-dihydroquinoline
eq equivalent(s)
Et ethyl
Et$_2$O diethyl ether
EtOH ethanol
EtOAc ethyl acetate
HATU 1-[bis(dimethylamino)methylene]-1H-1,2,3-triazolo[4,5-b]pyridinium 3-oxid hexafluorophosphate
HMPA hexamethylphosphoramide
HPLC high performance liquid chromatography
KHMDS potassium bis(trimethylsilyl)amide
NaHMDS sodium bis(trimethylsilyl)amide
LiHMDS lithium bis(trimethylsilyl)amide
LAH lithium aluminum anhydride
LCMS liquid chromatography mass spectrometry Me methyl
MeOH methanol
MS mass spectroscopy
Ms mesyl
NBS N-bromosuccinimide
NMM N-methyl-morpholine
NMP N-methyl-pyrrolidin-2-one
NMR nuclear magnetic resonance
PCC pyridinium chlorochromate
Ph phenyl
PPTS pyridium p-toluenesulfonate
iPr/i-Pr iso-propyl
TBS tert-butyldimethylsilyl
RP-HPLC reverse phase-high pressure liquid chromatography
TFA trifluoroacetic acid
TEA triethylamine
THF tetrahydrofuran
TLC thin layer chromatography Intermediate 1 trans-4-(4-Methoxy-3-methylphenyl)cyclohexanecarbaldehyde

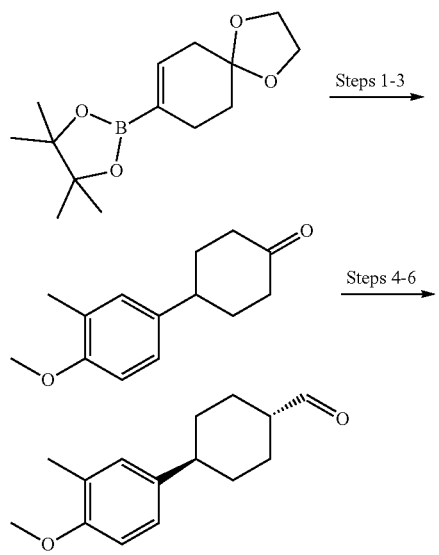

Step 1: 8-(4-Methoxy-3-methylphenyl)-1,4-dioxaspiro[4.5]dec-7-ene

A mixture of 1,4-dioxa-spiro[4,5]dec-7-en-8-boronic acid pinacol ester (25.0 g, 93.9 mmol), 4-iodo-2-methylanisole (28.0 g, 113 mmol), 1,1'-bis(diphenylphosphino)ferrocene dichlorlopalladium(II) (1.38 g, 1.89 mmol), dioxane (470 mL) and 1 M $Na_2CO_3$ (282 mL, 282 mmol) was degassed with 3 vacuum/$N_2$ cycles, stirred at 50° C. for 2.5 h, and then allowed to cool to rt. The mixture was diluted with EtOAc (500 mL) and washed with sat'd $NaHCO_3$ (2×500 mL). The aqueous layers were back extracted with EtOAc (200 mL). The combined EtOAc extracts were dried ($Na_2SO_4$), filtered, concentrated and purified by silica gel chromatography (0-5% EtOAc in hexanes) to give 8-(4-methoxy-3-methylphenyl)-1,4-dioxaspiro[4.5]dec-7-ene (19.9 g, 81%). $^1$H NMR (400 MHz, DMSO-$d_6$): δ 7.21-7.16 (m, 2H), 6.85 (d, 1H), 5.89-5.84 (m, 1H), 3.90 (s, 4H), 3.76 (s, 3H), 2.52-2.47 (m, 2H), 2.32 (br s, 2H), 2.13 (s, 3H), 1.77 (t, 2H); LCMS: 261.1 [M+H]$^+$.

Step 2: 8-(4-Methoxy-3-methylphenyl)-1,4-dioxaspiro[4.5]decane

Palladium on carbon (10 wt %, 8.08 g, 7.59 mmol) was added to a solution of 8-(4-methoxy-3-methylphenyl)-1,4-dioxaspiro[4.5]dec-7-ene (19.8 g, 76.1 mmol) in EtOAc (300 mL) at rt under $N_2$. The $N_2$ inlet was replaced with a balloon of $H_2$. The reaction was stirred for 4.5 h, filtered through Celite with EtOAc, and then concentrated to give 8-(4-methoxy-3-methylphenyl)-1,4-dioxaspiro[4.5]decane (18.2 g; contains 13% ketone) as a white solid. $^1$H NMR (400 MHz, DMSO-$d_6$): δ 7.00-6.95 (m, 2H), 6.81 (d, 1H), 3.91-3.84 (m, 4H), 3.73 (s, 3H), 2.49-2.42 (m, 1H), 2.11 (s, 3H), 1.76-1.68 (m, 4H), 1.67-1.55 (m, 4H); LCMS: 263.1 [M+H]$^+$.

Step 3: 4-(4-Methoxy-3-methylphenyl)cyclohexanone

Formic acid (96%, 14 mL, 356 mmol) and then water (2.20 mL, 122 mmol) were added to a solution of 8-(4-methoxy-3-methylphenyl)-1,4-dioxaspiro[4.5]decane (18.2 g) in toluene (60 mL) at rt under $N_2$. The reaction was heated at 120° C. for 4 h, allowed to cool to rt, and then poured into 200 mL $H_2O$ and 200 mL toluene. The toluene layer was washed with 200 mL $H_2O$ and then 200 mL sat'd $NaHCO_3$. The aqueous layers were back extracted with 100 mL toluene. The combined toluene extracts were dried ($Na_2SO_4$), filtered and concentrated to give 4-(4-methoxy-3-methylphenyl)cyclohexanone (15.5 g, 88% over 2 steps) as a white solid. $^1$H NMR (400 MHz, DMSO-$d_6$): δ 7.08-7.03 (m, 2H), 6.84 (d, 1H), 3.74 (s, 3H), 3.00-2.91 (m, 1H), 2.61-2.51 (m, 2H), 2.28-2.20 (m, 2H), 2.12 (s, 3H), 2.06-1.98 (m, 2H), 1.88-1.76 (m, 2H); LCMS: 219.0 [M+H]$^+$.

Step 4: 1-Methoxy-4-(4-(methoxymethylene)cyclohexyl)-2-methylbenzene

A mixture of (methoxymethyl)triphenylphosphonium chloride (35.74 g, 104.3 mmol) and THF (260 mL) under $N_2$ was cooled to −2.2° C. in an ice/brine bath. Sodium bis(trimethylsilyl)amide solution (2 M in THF, 50 mL, 100 mmol) was added dropwise via addition funnel over 12 min (internal temp ≤0.6° C.) with THF rinsing (5 mL). The reaction was stirred for 30 min, and then 4-(4-methoxy-3-methylphenyl)cyclohexanone (14.5 g, 66.6 mmol) was added portionwise over 5 min (exotherm to 7.3° C.). Residual cyclohexanone was rinsed into the reaction with THF (20 mL). The reaction was stirred at 0° C. for 25 min, and then poured into 400 mL $H_2O$ and 400 mL toluene. The toluene layer was washed with 400 mL $H_2O$, dried ($Na_2SO_4$), filtered, concentrated and purified by silica gel chromatography (0-5% EtOAc in hexanes) to give 1-methoxy-4-(4-(methoxymethylene)cylcohexyl)-2-methylbenzene (15.6 g, 95%) as a pale gold oil. $^1$H NMR (400 MHz, DMSO-$d_6$): δ 6.99-6.94 (m, 2H), 6.80 (d, 1H), 5.87 (s, 1H), 3.73 (s, 3H), 3.48 (s, 3H), 2.78-2.71 (m, 1H), 2.56-2.44 (m, 1H), 2.10 (s, 3H), 2.17-2.09 (m, 1H), 2.01-1.91 (m, 1H), 1.83-1.73 (m, 2H), 1.72-1.63 (m, 1H), 1.38-1.23 (m, 2H); LCMS: 247.1 [M+H]$^+$.

Step 5: 4-(4-Methoxy-3-methylphenyl)cyclohexanecarbaldehyde

Formic acid (96%, 12.5 mL, 331 mmol) and then water (2.5 mL, 139 mmol) were added to a solution of 1-methoxy- 4-(4-(methoxymethylene)cylcohexyl)-2-methylbenzene (16.05 g, 65.15 mmol) in toluene (130 mL) under $N_2$. The reaction was heated at 120° C. for 2 h, allowed to cool to rt, and then poured into 350 mL EtOAc and 350 mL $H_2O$. The organic layer was washed with 350 mL $H_2O$, dried ($Na_2SO_4$), filtered and concentrated to give 4-(4-methoxy-3-methylphenyl)cyclohexanecarbaldehyde (15.05 g) as a 1:1 mixture of stereoisomers.

Step 6: trans-4-(4-Methoxy-3-methylphenyl)cyclohexanecarbaldehyde

Aqueous sodium hydroxide (3.2 M, 31 mL, 99 mmol) was added to the crude mixture from Step 5 (14.68 g, 63.19 mmoL), toluene (60 mL) and ethanol (250 mL) at rt. The reaction was stirred for 5.5 hours (equilibration monitored by NMR) and then poured into 350 mL $H_2O$ and 350 mL EtOAc. The organic layer was washed with 350 mL $H_2O$, and the aqueous layers were back extracted with 150 mL EtOAc. The combined extracts were dried ($Na_2SO_4$), filtered, concentrated and purified by silica gel chromatography (0-5% EtOAc in hexanes) to give trans-4-(4-methoxy-3-methylphenyl)cyclohexanecarbaldehyde (10.17 g, 69%) as a white solid. $^1$H NMR (400 MHz, DMSO-$d_6$): δ 9.60 (s, 1H), 7.01-6.97 (m, 2H), 6.82 (d, 1H), 3.74 (s, 3H), 2.41-2.27 (m, 2H), 2.12 (s, 3H), 2.03-1.96 (m, 2H), 1.87-1.80 (m, 2H), 1.51-1.39 (m, 2H), 1.35-1.23 (m, 2H); LCMS: 233.0 $[M+H]^+$.

The Intermediates below were synthesized from the appropriate aryl halide (SM or Intermediate) following the procedures described for Intermediate 1.

| Int | Structure | Name | $[M + H]^+$ |
|---|---|---|---|
| 1.01 | 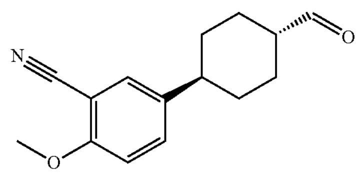 [SMILES: COc1ccc([C@H]2CC[C@H](C=O)CC2)cc1C#N] | 5-(trans-4-Formylcyclohexyl)-2-methoxybenzonitrile | 244.1 |
| 1.02 | 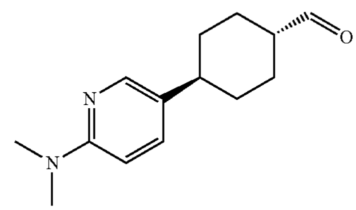 [SMILES: CN(C)c1ccc([C@H]2CC[C@H](C=O)CC2)cn1] | trans-4-(6-(Dimethylamino)pyridin-3-yl)cyclohexanecarbaldehyde | 233.2 |
| 1.03[6,10] | 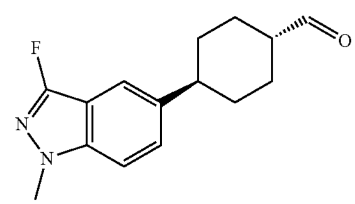 [SMILES: Cn1nc(F)c2cc([C@H]3CC[C@H](C=O)CC3)ccc21] | trans-4-(3-Fluoro-1-methyl-1H-indazol-5-yl)cyclohexanecarbaldehyde | 261.2 |
| 1.04[1,8,10,11,12] | 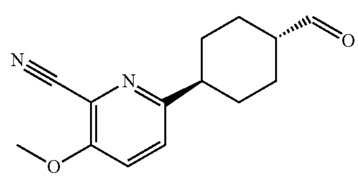 [SMILES: COc1ccc([C@H]2CC[C@H](C=O)CC2)nc1C#N] | 6-(trans-4-Formylcyclohexyl)-3-methoxypicolinonitrile | 245.4 |
| 1.05[10,11,12] | 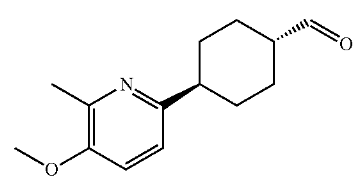 [SMILES: COc1ccc([C@H]2CC[C@H](C=O)CC2)nc1C] | trans-4-(5-Methoxy-6-methylpyridin-2-yl)cyclohexanecarbaldehyde | 234.4 |
| 1.06[9,10,11] | 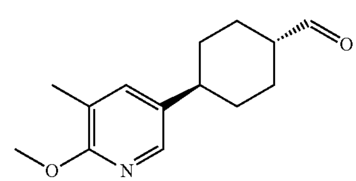 [SMILES: COc1ncc([C@H]2CC[C@H](C=O)CC2)cc1C] | trans-4-(6-Methoxy-5-methylpyridin-3-yl)cyclohexanecarbaldehyde | 234.1 |

| Int | Structure | Name | [M + H]⁺ |
|---|---|---|---|
| 1.07[2,9,10,11,12] | 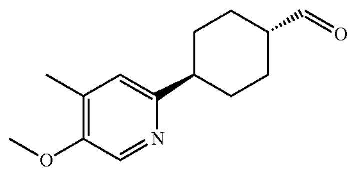 [SMILES: COc1cnc([C@H]2CC[C@H](C=O)CC2)cc1C] | trans-4-(5-Methoxy-4-methylpyridin-2-yl)cyclohexanecarbaldehyde | 234.2 |
| 1.08[3,7,10] | 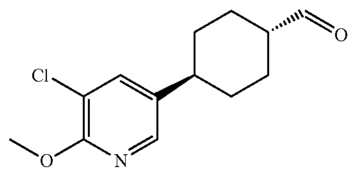 [SMILES: COc1ncc([C@H]2CC[C@H](C=O)CC2)cc1Cl] | trans-4-(5-Chloro-6-methoxypyridin-3-yl)cyclohexanecarbaldehyde | 254.4 |
| 1.09[4,9,10,11,12] | 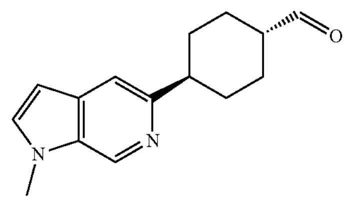 [SMILES: Cn1ccc2cc([C@H]3CC[C@H](C=O)CC3)ncc21] | trans-4-(1-Methyl-1H-pyrrolo[2,3-c]pyridin-5-yl)cyclohexanecarbaldehyde | 243.2 |
| 1.10[10,11] | 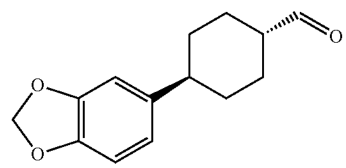 [SMILES: O=C[C@H]1CC[C@H](c2ccc3c(c2)OCO3)CC1] | trans-4-(Benzo[d][1,3]dioxol-5-yl)cyclohexanecarbaldehyde | 233.0 |
| 1.11[5,10,11] | 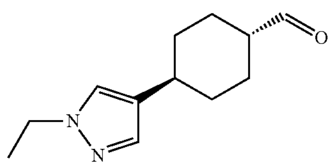 | trans-4-(1-Ethyl-1H-pyrazol-4-yl)cyclohexanecarbaldehyde | 207.2 |

Alternate conditions:

Step 1:

[1] EtOH, DME, 100° C., 5 h;

[2] EtOH, dioxane, 100° C., overnight;

[3] Cs$_2$CO$_3$, dioxane, 100° C., 6 h;

[4] Pd(PPh$_3$)$_4$, 100° C., 5 h;

[5] Pd(PPh$_3$)$_4$, CH$_3$CN/H$_2$O, reflux, overnight;

Step 2:

[6] MeOH;

[7] HCl, EtOAc;

Step 3:

[8] PPTS, acetone, H$_2$O, 60° C. 10 h;

[9] 3M HCl, THF, 60° C., 3 h to overnight;

Step 4:

[10] LiHMDS (1M THF), 0° C. or rt, 0.5-2 h;

Step 5:

[11] 3M HCl, THF, rt or 60° C., 1-6 h;

Step 6:

[12] NaOMe, MeOH, rt, 4 h to overnight.

Intermediate 2 trans-4-(3-Chloro-4-methoxyphenyl)cyclohexanecarbaldehyde

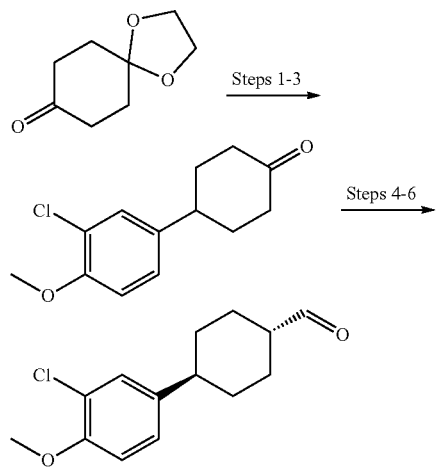

Step 1: 8-(3-Chloro-4-methoxyphenyl)-1,4-dioxaspiro[4.5]decan-8-ol

To a 3-necked round bottom flask was added 4-bromo-2-chloro-1-methoxy-benzene (45.00 g, 203.18 mmol) and THF (450 mL), n-Butyllithium (2.5 M in hexanes, 90.21 mL, 1.11 eq) was added at −78° C. The mixture was stirred for 2 h at −78° C. A solution of 1,4-dioxaspiro[4.5]decan-8-one (34.91 g, 223.50 mmol) in THF (90 mL) was added dropwise to the reaction mixture. The resulting mixture was stirred for 3 h at −78° C. The reaction was quenched with aqueous NH$_4$Cl (100 mL) and extracted with EtOAc (500 mL). The organic layer was dried (Na$_2$SO$_4$), filtered and concentrated. The residue was washed with hexanes (350 mL), filtered and dried under high vacuum. The solid was triturated with hexanes (15 mL), filtered and dried under high vacuum to give 8-(3-chloro-4-methoxy-phenyl)-1,4-dioxaspiro[4.5]decan-8-ol (37 g, 61%) as a white solid. $^1$H NMR (400 MHz, CDCl$_3$): δ 7.31 (d, 1H), 7.29 (dd, 1H), 7.10 (d, 1H), 3.90-3.92 (m, 4H), 3.89 (s, 3H), 1.99-2.02 (m, 4H), 1.70-1.73 (m, 4H); LCMS: 281.2 [M-OH]+.

Step 2: 8-(3-Chloro-4-methoxyphenyl)-1,4-dioxaspiro[4.5]decane

A solution of triethylsilane (19.26 g, 165.6 mmol), TFA (25.18 g, 220.8 mmol), and DCM (100 mL) was added dropwise to a solution of 8-(3-chloro-4-methoxyphenyl)-1,4-dioxaspiro[4.5]decan-8-ol (31.0 g, 110.4 mmol) and DCM (200 mL) at 0° C. The reaction mixture was stirred at rt overnight and then cooled to 0° C. The pH was adjusted to ~8 with aqueous NaHCO$_3$ and the mixture was extracted with DCM (2×100 mL). The organic layer was dried (Na$_2$SO$_4$), filtered, and concentrated to dryness to give 8-(3-chloro-4-methoxyphenyl)-1,4-dioxaspiro[4.5]decane, containing a small amount of 8-(3-chloro-4-methoxyphenyl)-1,4-dioxaspiro[4.5]dec-7-ene, (38 g, crude) as a yellow oil. LCMS: 283.1 [M+H]+.

Step 3: 4-(3-Chloro-4-methoxyphenyl)cyclohexanone 8-(3-chloro-4-methoxyphenyl)-1,4-dioxaspiro[4.5]decane (38.0 g, 134 mmol), formic acid (32.3 g, 672 mmol), H$_2$O (4.84 g, 269 mmol), and toluene (400 mL) was degassed with 3 vacuum/N$_2$ cycles, stirred at 130° C. overnight and then washed with H$_2$O (200 mL) and sat'd NaHCO$_3$ (200 mL). The combined aqueous layers were extracted with toluene (300 mL). The organic layer was dried (Na$_2$SO$_4$), filtered, and concentrated to dryness. The residue was triturated (PE:EtOAc=10:1, 80 mL) to give 4-(3-chloro-4-methoxyphenyl)cyclohexanone, containing a small amount of 3'-chloro-4'-methoxy-5,6-dihydro-[1,1'-biphenyl]-4(3H)-one, (20 g, 54%) as a light yellow solid. This solid (5.00 g, 21.12 mmol) was added to a mixture of Pd/C (10 wt. %, 820 mg, 0.77 mmol), HCl (12 M, 1.00 mL), and EtOAc (100 mL). The resulting mixture was degassed with 3 vacuum/H$_2$ cycles, stirred at rt for 30 min under H$_2$ (15 psi), filtered and then diluted with EtOAc (50 mL). The mixture was washed water (100 mL) and washed with sat'd NaHCO$_3$ (100 mL). The aqueous phase was extracted with EtOAc (100 mL). The combined organic layers were dried (Na$_2$SO$_4$), filtered, and concentrated to dryness to give 4-(3-chloro-4-methoxyphenyl)cyclohexanone (4.60 g, 84%) as a yellow solid. $^1$H NMR (400 MHz, CDCl$_3$): δ 7.24 (d, 1H), 7.09 (dd, 1H), 6.88 (d, 1H), 3.90 (s, 3H), 2.88-3.05 (m, 1H), 2.44-2.54 (m, 4H), 2.12-2.25 (m, 2H), 1.79-1.96 (m, 2H); LCMS: 239.1 [M+H]+.

Step 4: 2-Chloro-1-methoxy-4-(4-(methoxymethylene)cyclohexyl)benzene

Lithium bis(trimethylsilyl)amide (1 M, 36 mL) was added dropwise to a mixture of methoxymethyl(triphenyl)phosphonium chloride (12.24 g, 35.71 mmol) and THF (80 mL) at 0° C. The mixture was stirred for 2 h at 0° C. A solution of 4-(3-chloro-4-methoxy-phenyl)cyclohexanone (5.50 g, 23.04 mmol) in THF (20 mL) was added dropwise at 0° C. The resulting mixture was stirred for 3 h at 0° C. The reaction mixture was quenched by H$_2$O (100 mL) and extracted with EtOAc (3×100 mL). The combined organic layers were washed with brine (200 mL), dried (Na$_2$SO$_4$), filtered, concentrated, and purified by silica gel chromatography (petroleum ether/ethyl acetate=20:1) to give 2-chloro-1-methoxy-4-(4-(methoxymethylene)cyclohexyl)benzene (5 g, 77%) as yellow oil. LCMS: 267.1 [M+H]+.

Step 5: 4-(3-Chloro-4-methoxyphenyl)cyclohexanecarbaldehyde

A mixture of 2-chloro-1-methoxy-4-(4-(methoxymethylene)cyclohexyl)benzene (5.00 g, 18.74 mmol), formic acid (4.50 g, 93.7 mmol), H$_2$O (675.5 mg, 37.48 mmol), and toluene (100 mL) was degassed with 3 vacuum/N$_2$ cycles, stirred at 130° C. overnight, allowed to cool to rt, and then washed with H$_2$O (200 mL), and washed with sat'd NaHCO$_3$ (200 mL). The combined aqueous layers were extracted with toluene (300 mL). The organic layer was dried (Na$_2$SO$_4$), filtered, and concentrated to dryness to give 4-(3-chloro-4-methoxy-phenyl)cyclohexanecarbaldehyde (5.60 g, crude), a mixture of cis/trans isomers, as a yellow oil.

Step 6: trans-4-(3-Chloro-4-methoxyphenyl)cyclohexanecarbaldehyde

A solution of NaOH (992.6 mg, 24.82 mmol) in H$_2$O (12 mL) was added to the crude mixture from Step 5 (5.60 g, 15.51 mmol), EtOH (90 mL), and toluene (15 mL). The mixture was stirred at rt overnight, quenched with H₂O (100 mL), and then extracted with EtOAc (3×100 mL). The combined organic layers were washed by brine (200 mL), dried (Na₂SO₄), filtered and concentrated to dryness to give a residue. The residue was purified by silica gel chromatography (petroleum ether/ethyl acetate=20:1) and then triturated with MTBE (20 mL) to give trans-4-(3-chloro-4-methoxyphenyl)cyclohexanecarbaldehyde (1.96 g, 49%) as a white solid. ¹H NMR (400 MHz, DMSO-d6): δ 9.60 (s, 1H), 7.27 (d, 1H), 7.16 (dd, 1H), 7.05 (d, 1H), 3.81 (s, 3H), 2.43 (m, 1H), 2.27-2.37 (m, 1H), 1.95-2.05 (m, 2H), 1.84 (m, 2H), 1.45 (m, 2H), 1.21-1.35 (m, 2H); LCMS: 253.1 [M+H]⁺.

The Intermediate below was synthesized from 4-bromo-1-methoxy-2-methylbenzene following the procedures described for Intermediate 2.

| Int | Structure | Name | [M + H]⁺ |
|---|---|---|---|
| 1 | 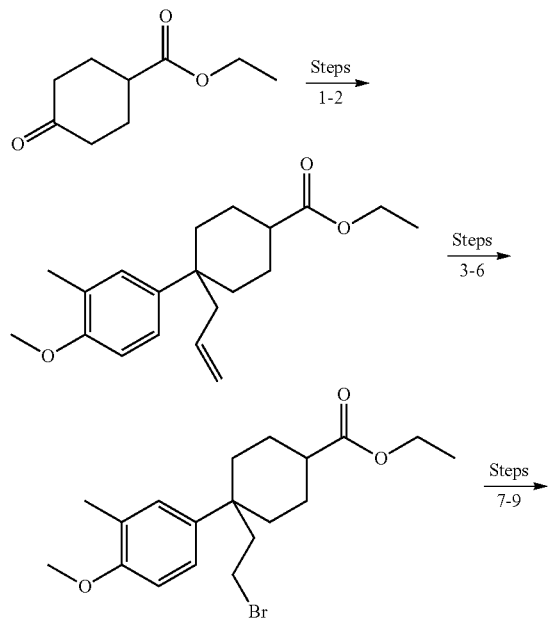 | trans-4-(4-Methoxy-3-methylphenyl)cyclohexanecarbaldehyde | 233.0 |

Alternate conditions:
Step 1: −60° C.;
Step 2: 0° C., 1 h;
Step 3a: THF in place of PhMe, 80° C., 18 h;
Step 3b: no HCl, 30 psi H₂, 18 h;
Step 4: 15 h;
Step 5: 3N HCl, THF, 60° C., 1 h;
Step 6: THF in place of PhMe.

Intermediate 3

4-(4-Methoxy-3-methylphenyl)bicyclo[2.2.2]octane-1-carbaldehyde

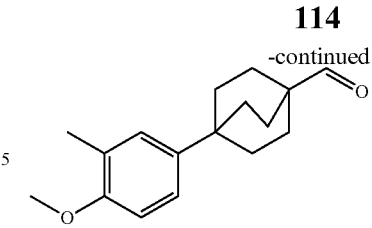

Step 1: Ethyl 4-hydroxy-4-(4-methoxy-3-methylphenyl)cyclohexanecarboxylate n-Butyllithium (2.5 M in hexanes, 60 mL, 150.0 mmol) was added dropwise to a solution of 4-bromo-1-methoxy-2-methylbenzene (27.78 g, 138.2 mmol) in THF (300 mL) at −78° C. The mixture was stirred at −78° C. for 1 h and then added dropwise to a solution of ethyl 4-oxocyclohexanecarboxylate (22.34 g, 131.3 mmol) in THF (300 mL) at −78 OC. The mixture was stirred at −78° C. for 2 h, added to sat'd NH₄Cl (600 mL) and then extracted with EtOAc (2×600 mL). The combined organic extracts were washed with water (400 mL), washed with brine (400 mL), dried (Na₂SO₄), filtered, concentrated, and purified by silica gel chromatography (petroleum ether/EtOAc=10/1) to give ethyl 4-hydroxy-4-(4-methoxy-3-methylphenyl)cyclohexanecarboxylate (18.9 g, 45%) as a yellow oil. ¹H NMR (400 MHz, DMSO): δ 7.11-7.26 (m, 2H), 6.75-6.84 (m, 1H), 4.59-4.64 (m, 1H), 3.98-4.11 (m, 2H), 3.72 (s, 3H), 2.25-2.39 (m, 1H), 2.07-2.13 (s, 2H), 1.77-1.93 (m, 3H), 1.42-1.75 (m, 5H), 1.11-1.23 (m, 3H); LCMS: 275.2 [M-OH]⁺.

Step 2: Ethyl 4-allyl-4-(4-methoxy-3-methylphenyl)cyclohexanecarboxylate

Boron trifluoride diethyl etherate (24.85 g, 84.03 mmol) was added to a solution of ethyl 4-hydroxy-4-(4-methoxy-3-methylphenyl)cyclohexanecarboxylate (18.90 g, 64.64 mmol) and allyltrimethylsilane (11.82 g, 103.42 mmol) in DCM (400 mL) at −78° C. The mixture was stirred at −78° C. for 1 h, stirred at rt overnight, and then added to brine (200 mL) and DCM (200 mL). The organic layer was separated, washed with sat'd NaHCO₃ (2×200 mL), washed with brine (200 mL), dried (Na₂SO₄), filtered, concentrated, and purified by silica gel chromatography (petroleum ether/EtOAc=20/1) to give ethyl 4-allyl-4-(4-methoxy-3-methylphenyl)cyclohexanecarboxylate (15 g, 71%) as a yellow oil. ¹H NMR (400 MHz, CDCl₃): δ 7.00-7.10 (m, 2H), 6.76 (d, 1H), 5.26-5.50 (m, 1H), 4.81-4.98 (m, 2H), 4.15 (q, 0.5H), 4.03 (q, 1.5H), 3.81 (s, 3H), 2.26-2.42 (m, 3H), 2.21 (s, 3H), 2.15 (d, 1.5H), 1.98 (d, 0.5H), 1.75-1.88 (m, 2.5H), 1.60-1.72 (m, 0.5H), 1.33-1.55 (m, 3H), 1.27 (t, 0.8H), 1.18 (t, 2.2H); LCMS: 339.3 [M+Na]⁺.

Step 3: Ethyl 4-(2,3-dihydroxypropyl)-4-(4-methoxy-3-methylphenyl)cyclohexanecarboxylate Osmium tetroxide (0.1 M in tert-butanol, 7.6 mL, 0.76 mmol) was added to a solution of ethyl 4-allyl-4-(4-methoxy-3-methylphenyl)cyclohexanecarboxylate (4.81 g, 15.2 mmol), 4-methylmorpholine N-oxide (2.67 g, 22.8 mmol), $CH_3CN$ (100 mL) and $H_2O$ (25 mL) at 0° C. The mixture was stirred at rt overnight. Saturated $Na_2SO_3$ (50 mL) was added to the mixture. The mixture was stirred at rt for 30 min, concentrated, dissolved in water (80 mL) and extracted with EtOAc (2×100 mL). The organic layers were dried ($Na_2SO_4$), filtered, concentrated, and purified by silica gel chromatography (petroleum ether/EtOAc=1/1) to give ethyl 4-(2,3-dihydroxypropyl)-4-(4-methoxy-3-methylphenyl)cyclohexanecarboxylate (5.23 g, 94%) as a yellow oil. ¹H NMR (400 MHz, $CDCl_3$): δ 7.05-7.16 (m, 2H), 6.78 (d, 1H), 4.06-4.17 (m, 0.5H), 3.95-4.05 (m, 1.5H), 3.80 (s, 3H), 3.48-3.66 (m, 1H), 3.18-3.32 (m, 2H), 2.40-2.53 (m, 2H), 2.27-2.37 (m, 1H), 2.19 (s, 3H), 1.80 (t, 3H), 1.32-1.68 (m, 7H), 1.24-1.25 (m, 0.8H), 1.17 (t, 2.2H); LCMS: 373.3 [M+Na]⁺.

Step 4: Ethyl 4-(4-methoxy-3-methylphenyl)-4-(2-oxoethyl)cyclohexanecarboxylate

Sodium periodate (3.83 g, 17.90 mmol) was added to a solution of ethyl 4-(2,3-dihydroxypropyl)-4-(4-methoxy-3-methylphenyl)cyclohexanecarboxylate (5.23 g, 14.9 mmol), THF (70 mL), and $H_2O$ (35 mL) at 0° C. The mixture was stirred at rt overnight and then added to water (50 mL) and EtOAc (2×100 mL). The organic layer was separated, washed with water (80 mL), washed with brine (80 mL), dried ($Na_2SO_4$), filtered, concentrated and purified by silica gel chromatography (petroleum ether/EtOAc=5/1) to give ethyl 4-(4-methoxy-3-methylphenyl)-4-(2-oxoethyl)cyclohexanecarboxylate (3.95 g, 82%) as a yellow oil. ¹H NMR (400 MHz, $CDCl_3$): δ 9.28-9.42 (m, 1H), 7.07-7.19 (m, 2H), 6.79 (d, 1H), 4.15 (q, 0.5H), 4.04 (q, 1.5H), 3.82 (s, 3H), 2.41-2.52 (m, 3H), 2.33 (s, 1H), 2.21 (s, 3H), 1.75-1.92 (m, 3H), 1.46-1.63 (m, 4H), 1.23-1.31 (t, 0.5H), 1.19 (t, 2.5H); LCMS: 341.3 [M+Na]⁺.

Step 5: Ethyl 4-(2-hydroxyethyl)-4-(4-methoxy-3-methylphenyl)cyclohexanecarboxylate Sodium borohydride (704 mg, 18.6 mmol) was added to a solution of ethyl 4-(4-methoxy-3-methylphenyl)-4-(2-oxoethyl)cyclohexanecarboxylate (3.95 g, 12.41 mmol) in THF (100 mL) at 0° C. The mixture was stirred at 0° C. for 1 h, stirred at rt overnight, and then diluted with water (100 mL). The organic solvent was removed under reduced pressure, and the aqueous layer was extracted with DCM (2×300 mL). The organic extracts were dried ($Na_2SO_4$), filtered, concentrated, and purified by silica gel chromatography (petroleum ether:EtOAc=3:1) to give ethyl 4-(2-hydroxyethyl)-4-(4-methoxy-3-methylphenyl)cyclohexanecarboxylate (3.11 g, 67%) as a yellow oil. ¹H NMR (400 MHz, $CDCl_3$): δ 6.96-7.04 (m, 2H), 6.71 (d, 1H), 4.03-4.12 (q, 0.4H), 3.97 (q, 1.6H), 3.74 (s, 3H), 3.28-3.38 (m, 2H), 2.19-2.39 (m, 3H), 2.14 (s, 3H), 1.71-1.80 (m, 2H), 1.60-1.70 (m, 2H), 1.28-1.50 (m, 4H), 1.17-1.24 (t, 1H), 1.12 (t, 2H), (The OH proton was not detected); LCMS: 343.2 [M+Na]⁺.

Step 6: Ethyl 4-(2-bromoethyl)-4-(4-methoxy-3-methylphenyl)cyclohexanecarboxylate Triphenylphosphine (4.60 g, 17.54 mmol) in DCM (20 mL) was added dropwise to a solution of ethyl 4-(2-hydroxyethyl)-4-(4-methoxy-3-methylphenyl)cyclohexanecarboxylate (2.81 g, 8.77 mmol), $CBr_4$ (4.36 g, 13.16 mmol), and DCM (40 mL) at 0° C. The mixture was stirred at 0° C. for 1 h, stirred at rt overnight, concentrated and then purified by silica gel chromatography (petroleum ether/EtOAc=20/1) to give ethyl 4-(2-bromoethyl)-4-(4-methoxy-3-methylphenyl)cyclohexanecarboxylate (2.62 g, 77%) as a yellow oil. ¹H NMR (400 MHz, $CDCl_3$): δ 6.96-7.08 (m, 2H), 6.77 (d, 1H), 4.15 (q, 0.3H), 4.03 (q, 1.7H), 3.81 (s, 3H), 2.91-3.06 (m, 2H), 2.24-2.41 (m, 3H), 2.15-2.24 (s, 3H), 1.95-2.06 (m, 2H), 1.77-1.87 (m, 2H), 1.34-1.53 (m, 4H), 1.27 (t, 1H), 1.18 (t, 2H); LCMS: 405.1 [M+Na]⁺.

Step 7: Ethyl 4-(4-methoxy-3-methylphenyl)bicyclo[2.2.2]octane-1-carboxylate

Lithium diisopropylamide (2 M in THF, 4.8 mL, 9.60 mmol) was added dropwise to a solution of ethyl 4-(2-bromoethyl)-4-(4-methoxy-3-methylphenyl)cyclohexanecarboxylate (1.81 g, 4.72 mmol), HMPA (4.23 g, 23.61 mmol), and THF (90 mL) at −78° C. The mixture was stirred at −78° C. for 3 h, added to sat'd $NH_4Cl$ (90 mL) and then extracted with EtOAc (2×150 mL). The combined organic layers were washed with water (100 mL), washed with brine (100 mL), dried ($Na_2SO_4$), filtered, concentrated, and purified by silica gel chromatography (petroleum ether/EtOAc=30/1) to give ethyl 4-(4-methoxy-3-methylphenyl)bicyclo[2.2.2]octane-1-carboxylate (1.17 g, 82%) as a yellow solid. ¹H NMR (400 MHz, $CDCl_3$): δ 6.98-7.05 (m, 2H), 6.69 (d, 1H), 4.05 (q, 2H), 3.73 (s, 3H), 2.14 (s, 3H), 1.70-1.87 (m, 12H), 1.18 (t, 3H); LCMS: 303.3 [M+H]⁺.

Step 8: (4-(4-Methoxy-3-methylphenyl)bicyclo[2.2.2]octan-1-yl)methanol

Diisobutylaluminum hydride (1 M in toluene, 14 mL, 14.0 mmol) was added to a solution of ethyl 4-(4-methoxy-3-methylphenyl)bicyclo[2.2.2]octane-1-carboxylate (1.64 g, 5.42 mmol) in DCM (100 mL) at −78° C. The mixture was stirred at −78° C. for 1 h, stirred at rt for 2 h, and then added to ice water (80 mL). The mixture was adjusted to (pH=6) with 1 N HCl and filtered. The organic layer was separated, and the aqueous layer was extracted with DCM (2×200 mL). The combined organic layers were washed with water (100 mL), washed with brine (100 mL), dried ($Na_2SO_4$), filtered and concentrated. The residue was purified by silica gel chromatography (petroleum ether/EtOAc=10/1) to give (4-(4-methoxy-3-methylphenyl)bicyclo[2.2.2]octan-1-yl)methanol (1.22 g, 82%) as a yellow solid. ¹H NMR (400 MHz, $CDCl_3$): δ 6.99-7.07 (m, 2H), 6.64-6.72 (m, 1H), 3.73 (s, 3H), 3.25 (s, 2H), 2.14 (s, 3H), 1.69-1.81 (m, 6H), 1.40-1.50 (m, 6H); LCMS: 261.2 [M+H]⁺.

Step 9: 4-(4-Methoxy-3-methylphenyl)bicyclo[2.2.2]octane-1-carbaldehyde

Pyridinium chlorochromate (1.03 g, 4.78 mmol) was added to a mixture of (4-(4-methoxy-3-methylphenyl)bicyclo[2.2.2]octan-1-yl)methanol (621.1 mg, 2.39 mmol), SiO$_2$ (1.93 g, 32.19 mmol) and DCM (120 mL). The mixture was stirred at rt for 2 h, filtered through a neutral alumina plug and concentrated to give 4-(4-methoxy-3-methylphenyl)bicyclo[2.2.2]octane-1-carbaldehyde (601.3 mg, 93%) as a white solid. $^1$H NMR (400 MHz, CDCl$_3$): δ 9.48-9.56 (s, 1H), 7.06-7.11 (m, 2H), 6.72-6.78 (m, 1H), 3.81 (s, 3H), 2.22 (s, 3H), 1.83-1.91 (m, 6H), 1.71-1.80 (m, 6H); LCMS: 259.3 [M+H]$^+$.

The Intermediate below was synthesized from 5-bromo-N,N-dimethylpyridin-2-amine following the procedures described for Intermediate 3.

min was 72° C.). The reaction was allowed to cool to rt, diluted with EtOAc (800 mL) and H$_2$O (800 mL), and then filtered through Celite with EtOAc washing (~400 mL). The layers were separated, and the organic layer was washed (800 mL H$_2$O), dried (Na$_2$SO$_4$), filtered, and concentrated (73.88 g). The residue was dry loaded onto silica gel and purified by silica gel chromatography (20-60% EtOAc in hexanes) to give 3-(1-cyclopropyl-1H-pyrazol-4-yl)aniline (31.5 g, 82%) as a beige solid. $^1$H NMR (400 MHz, DMSO-d$_6$): δ 8.03 (s, 1H), 7.66 (d, 1H), 6.97 (t, 1H), 6.73-6.72 (m, 1H), 6.71-6.68 (m, 1H), 6.42-6.38 (m, 1H), 5.00 (s, 2H), 3.75-3.68 (m, 1H), 1.08-1.00 (m, 2H), 1.00-0.92 (m, 2H); LCMS: 200.3 [M+H]$^+$.

The Intermediates below were synthesized from the appropriate aryl halide and the appropriate boronic acid/ester following the procedure described for Intermediate 4.

| Int | Structure | Name | [M + H]$^+$ |
|---|---|---|---|
| 3.01 | 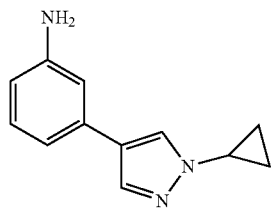 [SMILES: Nc1cccc(-c2cnn(C3CC3)c2)c1] | 4-(6-(Dimethylamino)pyridin-3-yl)bicyclo[2.2.2]octane-1-carbaldehyde | 259.5 |

Alternate conditions:
Step 2: 0° C., overnight;
Step 3: K$_2$OsO$_4$•2H$_2$O;
Step 7: −78° C., 1 h then rt, overnight;
Step 9: oxalyl chloride, DMSO, Et$_3$N, −78° C.

Intermediate 4

3-(1-Cyclopropyl-1H-pyrazol-4-yl)aniline

A mixture of 3-iodoaniline (63.36 g, 289.9 mmol), Pd(dppf)Cl$_2$ (7.05 g, 9.63 mmol), K$_2$CO$_3$ (2.2 M, 265 mL, 583.0 mmol), and dioxane (340 mL) was degassed with vacuum/N$_2$ cycles (3×). 1-cyclopropyl-4-(4,4,5,5-tetramethyl-1,3,2-dioxaborolan-2-yl)-1H-pyrazole (~90%, 50.09 g, 192.6 mmol) was added, and the mixture was heated in a pre-heated oil bath (90° C.) for 20 min (internal temp @ 20

| Int | Structure | Name | [M + H]$^+$ |
|---|---|---|---|
| 4.01$^1$ | | 4-(1-Cyclopropyl-1H-pyrazol-4-yl)pyridin-2-amine | 201.3 |
| 4.02$^1$ | | 4-(1-Isopropyl-1H-pyrazol-4-yl)pyridin-2-amine | 203.0 |
| 4.03 | | 3-(1-Isopropyl-1H-pyrazol-4-yl)aniline | 202.0 |

| Int | Structure | Name | [M + H]⁺ |
|---|---|---|---|
| 4.04 | 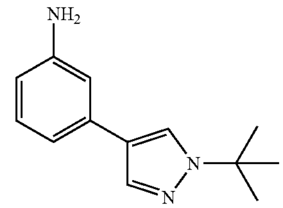 [SMILES: CC(C)(C)n1cc(-c2cccc(N)c2)cn1] | 3-(1-(tert-Butyl)-1H-pyrazol-4-yl)aniline | 216.4 |
| 4.05 | 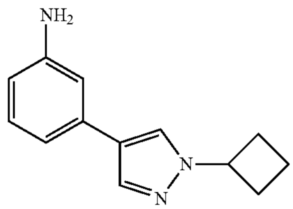 [SMILES: Nc1cccc(-c2cnn(C3CCC3)c2)c1] | 3-(1-Cyclobutyl-1H-pyrazol-4-yl)aniline | 214.4 |
| 4.06[2] | 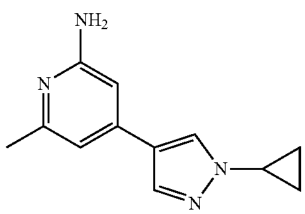 [SMILES: Cc1cc(-c2cnn(C3CC3)c2)cc(N)n1] | 4-(1-Cyclopropyl-1H-pyrazol-4-yl)-6-methylpyridin-2-amine | 215.1 |

[1] 4-bromopyridin-2-amine was used.
[2] 4-bromo-6-methylpyridin-2-amine was used.

Intermediate 5

3-(3-Methyl-1H-pyrazol-1-yl)aniline

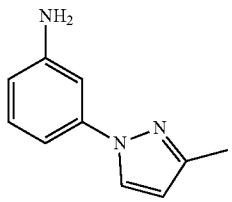

Step 1: 3-Methyl-1-(3-nitrophenyl)-1H-pyrazole

A mixture of 1-fluoro-3-nitrobenzene (2.00 g, 14.17 mmol), 3-methyl-1H-pyrazole (2.33 g, 28.34 mmol), K$_2$CO$_3$ (1.96 g, 14.17 mmol), and DMSO (20 mL) was heated to 120° C. overnight. The reaction mixture was filtered, and the filtrate was purified by RP-HPLC [water (10 mM NH$_4$HCO$_3$)-MeCN] to give 3-methyl-1-(3-nitrophenyl)-1H-pyrazole (2.0 g, 69%) as a light yellow solid. $^1$H NMR (400 MHz, CDCl$_3$): δ: 8.50 (t, 1H), 7.99-8.14 (m, 2H), 7.91 (d, 1H), 7.60 (t, 1H), 6.32 (d, 1H), 2.39 (s, 3H); LCMS: 203.9 [M+H]⁺.

Step 2: 3-(3-Methyl-1H-pyrazol-1-yl)aniline

Palladium on carbon (10 wt. %, 50 mg, 0.047 mmol) was added to a solution of 3-methyl-1-(3-nitrophenyl)-1H-pyrazole (1.0 g, 4.92 mmol) in MeOH (5 mL) under N$_2$. The mixture was degassed with 3 vacuum/H$_2$ cycles, stirred at rt under H$_2$ (15 psi) for 2 h, filtered, and concentrated under high vacuum to give 3-(3-methyl-1H-pyrazol-1-yl)aniline (400 mg, crude) as a light yellow oil. $^1$H NMR (400 MHz, CDCl$_3$): δ: 7.77 (d, 1H), 7.18 (t, 1H), 7.07 (t, 1H), 6.95 (dd, 1H), 6.56 (dd, 1H), 6.22 (d, 1H), 3.81 (s, 2H), 2.37 (s, 3H); LCMS: 174.1 [M+H]⁺.

Intermediate 6

3-Iodo-N-((trans-4-(4-methoxy-3-methylphenyl)cyclohexyl)methyl)aniline

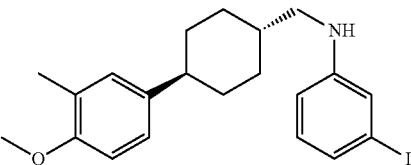 [SMILES: COc1ccc([C@H]2CC[C@H](CNc3cccc(I)c3)CC2)cc1C]

Sodium triacetoxyborohydride (3.74 g, 17.6 mmol) was added to a solution of Intermediate 1 (2.56 g, 11.0 mmol), 3-iodoaniline (2.56 g, 11.7 mmol), acetic acid (1.3 mL, 23 mmol) and dichloroethane (45 mL) at rt under N$_2$. The reaction was stirred for 80 min, poured into 50 mL sat'd NaHCO$_3$ and extracted with 50 mL EtOAc. The EtOAc layer was washed with 50 mL sat'd NaHCO$_3$ and washed with 50 mL brine. The aqueous layers were combined and back extracted with 25 mL EtOAc. The combined organics were dried (Na$_2$SO$_4$), filtered, concentrated and purified by silica gel chromatography (0-5% EtOAc in hexanes) to give 3-iodo-N-((trans-4-(4-methoxy-3-methylphenyl)cyclohexyl)methyl)aniline (4.43 g, 88%) as a yellow oil. $^1$H NMR (400 MHz, DMSO-d$_6$): δ 7.01-6.95 (m, 2H), 6.91 (s, 1H), 6.86-6.77 (m, 3H), 6.57 (d, 1H), 5.92 (t, 1H), 3.73 (s, 3H), 2.85 (t, 2H), 2.42-2.31 (m, 1H), 2.11 (s, 3H), 1.94-1.85 (m, 2H), 1.82-1.73 (m, 2H), 1.63-1.50 (m, 1H), 1.45-1.31 (m, 2H), 1.14-1.00 (m, 2H); LCMS: 436.4 [M+H]⁺.

Intermediate 7

3-(1-Cyclopropyl-1H-pyrazol-4-yl)-N-((4-(4-methoxy-3-methylphenyl)bicyclo[2.2.2]octan-1-yl)methyl)aniline

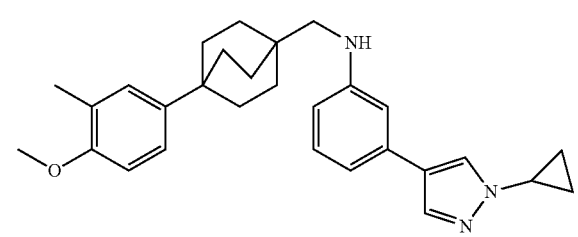 [SMILES: COc1ccc(C23CCC(CNc4cccc(-c5cnn(C6CC6)c5)c4)(CC2)CC3)cc1C]

Dichloroethane was cooled in an ice/water bath under N$_2$. Intermediate 3 (151 mg, 0.58 mmol), Intermediate 4 (118 mg, 0.59 mmol), and then sodium triacetoxyborohydride (198 mg, 0.93 mmol) were added to the reaction at 0° C. The reaction was allowed to warm to rt, stirred at rt for 85 min, poured into 20 mL saturated NaHCO$_3$, and then extracted with 20 mL EtOAc. The organic layer was washed with 20 mL brine, dried (Na$_2$SO$_4$), filtered, concentrated, and purified by silica gel chromatography (10-30% EtOAc in hexanes) to give 3-(1-cyclopropyl-1H-pyrazol-4-yl)-N-((4-(4-methoxy-3-methylphenyl)bicyclo[2.2.2]octan-1-yl)methyl)aniline (233 mg, 90%) as a white foam. $^1$H NMR (400 MHz, DMSO-$d_6$): δ 8.09 (s, 1H), 7.71 (s, 1H), 7.11-7.05 (m, 2H), 7.00 (t, 1H), 6.84-6.76 (m, 2H), 6.68 (d, 1H), 6.47 (d, 1H), 5.32 (t, 1H), 3.75-3.68 (m, 4H), 2.83 (d, 2H), 2.12 (s, 3H), 1.78-1.69 (m, 6H), 1.62-1.52 (m, 6H), 1.10-1.04 (m, 2H), 1.00-0.93 (m, 2H); LCMS: 442.3 [M+H]$^+$.

The Intermediates below were synthesized from the appropriate amine (SM or Intermediate) and the appropriate aldehyde Intermediates following the procedures described for Intermediate 6 and Intermediate 7.

| Int | Structure | Name | [M + H]$^+$ |
|---|---|---|---|
| 7.01 | 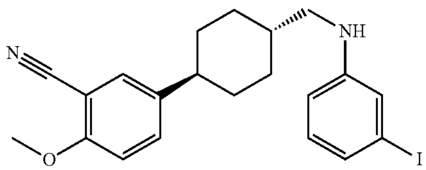 [SMILES: COc1ccc([C@H]2CC[C@H](CNc3cccc(I)c3)CC2)cc1C#N] | 5-(trans-4-(((3-Iodophenyl)amino)methyl)cyclohexyl)-2-methoxybenzonitrile | 447.1 |
| 7.02[1] | 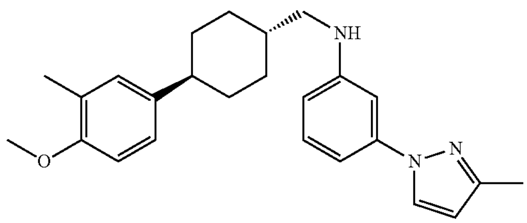 | N-((trans-4-(4-Methoxy-3-methylphenyl)cyclohexyl)methyl)-3-(3-methyl-1H-pyrazol-1-yl)aniline | 390.3 |
| 7.03 | 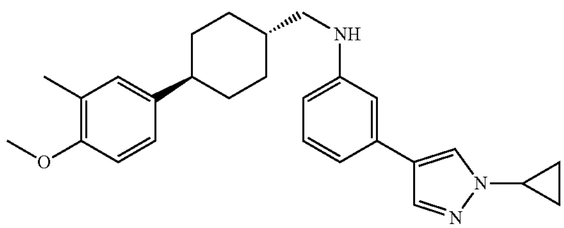 [SMILES: COc1ccc([C@H]2CC[C@H](CNc3cccc(-c4cnn(C5CC5)c4)c3)CC2)cc1C] | 3-(1-Cyclopropyl-1H-pyrazol-4-yl)-N-((trans-4-(4-methoxy-3-methylphenyl)cyclohexyl)methyl)aniline | 416.3 |
| 7.04 | 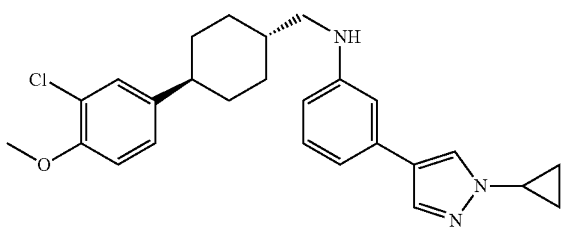 [SMILES: COc1ccc([C@H]2CC[C@H](CNc3cccc(-c4cnn(C5CC5)c4)c3)CC2)cc1Cl] | N-((trans-4-(3-Chloro-4-methoxyphenyl)cyclohexyl)methyl)-3-(1-cyclopropyl-1H-pyrazol-4-yl)aniline | 436.6 |
| 7.05 | 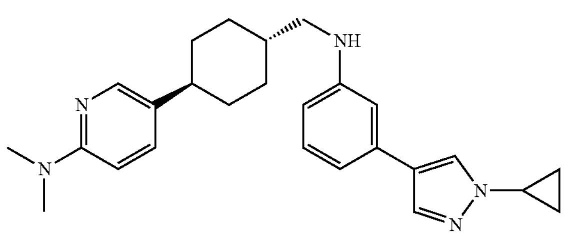 [SMILES: CN(C)c1ccc([C@H]2CC[C@H](CNc3cccc(-c4cnn(C5CC5)c4)c3)CC2)cn1] | 5-(trans-4-(((3-(1-Cyclopropyl-1H-pyrazol-4-yl)phenyl)amino)methyl)cyclohexyl)-N,N-dimethylpyridin-2-amine | 416.3 |
| 7.06 | 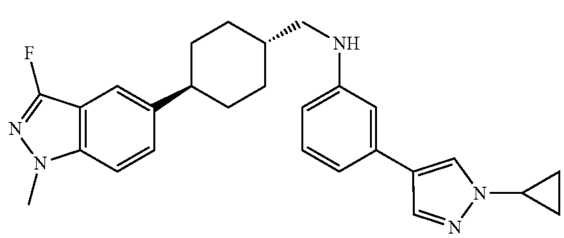 [SMILES: Cn1nc(F)c2cc([C@H]3CC[C@H](CNc4cccc(-c5cnn(C6CC6)c5)c4)CC3)ccc21] | 3-(1-Cyclopropyl-1H-pyrazol-4-yl)-N-((trans-4-(3-fluoro-1-methyl-1H-indazol-5-yl)cyclohexyl)methyl)aniline | 444.6 |

-continued

| Int | Structure | Name | [M + H]⁺ |
|---|---|---|---|
| 7.07 | 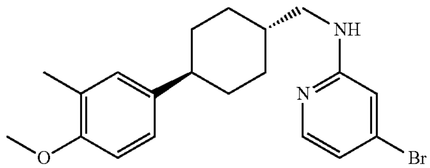 [SMILES: COc1ccc([C@H]2CC[C@H](CNc3cc(Br)ccn3)CC2)cc1C] | 4-Bromo-N-((trans-4-(4-methoxy-3-methylphenyl)cyclohexyl)methyl)pyridin-2-amine | 389.1 |
| 7.08 | 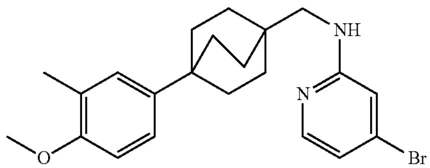 [SMILES: COc1ccc(C23CCC(CNc4cc(Br)ccn4)(CC2)CC3)cc1C] | 4-Bromo-N-((4-(4-methoxy-3-methylphenyl)bicyclo[2.2.2]octan-1-yl)methyl)pyridin-2-amine | 415.2 |
| 7.09 | 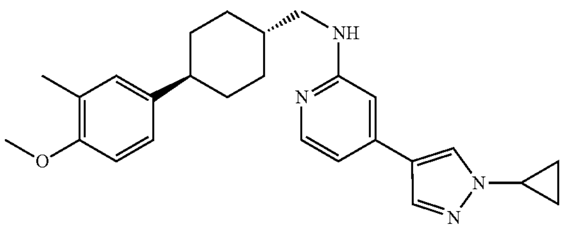 [SMILES: COc1ccc([C@H]2CC[C@H](CNc3cc(-c4cnn(C5CC5)c4)ccn3)CC2)cc1C] | 4-(1-Cyclopropyl-1H-pyrazol-4-yl)-N-((trans-4-(4-methoxy-3-methylphenyl)cyclohexyl)methyl)pyridin-2-amine | 417.1 |
| 7.10 | 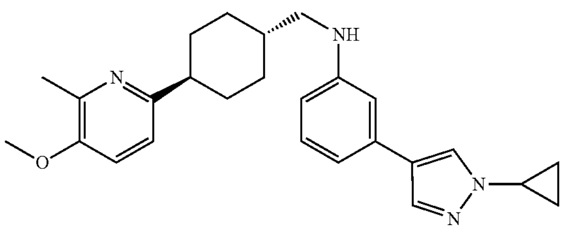 [SMILES: COc1ccc([C@H]2CC[C@H](CNc3cccc(-c4cnn(C5CC5)c4)c3)CC2)nc1C] | 3-(1-Cyclopropyl-1H-pyrazol-4-yl)-N-((trans-4-(5-methoxy-6-methylpyridin-2-yl)cyclohexyl)methyl)aniline | 417.1 |
| 7.11 | 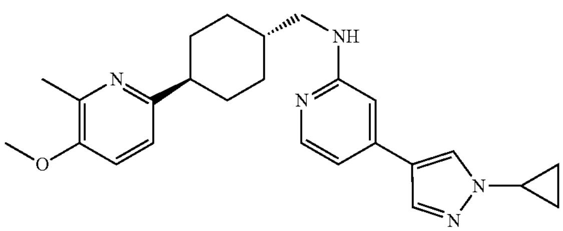 [SMILES: COc1ccc([C@H]2CC[C@H](CNc3cc(-c4cnn(C5CC5)c4)ccn3)CC2)nc1C] | 4-(1-Cyclopropyl-1H-pyrazol-4-yl)-N-((trans-4-(5-methoxy-6-methylpyridin-2-yl)cyclohexyl)methyl)pyridin-2-amine | 418.3 |
| 7.12 | 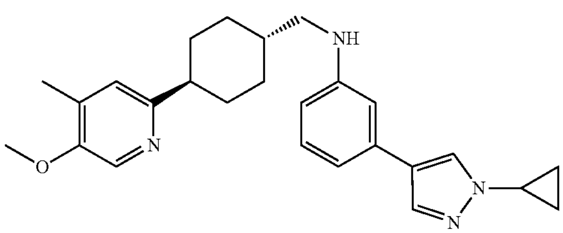 [SMILES: COc1cnc([C@H]2CC[C@H](CNc3cccc(-c4cnn(C5CC5)c4)c3)CC2)cc1C] | 3-(1-Cyclopropyl-1H-pyrazol-4-yl)-N-(((1r,4r)-4-(5-methoxy-4-methylpyridin-2-yl)cyclohexyl)methyl)aniline | 417.3 |
| 7.13 | 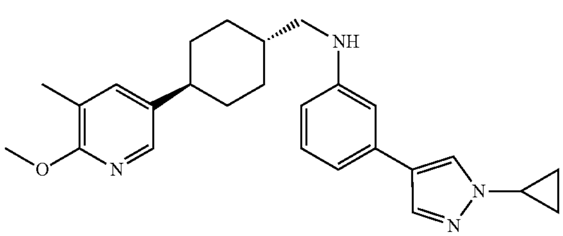 [SMILES: COc1ncc([C@H]2CC[C@H](CNc3cccc(-c4cnn(C5CC5)c4)c3)CC2)cc1C] | 3-(1-Cyclopropyl-1H-pyrazol-4-yl)-N-((trans-4-(6-methoxy-5-methylpyridin-3-yl)cyclohexyl)methyl)aniline | 417.3 |

-continued

| Int | Structure | Name | [M + H]⁺ |
|---|---|---|---|
| 7.14 | 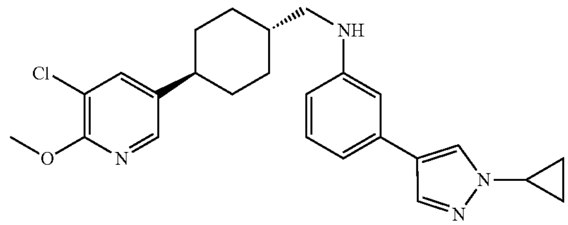 [SMILES: COc1ncc([C@H]2CC[C@H](CNc3cccc(-c4cnn(C5CC5)c4)c3)CC2)cc1Cl] | N-((trans-4-(5-Chloro-6-methoxypyridin-3-yl)cyclohexyl)methyl)-3-(1-cyclopropyl-1H-pyrazol-4-yl)aniline | 437.4 |
| 7.15 | 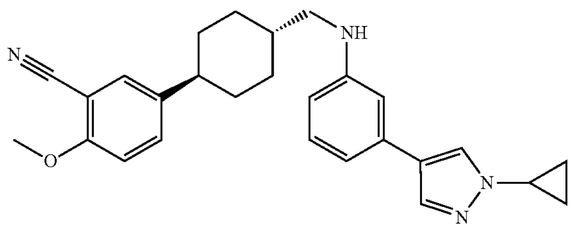 [SMILES: COc1ccc([C@H]2CC[C@H](CNc3cccc(-c4cnn(C5CC5)c4)c3)CC2)cc1C#N] | 5-(trans-4-(((3-(1-Cyclopropyl-1H-pyrazol-4-yl)phenyl)amino)methyl)cyclohexyl)-2-methoxybenzonitrile | 427.3 |
| 7.16 | 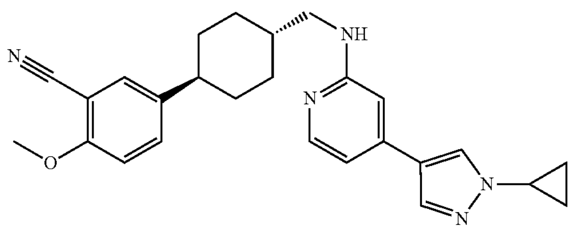 [SMILES: COc1ccc([C@H]2CC[C@H](CNc3cc(-c4cnn(C5CC5)c4)ccn3)CC2)cc1C#N] | 5-(trans-4-(((4-(1-Cyclopropyl-1H-pyrazol-4-yl)pyridin-2-yl)amino)methyl)cyclohexyl)-2-methoxybenzonitrile | 428.3 |
| 7.17 | 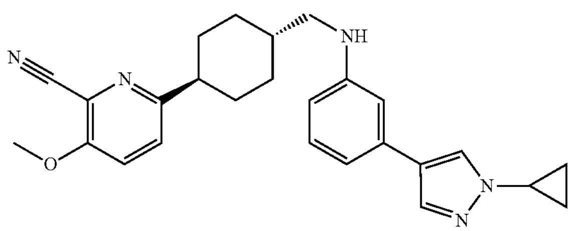 [SMILES: COc1ccc([C@H]2CC[C@H](CNc3cccc(-c4cnn(C5CC5)c4)c3)CC2)nc1C#N] | 6-(trans-4-(((3-(1-Cyclopropyl-1H-pyrazol-4-yl)phenyl)amino)methyl)cyclohexyl)-3-methoxypicolinonitrile | 428.3 |
| 7.18 | 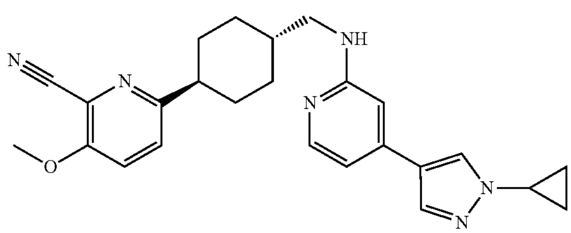 [SMILES: COc1ccc([C@H]2CC[C@H](CNc3cc(-c4cnn(C5CC5)c4)ccn3)CC2)nc1C#N] | 6-(trans-4-(((4-(1-Cyclopropyl-1H-pyrazol-4-yl)pyridin-2-yl)amino)methyl)cyclohexyl)-3-methoxypicolinonitrile | 429.4 |
| 7.19 | 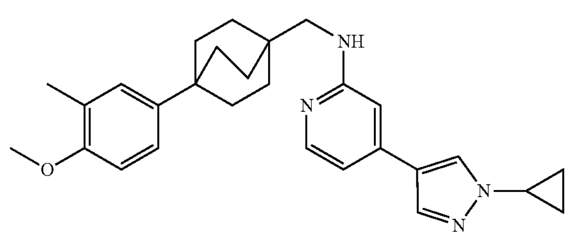 [SMILES: COc1ccc(C23CCC(CNc4cc(-c5cnn(C6CC6)c5)ccn4)(CC2)CC3)cc1C] | 4-(1-Cyclopropyl-1H-pyrazol-4-yl)-N-((4-(4-methoxy-3-methylphenyl)bicyclo[2.2.2]octan-1-yl)methyl)pyridin-2-amine | 443.1 |

-continued

| Int | Structure | Name | [M + H]⁺ |
|---|---|---|---|
| 7.20 | 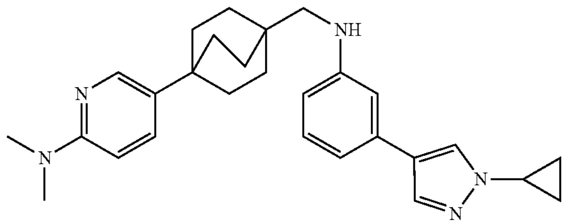 [SMILES: CN(C)c1ccc(C23CCC(CNc4cccc(-c5cnn(C6CC6)c5)c4)(CC2)CC3)cn1] | 5-(4-(((3-(1-Cyclopropyl-1H-pyrazol-4-yl)phenyl)amino)methyl)bicyclo[2.2.2]octan-1-yl)-N,N-dimethylpyridin-2-amine | 442.4 |
| 7.21 | 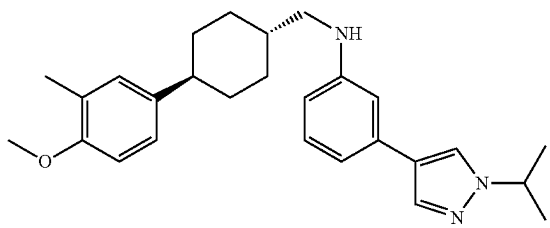 [SMILES: COc1ccc([C@H]2CC[C@H](CNc3cccc(-c4cnn(C(C)C)c4)c3)CC2)cc1C] | 3-(1-Isopropyl-1H-pyrazol-4-yl)-N-((trans-4-(4-methoxy-3-methylphenyl)cyclohexyl)methyl)aniline | 418.3 |
| 7.22 | 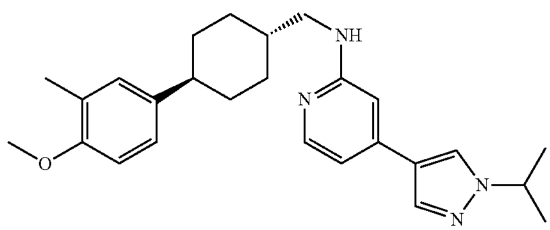 [SMILES: COc1ccc([C@H]2CC[C@H](CNc3cc(-c4cnn(C(C)C)c4)ccn3)CC2)cc1C] | 4-(1-Isopropyl-1H-pyrazol-4-yl)-N-((trans-4-(4-methoxy-3-methylphenyl)cyclohexyl)methyl)pyridin-2-amine | 419.3 |
| 7.23 | 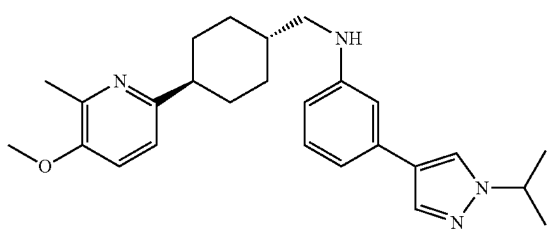 [SMILES: COc1ccc([C@H]2CC[C@H](CNc3cccc(-c4cnn(C(C)C)c4)c3)CC2)nc1C] | 3-(1-Isopropyl-1H-pyrazol-4-yl)-N-((trans-4-(5-methoxy-6-methylpyridin-2-yl)cyclohexyl)methyl)aniline | 419.7 |
| 7.24 | 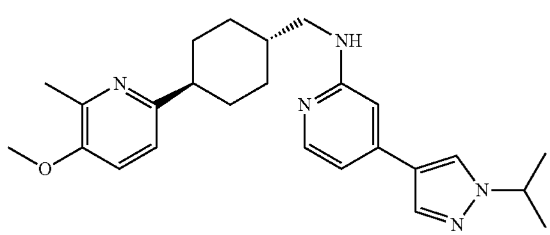 [SMILES: COc1ccc([C@H]2CC[C@H](CNc3cc(-c4cnn(C(C)C)c4)ccn3)CC2)nc1C] | 4-(1-Isopropyl-1H-pyrazol-4-yl)-N-((trans-4-(5-methoxy-6-methylpyridin-2-yl)cyclohexyl)methyl)pyridin-2-amine | 420.3 |
| 7.25 | 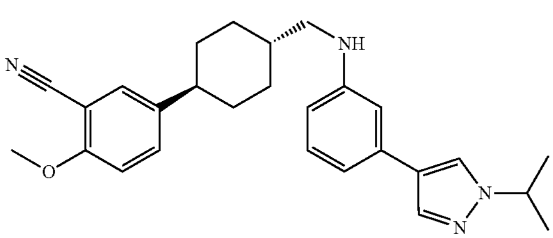 [SMILES: COc1ccc([C@H]2CC[C@H](CNc3cccc(-c4cnn(C(C)C)c4)c3)CC2)cc1C#N] | 5-(trans-4-(((3-(1-Isopropyl-1H-pyrazol-4-yl)phenyl)amino)methyl)cyclohexyl)-2-methoxybenzonitrile | 429.5 |

-continued

| Int | Structure | Name | [M + H]⁺ |
|---|---|---|---|
| 7.26 | 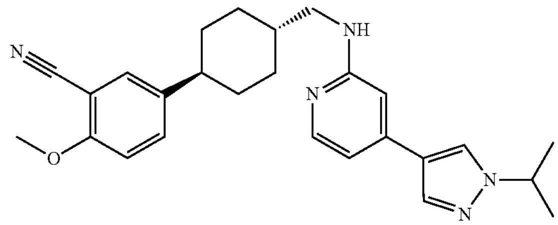 [SMILES: COc1ccc([C@H]2CC[C@H](CNc3cc(-c4cnn(C(C)C)c4)ccn3)CC2)cc1C#N] | 5-(trans-4-(((4-(1-Isopropyl-1H-pyrazol-4-yl)pyridin-2-yl)amino)methyl)cyclohexyl)-2-methoxybenzonitrile | 430.4 |
| 7.27 | 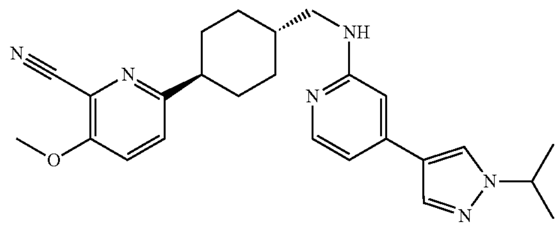 [SMILES: COc1ccc([C@H]2CC[C@H](CNc3cc(-c4cnn(C(C)C)c4)ccn3)CC2)nc1C#N] | 6-(trans-4-(((4-(1-Isopropyl-1H-pyrazol-4-yl)pyridin-2-yl)amino)methyl)cyclohexyl)-3-methoxypicolinonitrile | 431.4 |
| 7.28 | 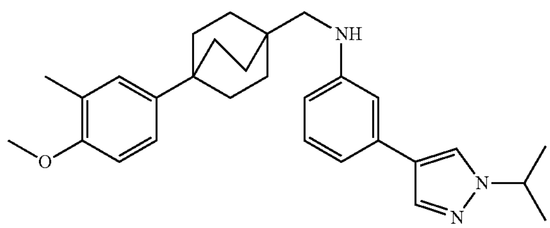 [SMILES: COc1ccc(C23CCC(CNc4cccc(-c5cnn(C(C)C)c5)c4)(CC2)CC3)cc1C] | 3-(1-Isopropyl-1H-pyrazol-4-yl)-N-((4-(4-methoxy-3-methylphenyl)bicyclo[2.2.2]octan-1-yl)methyl)aniline | 444.4 |
| 7.29 | 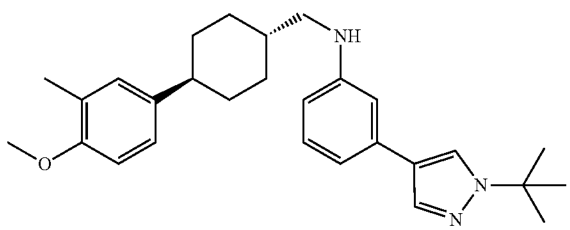 [SMILES: COc1ccc([C@H]2CC[C@H](CNc3cccc(-c4cnn(C(C)(C)C)c4)c3)CC2)cc1C] | 3-(1-(tert-Butyl)-1H-pyrazol-4-yl)-N-((trans-4-(4-methoxy-3-methylphenyl)cyclohexyl)methyl)aniline | 432.3 |
| 7.30 | 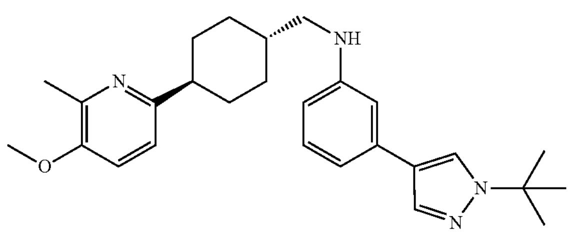 [SMILES: COc1ccc([C@H]2CC[C@H](CNc3cccc(-c4cnn(C(C)(C)C)c4)c3)CC2)nc1C] | 3-(1-(tert-Butyl)-1H-pyrazol-4-yl)-N-((trans-4-(5-methoxy-6-methylpyridin-2-yl)cyclohexyl)methyl)aniline | 433.4 |
| 7.31 | 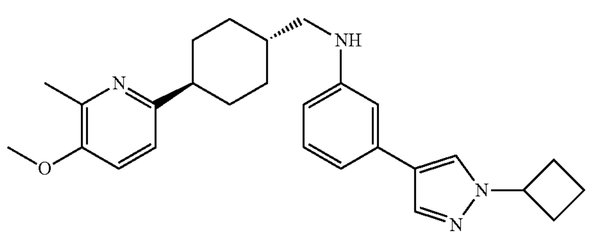 [SMILES: COc1ccc([C@H]2CC[C@H](CNc3cccc(-c4cnn(C5CCC5)c4)c3)CC2)nc1C] | 3-(1-Cyclobutyl-1H-pyrazol-4-yl)-N-((trans-4-(5-methoxy-6-methylpyridin-2-yl)cyclohexyl)methyl)aniline | 431.8 |

-continued

| Int | Structure | Name | [M + H]⁺ |
|---|---|---|---|
| 7.32 | 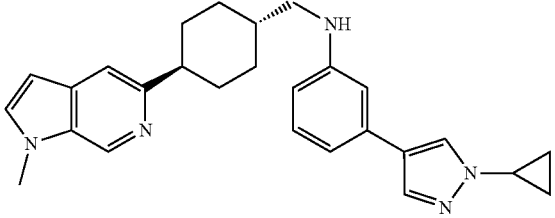 [SMILES: Cn1ccc2cc([C@H]3CC[C@H](CNc4cccc(-c5cnn(C6CC6)c5)c4)CC3)ncc21] | 3-(1-Cyclopropyl-1H-pyrazol-4-yl)-N-((trans-4-(1-methyl-1H-pyrrolo[2,3-c]pyridin-5-yl)cyclohexyl)methyl)aniline | 426.3 |
| 7.33 | 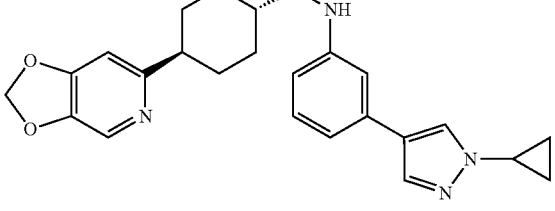 | N-((trans-4-(Benzo[d][1,3]dioxol-5-yl)cyclohexyl)methyl)-3-(1-cyclopropyl-1H-pyrazol-4-yl)aniline | 416.3 |
| 7.34 | 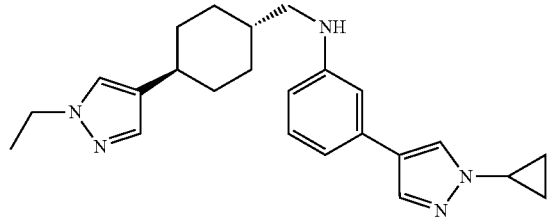 [SMILES: CCn1cc([C@H]2CC[C@H](CNc3cccc(-c4cnn(C5CC5)c4)c3)CC2)cn1] | 3-(1-Cyclopropyl-1H-pyrazol-4-yl)-N-((trans-4-(1-ethyl-1H-pyrazol-4-yl)cyclohexyl)methyl)aniline | 390.3 |
| 7.35[2] | 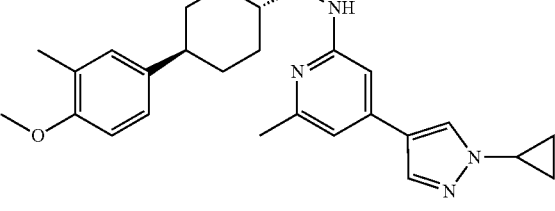 | 4-(1-Cyclopropyl-1H-pyrazol-4-yl)-N-((trans-4-(4-methoxy-3-methylphenyl)cyclohexyl)methyl)-6-methylpyridin-2-amine | 431.6 |
| 7.36[2] | 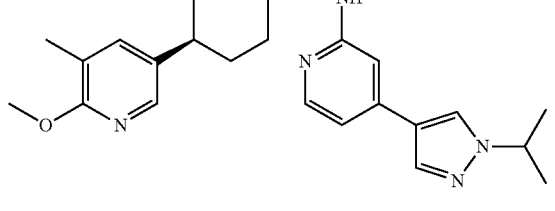 | 4-(1-Isopropyl-1H-pyrazol-4-yl)-N-((trans-4-(6-methoxy-5-methylpyridin-3-yl)cyclohexyl)methyl)pyridin-2-amine | 420.4 |
| 7.37[2] | 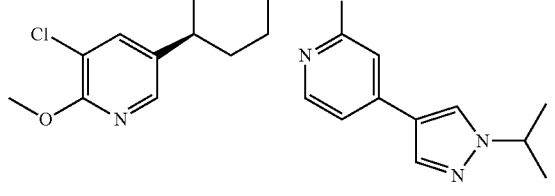 | N-((trans-4-(5-Chloro-6-methoxypyridin-3-yl)cyclohexyl)methyl)-4-(1-isopropyl-1H-pyrazol-4-yl)pyridin-2-amine | 440.4 |

[1]Alternate conditions: NaBH₃CN, AcOH, MeOH, rt, overnight;
[2]solvent was DCM.

Intermediate 8 trans-4-((tert-Butyldimethylsilyl)oxy)cyclohexanecarbonyl chloride

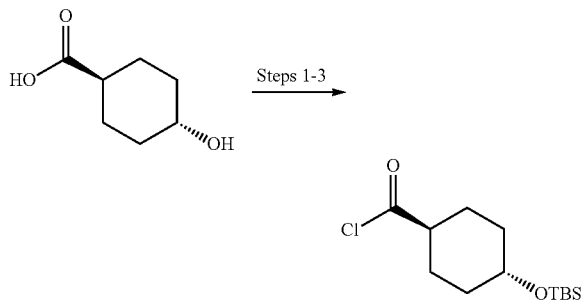

Step 1: trans-tert-Butyldimethylsilyl 4-((tert-butyldimethylsilyl)oxy)cyclohexanecarboxylate tert-Butyldimethylsilyl chloride (31.47 g, 208.8 mmol) was added to a mixture of trans-4-hydroxy-cyclohexanecarboxylic acid (10.03 g, 69.57 mmol), imidazole (18.96 g, 278.5 mmol), and DMF (140 mL) at rt under $N_2$ (reaction exothermed to 32° C.). The reaction was stirred at rt for 2 h and then diluted with 300 mL diethyl ether. The organic layer was washed with 1 N HCl (2×300 mL), washed with 300 mL brine, dried ($Na_2SO_4$), filtered and concentrated to give trans-tert-butyldimethylsilyl 4-((tert-butyldimethylsilyl)oxy)cyclohexanecarboxylate (31.5 g) as a clear oil. $^1$H NMR (400 MHz, DMSO-$d_6$): δ 3.61-3.53 (m, 1H), 2.26-2.18 (m, 1H), 2.04-1.96 (m, 2H), 1.92-1.85 (m, 2H), 1.51-1.39 (m, 2H), 1.39-1.27 (m, 2H), 0.94 (s, 9H), 0.89 (s, 9H), 0.26 (s, 6H), 0.06 (s, 6H).

Step 2: trans-4-((tert-Butyldimethylsilyl)oxy)cyclohexanecarboxylic acid

Potassium carbonate (58.01 g, 419.7 mmol) in water (300 mL) was added to a mixture of trans-tert-butyldimethylsilyl 4-((tert-butyldimethylsilyl)oxy)cyclohexanecarboxylate (31.5 g crude, 69.6 mmol), ethanol (1000 mL) and THF (300 mL) at rt under $N_2$. The reaction was stirred at rt for 3 h, concentrated until 300 mL remained, diluted with 600 mL brine, and then acidified to pH 2-3 with 20% $NaHSO_4$ (550 mL). The aqueous layer was extracted with 800 mL diethyl ether. The organic layer was washed with 800 mL brine, dried ($Na_2SO_4$), filtered and concentrated to give trans-4-((tert-butyldimethylsilyl)oxy)cyclohexanecarboxylic acid (17.3 g, 96% over 2 steps) as a white solid. $^1$H NMR (400 MHz, DMSO-$d_6$): δ 12.30 (br s, 1H), 3.59-3.51 (m, 1H), 2.15-2.05 (m, 1H), 1.88-1.74 (m, 4H), 1.41-1.29 (m, 2H), 1.28-1.16 (m, 2H), 0.84 (s, 9H), 0.02 (s, 6H).

Step 3: trans-4-((tert-Butyldimethylsilyl)oxy)cyclohexanecarbonyl chloride (Chloromethylene)dimethyl iminium chloride (34.02 g, 265.78 mmol) was weighed into a 1000 mL round bottom flask (3 neck) and degassed with vacuum/$N_2$ cycles (3×). Toluene (240 mL) was added to the flask, and the mixture was cooled (1.3° C.) in an ice bath. Anhydrous potassium carbonate* (68.71 g, 497.14 mmol) and trans-4-((tert-butyldimethylsilyl)oxy)cyclohexanecarboxylic acid (34.29 g, 132.69 mmol) were sequentially added to the reaction. The ice bath was removed, and the mixture was stirred for 35 min. Celite (7 g) was added to the reaction, and then the reaction was filtered through Celite (70 g, Chemglass 465 mL fritted funnel) with toluene washes (3×100 mL). This solution (451 g, 8.5% acid chloride, 100% yield, 72 mg/mL) was used immediately in the acylation reaction. $^1$H NMR (400 MHz, CDCl$_3$): δ 3.77-3.68 (m, 1H), 2.83-2.74 (m, 1H), 2.31-2.22 (m, 2H), 2.09-1.99 (m, 2H), 1.76-1.63 (m, 2H), 1.54-1.42 (m, 2H), 1.02 (s, 9H), 0.20 (s, 6H).

*Potassium carbonate was dried under vacuum by heating with a heat gun for ~5 min and then allowing to cool overnight.

The Intermediates below were synthesized from the appropriate starting materials following the procedure described for Intermediate 8.

| Int | Structure | Name |
|---|---|---|
| 8.01[1] | 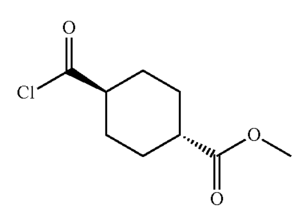 | trans-Methyl 4-(chlorocarbonyl)cyclohexanecarboxylate |
| 8.02[1] | 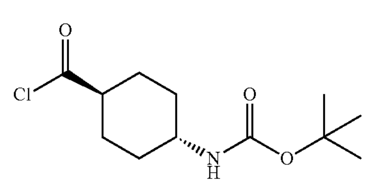 [SMILES: CC(C)(C)OC(=O)N[C@H]1CC[C@H](C(=O)Cl)CC1] | tert-Butyl (trans-4-(chlorocarbonyl)cyclohexyl)carbamate |

US 10,961,198 B2

-continued

| Int | Structure | Name |
|---|---|---|
| 8.03 | 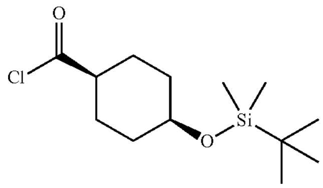 [SMILES: CC(C)(C)[Si](C)(C)O[C@H]1CC[C@@H](C(=O)Cl)CC1] | cis-4-((tert-Butyldimethylsilyl)oxy)cyclohexanecarbonyl chloride |
| 8.04[2] | 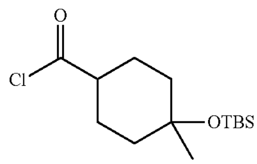 [SMILES: CC1(O[Si](C)(C)C(C)(C)C)CCC(C(=O)Cl)CC1] | 4-((tert-butyldimethylsilyl)oxy)-4-methylcyclohexanecarbonyl chloride |

[1] Step 3 only.
[2] Step 1: Ethyl 4-oxocyclohexanecarboxylate, AlMe₃, toluene, 0° C., 1 h gave ethyl 4-hydroxy-4-methylcyclohexanecarboxylate as a cis/trans mixture;
Step 2: TBSOTf, 2,6-lutidine, DCM, 0° C.-rt, overnight;
Step 3: LiOH·H₂O, H₂O, THF;
Step 4: Step 3 for Intermediate 8.

Intermediate 9 trans-4-((tert-Butyldimethylsilyl)oxy)-N-(3-iodophenyl)-N-((trans-4-(4-methoxy-3-methylphenyl)cyclohexyl)methyl)cyclohexanecarboxamide

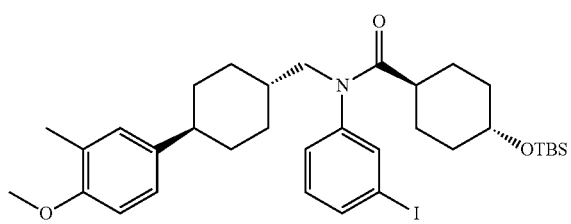 [SMILES: COc1ccc([C@H]2CC[C@H](CN(c3cccc(I)c3)C(=O)[C@H]3CC[C@H](O[Si](C)(C)C(C)(C)C)CC3)CC2)cc1C]

Intermediate 8 (74 mg/mL in toluene, 43 mL, 11.49 mmol) was added to a solution of Intermediate 6 (3.32 g, 7.63 mmol), pyridine (2.5 mL, 31 mmol), and toluene (15 mL). The mixture was stirred at rt for 90 min, diluted with EtOAc (50 mL), and washed (50 mL H₂O, 50 mL sat'd NaHCO₃ and then 50 mL brine). The organic layer was dried (Na₂SO₄), filtered, concentrated, and purified by silica gel chromatography (0-10% EtOAc in hexanes) to give trans-4-((tert-butyldimethylsilyl)oxy)-N-(3-iodophenyl)-N-((trans-4-(4-methoxy-3-methylphenyl)cyclohexyl)methyl) cyclohexanecarboxamide (4.05 g, 79%) as a white foam. $^1$H NMR (400 MHz, DMSO-d₆): δ 7.76 (d, 1H), 7.72 (s, 1H), 7.31 (d, 1H), 7.27 (t, 1H), 6.97-6.92 (m, 2H), 6.80-6.76 (m, 1H), 3.72 (s, 3H), 3.60-3.40 (m, 3H), 2.37-2.27 (m, 1H), 2.09 (s, 3H), 2.01-1.91 (m, 1H), 1.78-1.67 (m, 6H), 1.65-1.56 (m, 2H), 1.49-1.21 (m, 5H), 1.10-0.94 (m, 2H), 0.92-0.76 (m, 11H), −0.01 (s, 6H); LCMS: 676.6 [M+H]⁺.

The Intermediates below were synthesized from the appropriate Intermediate following the procedure described for Intermediate 9.

| Int | Structure | Name | [M + H]⁺ |
|---|---|---|---|
| 9.01 | 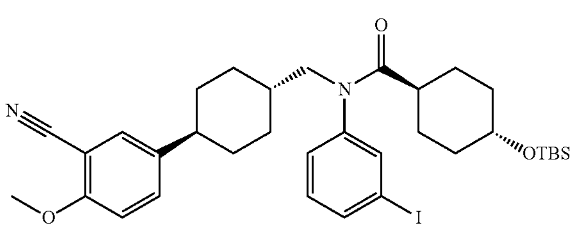 [SMILES: COc1ccc([C@H]2CC[C@H](CN(c3cccc(I)c3)C(=O)[C@H]3CC[C@H](O[Si](C)(C)C(C)(C)C)CC3)CC2)cc1C#N] | trans-4-((tert-Butyldimethylsilyl)oxy)-N-((trans-4-(3-cyano-4-methoxyphenyl)cyclohexyl)methyl)-N-(3-iodophenyl)cyclohexanecarboxamide | 687.5 |
| 9.02[1] | 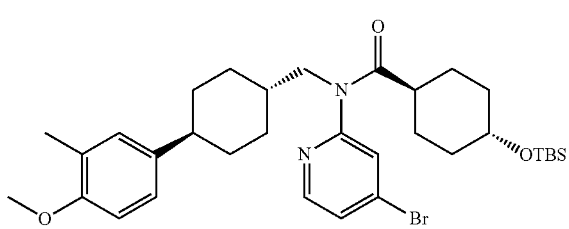 [SMILES: COc1ccc([C@H]2CC[C@H](CN(c3cc(Br)ccn3)C(=O)[C@H]3CC[C@H](O[Si](C)(C)C(C)(C)C)CC3)CC2)cc1C] | trans-N-(4-Bromopyridin-2-yl)-4-((tert-butyldimethylsilyl)oxy)-N-((trans-4-(4-methoxy-3-methylphenyl)cyclohexyl)methyl)cyclohexanecarboxamide | 629.2 |

| Int | Structure | Name | [M + H]+ |
|---|---|---|---|
| 9.03[1] | 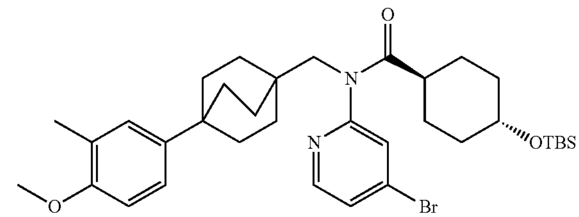 [SMILES: COc1ccc(C23CCC(CN(c4cc(Br)ccn4)C(=O)[C@H]4CC[C@H](O[Si](C)(C)C(C)(C)C)CC4)(CC2)CC3)cc1C] | trans-N-(4-Bromopyridin-2-yl)-4-((tert-butyldimethylsilyl)oxy)-N-((4-(4-methoxy-3-methylphenyl)bicyclo[2.2.2]octan-1-yl)methyl)cyclohexanecarboxamide | 655.2 |

[1]Alternate conditions used: TEA, DCM, rt, overnight.

Intermediate 10 trans-4-((tert-Butyldimethylsilyl)oxy)-N-((trans-4-(4-methoxy-3-methylphenyl)cyclohexyl)methyl)-N-(3-(4,4,5,5-tetramethyl-1,3,2-dioxaborolan-2-yl)phenyl)cyclohexanecarboxamide

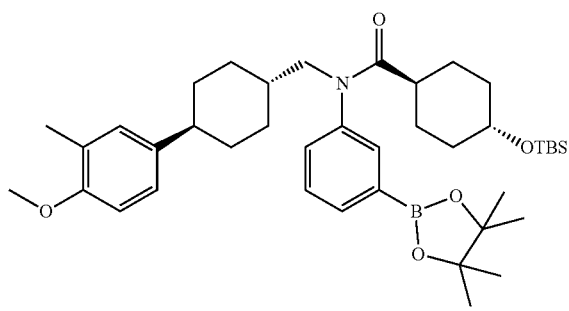 [SMILES: COc1ccc([C@H]2CC[C@H](CN(c3cccc(B4OC(C)(C)C(C)(C)O4)c3)C(=O)[C@H]3CC[C@H](O[Si](C)(C)C(C)(C)C)CC3)CC2)cc1C]

A mixture of bis(pinacolato)diboron (1.42 g, 5.59 mmol), potassium acetate (1.45 g, 14.8 mmol), Pd(dppf)Cl$_2$ (135 mg, 0.18 mmol), and toluene (23 mL) was degassed with 3 vacuum/N$_2$ cycles. Intermediate 9 (2.50 g, 3.70 mmol) was added to the mixture, and the reaction was degassed with 2 vacuum/N$_2$ cycles, heated at 115° C. for 3.5 h, and then allowed to cool to rt. The mixture was diluted with 75 mL EtOAc. The organics were washed with sat'd NaHCO$_3$ (2×75 mL), dried (Na$_2$SO$_4$), filtered, concentrated, and dried on high vacuum overnight to give trans-4-((tert-butyldimethylsilyl)oxy)-N-((trans-4-(4-methoxy-3-methylphenyl)cyclohexyl)methyl)-N-(3-(4,4,5,5-tetramethyl-1,3,2-dioxaborolan-2-yl)phenyl)cyclohexanecarboxamide (2.99 g, 120% crude product) as a brown solid. $^1$H NMR (400 MHz, CDCl$_3$): δ 7.82-7.78 (m, 1H), 7.61-7.57 (m, 1H), 7.43 (t, 1H), 7.27-7.24 (m, 1H), 6.99-6.94 (m, 2H), 6.74 (d, 1H), 3.80 (s, 3H), 3.72-3.45 (m, 3H), 2.44-2.33 (m, 1H), 2.20 (s, 3H), 2.11-2.01 (m, 1H), 1.90-1.76 (m, 6H), 1.75-1.65 (m, 3H), 1.58-1.47 (m, 2H), 1.42-1.32 (m, 14H), 1.24-1.10 (m, 2H), 1.06-0.92 (m, 2H), 0.84 (s, 9H), 0.01 (s, 6H); LCMS: 676.6 [M+H]+. Note: Intermediate 10 was also synthesized from the bromide version of Intermediate 9.

Intermediate 11 trans-4-((tert-Butyldimethylsilyl)oxy)-N-(3-ethynylphenyl)-N-((trans-4-(4-methoxy-3-methylphenyl)cyclohexyl)methyl)cyclohexanecarboxamide

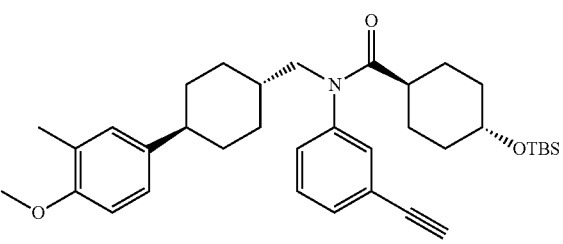 [SMILES: C#Cc1cccc(N(C[C@H]2CC[C@H](c3ccc(OC)c(C)c3)CC2)C(=O)[C@H]2CC[C@H](O[Si](C)(C)C(C)(C)C)CC2)c1]

Step 1: trans-4-((tert-Butyldimethylsilyl)oxy)-N-((trans-4-(4-methoxy-3-methylphenyl) cyclohexyl)methyl)-N-(3-((trimethylsilyl)ethynyl)phenyl)cyclohexanecarboxamide Ethynyl(trimethyl)silane (7.56 g, 76.95 mmol, 10.65 mL), CuI (733 mg, 3.85 mmol), and Pd(PPh$_3$)$_2$Cl$_2$ (2.70 g, 3.85 mmol) were added to a solution of Intermediate 9 (26 g, 38.48 mmol) in Et$_3$N (260 mL) under N$_2$. The mixture was stirred at 90° C. for 6 h, cooled to rt, and then diluted with ethyl acetate (250 mL). The mixture was washed with 250 mL H$_2$O. The organic layer was dried (Na$_2$SO$_4$), filtered, and concentrated. The crude was purified by silica gel chromatography (petroleum ether/ethyl acetate=20:1 to 5:1) to give trans-4-((tert-butyldimethylsilyl)oxy)-N-((trans-4-(4-methoxy-3-methylphenyl)cyclohexyl)methyl)-N-(3-((trimethylsilyl)ethynyl)phenyl)cyclohexanecarboxamide (21.5 g, 78% yield) as a yellow oil. $^1$H NMR (400 MHz, CDCl$_3$): δ 7.45-7.47 (m, 1H), 7.34-7.38 (m, 1H), 7.26-7.27 (m, 1H), 7.12-7.14 (m, 1H), 6.95-6.97 (m, 2H), 6.73-6.75 (m, 1H), 3.80 (s, 3H), 3.50-3.58 (m, 3H), 2.35-2.38 (m, 1H), 2.19 (s, 3H), 1.84-1.88 (m, 1H), 1.77-1.84 (m, 6H), 1.56-1.66 (m, 4H), 1.34-1.37 (m, 3H), 1.13-1.16 (m, 2H), 1.00-1.04 (m, 2H), 0.84 (s, 9H), 0.29 (s, 9H), 0.01 (s, 6H); LCMS: 646.5 [M+H]+.

Step 2: trans-4-((tert-Butyldimethylsilyl)oxy)-N-(3-ethynylphenyl)-N-((trans-4-(4-methoxy-3-methylphenyl)cyclohexyl)methyl)cyclohexanecarboxamide Ammonium fluoride (2.87 g, 77.39 mmol) was added to a solution of trans-4-((tert-butyldimethyl silyl)oxy)-N-

((trans-4-(4-methoxy-3-methylphenyl)cyclohexyl)methyl)-N-(3-((trimethylsilyl)ethynyl)phenyl)cyclohexanecarboxamide (10 g, 15.48 mmol) in MeOH (100 mL). The mixture was stirred at 60° C. for 1 h and then concentrated. The crude was purified by silica gel chromatography (petroleum ether/ethyl acetate=100/1 to 10:1) to give trans-4-((tert-butyldimethyl silyl)oxy)-N-(3-ethynylphenyl)-N-((trans-4-(4-methoxy-3-methylphenyl)cyclohexyl)methyl) cyclohexanecarboxamide (7.8 g, 88% yield) as yellow oil. $^1$H NMR (400 MHz, CDCl$_3$): δ 7.49-7.51 (m, 1H), 7.40-7.42 (m, 1H), 7.31 (s, 1H), 7.17-7.19 (m, 1H), 6.95-6.97 (m, 2H), 6.73-6.75 (m, 1H), 3.80 (s, 3H), 3.50-3.60 (m, 3H), 3.17 (s, 1H), 2.38-2.41 (m, 1H), 2.20 (s, 3H), 1.86-1.89 (m, 1H), 1.77-1.85 (m, 6H), 1.61-1.66 (m, 4H), 1.34-1.37 (m, 3H), 1.14-1.17 (m, 2H), 1.00-1.04 (m, 2H), 0.84 (s, 9H), 0.01 (s, 6H).

Intermediate 12; SM for Intermediate 1.04

6-Chloro-3-methoxypicolinonitrile

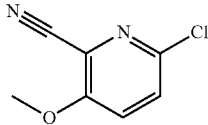

Step 1: 2-Cyano-3-methoxypyridine 1-oxide

3-Chloroperbenzoic acid (90.8 g, 447 mmol, 85% purity) was added to a solution of 3-methoxypicolinonitrile (50 g, 373 mmol) in DCE (500 mL) at rt. The reaction mixture was heated at 65° C. overnight and then allowed to cool to rt. The mixture was washed with NaHCO$_3$ (5×300 mL), dried over Na$_2$SO$_4$, filtered, concentrated, and then triturated in petroleum ether/EtOAc=5/1 (300 mL) to give 2-cyano-3-methoxypyridine 1-oxide (50 g, 89%) as a yellow solid. $^1$H NMR (400 MHz, CDCl$_3$): δ 7.95 (d, 1H), 7.37 (t, 1H), 6.90 (d, 1H), 4.03 (s, 3H); LCMS: 151.0 [M+H]$^+$.

Step 2: 6-Chloro-3-methoxypicolinonitrile

A mixture of 2-cyano-3-methoxypyridine 1-oxide (30 g, 200 mmol) and POCl$_3$ (333 g, 2.17 mol) was heated to 100° C. for 2 h under N$_2$. The mixture was concentrated to dryness, diluted with NaHCO$_3$ (300 mL), and extracted with EtOAc (2×100 ml). The organic layers were combined, dried (Na$_2$SO$_4$), filtered, concentrated, and then purified by silica gel chromatography (petroleum ether/EtOAc=2/1) to give 6-chloro-3-methoxypicolinonitrile (20 g, 59%) as a yellow solid. $^1$H NMR (400 MHz, CDCl$_3$): δ 7.51 (d, 1H), 7.38 (d, 1H), 3.99 (s, 3H); LCMS: 169.0 [M+H]+.

Intermediate 13; SM for Intermediate 1.09

5-Bromo-1-methyl-1H-pyrrolo[2,3-c]pyridine

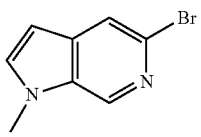

Sodium hydride (3.65 g, 91.36 mmol, 60% purity) was added to a solution of 5-bromo-1H-pyrrolo[2,3-c]pyridine (9 g, 45.68 mmol) in DMF (100 mL) at 0° C. under N$_2$. The reaction was stirred for 0.5 h, and then Me$_2$SO$_4$ (5.76 g, 45.68 mmol) was added dropwise at 0° C. under N$_2$. The reaction was allowed to warm to rt for 2 h, poured into water (200 mL), and extracted with EtOAc (5×100 mL). The combined organic layers were washed with water (2×100 mL), washed with brine (100 mL), dried over Na$_2$SO$_4$, filtered, concentrated, and then purified by chromatography on silica gel (petroleum ether/EtOAc=4/1) to give 5-bromo-1-methyl-1H-pyrrolo[2,3-c]pyridine (9.6 g, 99.5%) as a yellow solid. $^1$H NMR (400 MHz, DMSO-d$_6$): δ 8.64 (s, 1H), 7.73 (s, 1H), 7.63 (d, 1H), 6.47 (d, 1H), 3.89 (s, 3H); LCMS: 211.0 [M+H]$^+$.

Intermediate 14; SM for Intermediate 1.03

5-Bromo-3-fluoro-1-methyl-1H-indazole

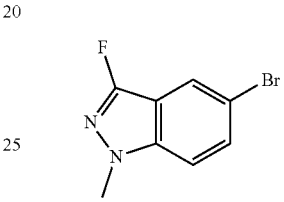

1-(Chloromethyl)-4-fluoro-1,4-diazabicyclo[2.2.2]octane-1,4-diium tetrafluoroborate (16.11 g, 45.48 mmol) was added to a solution of 5-bromo-1-methyl-1H-indazole (8.00 g, 37.90 mmol) in CH$_3$CN (80 mL) at rt. The mixture was stirred at 80° C. overnight, quenched with H$_2$O (50 mL) at rt, and then diluted with EtOAc (50 mL). The mixture was extracted with EtOAc (3×50 mL). The combined organic layers were dried over Na$_2$SO$_4$, filtered and concentrated under reduced pressure to give a residue. The residue was purified by column chromatography (petroleum ether/ethyl acetate=50 to 5:1) to give 5-bromo-3-fluoro-1-methyl-1H-indazole (3.95 g, 46%) as a white solid. $^1$H NMR (400 MHz, DMSO-d$_6$): δ 7.93 (s, 1H), 7.53-7.65 (m, 2H), 3.90 (s, 3H).

Compound 1 trans-4-Hydroxy-N-((trans-4-(4-methoxy-3-methylphenyl)cyclohexyl)methyl)-N-(3-(4-methyl-1H-pyrazol-1-yl)phenyl)cyclohexanecarboxamide

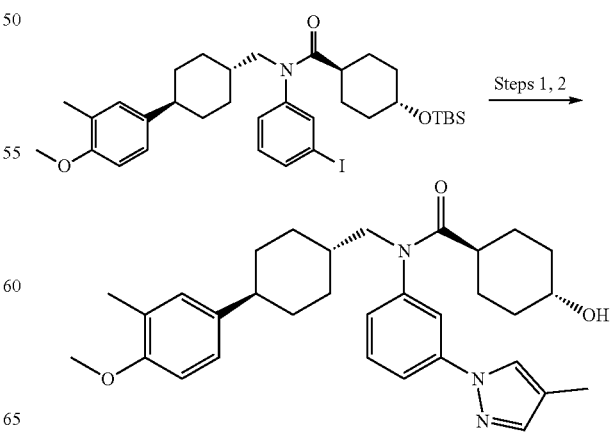

Steps 1, 2

141

Step 1: trans-4-((tert-Butyldimethylsilyl)oxy)-N-((trans-4-(4-methoxy-3-methylphenyl) cyclohexyl)methyl)-N-(3-(4-methyl-1H-pyrazol-1-yl)phenyl)cyclohexanecarboxamide A mixture of Cu$_2$O (2.6 mg, 0.019 mmol), Cs$_2$CO$_3$ (241 mg, 0.740 mmol), salicylaldoxime (10 mg, 0.074 mmol), and 4-methyl-1H-pyrazole (45.5 mg, 0.555 mmol) was added to a solution of Intermediate 9 (250 mg, 0.370 mmol) in CH$_3$CN (10 mL). The resulting mixture was stirred at 80° C. overnight under N$_2$, allowed to cool to rt, filtered, and concentrated in vacuo. The crude product was purified by prep-TLC (PE/EA=10/1) to give trans-4-((tert-butyldimethylsilyl)oxy)-N-((trans-4-(4-methoxy-3-methylphenyl)cyclohexyl)methyl)-N-(3-(4-methyl-1H-pyrazol-1-yl)phenyl)cyclohexanecarboxamide (100 mg, 43%) as a light yellow oil. LCMS: 630.5 [M+H]$^+$.

Step 2: trans-4-Hydroxy-N-((trans-4-(4-methoxy-3-methylphenyl)cyclohexyl)methyl)-N-(3-(4-methyl-1H-pyrazol-1-yl)phenyl)cyclohexanecarboxamide Aqueous hydrochloric acid (1 M, 0.5 mL) was added to a solution of trans-4-((tert-butyldimethyl silyl)oxy)-N-((trans-4-(4-methoxy-3-methylphenyl)cyclohexyl)methyl)-N-(3-(4-methyl-1H-pyrazol-1-yl)phenyl)cyclohexanecarboxamide (80.0 mg, 0.127 mmol) in MeOH (4 mL). The mixture was stirred at rt for 0.5 h, poured into 10 mL cold water, and then extracted with 5% MeOH in DCM (15 mL). The organic layer was washed with 10 mL brine, dried (Na$_2$SO$_4$), filtered, concentrated, and purified by prep-TLC (PE/EA=1/1) to give trans-4-hydroxy-N-((trans-4-(4-methoxy-3-methylphenyl)cyclohexyl)methyl)-N-(3-(4-methyl-1H-pyrazol-1-yl)phenyl)cyclohexanecarboxamide (21 mg, 32%) as a white solid. $^1$H NMR (400 MHz, DMSO-d$_6$): δ 8.37 (s, 1H), 7.77-7.86 (m, 1H), 7.73 (s, 1H), 7.52-7.62 (m, 2H), 7.20 (d, 1H), 6.92-6.96 (m, 2H), 6.78 (d, 1H), 4.35-4.42 (m, 1H), 3.72 (s, 3H), 3.54-3.61 (m, 2H), 3.26-3.30 (m, 1H), 2.00-2.12 (m, 7H), 1.69-1.80 (m, 6H), 1.59-1.68 (m, 2H), 1.22-1.49 (m, 6H), 0.99-1.12 (m, 2H), 0.70-0.85 (m, 2H); LCMS: 516.2 [M+H]$^+$.

Compound 2 trans-N-((trans-4-(3-Cyano-4-methoxyphenyl)cyclohexyl)methyl)-N-(3-(1-ethyl-1H-pyrazol-4-yl)phenyl)-4-hydroxycyclohexanecarboxamide

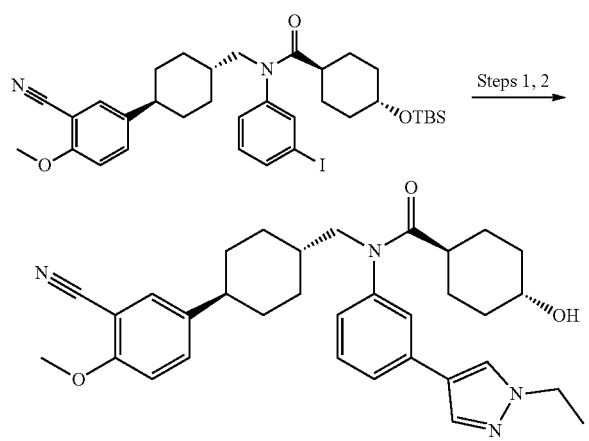

Step 1: trans-4-((tert-Butyldimethylsilyl)oxy)-N-((trans-4-(3-cyano-4-methoxyphenyl) cyclohexyl)methyl)-N-(3-(1-ethyl-1H-pyrazol-4-yl)phenyl)cyclohexanecarboxamide A mixture of Intermediate 9.01 (101 mg, 0.15 mmol), (1-ethyl-1H-pyrazol-4-yl)boronic acid (33 mg, 0.24 mmol), Pd(dppf)Cl$_2$ (15 mg, 0.02 mmol), dioxane (1.5 mL) and 0.4 M K$_2$CO$_3$ (1.1 mL, 0.44 mmol) was degassed with 3 vacuum/N$_2$ cycles, stirred at 80° C. for 25 min, allowed to cool to rt, poured into 20 mL sat'd NaHCO$_3$, and then extracted with 20 mL EtOAc. The organics were washed with 20 mL brine, dried (Na$_2$SO$_4$), filtered, concentrated, and purified by silica gel chromatography (20-50% ethyl acetate in hexanes) to give trans-4-((tert-butyldimethylsilyl)oxy)-N-((trans-4-(3-cyano-4-methoxyphenyl)cyclohexyl)methyl)-N-(3-(1-ethyl-1H-pyrazol-4-yl)phenyl)cyclohexanecarboxamide (79 mg, 81%). LCMS: 655.5 [M+H]$^+$.

Step 2: trans-N-((trans-4-(3-Cyano-4-methoxyphenyl)cyclohexyl)methyl)-N-(3-(1-ethyl-1H-pyrazol-4-yl)phenyl)-4-hydroxycyclohexanecarboxamide Aqueous hydrochloric acid (1N, 0.17 mL, 0.17 mmol) was added to a solution of trans-4-((tert-butyldimethylsilyl)oxy)-N-((trans-4-(3-cyano-4-methoxyphenyl)cyclohexyl)methyl)-N-(3-(1-ethyl-1H-pyrazol-4-yl)phenyl)cyclohexanecarboxamide (79 mg, 0.12 mmol), methanol (0.5 mL) and tetrahydrofuran (0.5 mL) at 0° C. The reaction was allowed to warm to rt, stirred at rt for 1 h, poured into 20 mL cold sat'd NaHCO$_3$, and then extracted with 20 mL EtOAc. The organics were washed with 20 mL sat'd NaHCO$_3$ and washed with 20 mL brine. The combined aqueous layers were back extracted with 20 mL EtOAc. The combined extracts were dried (Na$_2$SO$_4$), filtered, concentrated, and purified by silica gel chromatography (0-7% methanol in DCM) to give trans-N-((trans-4-(3-cyano-4-methoxyphenyl)cyclohexyl)methyl)-N-(3-(1-ethyl-1H-pyrazol-4-yl)phenyl)-4-hydroxycyclohexanecarboxamide (60 mg, 92%) as a yellow foam. $^1$H NMR (400 MHz, DMSO-d$_6$): δ 8.29 (s, 1H), 7.94 (s, 1H), 7.59 (d, 1H), 7.56-7.48 (m, 3H), 7.45 (t, 1H), 7.15-7.06 (m, 2H), 4.39 (d, 1H), 4.15 (q, 2H), 3.86 (s, 3H), 3.66-3.46 (m, 2H), 3.32-3.20 (m, 1H), 2.49-2.40 (m, 1H), 2.11-2.00 (m, 1H), 1.81-1.68 (m, 6H), 1.68-1.59 (m, 2H), 1.48-1.27 (m, 8H), 1.12-0.99 (m, 2H), 0.82-0.68 (m, 2H); LCMS: 541.4 [M+H]$^+$.

The Compounds below were synthesized from the appropriate Intermediate and the appropriate boronic acid or boronic ester following the procedures described for Compound 2.

| Cmpd | Structure | Name | [M + H]+ |
|---|---|---|---|
| 2.01[1,4] | 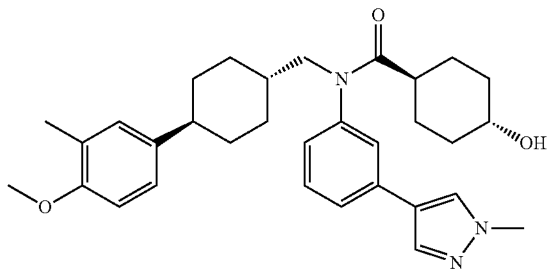 [SMILES: COc1ccc([C@H]2CC[C@H](CN(c3cccc(-c4cnn(C)c4)c3)C(=O)[C@H]3CC[C@H](O)CC3)CC2)cc1C] | trans-4-Hydroxy-N-((trans-4-(4-methoxy-3-methylphenyl)cyclohexyl)methyl)-N-(3-(1-methyl-1H-pyrazol-4-yl)phenyl)cyclohexanecarboxamide | 516.4 |
| 2.02[2,4] | 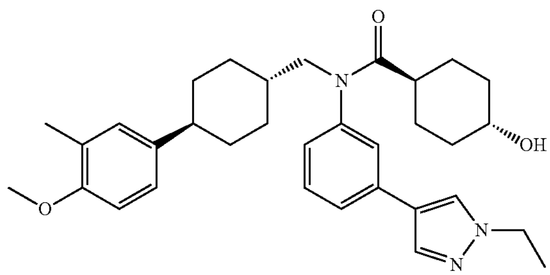 [SMILES: CCn1cc(-c2cccc(N(C[C@H]3CC[C@H](c4ccc(OC)c(C)c4)CC3)C(=O)[C@H]3CC[C@H](O)CC3)c2)cn1] | trans-N-(3-(1-Ethyl-1H-pyrazol-4-yl)phenyl)-4-hydroxy-N-((trans-4-(4-methoxy-3-methylphenyl)cyclohexyl)methyl)cyclohexanecarboxamide | 530.5 |
| 2.03 | 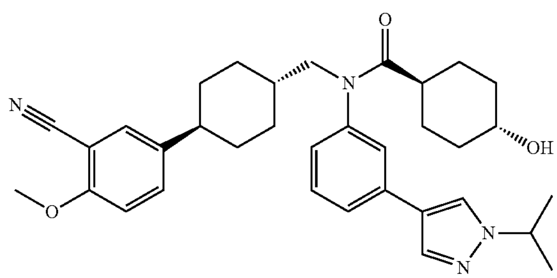 | trans-N-((trans-4-(3-Cyano-4-methoxyphenyl)cyclohexyl)methyl)-4-hydroxy-N-(3-(1-isopropyl-1H-pyrazol-4-yl)phenyl)cyclohexanecarboxamide | 555.5 |
| 2.04 | 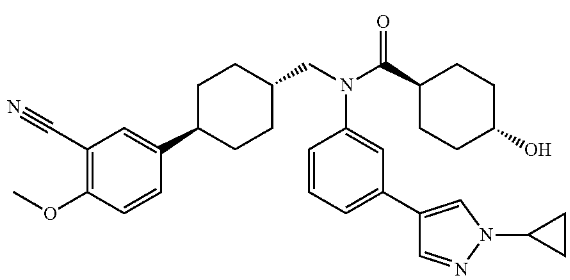 [SMILES: COc1ccc([C@H]2CC[C@H](CN(c3cccc(-c4cnn(C5CC5)c4)c3)C(=O)[C@H]3CC[C@H](O)CC3)CC2)cc1C#N] | trans-N-((trans-4-(3-Cyano-4-methoxyphenyl)cyclohexyl)methyl)-N-(3-(1-cyclopropyl-1H-pyrazol-4-yl)phenyl)-4-hydroxycyclohexanecarboxamide | 553.5 |
| 2.05 | 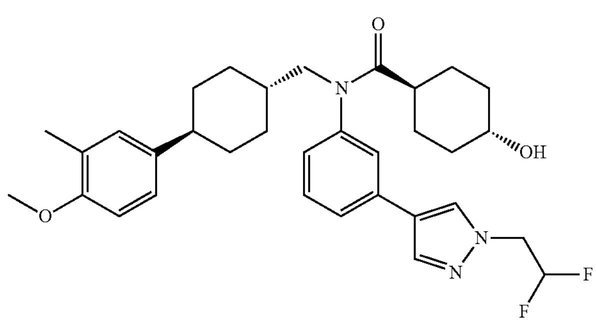 [SMILES: COc1ccc([C@H]2CC[C@H](CN(c3cccc(-c4cnn(CC(F)F)c4)c3)C(=O)[C@H]3CC[C@H](O)CC3)CC2)cc1C] | trans-N-(3-(1-(2,2-Difluoroethyl)-1H-pyrazol-4-yl)phenyl)-4-hydroxy-N-((trans-4-(4-methoxy-3-methylphenyl)cyclohexyl)methyl)cyclohexanecarboxamide | 566.4 |

| Cmpd | Structure | Name | [M + H]⁺ |
|---|---|---|---|
| 2.06 | 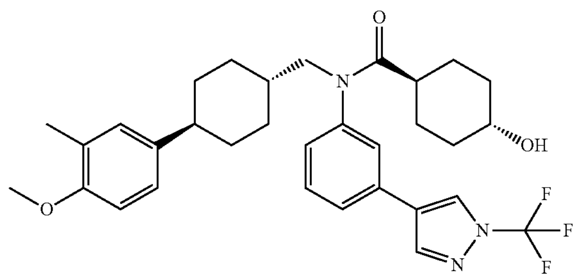 [SMILES: COc1ccc([C@H]2CC[C@H](CN(c3cccc(-c4cnn(C(F)(F)F)c4)c3)C(=O)[C@H]3CC[C@H](O)CC3)CC2)cc1C] | trans-4-Hydroxy-N-((trans-4-(4-methoxy-3-methylphenyl)cyclohexyl)methyl)-N-(3-(1-(trifluoromethyl)-1H-pyrazol-4-yl)phenyl)cyclohexanecarboxamide | 570.4 |
| 2.07[2] | 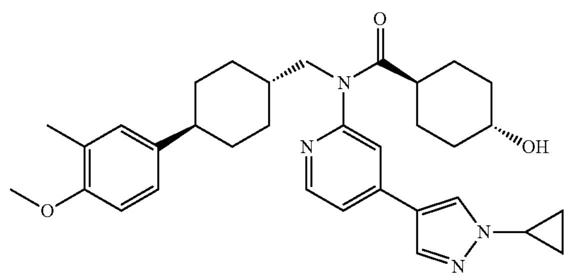 [SMILES: COc1ccc([C@H]2CC[C@H](CN(c3cc(-c4cnn(C5CC5)c4)ccn3)C(=O)[C@H]3CC[C@H](O)CC3)CC2)cc1C] | trans-N-(4-(1-Cyclopropyl-1H-pyrazol-4-yl)pyridin-2-yl)-4-hydroxy-N-((trans-4-(4-methoxy-3-methylphenyl)cyclohexyl)methyl)cyclohexanecarboxamide | 543.3 |
| 2.08 | 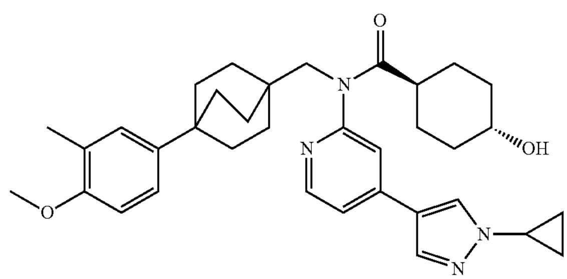 [SMILES: COc1ccc(C23CCC(CN(c4cc(-c5cnn(C6CC6)c5)ccn4)C(=O)[C@H]4CC[C@H](O)CC4)(CC2)CC3)cc1C] | trans-N-(4-(1-Cyclopropyl-1H-pyrazol-4-yl)pyridin-2-yl)-4-hydroxy-N-((4-(4-methoxy-3-methylphenyl)bicyclo[2.2.2]octan-1-yl)methyl)cyclohexanecarboxamide | 569.5 |
| 2.09[3] | 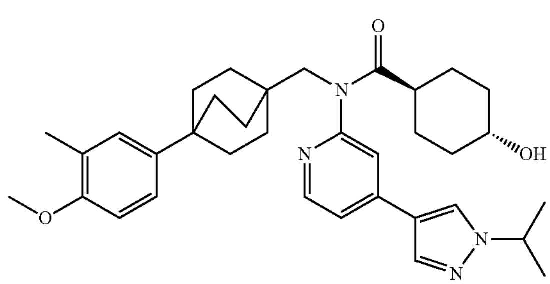 | trans-4-Hydroxy-N-(4-(1-isopropyl-1H-pyrazol-4-yl)pyridin-2-yl)-N-((4-(4-methoxy-3-methylphenyl)bicyclo[2.2.2]octan-1-yl)methyl)cyclohexanecarboxamide | 571.5 |

Alternate conditions:

Step 1:

[1] 1M Na$_2$CO$_3$, DMF, 50° C.,

[2] Cs$_2$CO$_3$, DMF (1-2% water), 50° C.,

[3] Pd(PPh$_3$)$_4$, Cs$_2$CO$_3$, DMF (2% water), 50° C.;

Step 2:

[4] 6N HCl.

Compound 3 trans-N-(3-(1-Cyclopropyl-1H-pyrazol-4-yl)phenyl)-4-hydroxy-N-((trans-4-(4-methoxy-3-methylphenyl)cyclohexyl)methyl)cyclohexanecarboxamide

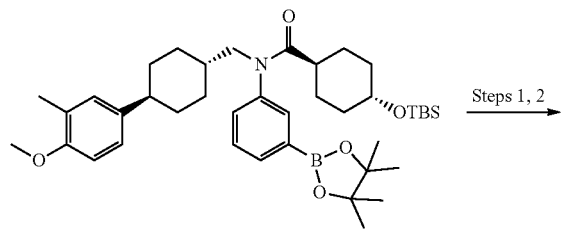

Steps 1, 2

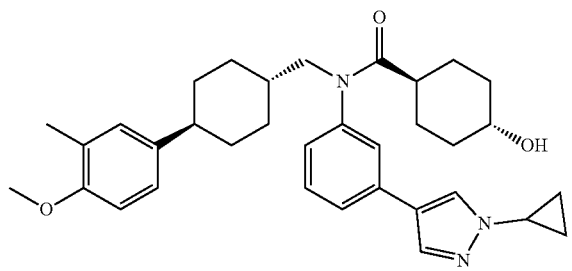

Step 1: trans-4-((tert-Butyldimethylsilyl)oxy)-N-(3-(1-cyclopropyl-1H-pyrazol-4-yl)phenyl)-N-((trans-4-(4-methoxy-3-methylphenyl)cyclohexyl)methyl)cyclohexanecarboxamide A mixture of 4-bromo-1-cyclopropyl-1H-pyrazole (65 mg, 0.35 mmol), Intermediate 10 (163 mg, 0.20 mmol), $Cs_2CO_3$ (196 mg, 0.60 mmol), $Pd(dppf)Cl_2$, DMF (2 mL), and $H_2O$ (20 μL) was degassed with 3 vacuum/$N_2$ cycles, heated at 80° C. for 110 min, and allowed to cool to rt. The reaction was poured into 20 mL sat'd $NaHCO_3$ and then extracted with EtOAc (2×20 mL). The combined organics were washed with 20 mL brine, dried ($Na_2SO_4$), filtered, concentrated, and purified by silica gel chromatography (10-30% ethyl acetate in hexanes) to give trans-4-((tert-butyldimethylsilyl)oxy)-N-(3-(1-cyclopropyl-1H-pyrazol-4-yl)phenyl)-N-((trans-4-(4-methoxy-3-methylphenyl)cyclohexyl)methyl)cyclohexanecarboxamide (63 mg, 48%) as a white foam.

$^1$H NMR (400 MHz, DMSO-$d_6$): δ 8.34 (s, 1H), 7.93 (s, 1H), 7.61 (d, 1H), 7.56-7.52 (m, 1H), 7.43 (t, 1H), 7.08 (d, 1H), 6.98-6.91 (m, 2H), 6.81-6.75 (m, 1H), 3.77-3.69 (m, 4H), 3.64-3.45 (m, 3H), 2.38-2.28 (m, 1H), 2.13-2.02 (m, 4H), 1.81-1.68 (m, 6H), 1.68-1.59 (m, 2H), 1.51-1.36 (m, 3H), 1.36-1.22 (m, 2H), 1.12-0.95 (m, 6H), 0.89-0.74 (m, 11H), −0.03 (s, 6H); LCMS: 656.6 [M+H]$^+$.

Step 2: trans-N-(3-(1-Cyclopropyl-1H-pyrazol-4-yl)phenyl)-4-hydroxy-N-((trans-4-(4-methoxy-3-methylphenyl)cyclohexyl)methyl)cyclohexanecarboxamide Aqueous hydrochloric acid (6 N, 0.13 mL, 0.78 mmol) was added to a solution of trans-4-((tert-butyldimethylsilyl)oxy)-N-(3-(1-cyclopropyl-1H-pyrazol-4-yl)phenyl)-N-((trans-4-(4-methoxy-3-methylphenyl)cyclohexyl)methyl)cyclohexanecarboxamide (62 mg, 0.095 mmol), methanol (0.5 mL) and tetrahydrofuran (0.5 mL) at 0° C. The reaction was allowed to warm to rt, stirred for 40 min, poured into 20 mL cold sat'd $NaHCO_3$, and then extracted with EtOAc. The organics were washed with 20 mL sat'd $NaHCO_3$ and washed with 20 mL brine. The first aqueous wash was back extracted with 20 mL EtOAc. The combined extracts were dried ($Na_2SO_4$), filtered, concentrated, and purified by silica gel chromatography (0-7% MeOH in DCM) to give trans-N-(3-(1-cyclopropyl-1H-pyrazol-4-yl)phenyl)-4-hydroxy-N-((trans-4-(4-methoxy-3-methylphenyl)cyclohexyl)methyl)cyclohexanecarboxamide (50 mg, 98%) as an off-white foam. $^1$H NMR (400 MHz, DMSO-$d_6$): δ 8.34 (s, 1H), 7.94 (s, 1H), 7.60 (d, 1H), 7.56-7.51 (m, 1H), 7.44 (t, 1H), 7.09 (d, 1H), 6.98-6.92 (m, 2H), 6.81-6.75 (m, 1H), 4.39 (d, 1H), 3.78-3.69 (m, 4H), 3.63-3.48 (m, 2H), 3.30-3.20 (m, 1H), 2.38-2.28 (m, 1H), 2.09 (s, 3H), 2.08-1.99 (m, 1H), 1.80-1.68 (m, 6H), 1.67-1.58 (m, 2H), 1.48-1.37 (m, 3H), 1.32-1.20 (m, 2H), 1.11-0.95 (m, 6H), 0.81-0.67 (m, 2H); LCMS: 542.5 [M+H]$^+$.

The Compounds below were synthesized from Intermediate 10 and the appropriate aryl halide following the procedures described for Compound 3.

| Cmpd | Structure | Name | [M + H]$^+$ |
|---|---|---|---|
| 3.01 | 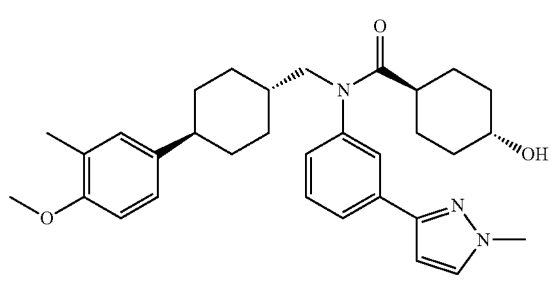 [SMILES: COc1ccc([C@H]2CC[C@H](CN(c3cccc(-c4ccn(C)n4)c3)C(=O)[C@H]3CC[C@H](O)CC3)CC2)cc1C] | trans-4-Hydroxy-N-((trans-4-(4-methoxy-3-methylphenyl)cyclohexyl)methyl)-N-(3-(1-methyl-1H-pyrazol-3-yl)phenyl)cyclohexanecarboxamide | 516.5 |

-continued

| Cmpd | Structure | Name | [M + H]+ |
|---|---|---|---|
| 3.02 | 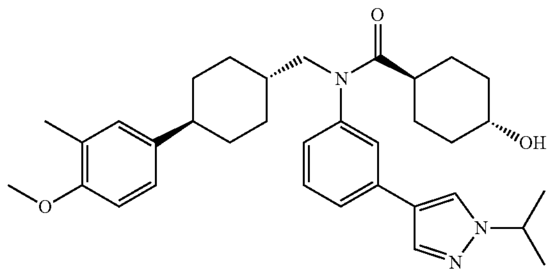 [SMILES: COc1ccc([C@H]2CC[C@H](CN(c3cccc(-c4cnn(C(C)C)c4)c3)C(=O)[C@H]3CC[C@H](O)CC3)CC2)cc1C] | trans-4-Hydroxy-N-(3-(1-isopropyl-1H-pyrazol-4-yl)phenyl)-N-((trans-4-(4-methoxy-3-methylphenyl)cyclohexyl)methyl)cyclohexanecarboxamide | 544.4 |
| 3.03 | 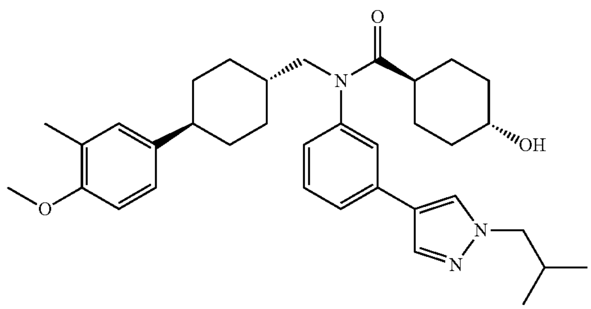 [SMILES: COc1ccc([C@H]2CC[C@H](CN(c3cccc(-c4cnn(CC(C)C)c4)c3)C(=O)[C@H]3CC[C@H](O)CC3)CC2)cc1C] | trans-4-Hydroxy-N-(3-(1-isobutyl-1H-pyrazol-4-yl)phenyl)-N-((trans-4-(4-methoxy-3-methylphenyl)cyclohexyl)methyl)cyclohexanecarboxamide | 558.5 |
| 3.04 | 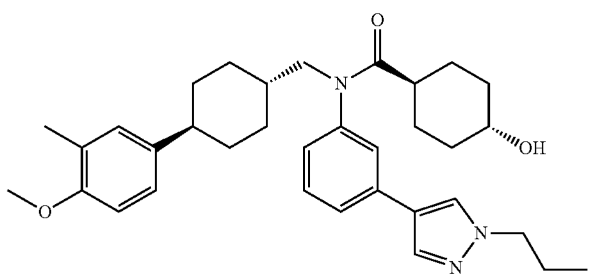 [SMILES: CCCn1cc(-c2cccc(N(C[C@H]3CC[C@H](c4ccc(OC)c(C)c4)CC3)C(=O)[C@H]3CC[C@H](O)CC3)c2)cn1] | trans-4-Hydroxy-N-((trans-4-(4-methoxy-3-methylphenyl)cyclohexyl)methyl)-N-(3-(1-propyl-1H-pyrazol-4-yl)phenyl)cyclohexanecarboxamide | 544.5 |
| 3.05 | 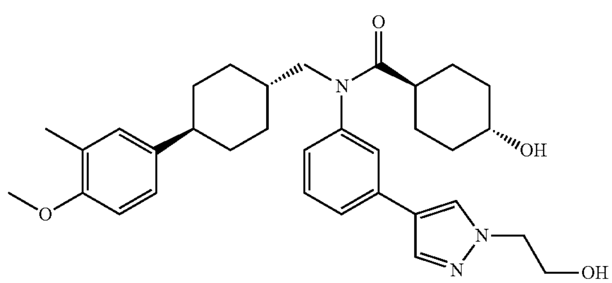 [SMILES: COc1ccc([C@H]2CC[C@H](CN(c3cccc(-c4cnn(CCO)c4)c3)C(=O)[C@H]3CC[C@H](O)CC3)CC2)cc1C] | trans-4-Hydroxy-N-(3-(1-(2-hydroxyethyl)-1H-pyrazol-4-yl)phenyl)-N-((trans-4-(4-methoxy-3-methylphenyl)cyclohexyl)methyl)cyclohexanecarboxamide | 546.5 |
| 3.06[1] | 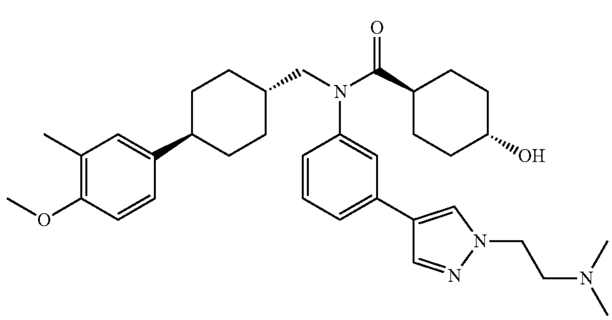 | trans-N-(3-(1-(2-(Dimethylamino)ethyl)-1H-pyrazol-4-yl)phenyl)-4-hydroxy-N-((trans-4-(4-methoxy-3-methylphenyl)cyclohexyl)methyl)cyclohexanecarboxamide | 573.5 |

-continued

| Cmpd | Structure | Name | [M + H]+ |
|---|---|---|---|
| 3.07 | 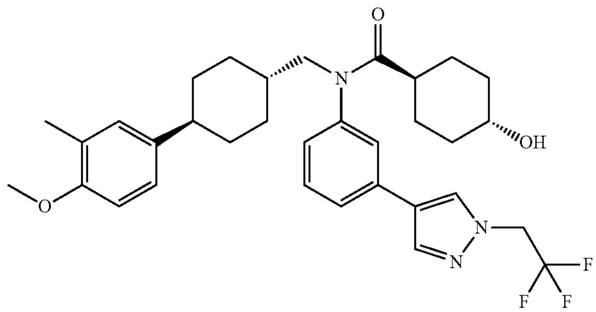 [SMILES: COc1ccc([C@H]2CC[C@H](CN(c3cccc(-c4cnn(CC(F)(F)F)c4)c3)C(=O)[C@H]3CC[C@H](O)CC3)CC2)cc1C] | trans-4-Hydroxy-N-((trans-4-(4-methoxy-3-methylphenyl)cyclohexyl)methyl)-N-(3-(1-(2,2,2-trifluoroethyl)-1H-pyrazol-4-yl)phenyl)cyclohexanecarboxamide | 584.4 |
| 3.08[2] | 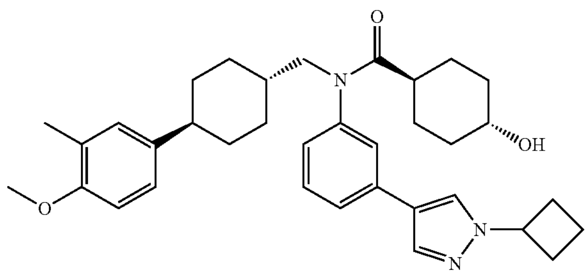 [SMILES: COc1ccc([C@H]2CC[C@H](CN(c3cccc(-c4cnn(C5CCC5)c4)c3)C(=O)[C@H]3CC[C@H](O)CC3)CC2)cc1C] | trans-N-(3-(1-Cyclobutyl-1H-pyrazol-4-yl)phenyl)-4-hydroxy-N-((trans-4-(4-methoxy-3-methylphenyl)cyclohexyl)methyl)cyclohexanecarboxamide | 556.4 |
| 3.09[1,2] | 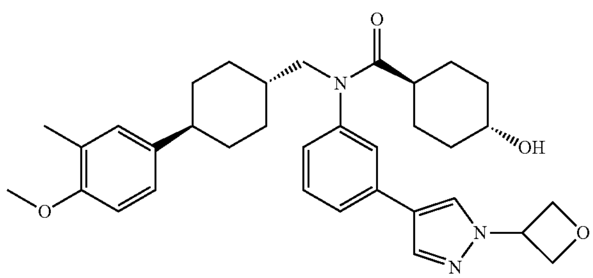 [SMILES: COc1ccc([C@H]2CC[C@H](CN(c3cccc(-c4cnn(C5COC5)c4)c3)C(=O)[C@H]3CC[C@H](O)CC3)CC2)cc1C] | trans-4-Hydroxy-N-((trans-4-(4-methoxy-3-methylphenyl)cyclohexyl)methyl)-N-(3-(1-(oxetan-3-yl)-1H-pyrazol-4-yl)phenyl)cyclohexanecarboxamide | 558.4 |
| 3.10[2] | 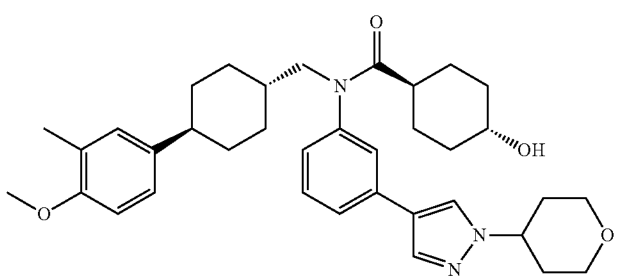 [SMILES: COc1ccc([C@H]2CC[C@H](CN(c3cccc(-c4cnn(C5CCOCC5)c4)c3)C(=O)[C@H]3CC[C@H](O)CC3)CC2)cc1C] | trans-4-Hydroxy-N-((trans-4-(4-methoxy-3-methylphenyl)cyclohexyl)methyl)-N-(3-(1-(tetrahydro-2H-pyran-4-yl)-1H-pyrazol-4-yl)phenyl)cyclohexanecarboxamide | 586.5 |
| 3.11[1,2] | 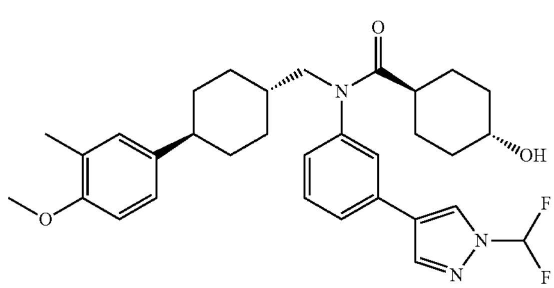 [SMILES: COc1ccc([C@H]2CC[C@H](CN(c3cccc(-c4cnn(C(F)F)c4)c3)C(=O)[C@H]3CC[C@H](O)CC3)CC2)cc1C] | trans-N-(3-(1-(Difluoromethyl)-1H-pyrazol-4-yl)phenyl)-4-hydroxy-N-((trans-4-(4-methoxy-3-methylphenyl)cyclohexyl)methyl)cyclohexanecarboxamide | 552.4 |

| Cmpd | Structure | Name | [M + H]+ |
|---|---|---|---|
| 3.12[1,2] | 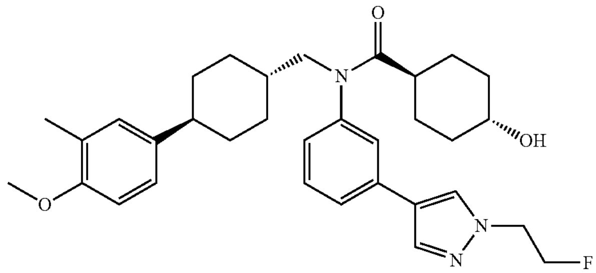 [SMILES: COc1ccc([C@H]2CC[C@H](CN(c3cccc(-c4cnn(CCF)c4)c3)C(=O)[C@H]3CC[C@H](O)CC3)CC2)cc1C] | trans-N-(3-(1-(2-Fluoroethyl)-1H-pyrazol-4-yl)phenyl)-4-hydroxy-N-((trans-4-(4-methoxy-3-methylphenyl)cyclohexyl)methyl)cyclohexanecarboxamide | 548.5 |
| 3.13[2] | 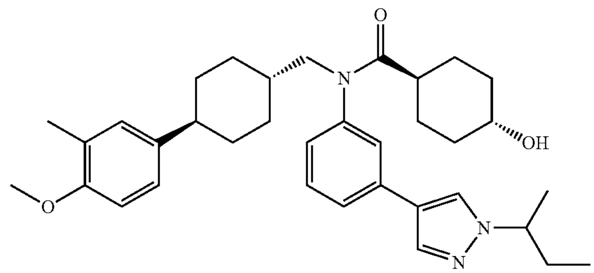 [SMILES: CCC(C)n1cc(-c2cccc(N(C[C@H]3CC[C@H](c4ccc(OC)c(C)c4)CC3)C(=O)[C@H]3CC[C@H](O)CC3)c2)cn1] | trans-N-(3-(1-(sec-Butyl)-1H-pyrazol-4-yl)phenyl)-4-hydroxy-N-((trans-4-(4-methoxy-3-methylphenyl)cyclohexyl)methyl)cyclohexanecarboxamide | 558.4 |

Alternate conditions:
Step 1:
[1] aq. $K_2CO_3$, dioxane, 80° C., 0.5-5 h;
Step 2:
[2] 1N HCl.

Compound 4 trans-4-Hydroxy-N-((trans-4-(4-methoxy-3-methylphenyl)cyclohexyl)methyl)-N-(3-((1-methyl-1H-pyrazol-4-yl)ethynyl)phenyl)cyclohexanecarboxamide

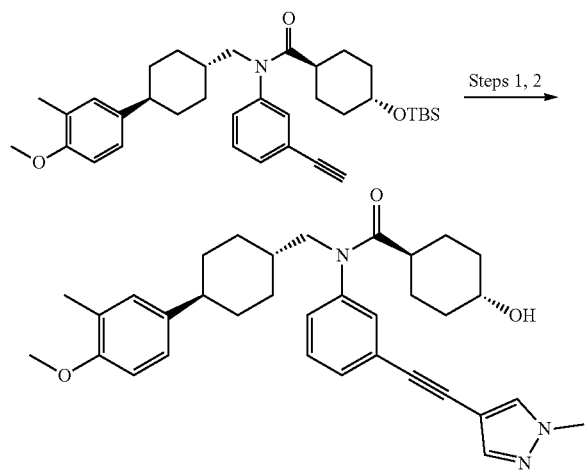

Step 1: trans-4-((tert-Butyldimethylsilyl)oxy)-N-((trans-4-(4-methoxy-3-methylphenyl) cyclohexyl)methyl)-N-(3-((1-methyl-1H-pyrazol-4-yl)ethynyl)phenyl)cyclohexane carboxamide A mixture of Intermediate 11 (301 mg, 0.525 mmol), 4-iodo-1-methyl-1H-pyrazole (131 mg, 0.629 mmol), CuI (10 mg, 0.053 mmol), Pd(PPh$_3$)$_2$Cl$_2$ (37 mg, 0.052 mmol), and Et$_3$N (5 mL) was stirred at 80° C. for 1 h under N$_2$, cooled to rt, poured into water (30 mL), and then extracted with EtOAc (3×20 mL). The combined organic layers were washed with brine (2×20 mL), dried (Na$_2$SO$_4$), filtered, and concentrated under reduced pressure. The residue was purified by silica gel chromatography (petroleum ether/ethyl acetate=25:1 to 5:1) to give trans-4-((tert-butyldimethylsilyl)oxy)-N-((trans-4-(4-methoxy-3-methylphenyl)cyclohexyl)methyl)-N-(3-((1-methyl-1H-pyrazol-4-yl)ethynyl)phenyl)cyclohexanecarboxamide (115 mg, 29%) as a yellow oil. $^1$H NMR (400 MHz, CDCl$_3$): δ 7.69 (s, 1H), 7.61 (s, 1H), 7.36-7.50 (m, 2H), 7.28-7.33 (m, 1H), 7.12 (d, 1H), 6.91-7.02 (m, 2H), 6.75 (d, 1H), 3.94 (s, 3H), 3.80 (s, 3H), 3.48-3.65 (m, 3H), 2.35-2.43 (m, 1H), 2.20 (s, 3H), 2.05-2.14 (m, 1H), 1.77-1.90 (m, 8H), 1.49-1.73 (m, 8H), 1.25-1.42 (m, 3H), 1.11-1.22 (m, 2H), 0.97-1.09 (m, 2H), 0.81-0.89 (m, 9H); LCMS: 654.3 [M+H]+.

Step 2: trans-4-Hydroxy-N-((trans-4-(4-methoxy-3-methylphenyl)cyclohexyl)methyl)-N-(3-((1-methyl-1H-pyrazol-4-yl)ethynyl)phenyl)cyclohexanecarboxamide Aqueous hydrochloric acid (1 M, 0.30 mL) was added to a solution of trans-4-((tert-butyldimethyl silyl)oxy)-N-((trans-4-(4-methoxy-3-methylphenyl)cyclohexyl)methyl)-N-(3-((1-methyl-1H-pyrazol-4-yl)ethynyl)phenyl)cyclohexanecarboxamide (111 mg, 0.170 mmol), MeOH (2 mL), and THF (2 mL) at 0° C. The ice/water bath was removed and the reaction was allowed to warm to rt. The mixture was stirred at rt for 1 h, poured into sat'd NaHCO$_3$ (40 mL), extracted with EtOAc (3×20 mL). The combined organic layers were washed with brine (2×20 mL), dried (Na$_2$SO$_4$), filtered and concentrated under reduced pressure. The residue was purified by RP-HPLC [water (10 mM NH$_4$HCO$_3$)-

MeCN] to give trans-4-hydroxy-N-((trans-4-(4-methoxy-3-methylphenyl)cyclohexyl)methyl)-N-(3-((1-methyl-1H-pyrazol-4-yl)ethynyl)phenyl)cyclohexanecarboxamide (47.8 mg, 52%) as a white solid. $^1$H NMR (400 MHz, DMSO-d$_6$): δ 8.09 (s, 1H), 7.71 (s, 1H), 7.48-7.52 (m, 2H), 7.42 (s, 1H), 7.32 (s, 1H), 6.93-6.95 (m, 2H), 6.72-6.83 (m, 1H), 4.34-4.47 (m, 1H), 3.86 (s, 3H), 3.72 (s, 3H), 3.51-3.61 (m, 2H), 3.30-3.32 (m, 1H), 2.24-2.38 (m, 1H), 2.09 (s, 3H), 1.90-2.01 (m, 1H), 1.67-1.79 (m, 6H), 1.55-1.67 (m, 2H), 1.21-1.49 (m, 5H), 0.97-1.12 (m, 2H), 0.70-0.84 (m, 2H); LCMS: 540.3 [M+H]$^+$.

The Compounds below were synthesized from Intermediate 11 and appropriate halide following the procedures described for Compound 4.

| Cmpd | Structure | Name | [M + H]$^+$ |
|---|---|---|---|
| 4.01 | 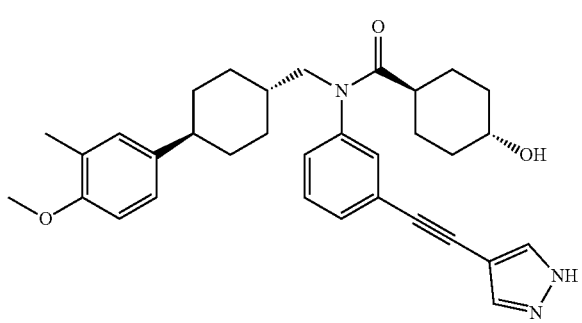 [SMILES: COc1ccc([C@H]2CC[C@H](CN(c3cccc(C#Cc4cn[nH]c4)c3)C(=O)[C@H]3CC[C@H](O)CC3)CC2)cc1C] | trans-N-(3-((1H-Pyrazol-4-yl)ethynyl)phenyl)-4-hydroxy-N-((trans-4-(4-methoxy-3-methylphenyl)cyclohexyl)methyl) cyclohexanecarboxamide | 526.5 |
| 4.02 | 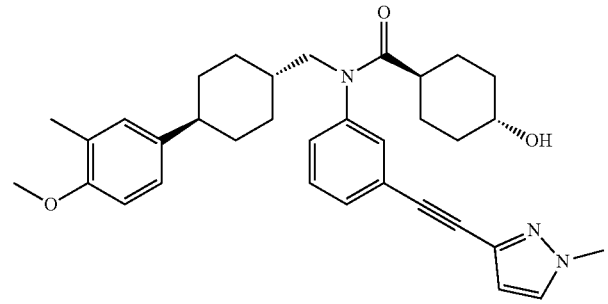 | trans-4-Hydroxy-N-((trans-4-(4-methoxy-3-methylphenyl)cyclohexyl)methyl)-N-(3-((1-methyl-1H-pyrazol-3-yl)ethynyl)phenyl)cyclohexane-carboxamide | 540.4 |
| 4.03 | 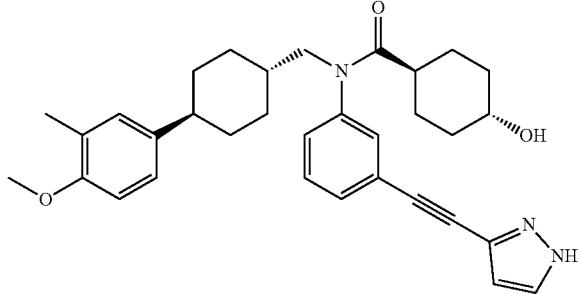 [SMILES: COc1ccc([C@H]2CC[C@H](CN(c3cccc(C#Cc4cc[nH]n4)c3)C(=O)[C@H]3CC[C@H](O)CC3)CC2)cc1C] | trans-N-(3-((1H-Pyrazol-3-yl)ethynyl)phenyl)-4-hydroxy-N-((trans-4-(4-methoxy-3-methylphenyl)cyclohexyl)methyl) cyclohexanecarboxamide | 526.4 |

Compound 5 trans-N-(3-(1-Cyclopropyl-1H-pyrazol-4-yl)phenyl)-N-((trans-4-(3-fluoro-1-methyl-1H-indazol-5-yl)cyclohexyl)methyl)-4-hydroxycyclohexanecarboxamide

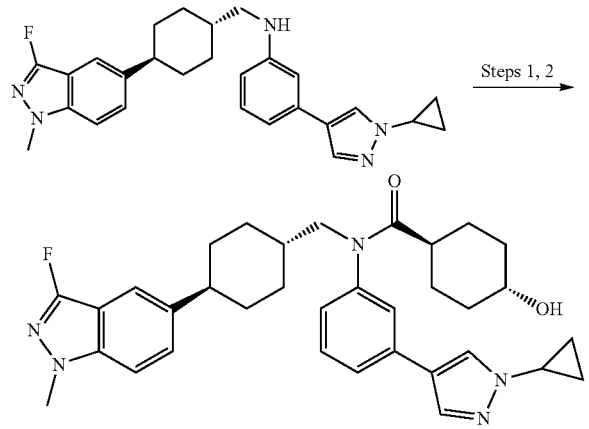

Step 1: trans-4-((tert-Butyldimethylsilyl)oxy)-N-(3-(1-cyclopropyl-1H-pyrazol-4-yl)phenyl)-N-((trans-4-(3-fluoro-1-methyl-1H-indazol-5-yl)cyclohexyl)methyl)cyclohexanecarboxamide Intermediate 8 (75 mg/mL toluene solution, 1.7 mL, 0.461 mmol) was added to a solution of Intermediate 7.06 (130 mg, 0.293 mmol), pyridine (95 μL, 1.17 mmol), and toluene (2.5 mL) in an rt water bath. The mixture was stirred at rt for 2 h, diluted with EtOAc (20 mL), washed (20 mL saturated NaHCO₃ and then 20 mL brine), dried (Na₂SO₄), filtered, and concentrated. The residue was purified by silica gel chromatography (0-40% EtOAc in hexanes) to give trans-4-((tert-butyldimethylsilyl)oxy)-N-(3-(1-cyclopropyl-1H-pyrazol-4-yl)phenyl)-N-((trans-4-(3-fluoro-1-methyl-1H-indazol-5-yl)cyclohexyl)methyl)cyclohexanecarboxamide (184 mg, 90%) as a white foam. $^1$H NMR (400 MHz, DMSO-$d_6$): δ 8.34 (s, 1H), 7.93 (s, 1H), 7.60 (d, 1H), 7.54 (s, 1H), 7.50 (dd, 1H), 7.48-7.41 (m, 2H), 7.36 (d, 1H), 7.10 (d, 1H), 3.86 (s, 3H), 3.77-3.70 (m, 1H), 3.68-3.42 (m, 3H), 2.61-2.52 (m, 1H), 2.13-2.02 (m, 1H), 1.84-1.75 (m, 4H), 1.75-1.68 (m, 2H), 1.68-1.59 (m, 2H), 1.54-1.33 (m, 5H), 1.14-1.03 (m, 4H), 1.02-0.92 (m, 2H), 0.90-0.72 (m, 11H), −0.03 (s, 6H); LCMS: 684.2 [M+H]⁺.

Step 2: trans-N-(3-(1-Cyclopropyl-1H-pyrazol-4-yl)phenyl)-N-((trans-4-(3-fluoro-1-methyl-1H-indazol-5-yl)cyclohexyl)methyl)-4-hydroxycyclohexanecarboxamide Aqueous hydrochloric acid (1 N, 0.5 mL, 0.5 mmol) was added to a solution of trans-4-((tert-butyldimethylsilyl)oxy)-N-(3-(1-cyclopropyl-1H-pyrazol-4-yl)phenyl)-N-((trans-4-(3-fluoro-1-methyl-1H-indazol-5-yl)cyclohexyl)methyl)cyclohexanecarboxamide (180 mg, 0.263 mmol), THF (1 mL), and MeOH (1 mL) at 0° C. The ice bath was removed after 10 min, and the reaction was stirred for 50 min. The mixture was diluted with EtOAc (20 mL), washed (2×20 mL saturated NaHCO₃ and then 20 mL brine), dried (Na₂SO₄), filtered, and concentrated. The residue was purified by silica gel chromatography (0-5% MeOH in DCM) to give trans-N-(3-(1-cyclopropyl-1H-pyrazol-4-yl)phenyl)-N-((trans-4-(3-fluoro-1-methyl-1H-indazol-5-yl)cyclohexyl)methyl)-4-hydroxycyclohexanecarboxamide (150 mg, 100%, 95% pure) as a white foam. $^1$H NMR (400 MHz, DMSO-$d_6$): δ 8.34 (s, 1H), 7.94 (s, 1H), 7.60 (d, 1H), 7.54 (s, 1H), 7.50 (dd, 1H), 7.48-7.41 (m, 2H), 7.36 (dd, 1H), 7.10 (d, 1H), 4.38 (d, 1H), 3.86 (s, 3H), 3.77-3.70 (m, 1H), 3.68-3.43 (m, 2H), 3.31-3.20 (m, 1H), 2.61-2.52 (m, 1H), 2.16-2.00 (m, 1H), 1.84-1.68 (m, 6H), 1.68-1.59 (m, 2H), 1.52-1.33 (m, 5H), 1.15-1.04 (m, 4H), 1.02-0.96 (m, 2H), 0.81-0.67 (m, 2H); LCMS: 570.4 [M+H]⁺.

The Compounds below were synthesized from the appropriate Intermediate following the procedures described for Compound 5.

| Cmpd | Structure | Name | [M + H]⁺ |
|---|---|---|---|
| 3 | 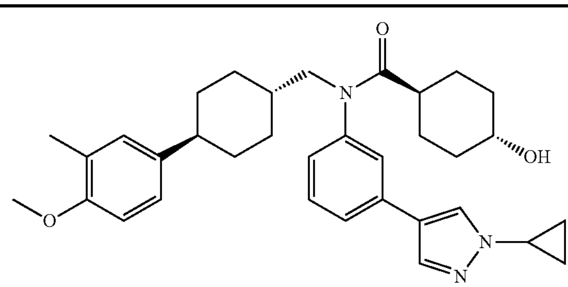 | trans-N-(3-(1-Cyclopropyl-1H-pyrazol-4-yl)phenyl)-4-hydroxy-N-((trans-4-(4-methoxy-3-methylphenyl)cyclohexyl)methyl)cyclohexanecarboxamide | 542.5 |
| 3.02 | 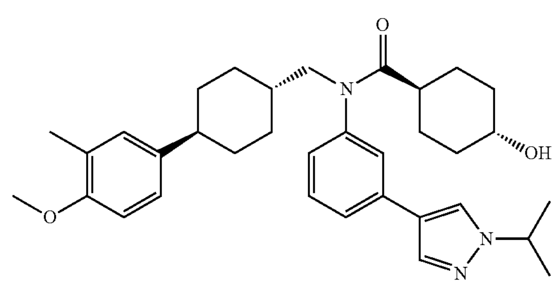 | trans-4-Hydroxy-N-(3-(1-isopropyl-1H-pyrazol-4-yl)phenyl)-N-((trans-4-(4-methoxy-3-methylphenyl)cyclohexyl)methyl)cyclohexanecarboxamide | 544.4 |

-continued

| Cmpd | Structure | Name | [M + H]+ |
|---|---|---|---|
| 5.01[1,6] | 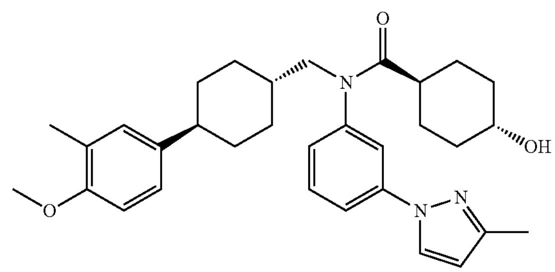 [SMILES: COc1ccc([C@H]2CC[C@H](CN(c3cccc(-n4ccc(C)n4)c3)C(=O)[C@H]3CC[C@H](O)CC3)CC2)cc1C] | trans-4-Hydroxy-N-((trans-4-(4-methoxy-3-methylphenyl)cyclohexyl)methyl)-N-(3-(3-methyl-1H-pyrazol-1-yl)phenyl)cyclohexanecarboxamide | 516.1 |
| 5.02 | 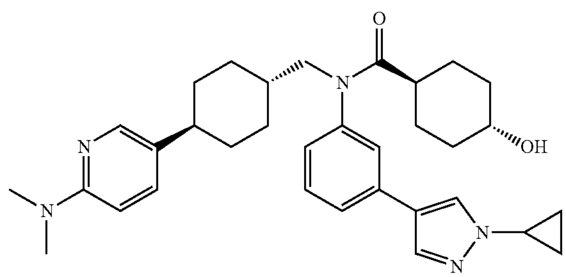 [SMILES: CN(C)c1ccc([C@H]2CC[C@H](CN(c3cccc(-c4cnn(C5CC5)c4)c3)C(=O)[C@H]3CC[C@H](O)CC3)CC2)cn1] | trans-N-(3-(1-Cyclopropyl-1H-pyrazol-4-yl)phenyl)-N-((trans-4-(6-(dimethylamino)pyridin-3-yl)cyclohexyl)methyl)-4-hydroxycyclohexanecarboxamide | 542.4 |
| 5.03[1] | 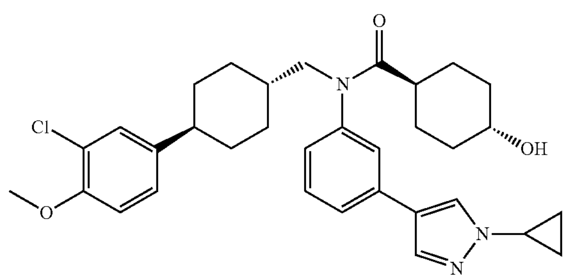 [SMILES: COc1ccc([C@H]2CC[C@H](CN(c3cccc(-c4cnn(C5CC5)c4)c3)C(=O)[C@H]3CC[C@H](O)CC3)CC2)cc1Cl] | trans-N-((trans-4-(3-Chloro-4-methoxyphenyl)cyclohexyl)methyl)-N-(3-(1-cyclopropyl-1H-pyrazol-4-yl)phenyl)-4-hydroxycyclohexanecarboxamide | 562.4 |
| 5.04 | 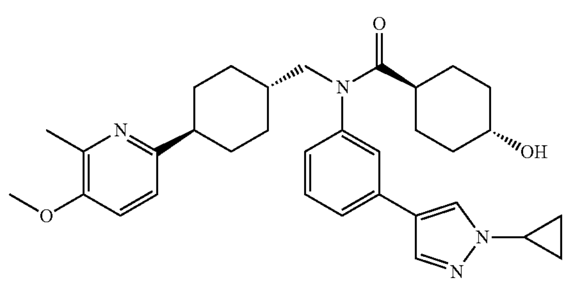 [SMILES: COc1ccc([C@H]2CC[C@H](CN(c3cccc(-c4cnn(C5CC5)c4)c3)C(=O)[C@H]3CC[C@H](O)CC3)CC2)nc1C] | trans-N-(3-(1-cyclopropyl-1H-pyrazol-4-yl)phenyl)-4-hydroxy-N-((trans-4-(5-methoxy-6-methylpyridin-2-yl)cyclohexyl)methyl)cyclohexanecarboxamide | 543.5 |
| 5.05[1] | 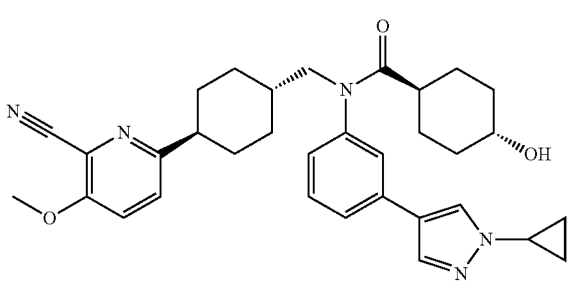 [SMILES: COc1ccc([C@H]2CC[C@H](CN(c3cccc(-c4cnn(C5CC5)c4)c3)C(=O)[C@H]3CC[C@H](O)CC3)CC2)nc1C#N] | trans-N-((trans-4-(6-Cyano-5-methoxypyridin-2-yl)cyclohexyl)methyl)-N-(3-(1-cyclopropyl-1H-pyrazol-4-yl)phenyl)-4-hydroxycyclohexanecarboxamide | 554.5 |

-continued

| Cmpd | Structure | Name | [M + H]+ |
|---|---|---|---|
| 5.06[1] | 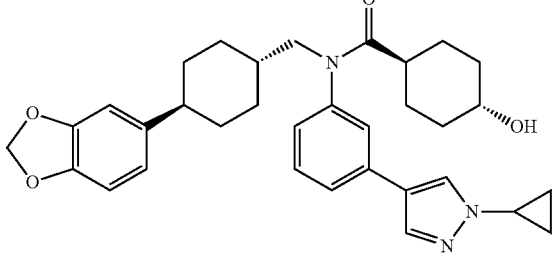 | trans-N-((trans-4-(Benzo[d][1,3]dioxol-5-yl)cyclohexyl)methyl)-N-(3-(1-cyclopropyl-1H-pyrazol-4-yl)phenyl)-4-hydroxycyclohexanecarboxamide | 542.5 |
| 5.07[1] | 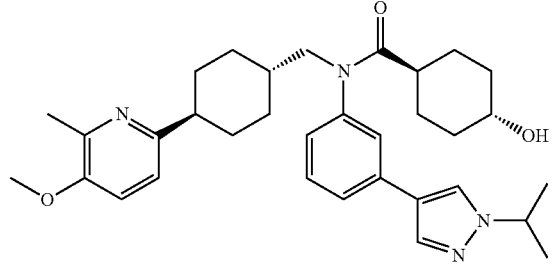 | trans-4-Hydroxy-N-(3-(1-isopropyl-1H-pyrazol-4-yl)phenyl)-N-((trans-4-(5-methoxy-6-methylpyridin-2-yl)cyclohexyl)methyl)cyclohexanecarboxamide | 545.5 |
| 5.08[1] | 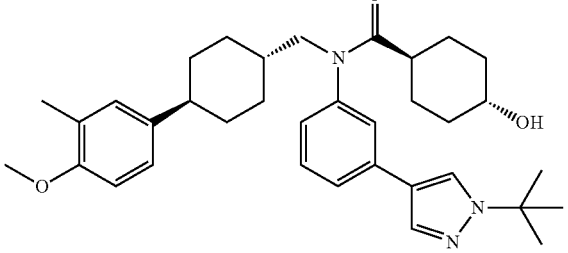 | trans-N-(3-(1-(tert-Butyl)-1H-pyrazol-4-yl)phenyl)-4-hydroxy-N-((trans-4-(4-methoxy-3-methylphenyl)cyclohexyl)methyl)cyclohexanecarboxamide | 558.3 |
| 5.09[2] | 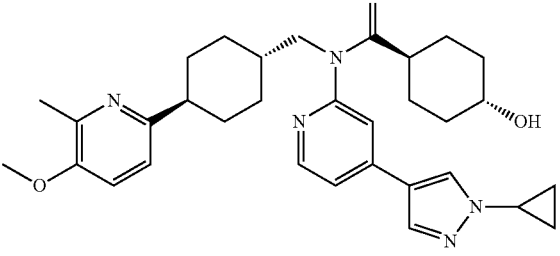 | trans-N-(4-(1-Cyclopropyl-1H-pyrazol-4-yl)pyridin-2-yl)-4-hydroxy-N-((trans-4-(5-methoxy-6-methylpyridin-2-yl)cyclohexyl)methyl)cyclohexanecarboxamide | 544.5 |
| 5.10[1] | 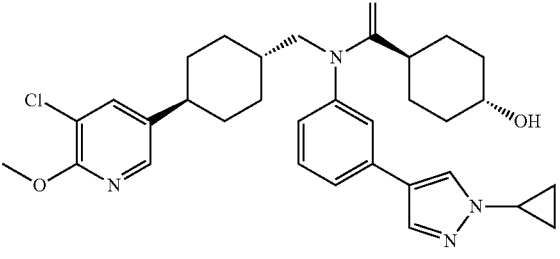 | trans-N-((trans-4-(5-Chloro-6-methoxypyridin-3-yl)cyclohexyl)methyl)-N-(3-(1-cyclopropyl-1H-pyrazol-4-yl)phenyl)-4-hydroxycyclohexanecarboxamide | 563.5 |

-continued

| Cmpd | Structure | Name | [M + H]+ |
|---|---|---|---|
| 5.11[2] | 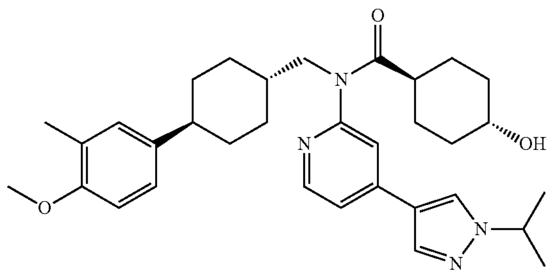 | trans-4-Hydroxy-N-(4-(1-isopropyl-1H-pyrazol-4-yl)pyridin-2-yl)-N-((trans-4-(4-methoxy-3-methylphenyl)cyclohexyl)methyl)cyclohexanecarboxamide | 545.5 |
| 5.12[1] | 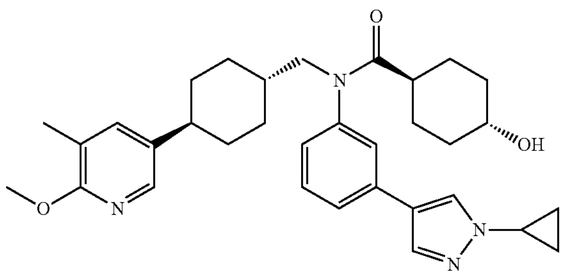 | trans-N-(3-(1-Cyclopropyl-1H-pyrazol-4-yl)phenyl)-4-hydroxy-N-((trans-4-(6-methoxy-5-methylpyridin-3-yl)cyclohexyl)methyl)cyclohexanecarboxamide | 543.4 |
| 5.13[2] | 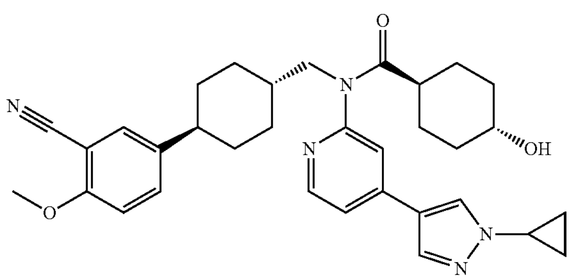 | trans-N-((trans-4-(3-Cyano-4-methoxyphenyl)cyclohexyl)methyl)-N-(4-(1-cyclopropyl-1H-pyrazol-4-yl)pyridin-2-yl)-4-hydroxycyclohexanecarboxamide | 554.4 |
| 5.14[2] | 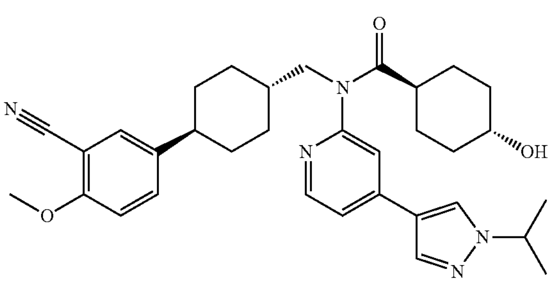 | trans-N-((trans-4-(3-Cyano-4-methoxyphenyl)cyclohexyl)methyl)-4-hydroxy-N-(4-(1-isopropyl-1H-pyrazol-4-yl)pyridin-2-yl)cyclohexanecarboxamide | 556.4 |
| 5.15[1] | 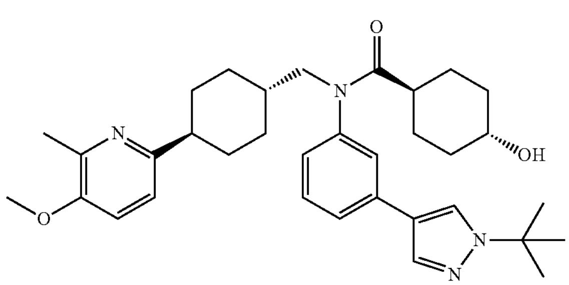 [SMILES: COc1ccc([C@H]2CC[C@H](CN(c3cccc(-c4cnn(C(C)(C)C)c4)c3)C(=O)[C@H]3CC[C@H](O)CC3)CC2)cc1C] | trans-N-(3-(1-(tert-Butyl)-1H-pyrazol-4-yl)phenyl)-4-hydroxy-N-((trans-4-(5-methoxy-6-methylpyridin-2-yl)cyclohexyl)methyl)cyclohexanecarboxamide | 559.5 |

-continued

| Cmpd | Structure | Name | [M + H]⁺ |
|---|---|---|---|
| 5.16 | 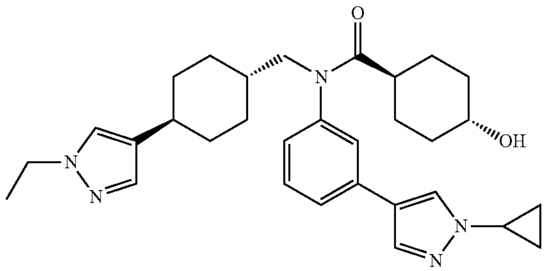 [SMILES: CCn1cc([C@H]2CC[C@H](CN(c3cccc(-c4cnn(C5CC5)c4)c3)C(=O)[C@H]3CC[C@H](O)CC3)CC2)cn1] | trans-N-(3-(1-Cyclopropyl-1H-pyrazol-4-yl)phenyl)-N-((trans-4-(1-ethyl-1H-pyrazol-4-yl)cyclohexyl)methyl)-4-hydroxycyclohexanecarboxamide | 516.5 |
| 5.17[1] | 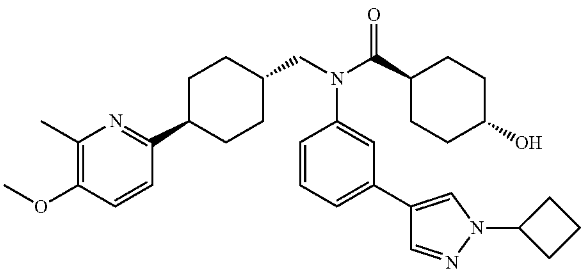 | trans-N-(3-(1-Cyclobutyl-1H-pyrazol-4-yl)phenyl)-4-hydroxy-N-((trans-4-(5-methoxy-6-methylpyridin-2-yl)cyclohexyl)methyl)cyclohexanecarboxamide | 557.5 |
| 5.18 | 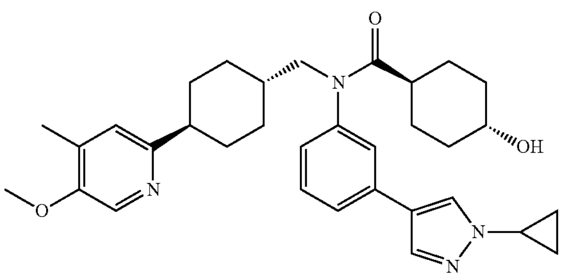 [SMILES: COc1cnc([C@H]2CC[C@H](CN(c3cccc(-c4cnn(C5CC5)c4)c3)C(=O)[C@H]3CC[C@H](O)CC3)CC2)cc1C] | trans-N-(3-(1-Cyclopropyl-1H-pyrazol-4-yl)phenyl)-4-hydroxy-N-((trans-4-(5-methoxy-4-methylpyridin-2-yl)cyclohexyl)methyl)cyclohexanecarboxamide | 543.5 |
| 5.19[3] | 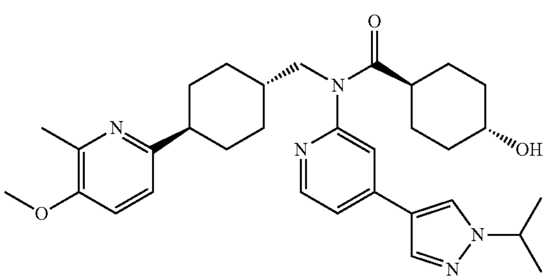 [SMILES: COc1ccc([C@H]2CC[C@H](CN(c3cc(-c4cnn(C(C)C)c4)ccn3)C(=O)[C@H]3CC[C@H](O)CC3)CC2)nc1C] | trans-4-Hydroxy-N-(4-(1-isopropyl-1H-pyrazol-4-yl)pyridin-2-yl)-N-((trans-4-(5-methoxy-6-methylpyridin-2-yl)cyclohexyl)methyl)cyclohexanecarboxamide | 546.5 |
| 5.20[2] | 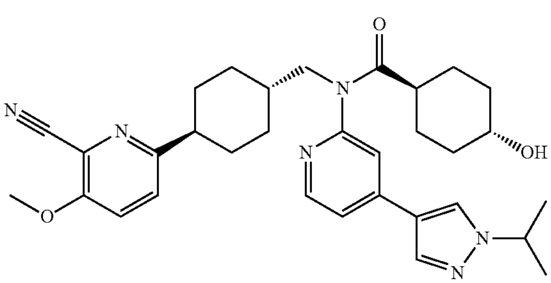 | trans-N-((trans-4-(6-Cyano-5-methoxypyridin-2-yl)cyclohexyl)methyl)-4-hydroxy-N-(4-(1-isopropyl-1H-pyrazol-4-yl)pyridin-2-yl)cyclohexanecarboxamide | 557.4 |

-continued

| Cmpd | Structure | Name | [M + H]+ |
|---|---|---|---|
| 5.21[1] | 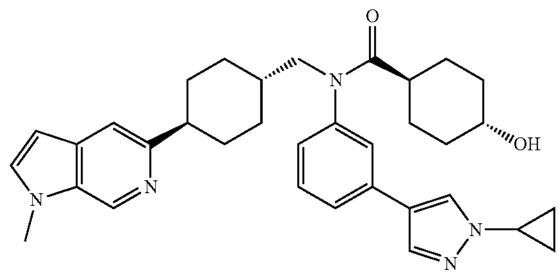 [SMILES: Cn1ccc2cc([C@H]3CC[C@H](CN(c4cccc(-c5cnn(C6CC6)c5)c4)C(=O)[C@H]4CC[C@H](O)CC4)CC3)ncc21] | trans-N-(3-(1-Cyclopropyl-1H-pyrazol-4-yl)phenyl)-4-hydroxy-N-((trans-4-(1-methyl-1H-pyrrolo[2,3-c]pyridin-5-yl)cyclohexyl)methyl)cyclohexanecarboxamide | 552.5 |
| 5.22[2] | 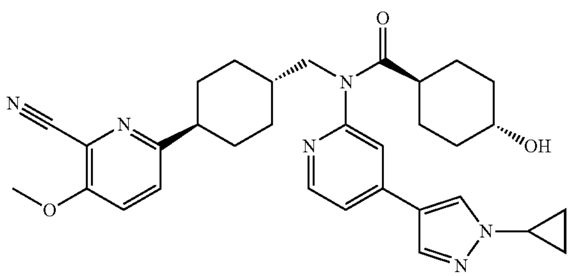 [SMILES: COc1ccc([C@H]2CC[C@H](CN(c3cc(-c4cnn(C5CC5)c4)ccn3)C(=O)[C@H]3CC[C@H](O)CC3)CC2)nc1C#N] | trans-N-((trans-4-(6-Cyano-5-methoxypyridin-2-yl)cyclohexyl)methyl)-N-(4-(1-cyclopropyl-1H-pyrazol-4-yl)pyridin-2-yl)-4-hydroxycyclohexanecarboxamide | 555.5 |
| 5.23[1] | 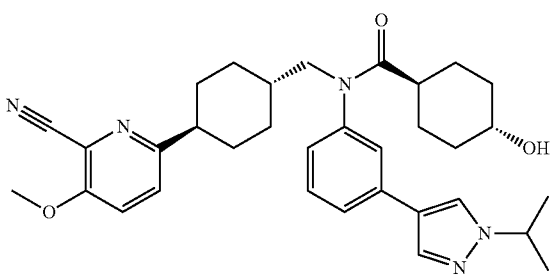 | trans-N-((trans-4-(6-Cyano-5-methoxypyridin-2-yl)cyclohexyl)methyl)-4-hydroxy-N-(3-(1-isopropyl-1H-pyrazol-4-yl)phenyl)cyclohexanecarboxamide | 556.5 |
| 5.24[1] | 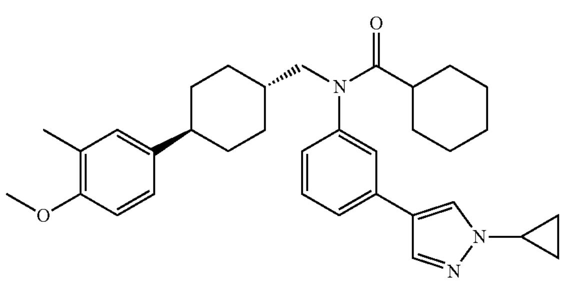 [SMILES: COc1ccc([C@H]2CC[C@H](CN(C(=O)C3CCCCC3)c3cccc(-c4cnn(C5CC5)c4)c3)CC2)cc1C] | N-(3-(1-Cyclopropyl-1H-pyrazol-4-yl)phenyl)-N-((trans-4-(4-methoxy-3-methylphenyl)cyclohexyl)methyl)cyclohexanecarboxamide | 526.4 |
| 5.25[1] | 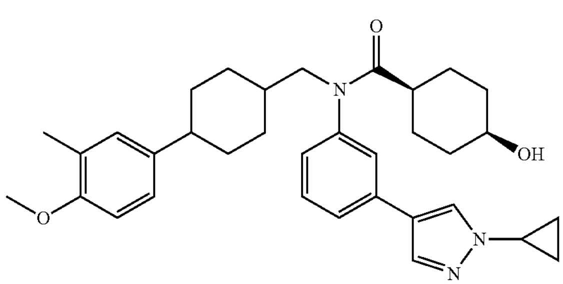 [SMILES: COc1ccc(C2CCC(CN(c3cccc(-c4cnn(C5CC5)c4)c3)C(=O)[C@H]3CC[C@@H](O)CC3)CC2)cc1C] | cis-N-(3-(1-Cyclopropyl-1H-pyrazol-4-yl)phenyl)-4-hydroxy-N-((4-(4-methoxy-3-methylphenyl)cyclohexyl)methyl)cyclohexanecarboxamide | 542.4 |

-continued

| Cmpd | Structure | Name | [M + H]+ |
|---|---|---|---|
| 5.26[2] | 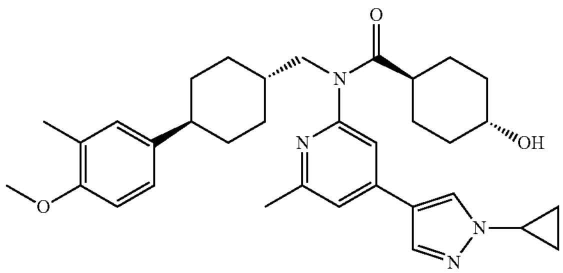 [SMILES: COc1ccc([C@H]2CC[C@H](CN(c3cc(-c4cnn(C5CC5)c4)cc(C)n3)C(=O)[C@H]3CC[C@H](O)CC3)CC2)cc1C] | trans-N-(4-(1-Cyclopropyl-1H-pyrazol-4-yl)-6-methylpyridin-2-yl)-4-hydroxy-N-((trans-4-(4-methoxy-3-methylphenyl)cyclohexyl)methyl)cyclohexanecarboxamide | 557.7 |
| 5.27[1,5] | 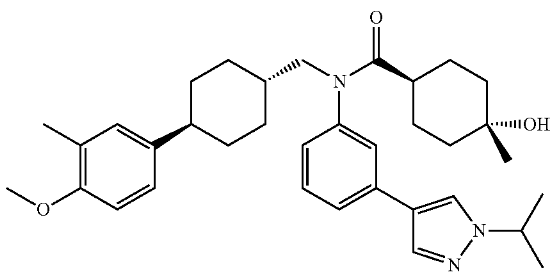 [SMILES: COc1ccc([C@H]2CC[C@H](CN(c3cccc(-c4cnn(C(C)C)c4)c3)C(=O)[C@H]3CC[C@](C)(O)CC3)CC2)cc1C] | (1r,4r)-4-Hydroxy-N-(3-(1-isopropyl-1H-pyrazol-4-yl)phenyl)-N-((trans-4-(4-methoxy-3-methylphenyl)cyclohexyl)methyl)-4-methylcyclohexanecarboxamide | 558.3 |
| 5.28[7] | 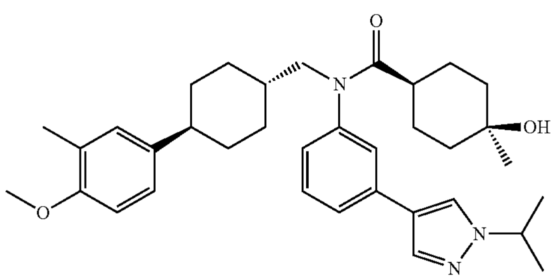 [SMILES: COc1ccc([C@H]2CC[C@H](CN(c3cccc(-c4cnn(C(C)C)c4)c3)C(=O)[C@H]3CC[C@@](C)(O)CC3)CC2)cc1C] | (1s,4s)-4-Hydroxy-N-(3-(1-isopropyl-1H-pyrazol-4-yl)phenyl)-N-((trans-4-(4-methoxy-3-methylphenyl)cyclohexyl)methyl)-4-methylcyclohexanecarboxamide | 558.3 |
| 5.29[4] | 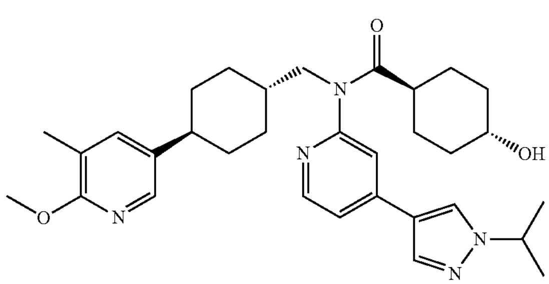 | trans-4-Hydroxy-N-(4-(1-Isopropyl-1H-pyrazol-4-yl)pyridin-2-yl)-N-((trans-4-(6-methoxy-5-methylpyridin-3-yl)cyclohexyl)methyl)cyclohexanecarboxamide | 546.5 |

| Cmpd | Structure | Name | [M + H]⁺ |
|---|---|---|---|
| 5.30[4] | 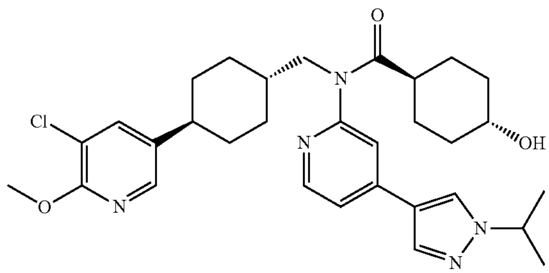 | trans-N-((trans-4-(5-Chloro-6-methoxypyridin-3-yl)cyclohexyl)methyl)-4-hydroxy-N-(4-(1-isopropyl-1H-pyrazol-4-yl)pyridin-2-yl)cyclohexanecarboxamide | 566.5 |

Alternate conditions:
Step 1:
[1]solvent was DCM;
[2]DMAP, pyridine, 80° C.;
[3]TEA, DCM, rt;
[4]DMAP, TEA, 80° C., 1 h;
Step 2:
[5]3M HCl, THF, MeOH, 45° C.
[6]TBS was cleaved during acylation.
[7]Isolated during the purification of Compound 5.27.

Compound 6 trans-N-(3-(1-Cyclopropyl-1H-pyrazol-4-yl)phenyl)-4-hydroxy-N-((4-(4-methoxy-3-methylphenyl)bicyclo[2.2.2]octan-1-yl)methyl)cyclohexanecarboxamide

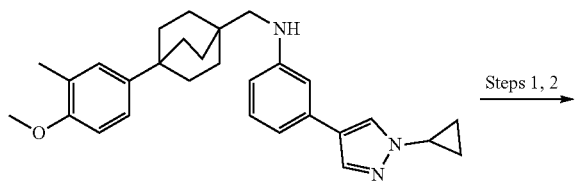

Steps 1, 2

Step 1: trans-4-((tert-Butyldimethylsilyl)oxy)-N-(3-(1-cyclopropyl-1H-pyrazol-4-yl)phenyl)-N-((4-(4-methoxy-3-methylphenyl)bicyclo[2.2.2]octan-1-yl)methyl)cyclohexanecarboxamide A solution of Intermediate 8 (44 mg/mL toluene solution, 2.5 mL, 0.397 mmol) was added to a solution of Intermediate 7 (114 mg, 0.258 mmol), pyridine (0.1 mL, 1.2 mmol), and DCM (2.0 mL) at rt. The mixture was stirred at rt for 135 min, and additional Intermediate 8 (44 mg/mL toluene solution, 0.5 mL, 0.079 mmol) was added. The mixture was stirred for 90 min, diluted with EtOAc (20 mL), washed (2×15 mL saturated NaHCO₃ and then 15 mL brine), dried (Na₂SO₄), filtered, and concentrated. The residue was purified by silica gel chromatography (0-35% EtOAc in hexanes) to give trans-4-((tert-butyldimethylsilyl)oxy)-N-(3-(1-cyclopropyl-1H-pyrazol-4-yl)phenyl)-N-((4-(4-methoxy-3-methylphenyl)bicyclo[2.2.2]octan-1-yl)methyl)cyclohexanecarboxamide (155 mg, 88%) as a white foam. LCMS: 682.5 [M+H]⁺.

Step 2: trans-N-(3-(1-Cyclopropyl-1H-pyrazol-4-yl)phenyl)-4-hydroxy-N-((4-(4-methoxy-3-methylphenyl)bicyclo[2.2.2]octan-1-yl)methyl)cyclohexanecarboxamide Aqueous hydrochloric acid (1 M, 0.5 mL, 0.5 mmol) was added to a mixture of trans-4-((tert-butyldimethylsilyl)oxy)-N-(3-(1-cyclopropyl-1H-pyrazol-4-yl)phenyl)-N-((4-(4-methoxy-3-methylphenyl)bicyclo[2.2.2]octan-1-yl)methyl)cyclohexanecarboxamide (150 mg, 0.220 mmol), THF (1 mL), and MeOH (1 mL) at 0° C. The reaction was stirred for 1 h, diluted with EtOAc (20 mL), washed (2×20 mL saturated NaHCO₃ and then 20 mL brine), dried (Na₂SO₄), filtered, and concentrated. The residue was purified by silica gel chromatography (0-5% MeOH in DCM) to give trans-N-(3-(1-cyclopropyl-1H-pyrazol-4-yl)phenyl)-4-hydroxy-N-((4-(4-methoxy-3-methylphenyl)bicyclo[2.2.2]octan-1-yl)methyl)cyclohexanecarboxamide (109 mg, 89%) as a white foam. $^1$H NMR (400 MHz, DMSO-d₆): δ 8.34 (s, 1H), 7.94 (s, 1H), 7.59 (s, 1H), 7.54 (d, 1H), 7.40 (t, 1H), 7.16 (d, 1H), 7.03-6.97 (m, 2H), 6.76 (d, 1H), 4.40 (s, 1H), 3.76-3.71 (m, 2H), 3.70 (s, 3H), 3.62-3.32 (m, 1H), 3.31-3.20 (m, 1H), 2.22-2.11 (m, 1H), 2.08 (s, 3H), 1.80-1.68 (m, 2H), 1.66-1.55 (m, 8H), 1.46-1.31 (m, 8H), 1.11-0.99 (m, 4H), 0.83-0.66 (m, 2H); LCMS: 568.4 [M+H]+.

The Compounds below were synthesized from the appropriate Intermediate following the procedures described for Compound 6.

| Cmpd | Structure | Name | [M + H]+ |
|---|---|---|---|
| 6.01[1,2] | 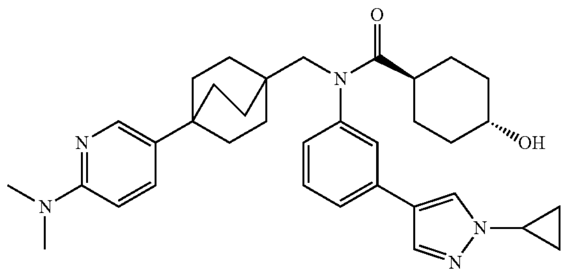 [SMILES: CN(C)c1ccc(C23CCC(CN(c4cccc(-c5cnn(C6CC6)c5)c4)C(=O)[C@H]4CC[C@H](O)CC4)(CC2)CC3)cn1] | trans-N-(3-(1-Cyclopropyl-1H-pyrazol-4-yl)phenyl)-N-((4-(6-(dimethylamino)pyridin-3-yl)bicyclo[2.2.2]octan-1-yl)methyl)-4-hydroxycyclohexanecarboxamide | 568.5 |
| 6.02[1] | 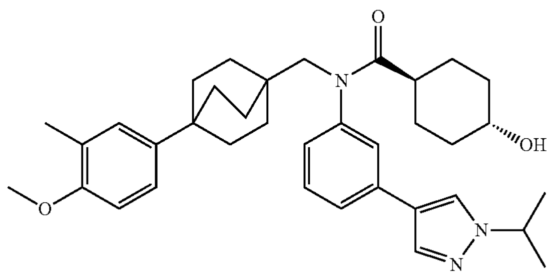 | trans-4-Hydroxy-N-(3-(1-isopropyl-1H-pyrazol-4-yl)phenyl)-N-((4-(4-methoxy-3-methylphenyl)bicyclo[2.2.2]octan-1-yl)methyl)cyclohexanecarboxamide | 570.4 |

Alternate conditions:
Step 1:
[1]DMAP with pyridine as solvent;
[2]50° C.

Compound 7 trans-4-Amino-N-(3-(1-isopropyl-1H-pyrazol-4-yl)phenyl)-N-((trans-4-(4-methoxy-3-methylphenyl)cyclohexyl)methyl)cyclohexanecarboxamide

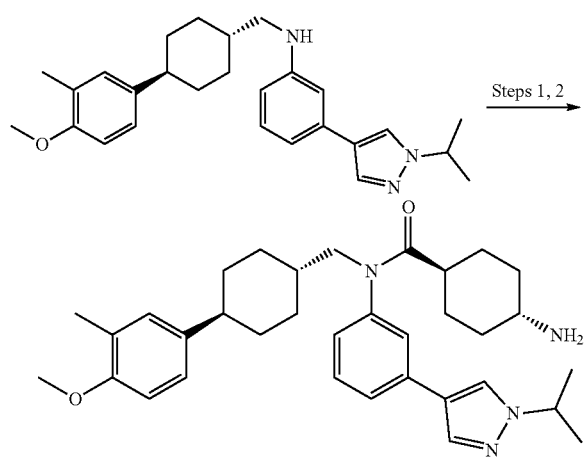

Steps 1, 2

Step 1: tert-Butyl (trans-4-((3-(1-isopropyl-1H-pyrazol-4-yl)phenyl)((trans-4-(4-methoxy-3-methylphenyl)cyclohexyl)methyl)carbamoyl)cyclohexyl)carbamate Intermediate 8.02 (58 mg/mL in toluene, 9 mL, 2.006 mmol) was added to a solution of Intermediate 7.21 (418 mg, 1.001 mmol), pyridine (0.33 mL, 4.08 mmol), and DCM (4 mL) at rt. The resulting mixture was stirred at rt for 60 min, diluted with 50 mL EtOAc, washed (50 mL H$_2$O, 50 mL saturated NaHCO$_3$ and then 50 mL brine), dried (Na$_2$SO$_4$), filtered, and then concentrated. The residue was purified by silica gel chromatography (10-50% EtOAc in hexanes) to give tert-butyl (trans-4-((3-(1-isopropyl-1H-pyrazol-4-yl)phenyl)((trans-4-(4-methoxy-3-methylphenyl)cyclohexyl)methyl)carbamoyl)cyclohexyl)carbamate (622 mg, 96%) as a white foam. $^1$H NMR (400 MHz, DMSO-d$_6$): δ 8.32 (s, 1H), 7.94 (s, 1H), 7.60 (d, 1H), 7.55-7.52 (m, 1H), 7.44 (t, 1H), 7.09 (d, 1H), 6.98-6.92 (m, 2H), 6.81-6.75 (m, 1H), 6.53 (d, 1H), 4.56-4.44 (m, 1H), 3.71 (s, 3H), 3.68-3.35 (m, 2H), 3.20-3.00 (m, 1H), 2.38-2.28 (m, 1H), 2.12-2.00 (m, 4H), 1.80-1.62 (m, 8H), 1.50-1.21 (m, 20H), 1.13-0.98 (m, 2H), 0.89-0.79 (m, 2H); LCMS: 665.5 [M+Na]+.

Step 2: trans-4-Amino-N-(3-(1-Isopropyl-1H-pyrazol-4-yl)phenyl)-N-((trans-4-(4-methoxy-3-methylphenyl)cyclohexyl)methyl)cyclohexanecarboxamide A solution of tert-butyl (trans-4-((3-(1-isopropyl-1H-pyrazol-4-yl)phenyl)((trans-4-(4-methoxy-3-methylphenyl)cyclohexyl)methyl)carbamoyl)cyclohexyl)carbamate (617 mg, 0.960 mmol) and trifluoroacetic acid (20% in DCM, 10 mL) was stirred at rt for 35 min, diluted with DCM (50 mL), and washed (2×50 mL saturated NaHCO$_3$ and then 50 mL brine). The organic layer was dried (Na$_2$SO$_4$), filtered, and then concentrated to give trans-4-Amino-N-(3-(1-isopropyl-1H-pyrazol-4-yl)phenyl)-N-((trans-4-(4-methoxy-3-methylphenyl)cyclohexyl)methyl)cyclohexanecarboxamide (515 mg, 99%) as a white foam. $^1$H NMR (400 MHz, DMSO-d$_6$): δ 8.32 (s, 1H), 7.94 (s, 1H), 7.60 (d, 1H), 7.56-7.52 (m, 1H), 7.44 (t, 1H), 7.09 (d, 1H), 6.97-6.92 (m, 2H), 6.80-6.76 (m, 1H), 4.56-4.44 (m, 1H), 3.71 (s, 3H), 3.66-3.37 (m, 2H), 3.11-2.87 (m, 2H), 2.48-2.40 (m, 1H), 2.38-2.28 (m, 1H), 2.13-2.00 (m, 4H), 1.80-1.60 (m, 8H), 1.49-1.35 (m, 9H), 1.35-1.21 (m, 2H), 1.13-0.99 (m, 2H), 0.77-0.60 (m, 2H); LCMS: 543.6 [M+H]+.

The Compound below was synthesized from Intermediate 7 following the procedures described for Compound 7.

| Cmpd | Structure | Name | [M + H]⁺ |
|---|---|---|---|
| 7.01 | (structure shown) | trans-4-Amino-N-(3-(1-cyclopropyl-1H-pyrazol-4-yl)phenyl)-N-((4-(4-methoxy-3-methylphenyl)bicyclo[2.2.2]octan-1-yl)methyl)cyclohexanecarboxamide | 567.6 |

Compound 8 trans-N-(3-(1-Cyclopropyl-1H-pyrazol-4-yl)phenyl)-4-hydroxy-N-((trans-4-(4-hydroxy-3-methylphenyl)cyclohexyl)methyl)cyclohexanecarboxamide

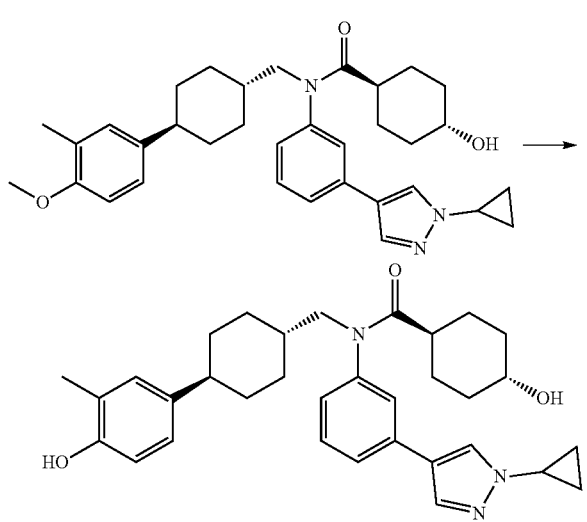

A solution of BBr₃ (4.0 mL, 1 M in DCM) was added dropwise over 2 min to a solution of Compound 3 (1.007 g, 1.858 mmol) and anhydrous DCM (40 mL) at 30° C. The reaction became thick with a white, clumpy solid and was stirred vigorously. After 6 h, additional DCM (5 mL) and BBr₃ (1 mL) were added. After 24 h total reaction time, a CH₃OH/H₂O mixture (20 mL, 19:1) was added. The reaction was concentrated and then purified by silica gel chromatography (1-20% CH₃OH in DCM) to give a mixture containing secondary amine (de-acylation). This mixture was purified by reverse-phase HPLC (Waters SunFire column; 55% CH₃CN/45% H₂O containing 0.1% TFA), and the concentrated fractions were diluted with EtOAc (60 mL) and washed with sat'd NaHCO₃ (50 mL). The organic layer was dried (MgSO₄), filtered, concentrated, and then held under vacuum (0.1 mTorr) for several days to give trans-N-(3-(1-cyclopropyl-1H-pyrazol-4-yl)phenyl)-4-hydroxy-N-((trans-4-(4-hydroxy-3-methylphenyl)cyclohexyl)methyl)cyclohexanecarboxamide as a white foam. ¹H NMR (400 MHz, DMSO-d₆): δ 8.92 (s, 1H), 8.34 (s, 1H), 7.93 (s, 1H), 7.60 (d, 1H), 7.53 (s, 1H), 7.44 (t, 1H), 7.08 (d, 1H), 6.85 (s, 1H), 6.77 (d, 1H), 6.63 (d, 1H), 4.38 (d, 1H), 3.78-3.71 (m, 1H), 3.55 (br, 2H), 3.32-3.21 (m, 1H), 2.33-2.23 (m, 1H), 2.06 (s, 3H), 2.08-1.99 (m, 1H), 1.79-1.67 (m, 6H), 1.67-1.58 (m, 2H), 1.48-1.33 (m, 3H), 1.33-1.20 (m, 2H), 1.10-0.95 (m, 6H), 0.81-0.68 (m, 2H); LCMS: 528.4 [M+H]⁺.

Example A-1: Parenteral Pharmaceutical Composition

To prepare a parenteral pharmaceutical composition suitable for administration by injection (subcutaneous, intravenous), 1-1000 mg of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection Example A-2: Oral Solution To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound described herein, or a pharmaceutically acceptable salt thereof, is placed into Size 4 capsule, or size 1 capsule (hypromellose or hard gelatin) and the capsule is closed.

Example A-5: Topical Gel Composition

To prepare a pharmaceutical topical gel composition, a compound described herein, or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example B-1: In Vitro FXR Assay (TK)

Seeding

CV-1 cells were seeded at a density of 2,000,000 cells in a T175 flask with DMEM+10% charcoal double-stripped FBS and incubated at 37° C. in 5% $CO_2$ for 18 h (O/N).

Transfection

After 18 h of incubation, the medium in the T175 flask was changed with fresh DMEM+10% charcoal super-stripped serum. In a polypropylene tube, 2500 µL OptiMEM (Life Technologies, Cat #31985-062) was combined with expression plasmids for hFXR, hRXR, TK-ECRE-luc and pCMX-YFP. The tube was then briefly vortexed and incubated at room temperature for 5 minutes. Transfection reagent (X-tremeGENE HP from Roche, Cat #06 366 236 001) was added to the OptiMEM/plasmid mixture vortexed and incubated at room temperature for 20 minutes. Following incubation, the transfection reagent/DNA mixture complex was added to cells in the T175 flask and the cells were incubated at 37° C. in 5% $CO_2$ for 18 h (O/N).

Test Compounds

Compounds were serially diluted in DMSO and added to transfected CV-1 cells. The cells were then incubated for 18 hrs. The next day cells were lysed and examined for luminescence.

Representative data for exemplary compounds disclosed herein is presented in the following table.

TABLE 2

| Compound No | TK hFXR: $EC_{50}$ (uM) |
|---|---|
| 1 | ++ |
| 2 | +++ |
| 2.01 | +++ |
| 2.02 | +++ |
| 2.03 | +++ |
| 2.04 | +++ |
| 2.05 | +++ |
| 2.06 | +++ |
| 2.07 | +++ |
| 2.08 | +++ |
| 2.09 | +++ |
| 3 | +++ |
| 3.01 | + |
| 3.02 | +++ |
| 3.03 | +++ |
| 3.04 | +++ |
| 3.05 | + |
| 3.06 | + |
| 3.07 | +++ |
| 3.08 | +++ |
| 3.09 | +++ |
| 3.10 | +++ |
| 3.11 | +++ |
| 3.12 | +++ |
| 3.13 | +++ |
| 4 | +++ |
| 4.01 | +++ |
| 4.02 | +++ |
| 4.03 | +++ |
| 5 | +++ |
| 5.01 | ++ |
| 5.02 | +++ |
| 5.03 | +++ |
| 5.04 | +++ |
| 5.05 | +++ |
| 5.06 | +++ |
| 5.07 | +++ |
| 5.08 | +++ |
| 5.09 | ++ |
| 5.10 | +++ |
| 5.11 | +++ |
| 5.12 | +++ |
| 5.13 | +++ |
| 5.14 | +++ |
| 5.15 | +++ |
| 5.16 | ++ |
| 5.17 | +++ |
| 5.18 | ++ |
| 5.19 | +++ |
| 5.20 | ++ |
| 5.21 | + |
| 5.22 | ++ |
| 5.23 | +++ |
| 5.24 | +++ |
| 5.25 | +++ |
| 5.26 | ++ |
| 5.27 | +++ |
| 5.28 | +++ |
| 5.29 | +++ |
| 5.30 | +++ |
| 6 | +++ |
| 6.01 | +++ |
| 6.02 | +++ |
| 7 | + |
| 7.01 | ++ |
| 8 | ++ |

Where '+++' means $EC_{50}$ ≤0.25 uM; '++' means $EC_{50}$ >0.25 uM & <1 uM; '+' means $EC_{50}$ ≥1 uM. Compounds with a maximum efficacy of <25% of the Fexarmine control were classified as '+'.

Example B-2: In Vitro FXR Assay (hSHP) Seeding

CV-1 cells were seeded at a density of 2,000,000 cells in a T175 flask with DMEM+10% charcoal double-stripped FBS and incubated at 37° C. in 5% $CO_2$ for 18 h (O/N).

Transfection

After 18 h of incubation, the medium in the T175 flask was changed with fresh DMEM+10% charcoal super-stripped serum. In a polypropylene tube, 2500 µL OptiMEM (Life Technologies, Cat #31985-062) was combined with expression plasmids for hFXR, hRXR, hSHP-luc and pCMX-YFP. The tube was then briefly vortexed and incubated at room temperature for 5 minutes. Transfection reagent (X-tremeGENE HP from Roche, Cat #06 366 236 001) was added to the OptiMEM/plasmid mixture vortexed and incubated at room temperature for 20 minutes. Following incubation, the transfection reagent/DNA mixture complex was added to cells in the T175 flask and the cells were incubated at 37° C. in 5% $CO_2$ for 18 h (O/N).

Test Compounds

Compounds were serially diluted in DMSO and added to transfected CV-1 cells. The cells were then incubated for 18 hrs. The next day cells were lysed and examined for luminescence.

Example B-3: NASH Activity Study (STZ Model)

NASH can be induced in male C57BL/6 by a single subcutaneous injection of 200 ug STZ 2 days after birth followed by feeding high fat diet (HFD) ad libitum after 4 weeks of age. While continuing HFD, compounds can be dosed for 4-8 weeks to determine the effects on NASH. Fasting glucose can be measured throughout the study with a hand-held glucose meter. Serum alanine aminotransferase (ALT), aspartate aminotransferase (AST) and triglyceride (TG) can be measured by a clinical chemistry analyzer. The contents of TG in the liver tissue can be measured using the Triglyceride E-test kit (Wako, Tokyo, Japan). Histological analysis of liver sections can be performed on tissue embedded in Tissue-TEK O.C.T. compound, snap frozen in liquid nitrogen, and stored at −80 C. The sections can be cut (5 um), air dried and fixed in acetone. For hematoxylin and eosin staining, liver sections can be prefixed by Bouin's solution and then stained with hematoxylin and eosin solution. The degree of (zone-3) liver fibrosis can be assessed with Sirius red staining.

Example B-4: NASH Activity Study (AMLN Model)

NASH is induced in male C57BL/6 mice by diet-induction with AMLN diet (DIO-NASH) (D09100301, Research Diet, USA) (40% fat (18% trans-fat), 40% carbohydrates (20% fructose) and 2% cholesterol). The animals are kept on the diet for 29 weeks. After 26 weeks of diet induction, liver biopsies are performed for base line histological assessment of disease progression (hepatosteatosis and fibrosis), stratified and randomized into treatment groups according to liver fibrosis stage, steatosis score, and body weight. Three weeks after biopsy the mice are stratified into treatment groups and dosed daily by oral gavage with FXR agonists for 8 weeks. At the end of the study liver biopsies are performed to assess hepatic steatosis and fibrosis by examining tissue sections stained with H&E and Sirius Red, respectively. Total collagen content in the liver is measured by colorimetric determination of hydroxyproline residues by acid hydrolysis of collagen. Triglycerides and total cholesterol content in liver homogenates are measured in single determinations using autoanalyzer Cobas C-111 with commercial kit (Roche Diagnostics, Germany) according to manufacturer's instructions.

Example B-5: CCl$_4$ Fibrosis Model

Fibrosis can be induced in BALB/c male mice by bi-weekly administration of CCl$_4$ administered by intraperitoneal injection. CCl$_4$ is formulated 1:1 in oil and is injected IP at 1 ml/kg. After 2-4 weeks of fibrosis induction the compounds can be administered daily by oral gavage for 2-6 weeks of treatment while continuing CCl$_4$ administration. At study termination livers can be formalin fixed and stained with Sirius Red stain for histopathological evaluation of fibrosis. Total collagen content can be measured by colorimetric determination of hydroxyproline residues by acid hydrolysis of collagen. Serum alanine aminotransferase (ALT) and aspartate aminotransferase (AST) can be measured by a clinical chemistry analyzer.

Example B-6: Intrahepatic Cholestasis Model

Experimental intrahepatic cholestasis induced by 17a-ethynylestradiol (EE2) treatment in rodents is a widely used in vivo model to examine the mechanisms involved in estrogen-induced cholestasis. Intrahepatic cholestasis can be induced in adult male mice by subcutaneous injection of 10 mg/kg 17a-ethynylestradiol (E2) daily for 5 days. Testing of FXR ligands can be performed by administration of compounds during E2 induction of cholestasis. Cholestatic effects can be quantitated by assessing liver/body weight ratio and measuring serum total bile acids and alkaline phosphatase levels can be measured using reagents and controls from Diagnostic Chemicals Ltd. and the Cobas Mira plus CC analyzer (Roche Diagnostics). For histology and mitosis measurements, liver samples from each mouse can be fixed in 10% neutral buffered formalin. Slides are stained with hematoxylin and eosin using standard protocols and examined microscopically for structural changes. Hepatocyte proliferation is evaluated by immunohistochemical staining for Ki67.

Example B-7: Direct Target Gene Regulation

Direct target gene regulation by FXR ligands can be assessed by dosing mice either acutely or chronically with compounds and collecting tissues at various time points after dosing. RNA can be isolated from tissues such as the ileum and liver, and reverse transcribed to cDNA for quantitative PCR analysis of genes known in the literature to be directly and indirectly regulated by FXR such as SHP, BSEP, IBABP, FGF15, CYP7A1, CYP8B1 and C3.

Example B-8: Mouse PK Study

The plasma pharmacokinetics of any one of the compounds disclosed herein as a test article test article is measured following a single bolus intravenous and oral administration to mice (CD-1, C57BL, and diet induced obesity mice). Test article is formulated for intravenous administration in a vehicle solution of DMSO, PEG400, hydroxypropyl-β-cyclodextrin (HPβCD) and is administered (for example at a dose volume of 3 mL/kg) at selected dose levels. An oral dosing formulation is prepared in appropriate oral dosing vehicles (vegetable oils, PEG400, Solutol, citrate buffer, or carboxymethyl cellulose) and is administered at a dose volume of 5-10 mL/kg at selected dose levels. Blood samples (approximately 0.15 mL) are collected by cheek pouch method at pre-determined time intervals post intravenous or oral doses into tubes containing EDTA. Plasma is isolated by centrifugation of blood at 10,000 g for 5 minutes, and aliquots are transferred into a 96-well plate and stored at −60° C. or below until analysis.

Calibration standards of test article are prepared by diluting DMSO stock solution with DMSO in a concentration range. Aliquots of calibration standards in DMSO are combined with plasma from naïve mouse so that the final concentrations of calibration standards in plasma are 10-fold lower than the calibration standards in DMSO. PK plasma samples are combined with blank DMSO to match the matrix. The calibration standards and PK samples are combined with ice-cold acetonitrile containing an analytical internal standard and centrifuged at 1850 g for 30 minutes at 4° C. The supernatant fractions are analyzed by LC/MS/MS and quantitated against the calibration curve. Pharmacokinetic parameters (area under the curve (AUC), $C_{max}$, $T_{max}$, elimination half-life ($T_{1/2}$), clearance (CL), steady state volume of distribution ($V_{dss}$), and mean residence time (MRT)) are calculated via non-compartmental analysis using Microsoft Excel (version 2013).

Example B-9: Rat ANIT Model

A compound described herein is evaluated in a chronic treatment model of cholestasis over a range of doses (for example, doses in the range of 0.01 to 100 mg/kg). This model is used to evaluate the suitability of the use of FXR agonists, e.g. a compound described herein, for the treatment of cholestatic liver disorders such as bile acid malabsorption (e.g., primary or secondary bile acid diarrhea), bile reflux gastritis, collagenous colitis, lymphocytic colitis, diversion colitis, indeterminate colitis, Alagille syndrome, biliary atresia, ductopenic liver transplant rejection, bone marrow or stem cell transplant associated graft versus host disease, cystic fibrosis liver disease, and parenteral nutrition-associated liver disease.

Rats are treated with alpha-naphthylisothiocyanate (ANIT) (0.1% w/w) in food for 3 days prior to treatment with a compound described herein, at a range of doses (for example, doses in the range of 0.01 to 100 mg/kg). A noncholestatic control group is fed standard chow diet without ANIT and serves as the noncholestatic control animals ("Control"). After 14 days of oral dosing, rat serum is analyzed for levels of analytes. LLQ, lower limit of quantitation. Mean±SEM; n=5.

Levels of hepatobiliary injury indicators are measured in rat serum, such as elevated levels of circulating aspartate aminotransferase (AST), alanine aminotransferase (ALT), bilirubin and bile acids. ANIT exposure induces profound cholestasis and hepatocellular damage. A compound that improves many of these indicators is useful in the treatment of the aforementioned diseases or conditions.

Reductions in the accumulation of bile acids in the liver, enhancements in bile acid excretion in the biliary tract and inhibition of bile acid synthesis is consistent with the pharmacological action of a FXR agonist. An improvement in the serum conjugated bilirubin (a direct indicator for hepatic function) implies recovery from cholestasis with improved bile excretion.

Furthermore, an analysis is made to ascertain the effects of the compound described herein on serum FGF15 fibroblast growth factor 15 (FGF15 in rodent; FGF19 in human) expression, a hormone that is secreted in the portal blood and signals to the liver to repress CYP7A1 expression synergistically with SHP. The direct FXR-dependent induction of FGF15/19 along with FGF15/19's anti-cholestatic properties makes it a convenient serum biomarker for detecting target engagement of FXR agonists.

Serum FGF15 levels are quantified using an FGF15 Meso Scale Discovery (MSD) assay. For example, Mouse FGF15 antibody from R&D Systems (AF6755) is used both as capture and detection antibody in the assay. MSD SULFO-TAG NHS-Ester is used to label the FGF15 antibody. MSD standard 96-well plates are coated with the FGF15 capture antibody and the plates are blocked with MSD Blocker A (R93AA-2). After washing the plate with PBS+0.05% Tween 20, MSD diluent 4 is dispensed into each well and incubated for 30 min. 25 pi of calibrator dilutions or samples (serum or EDTA plasma) are dispensed into each well and incubated with shaking at RT.

After washing, detection antibody is added and incubated with shaking for 1 h at RT. After washing and the addition of MSD Read buffer (R92TC-2), the plate is read on an MSD SECTOR Imager 6000. Plots of the standard curve and unknown samples are calculated using MSD data analysis software.

The examples and embodiments described herein are for illustrative purposes only and various modifications or changes suggested to persons skilled in the art are to be included within the spirit and purview of this application and scope of the appended claims.

Example B-10: Mouse Chronic DSS Colitis Model

The chronic Dextran Sodium Sulfate (DSS)-induced mouse can be used to test the therapeutic potential of compounds against inflammatory bowel disease (IBD). Chronic colitis can be induced by feeding mice DSS in drinking water. For example, 2% DSS in drinking water for 5 days and regular drinking water for 5 days, then this feeding cycle can be repeated two more times with higher concentrations of DSS, 2.5% and 3%, respectively for a total of three cycles. Colitis develops approximately after the first cycle of DSS feeding, which can be monitored by loss of body weight, stool consistency and rectal bleeding. An FXR agonist can be tested by administering to mice at the same time of starting 2% DSS water feeding. Alternatively, testing of an FXR agonist can be performed post the first feeding cycle of 2% DSS water and regular water. During the period of administering the FXR agonist to mice, the therapeutic effects can be monitored by observations on body weights, stool consistency and rectal bleeding. After euthanasia, the disease development and effects of the FXR agonist can be further quantified by measuring colon weight and length, colon histology by H&E staining for inflammation and structural changes in mucosa, and protein and RNA expression of genes related to the disease.

Example B-11: Adoptive T-cell Transfer Colitis Mouse Model

The adoptive T-cell transfer colitis model is accepted as a relevant mouse model for human inflammatory bowel disease (IBD). To induce colitis in this model, the CD4 T-lymphocyte population is isolated from the spleens of donor mice, subsequently a subpopulation of CD4+CD45RB high T-cells is purified by cell sorting using flow cytometry. The purified CD4+CD45RB high T-cells are injected into the peritoneal cavity of the recipient SCID mice. Colitis develops approximately three to six weeks after T-cell transfer, which can be monitored by loss of body weight (although loss of body weight can be variable), inconsistent stool or bloody diarrhea. Testing of an FXR agonist can be initiated at the same time of injecting purified CD4+CD45RB high T-cells to the recipient SCID mice.

Alternatively, the FXR agonist can be administered two or three weeks post T-cell transfer, when colitis has already developed in the model. During the period of administering the FXR agonist to mice, the therapeutic effects can be monitored by observations on body weights, stool consistency and rectal bleeding. After euthanasia, the disease development and effects of the FXR agonist can be further quantified by measuring colon weight and length, colon and ileum histology by H&E staining for inflammation and structural changes in mucosa, and protein and RNA expression of genes related to the disease.

Example B-12: Mdr1a−/− Mouse Model

The Mdr1a−/− mouse model is a spontaneous colitis model that has been used in testing new therapies for human IBD. Loss of the Mdr1a gene in this model leads to impaired intestinal barrier function, which results in increased infiltration of gut bacteria and subsequent colitis. Under proper housing conditions, Mdr1a−/− mice can develop colitis at about 8 to 13 weeks of age. During disease progression, a disease activity index (DAI) summing the clinical observation scores on rectal prolapse, stool consistency and rectal bleeding can be used to monitor the disease. Testing of an FXR agonist can be started at the initial stage of disease, generally with DAI score less than 1.0. Alternatively, administration of an FXR agonist can be initiated when colitis has developed, typically with a DAI score above 2.0. Therapeutic effects of the FXR agonist can be monitored by measuring the DAI, and testing can be terminated when desired disease severity has been achieved, generally with a DAI score around 5.0. After euthanasia, the disease development and effects of the FXR agonist can be further quantified by measuring colon weight and length, colon histology by H&E staining for inflammation and structural changes in mucosa, and protein and RNA expression of genes related to the disease.

The examples and embodiments described herein are for illustrative purposes only and various modifications or changes suggested to persons skilled in the art are to be included within the spirit and purview of this application and scope of the appended claims.

What is claimed is:

1. A method of treating fatty liver in a mammal, comprising administering to the mammal with fatty liver a compound that has the following structure:

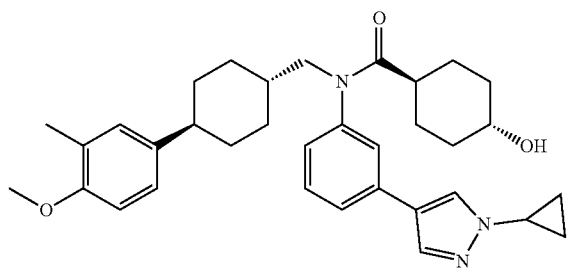

or a pharmaceutically acceptable salt or solvate thereof.

2. A method of treating a disease or condition in a mammal, comprising administering to the mammal in need thereof a compound that has the following structure:

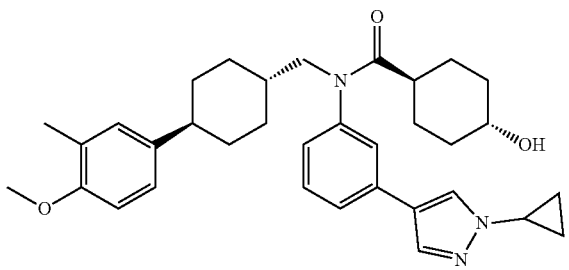

or a pharmaceutically acceptable salt or solvate thereof;

wherein the disease or condition is primary biliary cirrhosis, primary sclerosing cholangitis, cholestasis, nonalcoholic steatohepatitis (NASH), nonalcoholic fatty liver disease (NAFLD), inflammatory bowel disease, irritable bowel syndrome, or bile acid diarrhea.

3. The method of claim 2, further comprising administering at least one additional therapeutic agent to the mammal.

4. The method of claim 1, further comprising administering at least one additional therapeutic agent to the mammal.

* * * * *